United States Patent [19]
Oinuma et al.

[11] Patent Number: 5,679,671
[45] Date of Patent: Oct. 21, 1997

[54] AMINO ACID DERIVATIVE

[75] Inventors: Hitoshi Oinuma; Shinji Suda; Naoki Yoneda, all of Ibaraki; Makoto Kotake, Chiba; Kenji Hayashi, Ibaraki; Kazutoshi Miyake, Ibaraki; Nobuyuki Mori, Ibaraki; Mamoru Saito, Ibaraki; Toshiyuki Matsuoka, Ibaraki; Masayuki Namiki, Ibaraki; Takeshi Sudo, Ibaraki; Shigeru Souda, Ibaraki, all of Japan

[73] Assignee: Eisai Co., Ltd., Tokyo, Japan

[21] Appl. No.: 374,705

[22] Filed: Jan. 25, 1995

[30] Foreign Application Priority Data

| Jun. 11, 1993 | [JP] | Japan | 5-140346 |
| Jun. 14, 1993 | [JP] | Japan | 5-141841 |
| Jul. 6, 1993 | [JP] | Japan | 5-166692 |
| Oct. 28, 1993 | [JP] | Japan | 5-270283 |
| Oct. 28, 1993 | [JP] | Japan | 5-292830 |
| Nov. 8, 1993 | [JP] | Japan | 5-300807 |
| Nov. 16, 1993 | [JP] | Japan | 5-308577 |
| Dec. 17, 1993 | [JP] | Japan | 5-317665 |
| Feb. 8, 1994 | [JP] | Japan | 6-034300 |
| Feb. 8, 1994 | [JP] | Japan | 6-034301 |
| Mar. 7, 1994 | [JP] | Japan | 6-035511 |
| Mar. 7, 1994 | [JP] | Japan | 6-035512 |

[51] Int. Cl.⁶ ............................ A61K 31/55; C07D 495/06
[52] U.S. Cl. .................... 514/211; 514/213; 514/214; 514/215; 514/217; 514/218; 514/219; 514/220; 514/221; 514/279; 514/299; 514/359; 514/438; 514/439; 514/443; 514/444; 514/448; 540/521; 540/522; 546/38
[58] Field of Search .................... 514/211, 213, 514/214, 215, 217, 218, 219, 220, 221, 279, 299, 359, 438, 439, 443, 444, 448; 540/521, 522; 546/38

[56] References Cited

U.S. PATENT DOCUMENTS 5,238,932 8/1993 Flynn et al. .................... 514/214

FOREIGN PATENT DOCUMENTS

| 0481522 | 4/1992 | European Pat. Off. . |
| 0533084 | 3/1993 | European Pat. Off. . |
| 0534363 | 3/1993 | European Pat. Off. . |
| 0599444 | 6/1994 | European Pat. Off. . |

OTHER PUBLICATIONS

Flynn et al., J. Med. Chem., 36(16), pp. 2420–2423 (Aug. 1993).

*Primary Examiner*—John M. Cooney, Jr.
*Attorney, Agent, or Firm*—Birch, Stewart, Kolasch & Birch, LLP

[57] ABSTRACT

The present invention relates to an amino acid derivative having an angiotensin I-converting enzyme inhibition activity, a vasopressin antagonism and an atrial natriuretic peptide hydrolase inhibition activity.

This amino acid derivative is represented by the following general formula (I):

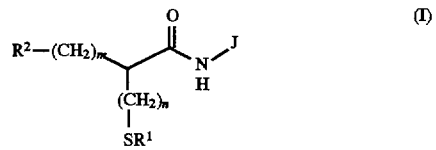

wherein $R^1$ represents a hydrogen atom or an acyl group;

$R^2$ represents a hydrogen atom, a lower alkyl group, a cycloalkyl group, an ary group which may have a substituent, a heteroaryl group which may have a substituent, an arylalkyl group which may have a substituent or a heteroarylalkyl group which may have a substituent;

m and n represent each independently an integer of 0, 1 or 2 and

J represents a cyclic group having an angiotensin I-converting enzyme inhibition activity.

61 Claims, No Drawings

AMINO ACID DERIVATIVE

FIELD OF THE INVENTION

The present invention relates to an amino acid derivative. More particularly, it relates to an amino acid derivative having excellent effects as a medicine.

DESCRIPTION OF THE RELATED ART

Among heart diseases generally called heart failure, not only acute heart failure but also a disease requiring no immediate treatment such as chronic heart failure when it has progressed, is directly fatal to us. Accordingly studies on remedies for this disease have been actively made for a long time. As a result, there have been developed, up to the present, a number of medicines for heart failure with various action mechanisms.

For example, cardiac glycosides represented by digitalis have been used for a long time as a medicine capable of improving cardiac contractile force and tolerance limit to exercise without elevating cardiac rate. However, these cardiac glycosides have such defects that they each has a narrow margin of safety and can administer to only limited patients. In addition, they exhibit some side effects of, for example, causing severe arrhythmia, which makes them less useful.

To relieve hemostasis due to backward heart failure, diuretics such as furosemide and spironolactone are sometimes employed. Although these medicines have such advantages that they are also applicable to a mild case of heart failure and relieve subjective symptoms, they have such disadvantages that they exhibit side effects of, for example, electrolyte disturbance and dysglycemia and are not directly related to the improvement of tolerance limit to exercise and the so-called "quality of life".

As a vasodilator for improving blood flow in the coronary vessel, there have also been employed nitrates such as isosorbide nitrate and α-receptor blocking agents represented by bunazosin and prazosin. Although the former has been widely used since it is characterized by relieving the preload and improving subjective symptoms and tolerance limit to exercise, exerting an immediate action and having no severe side effect, it has such a defect that it tends to be easily tolerated. On the other hand, the latter is characterized by relieving both of preload and postload and elevating the cardiac rate. However, it has been reported that these agents have no effect of improving subjective symptoms or tolerance limit to exercise.

Furthermore, there have been known β-stimulating drugs such as dopamine and dobutamine, each having a potent effect of enhancing cardiac contractility, as the first choice in the emergency care for acute heart failure. However, these drugs are liable to be tolerant and sometimes cause arrhythmia, etc. It is also known that they exert some side effects of inducing, for example, myocardial disorders. Accordingly care must be taken of the utilization of these drugs.

In recent years, atrial natriuretic peptide hydrolase (neutral endpeptidase: NEP 24, 11) inhibitors and angiotensin I-converting enzyme (hereinafter referred to simply as ACE) inhibitors have attracted attention as a novel remedy for heart failure.

The above-mentioned atrial natriuretic peptide (hereinafter referred to simply as ANP) is a hormone present in bionomics. In addition to a potent water diuretic/natriuretic effect, a vasodilator effect and so on, it exerts a suppressive effect on the liberation of norepinephrine through the suppression of the sympathetic nerve, a suppressive effect on the secretion of renin from the kidney and a suppressive effect on the secretion of aldosterone from the adrenal gland, and, further, excerts also an inhibitory effect on perfusion through the enhancement of the water permeability in the vein, etc. With respect to the function of ANP in a patient suffering from the congestive heart failure with an increase in preload, for example, it is considered that the secretion of ANP is accelerated in proportion to atrial-stretch stimulation and the amount of the circulating body fluid is thus compensatingly controlled. In fact, by the administration of ANP to patients with heart failure, decrease of the pulmonary wedge pressure and a diuretic effect are observed, and the improvements of the cardiac index and the stroke volume are also attained. Further, it is reported that ANP suppresses the liberation of endogenous hormones promoting the vicious circle in heart failure, for example, aldosterone and norepinephrine to thereby relieve the pathological conditions of heart failure from various angles. It is considered that these effects of ANP are favorable in treating not only heart failure but also hypertension.

Because of being a peptide, however, ANP cannot be orally administered and has only a poor metabolic stability, which brings about a problem that it can be clinically usable only in an acute stage at present. Also it is reported that the effects of ANP would be deteriorated during prolonged administration. Thus it should be carefully used.

Under taking the above-mentioned characteristics of ANP into consideration, much attention has been paid to the above-mentioned ANP hydrolase inhibitor (hereinafter referred to simply as NEP inhibitor) as an ANP-associated preparation for oral administration. It is reported that the administration of the NEP inhibitor to a patient with heart failure increases the blood ANP level and exerts a natriuretic effect. However, the existing NEP inhibitors only slightly affect the cardiovascular dynamics and cannot clearly exhibit the effect of relieving preload and postload.

On the other hand, there has been proved the usefulness of the ACE inhibitor which is one of vasodilators, because it suppresses the formation of angiotensin II (hereinafter referred to simply as AT-II) which is an increment factor of heart failure to thereby significantly improve the NYHA severity and enhance the tolerance limit to exercise in chronic heart failure, and thus exhibits life-prolongation effect. However, the effective ratio of the existing ACE inhibitors to the patients is not always high, and their efficacies widely vary from patient to patient. In addition, it is pointed out such problem that the ACE inhibitors have side effects of, for example, inducing hypotension, which restricts the administration thereof to those suffering from depression of renal function.

DISCLOSURE OF THE INVENTION

As discussed above, the existing NEP inhibitors and ACE inhibitors are each limited in usefulness, though they have attracted public attention as novel remedies for heart failure. Therefore, it has been urgently desired to study a medicine having the advantages of both of the NEP inhibition activity and the ACE inhibition activity.

Under these circumstances, the present inventors have conducted studies with respect to a medicine which can be orally administered, has a high metabolic stability and a high effective ratio and is also applicable widely to patients with complications. As a result, they have found that the desired object can be achieved by using an amino acid derivative or a pharmacologically acceptable salt thereof as will be shown hereinbelow, thus completing the present invention.

The present invention relates to a medicinal composition comprising a therapeutically or prophylactically available dose of an amino acid derivative represented by the general formula (I) or a pharmacologically acceptable salt thereof and a pharmacologically acceptable filler:

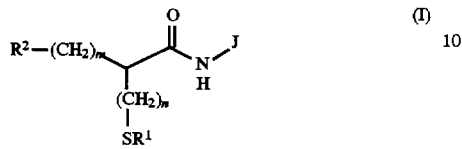

wherein $R^1$ represents a hydrogen atom or an acyl group;

$R^2$ represents a hydrogen atom, a lower alkyl group, a cycloalkyl group, an arylalkyl group which may have a substituent or a heteroarylalkyl group which may have a substituent, an aryl group which may have a substituent, or a heteroaryl group which may have a substituent;

m and n represent each independently an integer of 0, 1 or 2; and

J represents a cyclic group having an angiotensin I-converting enzyme inhibition activity.

The cyclic group having an ACE inhibition activity as given in the definition of J in the above general formula (I) involves every group each having an ACE inhibition activity and a saturated or unsaturated monocyclic or fused ring. Particular examples thereof include those represented by the following general formula, though the group is not restricted thereto:

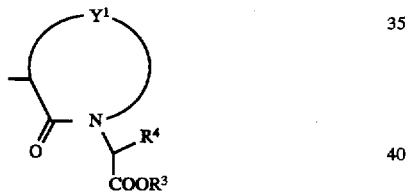

wherein $R^3$ represents a hydrogen atom or a carboxyl-protecting group;

$Y^1$ represents a group represented by the formula $-(CR^5R^6)_p-Z-(CR^7R^8)_q-$ [wherein $R^5$, $R^6$, $R^7$ and $R^8$ are the same or different from one another and each represents a hydrogen atom, a lower alkyl group, an aryl group which may have a substituent, a heteroaryl group which may have a substituent, an arylalkyl group which may have a substituent or a heteroarylalkyl group which may have a substituent; Z represents a group represented by the formula $-(CH_2)_r-$ (wherein r represents an integer of 0 or 1), a group represented by the formula $-S-$, a group represented by the formula $-SO-$, a group represented by the formula $-SO_2-$, a group represented by the formula $-O-$ or a group represented by the formula $-NR^9-$ (wherein $R^9$ represents a hydrogen atom or a lower alkyl group); and p and q represents each independently an integer of 0 or 1 to 4 and the sum of p and q is 6 or less;

with the proviso that in $R^5$, $R^6$, $R^7$, $R^8$ and $R^9$, when two carbon atoms each having an arbitrary substituent selected from among $R^5$ to $R^9$ bonded thereto are adjacent to each other, said two carbon atoms and said two substituents bonded thereto may be combined together to form a benzene ring or a heteroaryl ring, which may have a substituent;

and that when $R^2$ is an aryl group, p is 2, q is 2, Z represents a group represented by the formula $-(CH_2)_{r'}-$ (wherein r' is 0), and two substituents arbitrary selected from among $R^7$'s and $R^8$'s which are bonded to two adjacent carbon atoms are combined together to form a benzene ring, said benzene ring must be substituted by an aryl group which may have a substituent]; and $R^4$ represents a hydrogen atom, or a group used to form a 5- to 7-membered ring which may contain one sulfur or oxygen atom in combination with $R^7$ or $R^8$.

To further promote the understanding of the present invention, particular examples of the compounds according to the present invention will be given hereinbelow, though the present invention is not restricted thereto:

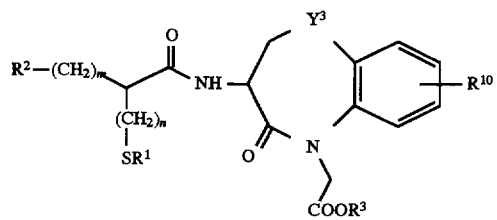

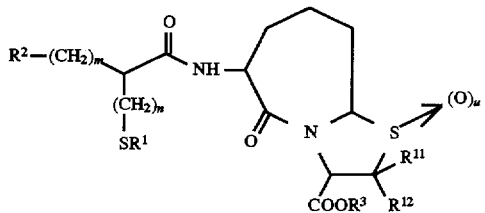

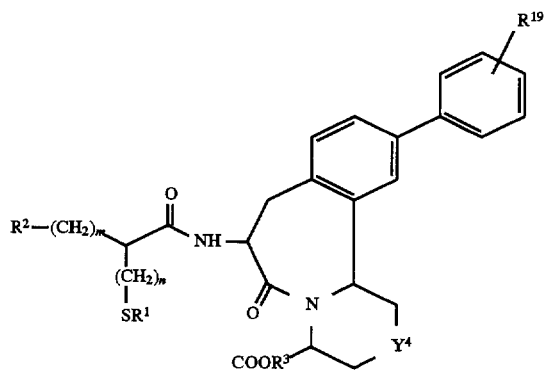

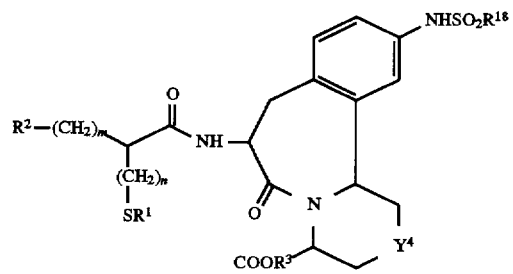

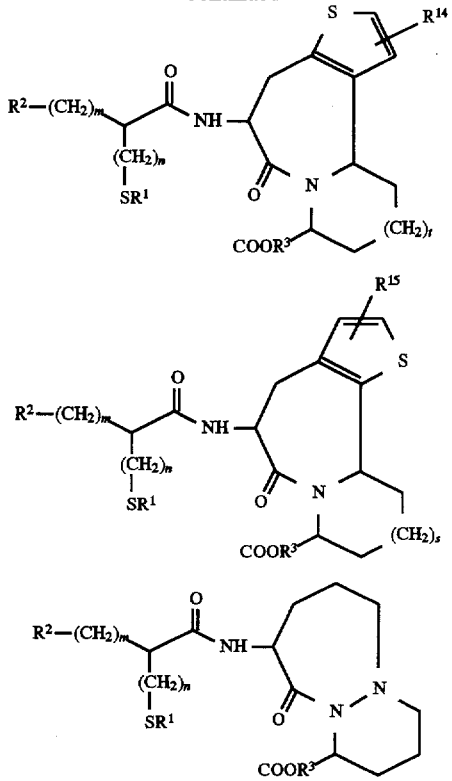

wherein R¹ represents a hydrogen atom or an acyl group;

R² represents a hydrogen atom, a lower alkyl group, a cycloalkyl group, an aryl group which may have a substituent, a heteroaryl group which may have a substituent, an arylalkyl group which may have a substituent or a heteroarylalkyl group which may have a substituent;

R³ represents a hydrogen atom or a carboxyl-protecting group;

R¹¹ and R¹² are the same or different from each other and each represents a hydrogen atom or a lower alkyl group;

u represents 0, 1 or 2;

R¹⁹ represents a hydrogen atom, a lower alkyl group, a lower alkoxy group, a hydroxyl group or a halogen atom;

m and n represent each independently 0, 1 or 2;

R¹⁴ and R¹⁵ represent each a hydrogen atom, a lower alkyl group, a lower alkoxy group, a hydroxyl group, a halogen atom, an aryl group which may have a substituent or a heteroaryl group which may have a substituent;

s and t represent each an integer of 0, 1 or 2;

Y⁹ represents a group represented by the formula —(CH₂)_w— (wherein w represents an integer of 0 or 1), a group represented by the formula —S—, a group represented by the formula —SO—, a group represented by the formula —SO₂—, a group represented by the formula —O— or a group represented by the formula —NR¹⁷— (wherein R¹⁷ represents a hydrogen atom or a lower alkyl group);

R¹⁰ represents a hydrogen atom, a lower alkyl group, a lower alkoxy group, a hydroxyl group, a halogen atom, an aryl group which may have a substituent or a heteroaryl group which may have a substituent;

Y⁴ represents a group represented by the formula —(CH₂)_x— (wherein x represents an integer of 0 or 1), a group represented by the formula —S—, a group represented by the formula —SO—, a group represented by the formula —SO₂—, a group represented by the formula —O— or a group represented by the formula —NR¹⁷— (wherein R¹⁷ represents a hydrogen atom or a lower alkyl group); and R¹⁸ represents a hydrogen atom, a lower alkyl group or an arylalkyl group which may have a substituent.

In the present invention, the lower alkyl group as given in the definition of R², R⁵, R⁶, R⁷, R⁸, R⁹, R¹⁰, R¹³, R¹⁴, R¹⁵, R¹⁶, R¹⁷, R¹⁸ and R¹⁹ means a linear or branched alkyl group having 1 to 8, preferably 1 to 6, carbon atoms. Examples thereof include methyl group, ethyl group, propyl group, isopropyl group, n-butyl group, isobutyl group, sec-butyl group, tert-butyl group, pentyl (amyl) group, isopentyl group, neopentyl group, tert-pentyl group, 1-methylbutyl group, 2-methylbutyl group, 1,2-dimethylpropyl group, n-hexyl group, isohexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,1,2-trimethylpropyl group, 1,2,2-trimethylpropyl group, 1-ethyl-1-methylpropyl group, 1-ethyl-2-methylpropyl group and so on. Preferable examples thereof include methyl group, ethyl group, propyl group, isopropyl group, n-butyl group, isobutyl group, sec-butyl group, tert-butyl group, n-pentyl group and isopeptyl group. As R², particularly isobutyl group, still preferably S-isobutyl group, i.e., 1(S)-methylpropyl group may be cited.

The lower alkoxy group as given in the definition of R¹⁰, R¹³, R¹⁴ and R¹⁵ means those derived from the above-mentioned lower alkyl groups, for example, methoxy, ethoxy, isopropoxy, n-butoxy, t-butoxy and so on.

In the aryl group which may have a substituent as given in the definition of R², R⁵, R⁶, R⁷, R⁸, R¹⁰, R¹⁴ and R¹⁵, phenyl, 2-naphthyl, 3-naphthyl, anthracenyl and so on may be exampled as aryl.

The substituent in this case may mean a lower alkyl group such as methyl group, ethyl group, propyl group and isopropyl group, a lower alkoxy group such as methoxy group, ethoxy group, propyloxy group and isopropyloxy group, an aryl group, an arylalkyl group, a heteroaryl group, a heteroarylalkyl group, nitro group, hydroxyl group, an amino group which may be mono- or di-substituted, an acyl group such as formyl group and acetyl group, a hydroxyalkyl group, an alkoxyalkyl group, an aminoalkyl group, carbamoyl group, thiol group, an alkylthio group, sulfinyl group, sulfonyl group, an alkylsulfinyl group, an alkylsulfonyl group, a halogen atom, a carboxyl group which may be protected, a carboxylalkyl group which may be protected, an acylalkyl group which may be protected, and so on.

The heteroaryl group which may have a substituent as given in the definition of R², R⁵, R⁶, R⁷, R⁸, R¹⁰, R¹⁴ and R¹⁵ means a 3- to 8-membered, preferably 5- to 6-membered, ring or fused ring containing at least one hetero atom such as oxygen atom, sulfur atom and nitrogen atom.

Particular examples thereof include thienyl, furanyl, pyranyl, 2H-pyrrolyl, pyrrolyl, imidazolyl, pyrazolyl, pyridyl, pyrazinyl, pyrimidyl, pyridazinyl, isothiazolyl, isoxazolyl, furazanyl, benzothienyl, isobenzofuranyl, chromenyl, Indolidinyl, isoindolyl, indolyl, purinyl, quinolidinyl, isoquinolyl, quinolyl, phthalazinyl, quinazolyl, carbazolyl, acridinyl, phenanthridinyl and so on.

In this case, the substituent has the same meaning as the one for the aryl as described above.

In the arylalkyl group which may have a substituent as given in the definition of $R^2$, $R^5$, $R^6$, $R^7$, $R^8$ and $R^{18}$, the aryl has the same meaning as the aryl as described above.

In this case, the alkyl has the same meaning as the lower alkyl as described above. Further, the substituent in this case has the same meaning as the one for the aryl group as described above.

In the heteroarylalkyl group which may have a substituent as given in the definition of $R^2$, $R^5$, $R^6$, $R^7$ and $R^8$, it has the same meaning as the heteroaryl as described above.

In this case, the alkyl has the same meaning as the lower alkyl as described above. Further, the substituent in this case has the same meaning as the one for the heteroaryl group as described.

The halogen atom as given in the definition of $R^{10}$, $R^{13}$, $R^{14}$, $R^{15}$ and $R^{19}$ means fluorine atom, chlorine atom, bromine atom, iodine atom and so on.

The carboxyl-protecting group as given in the definition of $R^3$ means those which can be hydrolyzed into a carboxyl group in vivo. Examples thereof include lower alkyl groups such as methyl, ethyl and t-butyl; lower alkyl groups substituted with a phenyl group which may have a substituent, such as p-methoxybenzyl, p-nitrobenzyl, 3,4-dimethoxybenzyl, diphenylmethyl, trityl and phenethyl; haloganated lower alkyl groups such as 2,2,2-trichloroethyl and 2-iodoethyl; lower alkanoyloxy lower alkyl groups such as pivaloyloxymethyl, acetoxymethyl, propionyloxymethyl, butyryloxymethyl, valeryloxymethyl, 1-acetoxyethyl, 2-acetoxyethyl, 1-pivaloyloxyethyl and 2-pivaloyloxyethyl; higher alkanoyloxy lower alkyl groups such as palmitoyloxyethyl, heptadecanoyloxymethyl and 1-palmitoyloxyethyl; lower alkoxycarbonyloxy lower alkyl groups such as methoxycarbonyloxymethyl, 1-butoxycarbonyloxyethyl and 1-(isopropoxycarbonyloxy) ethyl; carboxy lower alkyl groups such as carboxymethyl and 2-carboxyethyl; heterocyclic groups such as 3-phthalidyl; benzoyloxy lower alkyl groups which may have a substituent, such as 4-glycyloxybenzoyloxymethyl and 4-[N-(t-butoxycarbonyl)glycyloxy]benzoyloxymethyl; (substituted dioxolene) lower alkyl groups such as (5-methyl-2-oxo-1,3-dioxolen-4-yl)methyl; cycloalkyl-substituted lower alkanoyloxy lower alkyl groups such as 1-cyclohexylacetyloxyethyl; and cycloalkyloxycarbonyloxy lower alkyl groups such as 1-cyclohexyloxycarbonyloxyethyl.

The acyl group as given in the definition of $R^1$ includes aliphatic and aromatic acyl groups and those derived from heterocyclic groups, for examples, lower alkanoyl groups such as formyl group, acetyl group, propionyl group, butyryl group, valeryl group, isovaleryl group and pivaloyl group, aroyl groups such as benzoyl group, toluoyl group and naphthoyl group, heteroaroyl groups such as furoyl group, nicotinoyl group and isonicotinoyl group, and so on. Among them, formyl group, acetyl group, benzoyl group and so on may be cited as particularly preferable ones.

As examples of the pharmacologically acceptable salt in the present invention, inorganic acid salts such as hydrochloride, sulfate, hydrobromide and phosphate and organic acid salts such as formate, acetate, trifluoroacetate, maleate, fumarate, tartrate, methanesulfonate, benzenesulfonate and toluenesulfonate may be cited.

The compounds of the present invention occur as various stereoisomers due to the structures thereof. It is needless to say that they each falls within the scope of the present invention.

As preferable compounds among compounds of the present invention, those represented by the following general formula (VII) may be cited:

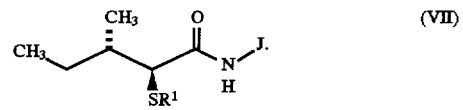

Although these compounds occur as optical isomers due to their structures as described above, the compounds represented by the following general formula (VII') have preferable stereostructures:

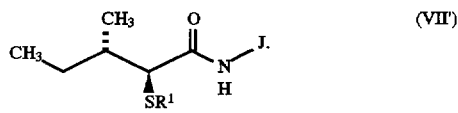

The compounds of the present invention, in which the side chain part:

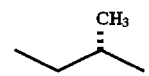

in common to the compounds represented by the general formula (VII) is bound to a cyclic group, can exert an enhanced effect as compared with other compounds being similar thereto in structure. As a matter of course, they can exert remarkably improved effects as compared with compounds being similar in structure thereto when they are intravenously administered. Further, they can exert remarkably improved effects as compared with compounds being similar in structure thereto when they are orally administered, since they have improved bioavailabilities.

Now, main processes for producing the compounds of the present invention will be given. Needless to say, the compounds of the present invention can be obtained by combining known reactions in addition to the production processes as will be given hereinafter.

Production process A-1

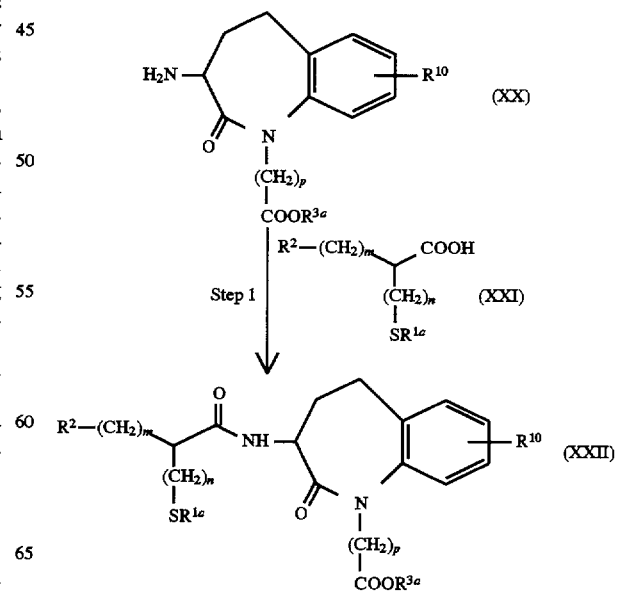

-continued

Step 2

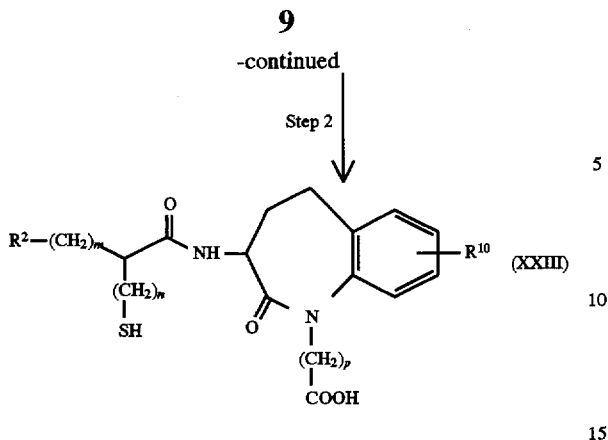
(XXIII)

wherein $R^2$ represents a hydrogen atom, a lower alkyl group, a cycloalkyl group, an aryl group which may have a substituent, a heteroaryl group which may have a substituent, an arylalkyl group which may have a substituent or a heteroarylalkyl group which may have a substituent;

$R^{10}$ represents a hydrogen atom, a lower alkyl group, a lower alkoxy group, a hydroxyl group, a halogen atom, an aryl group which may have a substituent or a heteroaryl group which may have a substituent;

$R^{1a}$ represents an acyl group;

$R^{3a}$ represents a carboxyl-protecting group;

p represents an integer of 1 or 2; and m and n represent each independently an integer of 0 to 2.

(Step 1)

This step is one wherein a 3-amino-benzazepin-2-one derivative (XX) is condensed with a carboxylic acid derivative (XXI) or an active derivative thereof such as an acid halide thereof to thereby give an amide derivative (XXII). The condensation is effected in the conventional manner. For example, the 3-amino-benzazepin-2-one derivative (XX) is reacted with the carboxylic acid derivative (XXI) in an inert solvent represented by methylene chloride, tetrahydrofuran and so on in the presence of a condensing reagent commonly employed in the art such as EEDQ (1-ethoxycarbonyl-2-ethoxy-1,2-dihydro-quinoline), DCC (1,3-dicyclohexylcarbodiimide), DEC [1-(3-dimethylaminopropyl)-3-ethylcarbodiimide hydrochloride] or diethyl cyanophosphonate to thereby give the amide derivative (XXII). When the condensation proceeds via an acid chloride of the carboxylic acid derivative (XXI), the carboxylic acid derivative (XXI) is converted into the acid chloride thereof in an appropriate inert solvent with the use of a chlorinating agent commonly employed in the art such as thionyl chloride and oxalyl chloride, followed by the reaction thereof with the 3-aminobenzazepin-2-one derivative (XX) to thereby give the compound (XXII).

(Step 2)

This step is one wherein the ester group and acylthio group in the amide derivative (XXII) obtained in the step 1 are deprotected by the conventional manner to thereby give the target compound (XXIII). The deprotection is effected by a method commonly employed in the art. For example, it may be effected by hydrolyzing the amide derivative (XXII) in a dilute aqueous solution of an alkali such as sodium hydroxide and lithium hydroxide or in a dilute aqueous solution of a mineral acid.

Production process A-2

When $R^{10}$ is an aryl group which may have a substituent, the compound (XX') can be synthesized by the following process:

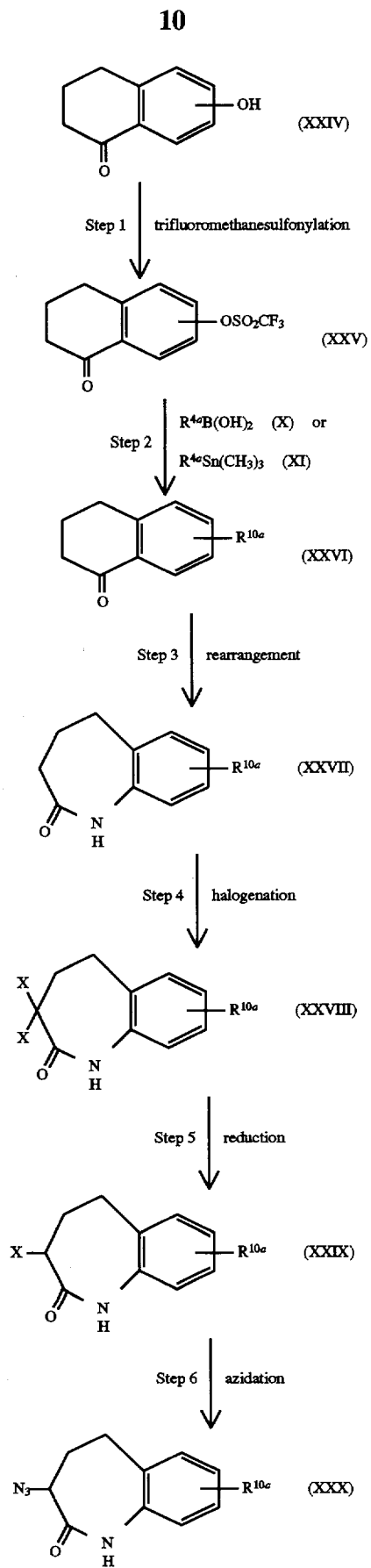

-continued

Step 7 | alkylation

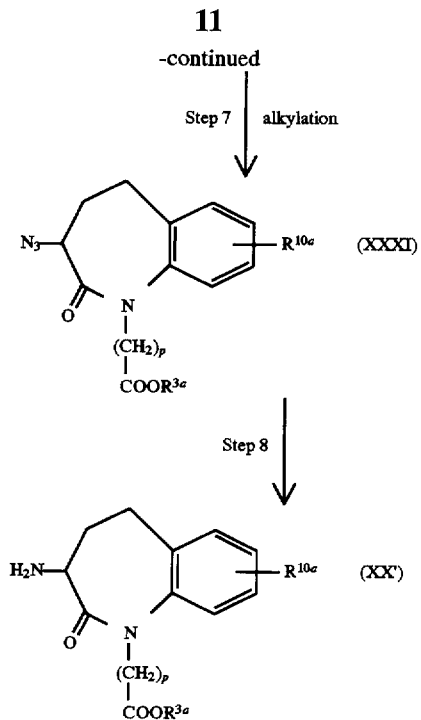

Step 8 wherein $R^{3a}$ and p have each the same meaning as the one defined above;

$R^{10a}$ represents an aryl group which may have a substituent; and

X represents a halogen atom.

(Step 1)

This step is one wherein a hydroxytetralone derivative (XXIV) is trifluoromethanesulfonylated to thereby give a trifluoromethanesulfonyloxy compound (XXV). The trifluoromethanesulfonylation is effected by reacting the derivative (XXIV) with trifluoromethanesulfonic anhydride or trifluoromethanesulfonyl chloride in an inert solvent represented by methylene chloride, tetrahydrofuran and so on in the presence of a base such as pyridine.

(Step 2)

This step is one wherein the trifluoromethanesulfonyloxy compound (XXV) obtained in the step 1 is coupled with an arylboric acid compound (X) or an aryltin compound (XI) to thereby give an aryltetralone derivative (XXVI). The coupling of the compound (XXV) with the compound (X) or (XI) is effected in an appropriate solvent which would not inhibit this reaction in the presence of an appropriate base and a palladium catalyst. As examples of the solvent, hydrocarbons such as toluene and amides such as N,N'-dimethylformamide may be cited. As examples of the base, alkali or alkaline earth metal carbonates such as potassium carbonate and calcium carbonate and organic bases such as triethylamine and N-methylmorpholine may be cited. As an example of the palladium catalyst, tetrakis (triphenylphosphine)palladium (0) may be cited.

(Step 3)

This step is one wherein a benzazepine derivative (XXVII) is obtained from the aryltetralone derivative (XXVI) obtained in the step 2 by a rearrangement reaction commonly employed in the art. The rearrangement can be carried out in accordance with a method commonly employed in the art, for example, the Beckmann rearrangement, the Schmidt rearrangement or the like. More particularly speaking, in the case of the Beckmann rearrangement, the benzazepine derivative (XXVII) can be obtained by treating the aryltetralone derivative (XXVI) with hydroxylamine hydrochloride to thereby give an oxime, and then, for example, heating the oxime in the presence of an appropriate acid. In the case of the Schmidt rearrangement, it is effected by, for example, a method which comprises reacting with hydrazoic acid or sodium azide in the presence of an appropriate acid. As the acid, every one commonly employed in the art may be used. Examples thereof include sulfuric acid, polyphosphoric acid, trichloroacetic acid, methanesulfonic acid and so on.

(Steps 4 and 5)

These steps are one wherein the benzazepine derivative (XXVII) obtained in the step 3 is halogenated and reduced to thereby give a 3-halo-benzazepine derivative (XXIX).

The dihalogenation and reduction can be proceeded each in accordance with a method commonly employed in the art. In particular, a preferable result can be achieved by carrying out these reactions in accordance with the method of Nagasawa et al. [J. Med. Chem., 14, 501 (1979)].

Namely, first, the benzazepine derivative (XXVII) obtained in the step 3 is reacted with $PX_5$ (wherein X is Br or Cl) to thereby give a dihalogen-substituted benzazepine derivative (XXVIII), and next, the compound (XXVIII) is catalytically hydrogenated in the presence of a palladium catalyst to thereby give a 3-halo-benzazepine derivative (XXIX).

(Step 6)

This step is one wherein the 3-halo-benzazepine derivative (XXIX) obtained in the step 5 is subjected to azidation to thereby give an azide (XXX).

The azidation is effected by a method commonly employed in the art. That is, it is effected by reacting the 3-halo-benzazepine derivative (XXIX) with sodium azide or lithium azide in an appropriate solvent, for example, ethanol, dimethylformamide or dimethyl sulfoxide.

(Step 7)

This step is one wherein the azide (XXX) obtained in the step 6 is alkylated by the conventional manner to thereby give an N-alkylated compound (XXXI).

The alkylation can be effected by a method commonly employed in the art. For example, it is effected by reacting the azide (XXX) with an iodoalkyl ester in an appropriate solvent, for example, dimethylformamide or tetrahydrofuran in the presence of a strong base such as sodium hydride. Alternatively, it is effected by reacting the azide (XXX) with an haloalkyl ester in tetrahydrofuran in the presence of a base such as potassium carbonate with the use of a phase transfer catalyst such as tetra n-butylammonium bromide and benzyltriethylammonium iodide.

(Step 8)

This step is one wherein the N-alkylated compound (XXXI) obtained in the step 7 is reduced by the convectional manner to thereby give an amine (XX').

The reduction can be effected by a method commonly employed in the art. It may be effected by catalytically hydrogenating the N-alkylated compound (XXXI) in an appropriate solvent, for example, methanol, ethanol or ethyl acetate in the presence of a catalyst such as palladium/carbon.

This amine (XX') is important as an intermediate for producing the compound of the general formula (II) wherein $Y^3$ is a group represented by —$CH_2$—.

Production process B-1
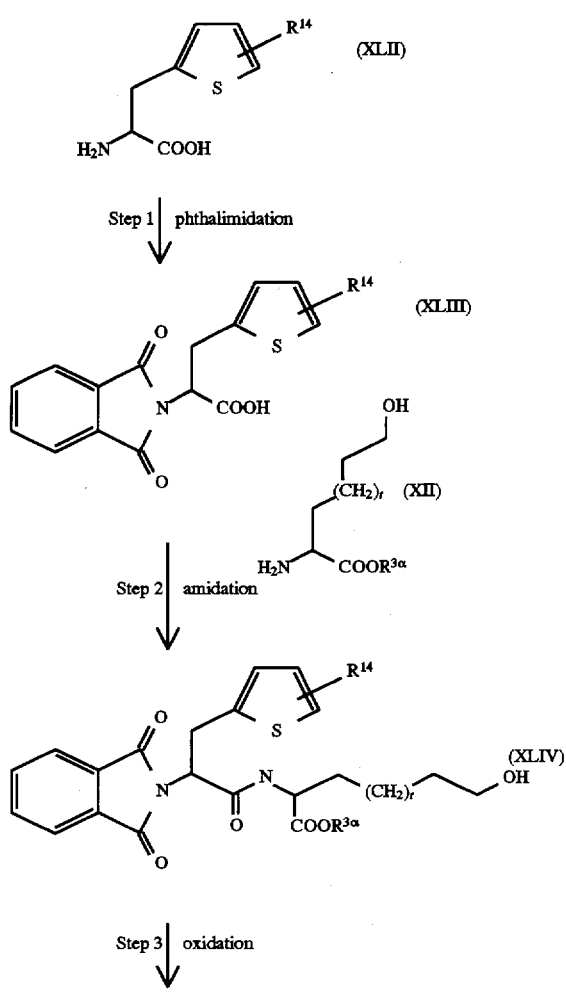
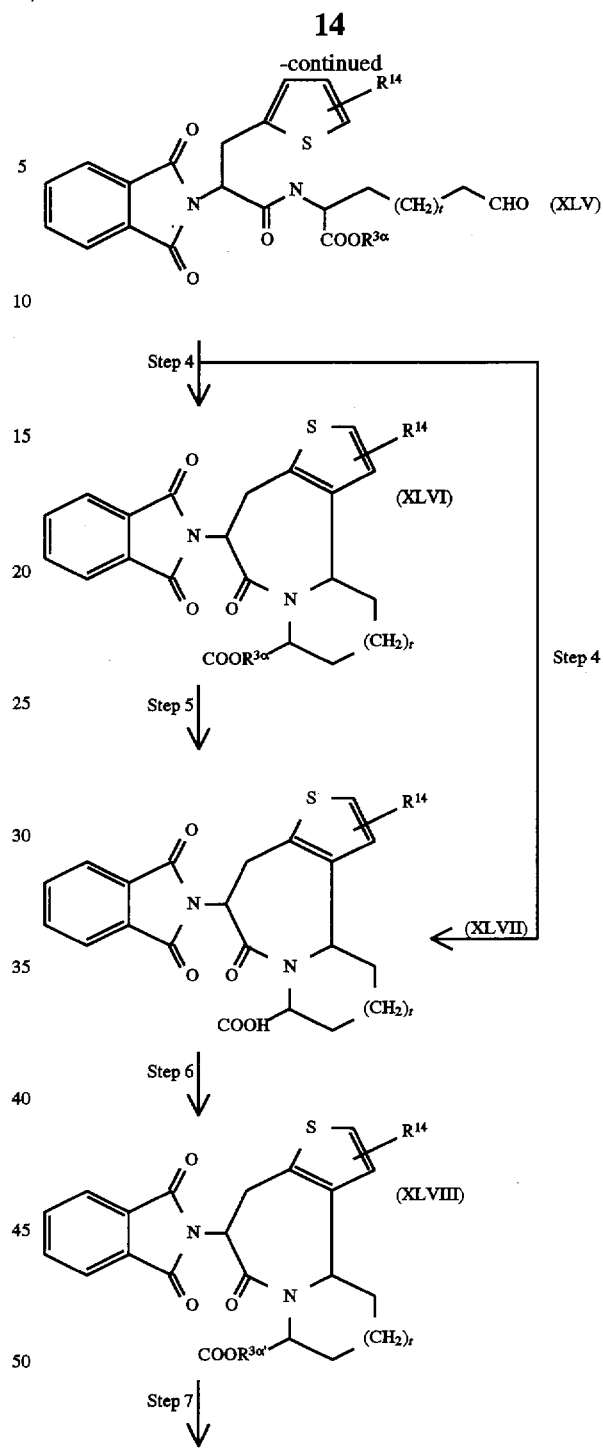

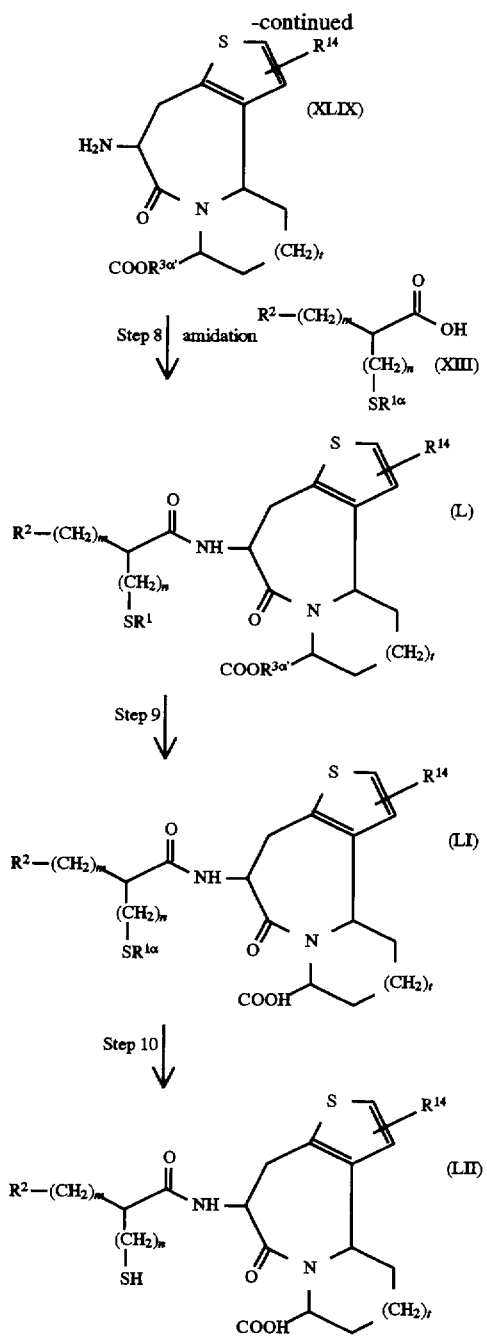

In a series of formulas, $R^{1a}$ represents an acyl group; $R^2$ represents a hydrogen atom, a lower alkyl group, a cycloalkyl group, an aryl group which may have a substituent, a heteroaryl group which may have a substituent, an arylalkyl group which may have a substituent or a heteroarylalkyl group which may have a substituent; $R^{3a}$ and $R^{3a'}$ represent carboxy-protecting groups; $R^{14}$ represents a hydrogen atom, a lower alkyl group, a lower alkoxy group, a hydroxyl group, a halogen atom, an aryl group which may have a substituent or a heteroaryl group which may have a substituent; t represents an integer of 0, 1 or 2; m represents an integer of 0, 1 or 2; and n represents an integer of 0, 1 or 2.

(Step 1)

This step is one wherein the amino group of a 2-thienylalanine derivative (XLVII) is protected through phthalimidation by the conventional manner to thereby give a phthalimide carboxylic acid derivative (XLIII). The compound (XLIII) can be obtained in accordance with a method for phthalimidation which is commonly employed in the art. For example, phthalic anhydride and the compound (XLII) are heated in an inert solvent, for example, dimethylformamide or aqueous dioxane or without using any solvent in the presence of a base such as triethylamine or without using any base to thereby give the phthalimide carboxylic acid derivative (XLIII). Alternately, a phthalimidating agent such as ethoxycarbonylphthalimide is reacted with the compound (XLII) in the presence of a base such as sodium carbonate and sodium hydrogencarbonate to thereby give the phthalimide carboxylic acid derivative (XLIII).

(Step 2)

This step is one wherein the phthalimide carboxylic acid derivative (XLIII) obtained in the step 1 or an active derivative thereof, such as an acid halide thereof, is condensed with an amino acid ester derivative (XII) by the conventional manner to thereby give an amide derivative (XLIV).

The condensation is effected by a method commonly employed in the art. For example, the compound (XLIII) is reacted with the amino acid ester derivative (XII) in an inert solvent represented by methylene chloride, tetrahydrofuran and so on in the presence of a commonly employed condensing reagent such as EEDQ (1-ethoxycarbonyl-2-ethoxy-1,2-dihydroquinoline), DCC (1,3-dicyclohexylcarbodiimide), DEC (1-(3-dimethylaminopropyl)-3-ethylcarbodiimide hydrochloride) or diethyl cyanophosphonate to thereby give the compound (XLIV).

When the condensation is to be carried out via an acid chloride of the compound (XLIII), the compound (XLIII) is converted into an acid chloride thereof in an appropriate inert solvent with the use of a commonly employed chlorinating agent such as thionyl chloride and oxalyl chloride, and then the acid chloride thus obtained is reacted with the amino acid ester derivative (XII) to thereby give the compound (XLIV).

(Step 3)

This step is one wherein the hydroxyl group of the amide derivative (XLIV) obtained in the step 2 is oxidized to thereby give an aldehyde derivative (XLV). The compound (XLV) can be obtained by a method commonly used for the oxidation of alkyl alcohols. For example, the aldehyde derivative (XLV) can be obtained by effecting the Swann oxidation with the use of oxalyl chloride and dimethyl sulfoxide or an oxidation with the use of manganese dioxide in an appropriate aprotic solvent such as dichloromethane and chloroform.

(Step 4)

This step is one wherein the aldehyde derivative (XLV) obtained in the step 3 is cyclized to thereby directly give, through an enamine derivative, an ester derivative (XLVI) or a carboxylic acid derivative (XLVII). For example, the ester derivative (XLVI) can be obtained by treating the compound (XLV) with trifluoroacetic acid in an appropriate aprotic solvent such as dichloromethane and chloroform. Alternatively, the carboxylic acid derivative (XLVII) can be obtained by treating the compound (XLV) with a mixture of trifluoromethanesulfonic acid and trifluoroacetic anhydride or trifluoromethanesulfonic acid alone in an appropriate aprotic solvent such as dichloromethane and chloroform.

(Step 5)

This step is one wherein the ester derivative (XLVI) directly obtained in the step 4 is subjected to deprotection by the conventional manner to thereby give a carboxylic acid derivative (XLVII). For example, the ester derivative (XLVI) is subjected to a protic strong acid treatment with trifluoromethanesulfonic acid in a protic solvent such as ethanol to thereby give the carboxylic acid derivative (XLVII).
(Step 6)

This step is one wherein the functional carboxylic acid group of the carboxylic acid derivative (XLVII) obtained in the steps 4 and 5 is protected by esterification to thereby give an ester derivative (XLVIII). As the ester group, a general alkyl group, a branched alkyl group or a group which can be selectively deprotected under such reaction conditions that the acylthio group of the compound (L) to be synthesized in the step 8 is not hydrolyzed is introduced. The esterification is effected by a method commonly employed in the art. For example, the derivative (XLVII) is reacted with an alcohol in the presence of a mineral acid such as hydrochloric acid and sulfuric acid. Alternatively, the derivative (XLVII) is reacted with, for example, diphenylbromomethane, triphenylbromomethane or trimethylsilylethanol in an inert solvent such as dimethylformamide and tetrahydrofuran in the presence of a base such as cesium carbonate and potassium carbonate. Thus the ester derivative (XLVIII) can be obtained.
(Step 7)

This step is one wherein the phthalimide group of the ester derivative (XLVIII) obtained in the step 6 is deprotected to thereby give an amine (XLIX). This method is one according to the conventional manner. For example, the ester derivative (XLVIII) is treated with hydrazine in a solvent such as water, an alcohol and tetrahydrofuran to thereby deprotect the phthalimide. Thus, the amine (XLIX) can be obtained.
(Step 8)

This step is one wherein the carboxylic acid derivative (XIII) or an active derivatine thereof, such as an acid halide thereof, is condensed with the amine (XLIX) obtained in the step 7 to thereby give an amide derivative (L). This reaction is effected by a method commonly employed in the art. For example, the carboxylic acid derivative (XIII) is reacted with the amine (XLIX) in an inert solvent such as methylene chloride and tetrehydrofuran in the presence of a commonly employed condensing reagent such as EEDQ, DCC, DEC or diethyl cyanophosphonate to thereby give the compound (L). When the reaction is to be carried out via an acid chloride of the carboxylic acid derivative (XIII), the carboxylic acid derivative (XIII) is converted into an acid halogenide thereof in an appropriate inert solvent with a halogenating agent commonly employed in the art, such as thionyl chloride and oxalyl chloride, and then the obtained acid halogenide is reacted with the amine (XLIX) to thereby give the compound (L).
(Step 9)

This step is one wherein either or both of the acylthio group and ester group of the amide derivative (L) obtained in the step 8 is(are) deprotected by the conventional manner to thereby give a carboxylic acid derivative (LI). When the group(s) to be eliminated is(are) usual alkyl group(s), branched alkyl group(s) or the like, for example, the amide derivative (L) is hydrolyzed in a dilute aqueous solution of an alkali such as sodium hydroxide and lithium hydroxide or in a dilute aqueous solution of a mineral acid to thereby give a mercapto carboxylic acid derivative (LI) having $R^{1a}$ representing hydrogen. When the group(s) to be eliminated is(are) t-butyl group(s), an arylalkyl group(s), a branched arylalkyl group(s) or the like, the deprotection is effected under such reaction conditions that the acylthio group remains stable, for example, by catalytically hydrogenating, treating with trifluoroacetic acid or the like, to thereby give an acylthio carboxylic acid derivative (LI).
(Step 10)

This step is one wherein the acylthio group, if contained, of the carboxylic acid derivative (LI) obtained in the step 9 is hydrolyzed to thereby give a mercapto carboxylic acid derivative (LII). The hydrolysis can be effected under conditions for hydrolysis commonly employed in the art, i.e., in a dilute aqueous solution of an alkali such as sodium hydroxide and lithium hydroxide or in a dilute aqueous solution of a mineral acid.

Production process B-2

When n is 0, the compound (LIV) can be also synthesized by the following process:

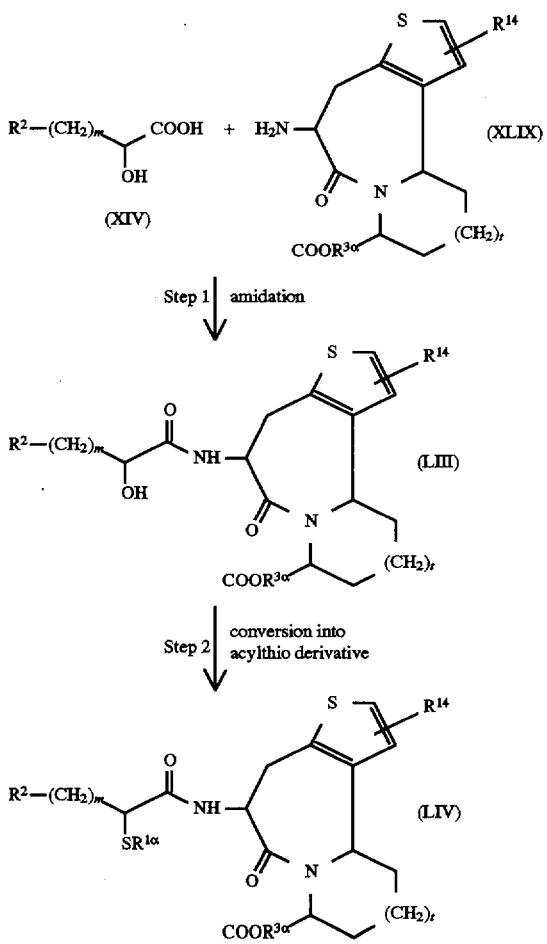

In a series of formulas, $R^{1a}$, $R^2$, $R^{3a}$, $R^{14}$, m and t have each the same meaning as the one defined above.
(Step 1)

This step is one wherein an α-hydroxy carboxylic acid derivative (XIV) is condensed with the amine (XLIX) obtained in the above-mentioned Production process B-1, step 7 by the conventional manner to thereby give an α-hydroxy carboxylic acid amide derivative (LIII). Similar to the Production process B-1, step 8, the compounds (LIII) and (XLIX) are reacted in an inert solvent such as methylene chloride and tetrahydrofuran in the presence of a condensing reagent commonly employed in the art, for example, EEDQ, DCC, DEC, diethyl cyanophosphonate or the like. Thus, the amide derivative (LIII) can be obtained.

(Step 2)

This step is one wherein the hydroxyl group of the amide derivative (LIII) obtained in the step 1 is converted into an acylthio group by the conventional manner to thereby give an acylthio derivative (LIV). The compound (LIV) can be synthesized in accordance with a method commonly employed for preparing an acylthio derivative. For example, the compound (LIII) is treated by a Mitsunobu type reaction in an inert solvent such as methylene chloride and tetrahydrofuran with the use of triphenylphosphine and an azodicarboxylic acid ester such as DIAD (diisopropyl azodicarboxylate). Thus, the acylthio derivative (LIV) can be obtained.

Production process B-3

A compound represented by the general formula (VIb) can be produced by the following process:

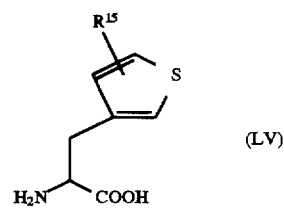
(LV)

Step 1 | phthalimidation

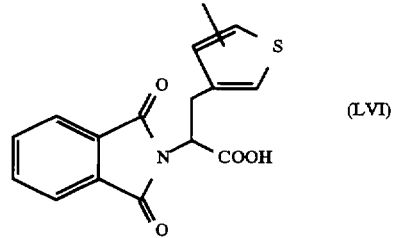
(LVI)

Step 2 | amidation

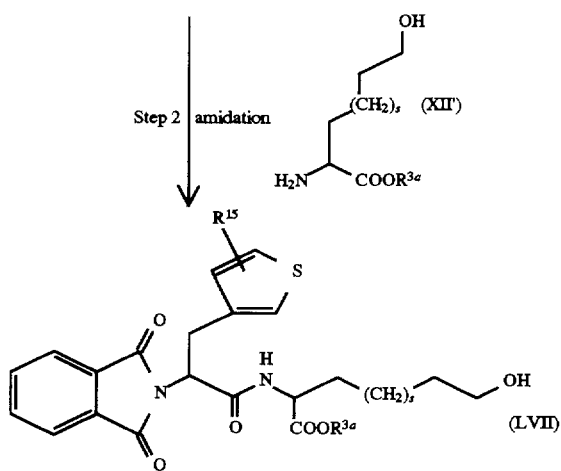

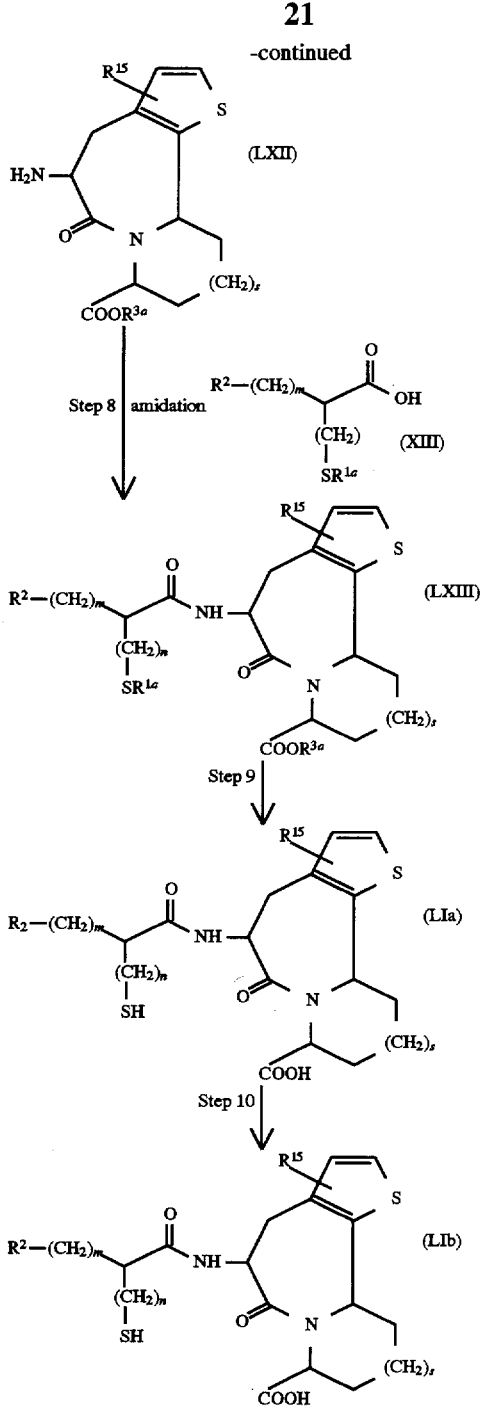

In a series of formulas, $R^{1a}$ represents an acyl group; $R^2$ represents a hydrogen atom, a lower alkyl group, a cycloalkyl group, an aryl group which may have a substituent, a heteroaryl group which may have a substituent, an arylalkyl group which may have a substituent or a heteroarylalkyl group which may have a substituent; $R^{3a}$ represents a carboxyl-protecting group; $R^{15}$ represents a hydrogen atom, a lower alkyl group, a lower alkoxy group, a hydroxyl group, a halogen atom, an aryl group which may have a substituent or a heteroaryl group which may have a substituent; s represents an integer of 0, 1 or 2; m represents an integer of 0, 1 or 2; and n represents an integer of 0, 1 or 2.

(Step 1)

This step is one wherein the amino group of a 3-thienylalanine acid derivative (LV) is protected through phthalimidation to thereby give a phthalimide carboxylic acid derivative (LVI). The compound (LVI) can be obtained by a method commonly employed in the art. For example, the phthalimide carboxylic acid derivative (LVI) can be obtained by heating phthalic anhydride together with the compound (LV) in an inert solvent such as dimethylformamide and aqueous dioxane or without using any solvent in the presence of a base such as triethylamine or without using any base. Alternatively, it can be obtained by heacting a phthalimidation agent such as ethoxycarbonylphthalimide together with the compound (LV) in the presence of a base such as sodium carbonate and sodium hydrogencarbonate.

(Step 2)

This step is one wherein the phthalimide carboxylic acid derivative (LVI) obtained in the step 1 or an active derivative thereof, such as an acid halide thereof, is condensed with an amino acid ester derivative (XII') by the conventional manner to thereby give an amide derivative (LVII).

The condensation may be effected by a method commonly employed in the art. For example, the compound (LVI) is reacted with the amino acid ester derivative (XII') in an inert solvent represented by methylene chloride, tetrahydrofuran and so on in the presence of a commonly employed condensing reagent such as EEDQ (1-ethoxycarbonyl-2-ethoxy-1,2-dihydroquinoline), DCC (1,3-dicyclohexylcarbodiimide), DEC (1-(3-dimethylaminopropyl)-3-ethylcarbodiimide hydrochloride) or diethyl cyanophosphonate. Thus, the compound (LVII) can be obtained. When the condensation is carried out via an acid chloride of the compound (LVI), the compound (LVI) is converted into an acid chloride in an appropriate inert solvent with the use of a commonly employed chlorinating agent such as thionyl chloride and oxalyl chloride, anf then the acid chloride thus obtained is reacted with the amino acid ester derivative (XII') to thereby give the compound (LVII).

(Step 3)

This step is one wherein the hydroxyl group of the amide derivative (LVII) obtained in the step 2 is oxidized by the conventional manner to thereby give an aldehyde derivative (LVIII). The compound (LVIII) can be obtained by a method commonly used for the oxidation of alkyl alcohols. For example, the aldehyde derivative (LVIII) can be obtained by effecting the Swann oxidation with the use of oxalyl chloride and dimethyl sulfoxide or an oxidation with the use of manganese dioxide in an appropriate aprotic solvent such as dichloromethane and chloroform.

(Step 4)

This step is one wherein the aldehyde derivative (LVIII) obtained in the step 3 is cyclized by the conventional manner to thereby give, through an enamine derivative, an ester derivative (LIX). Alternatively, this step is also one wherein the aldehyde derivative (LVIII) is cyclized to thereby directly give, through an enamine derivative, a carboxylic acid derivative (LX).

For example, the ester derivative (LIX) can be obtained by treating the compound (LVIII) with trifluoroacetic acid in an appropriate aprotic solvent such as dichloromethane and chloroform. Alternatively, the carboxylic acid derivative (LX) can be obtained by treating the compound (LVIII) with a mixture of trifluoromethanesulfonic acid and trifluoroacetic anhydride or trifluoromethanesulfonic acid alone in an appropriate aprotic solvent such as dichloromethane and chloroform.

(Step 5)

This step is one wherein the ester derivative (LIX) obtained in the step 4 is deprotected to thereby give a carboxylic acid derivative (LX). For example, the ester derivative (LIX) is treated with a protic strong acid such as trifluoromethanesulfonic acid in a protic solvent such as ethanol. Thus, the carboxylic acid derivative (LX) can be obtained.

(Step 6)

This step is one wherein the functional carboxylic acid group of the carboxylic acid derivative (LX) obtained in the steps 4 and 5 is protected by esterification to thereby give an ester derivative (LXIV).

As the protecting group, a general alkyl group, a branched alkyl group or a group which can be selectively deprotected under such reaction conditions that the acylthio group of the compound (LXIII) to be synthesized in the step 8 is not hydrolyzed may be introduced. The esterification is effected by a method commonly employed in the art. For example, the carboxylic acid derivative (LX) is reacted with an alcohol in the presence of a mineral acid such as hydrochloric acid or sulfuric acid. Alternatively, the derivative (LX) is reacted with, for example, diphenylbromomethane, triphenylbromomethane or trimethylsilylethanol in an inert solvent such as dimethylformamide and tetrahydrofuran in the presence of a base such as cesium carbonate and potassium carbonate. Thus, the ester derivative (LXIV) can be obtained.

(Step 7)

This step is one wherein the phthalimide group of the ester derivative (LXIV) obtained in the step 6 is deprotected to thereby give an amine (LXII). This reaction can be effected by the conventional manner. For example, the compound (LXIV) is treated with hydrazine in a solvent such as water, an alcohol and tetrahydrofuran to thereby deprotect the phthalimide. Thus, the amine (LXII) can be obtained.

(Step 8)

This step is one wherein the carboxylic acid derivative (XIII) or an active derivative thereof, such as an acid halide thereof, is condensed with the amine (LXII) obtained in the step 7 to thereby give an amide derivative (LXIII). This reaction is effected by a method commonly employed in the art. For example, the carboxylic acid derivative (XIII) is reacted with the amine (LXII) in an inert solvent such as methylene chloride and tetrahydrofuran in the presence of a commonly employed condensing reagent such as EEDQ, DCC, DEC or diethyl cyanophosphonate. Thus, the compound (LXIII) can be obtained. When the reaction is carried out via an acid chloride of the carboxylic acid derivative (XIII), for example, the carboxylic acid derivative (XIII) is converted into an acid halogenide in an appropriate inert solvent with a halogenating agent commonly employed in the art, for example, thionyl chloride, oxalyl chloride or the like, and then the obtained acid halogenide is reacted with the amine (LXII) to thereby give the compound (LXIII).

(Step 9)

This step is one wherein either or both of the acylthio group and ester group of the amide derivative (LXIII) obtained in the step 8 is(are) deprotected by the conventional manner to thereby give a carboxylic acid derivative (LIa). When the group(s) to be eliminated is(are) usual an alkyl group(s), a branched alkyl group(s) or the like, for example, the amide derivative (LXIII) is hydrolyzed in a dilute aqueous solution of an alkali such as sodium hydroxide and lithium hydroxide or in a dilute aqueous solution of a mineral acid to thereby give a mercapto carboxylic acid derivative (LIa) which is a compound having $R^{1a}$ representing hydrogen. When the group(s) to be eliminated is(are) t-butyl group(s), an allylalkyl group(s), a branched allylalkyl group(s) or the like, the deprotection is effected under such reaction conditions that the acylthio group remains stable, for example, by catalytically hydrogenating, treating with trifluoroacetic acid or the like, to thereby give an acylthio carboxylic acid derivative (LIa).

(Step 10)

This step is one wherein the acylthio group, if contained, of the carboxylic acid derivative (LIa) obtained in the step 9 is hydrolyzed to thereby give a mercapto carboxylic acid derivative (LIb). The hydrolysis can be effected under conditions for hydrolysis commonly employed in the art, i.e., in a dilute aqueous solution of an alkali such as sodium hydroxide and lithium hydroxide or in a dilute aqueous solution of a mineral acid.

Production process B-4

When n is 0, the compound (LVIa) can be also synthesized by the following process:

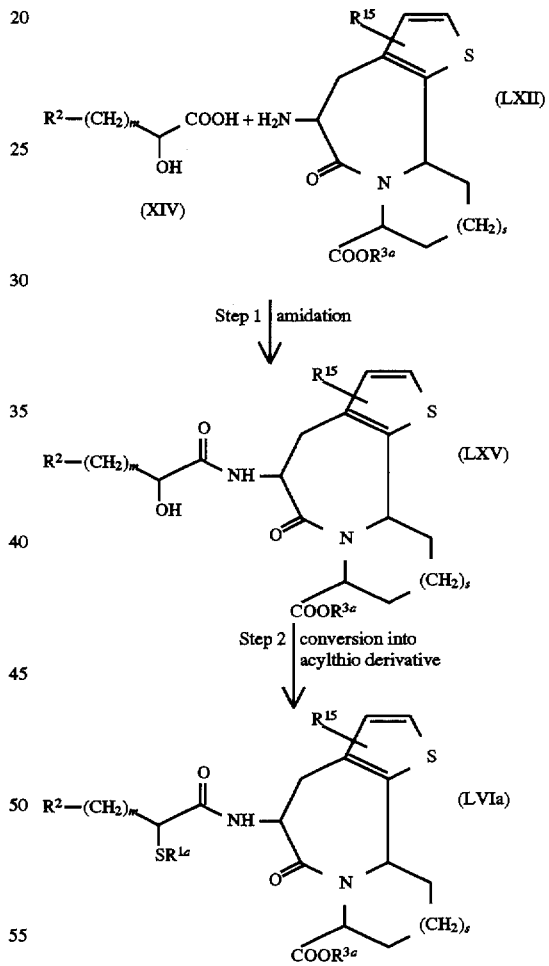

In a series of formulas, $R^{1a}$ represents an acyl group; $R^2$ represents a hydrogen atom, a lower alkyl group, a cycloalkyl group, an aryl group which may have a substituent, a heteroaryl group which may have a substituent, an arylalkyl group which may have a substituent or a heteroarylalkyl group which may have a substituent; $R^{3a}$ represents a carboxyl-protecting group; $R^{15}$ represents a hydrogen atom, a lower alkyl group, a lower alkoxy group, a hydroxyl group, a halogen atom, an aryl group which may have a substituent or a heteroaryl group which may have a substituent; s represents an integer of 0, 1 or 2; and m represents an integer of 0, 1 or 2.

(Step 1)

This step is one wherein an α-hydroxy carboxylic acid derivative (XIV) is condensed with the amine (LXII) obtained in the above-mentioned Production process B-3, step 7 by the conventional manner to thereby give an α-hydroxy carboxylic acid amide derivative (LXV). Similar to the Production process B-3, step 8, the compounds (XIV) and (LXII) are reacted in an inert solvent such as methylene chloride and tetrahydrofuran in the presence of a condensing reagent commonly employed in the art, for example, EEDQ, DDC, DEC or diethyl cyanophosphonate. Thus, the amide derivative (LXV) can be obtained.

(Step 2)

This step is one wherein the hydroxyl group of the amide derivative (LXV) obtained in the step 1 is converted into an acylthio group to thereby give an acylthio derivative (LVIa). The compound (LVIa) can be synthesized in accordance with a method commonly employed for converting a hydroxyl group into an acylthio group. For example, the compound (LXV) is treated by a Mitsunobu type reaction in an inert solvent such as methylene chloride and tetrahydrofuran with the use of triphenylphosphine and an azodicarboxylic acid ester such as DIAD (diisopropyl azodicarboxylate). Thus, the acylthio derivative (LVIa) can be obtained.

Production process C-1

A compound represented by the general formula (VII) can be produced by the following process:

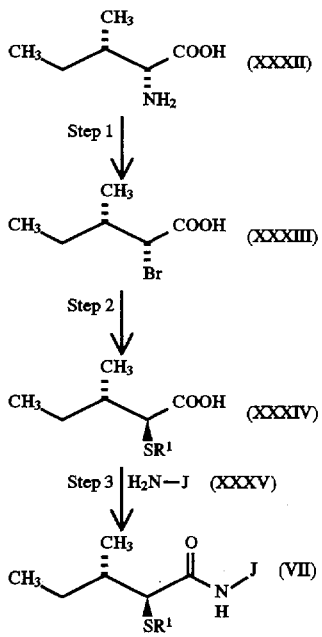

In a series of formulas, $R^1$ represents a hydrogen atom or an acyl group; and J represents a cyclic group having an ACE inhibition activity.

(Step 1)

That is, this step is one wherein the amino group of D-allo-isoleucine (XXXII) is brominated to thereby give a bromide (XXXIII). The bromide (XXXIII) can be obtained in accordance with a method commonly employed in the art for stereoselective bromination. For example, the compound (XXXII) is treated with a nitrite such as sodium nitrite and silver nitrite in an aqueous solution of hydrogen bromide. Thus, the bromide (XXXIII) can be obtained.

(Step 2)

That is, this step is one wherein the bromine group of the bromide (XXXIII) obtained in the step 1 is converted into an acylthio group to thereby give an acylthiopentanoic acid derivative (XXXIV). This reaction is effected in accordance with the conventional manner. For example, the bromide (XXXIII) is reacted with a thiocarboxylate such as potassium thioacetate and sodium thioacetate in a polar solvent such as acetonitrile and acetone. Alternatively, the bromide (XXXIII) is reacted with a thiocarboxylic acid such as thioacetic acid and thiobenzoic acid in the presence of a base such as potassium carbonate and cesium carbonate. Thus, the acylthiopentanoic acid derivative (XXXIV) can be obtained.

(Step 3)

That is, this step is one wherein the acylthiopentanoic acid derivative (XXXIV) obtained in the step 2 or an active derivative thereof, such as an acid halide thereof, is condensed with an amino acid ester derivative (XXXV) to thereby give an amide derivative (VII). For example, the acylthiopentanoic acid derivative (XXXIV) is reacted with the amino acid ester derivative (XXXV) in an inert solvent such as methylene chloride and tetrahydrofuran in the presence of a commonly employed condensing reagent such as EEDQ (1-ethoxycarbonyl-2-ethoxy-1,2-dihydroquinoline), DCC (1,3-dicyclohexylcarbodiimide), DEC (1-(3-dimethylaminopropyl)-3-ethylcarbodiimide hydrochloride) or diethyl cyanophosphonate. Thus, the amide derivative (VII) can be obtained. When the condensation is carried out via an acid chloride of the acylthiopentanoic acid derivative (XXXIV), the acylthiopentanoic acid derivative (XXXIV) is converted into an acid chloride in an appropriate inert solvent with the use of a commonly employed chlorinating agent such as thionyl chloride and oxalyl chloride, and then the acid chloride thus obtained is reacted with the amino acid ester derivative (XXXV) to thereby give the target compound (VII).

Production process C-2

A compound represented by the general formula (VII) can be also obtained by the following process:

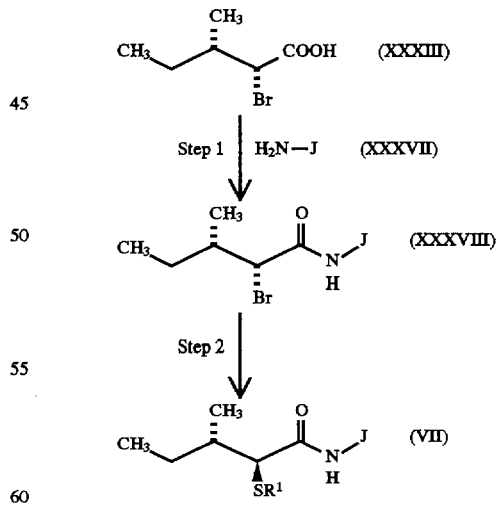

In a series of formulas, $R^1$ and J have each the same meaning as the one defined above.

(Step 1)

That is, this step is one wherein the brominated carboxylic acid derivative (XXXIII) obtained in the Production process C-1, step 1 or an active derivative thereof, such as an acid halide thereof, is condensed with an amino acid ester derivative (XXXVII) to thereby give an amide derivative (XXXVIII). The amide derivative (XXXVIII) can be obtained by the same treatment as the one in the Production process C-1, step 3.
(Step 2)

That is, this step is one wherein the bromine group in the amide derivative (XXXVIII) obtained in the step 1 is converted into an acylthio group to thereby give an amide derivative (VII) which is the same one as the compound obtained in the Production process C-1, step 3. The amide derivative (VII) can be obtained by the same treatment as the one in the Production process C-1, step 2.

Production process C-3

Among compounds represented by the general formula (VII), those wherein $R^3$ is a hydrogen atom can be also obtained by the following process:

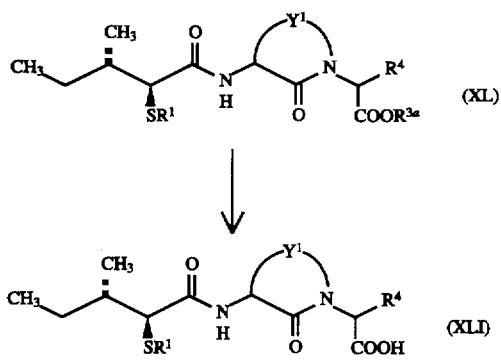

In a series of formulas, $R^1$ represents a hydrogen atom or an acyl group; $R^{3a}$ represents a carboxyl-protecting group; $R^4$ represents a hydrogen atom, a lower alkyl group or an arylalkyl group which may have a substituent; and $Y^1$ has the same meaning as the one defined above.

Namely, the ester alone or both of the ester and acylthio group of the compounds (XL) obtained by the Production processes C-1 and C-2 is(are) deprotected by the conventional manner to thereby give a carboxylic acid derivative (XLI). When the group(s) to be eliminated is(are) an usual alkyl or branched alkyl group or the like, the amide derivative (VII) is hydrolyzed in a dilute aqueous solution of an alkali such as sodium hydroxide and lithium hydroxide or in a dilute aqueous solution of a mineral acid to thereby give a carboxylic acid derivative (XLI) having $R^1$ representing hydrogen. When the group(s) to be eliminated is(are) t-butyl group(s), a branched allylalkyl group(s) such as benzhydryl group, a silylethyl group(s) such as trimethylsilylethyl group, or the like, only the part of the ester group is deprotected under such reaction conditions that the thioacyl group remains stable, for example, by treating with trifluoroacetic acid or an alkylammonium fluoride, to thereby give an acylthio carboxylic acid derivative (XLI).

Production process D-1

A compound represented by the following general formula (D) can be produced by the following process:

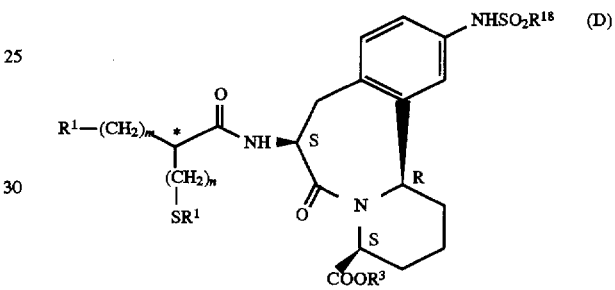

wherein $R^1$, $R^2$, $R^3$, $R^{18}$, m and n have each the same meaning as the one defined above;

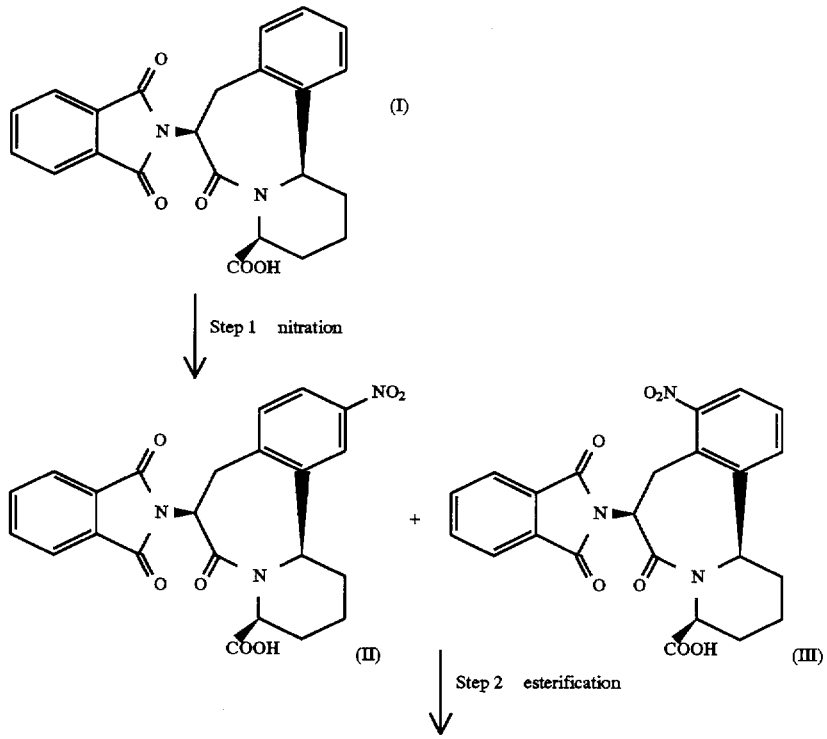

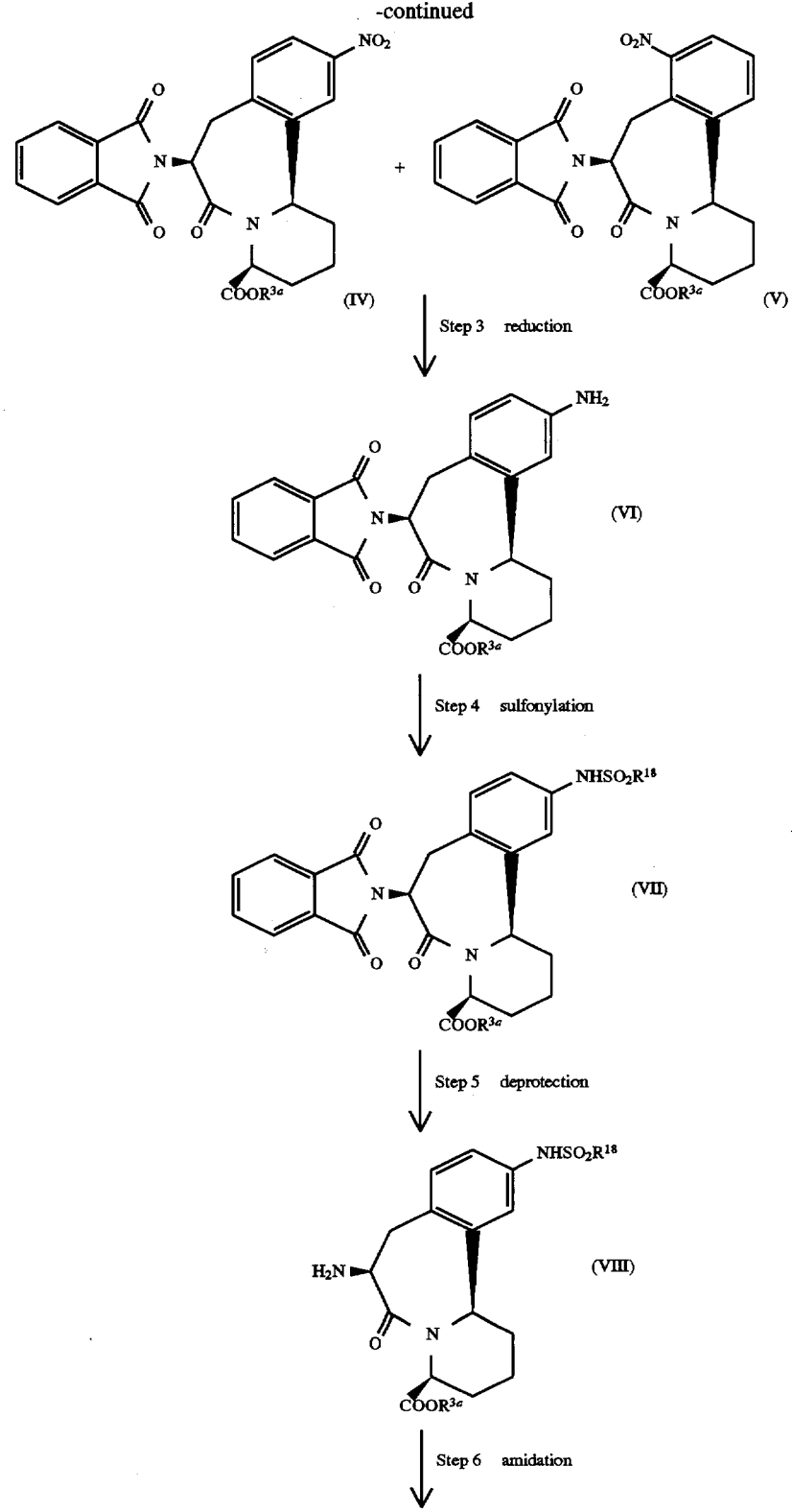

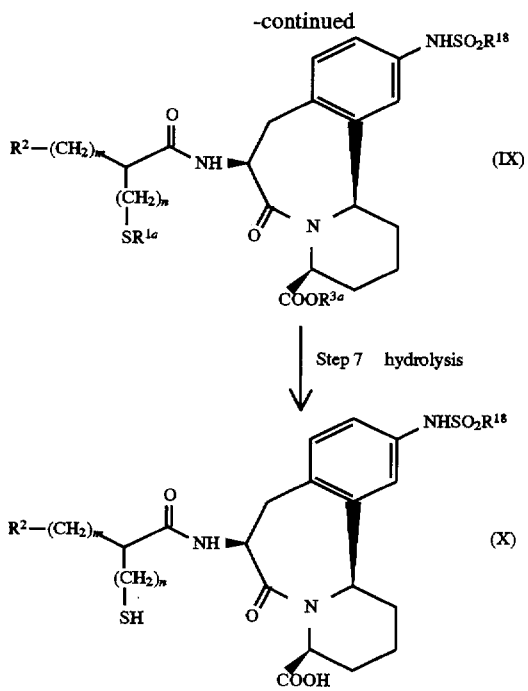

In a series of formulas which represent the above Production process D-1, $R^2$, $R^{3a}$, $R^{18}$ and n have each the same meaning as the one defined above; and $R^{1a}$ represents a group selected from those as given above in the definition of $R^1$ except a hydrogen atom.

(Step 1)

Namely, this is a step which comprises nitrating a publicly known cyclic amino acid derivative (I) or a cyclic amino acid derivative (I) obtained by a publicly known method by a publicly known method.

The nitration described above is effected by the conventional manner. Usually, a method which comprises treating with a nitrating agent commonly employed in the art, for example, nitronium tetrafluoroborate or the like in an inert organic solvent, for example, chloroform, dichloromethane or the like to effect nitration, a method which comprises effecting nitration with fuming nitric acid or the like in the presence of acetic acid, acetic anhydride, sulfuric acid or the like, and other methods may be cited.

(Step 2)

This is a step which comprises esterifying the functional carboxylic acid group of the nitro compound (II) obtained in the step 1.

As the above-mentioned ester, a lower alkyl group or a group which can be selectively deprotected under such reaction conditions that the thioacetyl group of the compound (IX) to be synthesized in the subsequent step 6 is not hydrolyzed, is introduced. The ester compound (IV) can be obtained by, for example, reacting the nitro compound (II) with an alcohol in the presence of a mineral acid such as hydrochloric acid and sulfuric acid or, alternatively, reacting the nitro compound (II) with diphenylbromomethane, triphenylbromomethane or trimethylsilylethanol in an inert solvent such as dimethylformamide and tetrahydrofuran in the presence of a base such as cesium carbonate and potassium carbonate.

(Step 3)

This is a step which comprises reducing the nitro group of the compound (IV) obtained in the step 2 by the conventional manner to thereby give an aniline compound (VI).

The reduction described above may be effected by a method commonly employed in the art. For example, catalytic reduction with the use of palladium, platinum or the like as a catalyst, or reduction with the use of a metal such as zinc and iron under acidic conditions may usually be cited.

(Step 4)

Namely, this is a step which comprises reacting the aniline compound (VI) obtained in the step 3 with a publicly known chlorosulfonic acid derivative or a chlorosulfonic acid derivative obtained by a publicly known method to thereby give a sulfonylamide derivative (VII).

For example, the sulfonylamide derivative (VII) can be obtained by reacting the aniline compound (VI) with the chlorosulfonic acid derivative with the use of an inert solvent such as acetonitrile, tetrahydrofuran, toluene and dichloromethane in the presence of a base such as pyridine, triethylamine and sodium carbonate.

(Step 5)

This is a step which comprises deprotecting the phthalimide group of the sulfonylamide derivative (VII) obtained in the step 4 to thereby give an amine compound (VIII).

The deprotection described above may be effected by the conventional manner. The amine compound (VIII) can be usually obtained by, for example, treating the compound (VII) with hydrazine in a solvent such as water, an alcohol and tetrahydrofuran to thereby deprotect the phthalimide group.

(Step 6)

This is a step which comprises condensing a publicly known carboxylic acid derivative or a carboxylic acid derivative obtained by a publicly known method or an active derivative thereof such as an acid halide thereof with the amine compound (VIII) obtained in the step 5 to thereby give an amide derivative (IX).

The condensation described above may be effected by the conventional manner. For example, the above-mentioned carboxylic acid derivative is reacted with the amine compound (VIII) in an inert solvent such as methylene chloride and tetrahydrofuran in the presence of a condensing reagent such as EEDQ (1-ethoxycarbonyl- 2-ethoxy-1,2-dihydroquinoline), DCC (1,3-dichlorohexylcarbodiimide hydrochloride), DEC or diethyl cyanophosphonate. Thus, the amide derivative (IX) can be obtained. When the condensation is carried out via an acid chloride of the carboxylic acid derivative, the carboxylic acid derivative is converted into an acid chloride in an appropriate inert solvent with a chlorinating agent such as thionyl chloride and oxalyl chloride, and then the acid chloride thus obtained is reacted with the amine compound (VIII) to thereby give the amide derivative (IX).

(Step 7)

This is a step which comprise deprotecting either or both of the ester group and thioacyl group of the amide derivative (IX) obtained in the above step 6 to thereby give the target compound (X). When the ester group is a usual alkyl group, a branched alkyl group or the like, the amide derivative (X) is hydrolyzed in a dilute aqueous solution of an alkali such as sodium hydroxide and lithium hydroxide or in a dilute aqueous solution of a mineral acid to thereby give a mercapto carboxylic acid derivative (X) having $R^1$ representing hydrogen. When the ester group is t-butyl group, an allylalkyl group, a branched allylalkyl group or the like, the deprotection is effected under such reaction conditions that the thioacyl group remains stable, for example, by catalytically hydrogenating or using trifluoroacetic acid or the like, to thereby give a thioacyl carboxylic acid (X).

Production process D-2

Among compounds represented by the above general formula (D), those wherein n is 0 can be also produced by the following process:

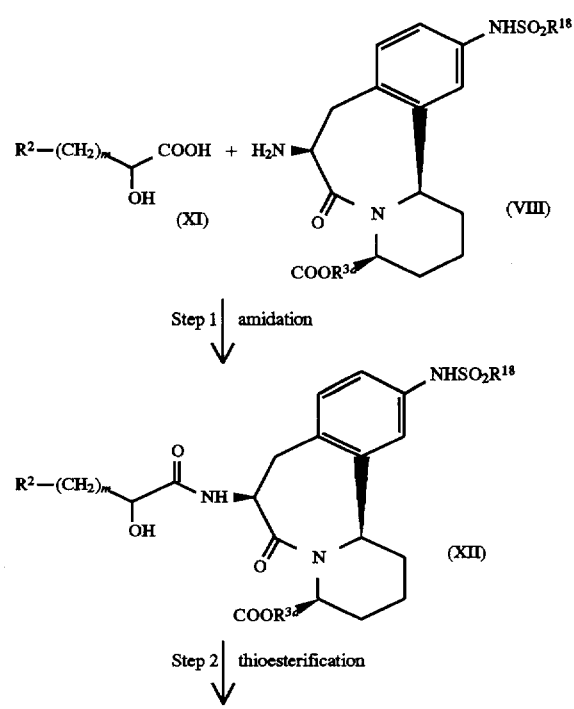

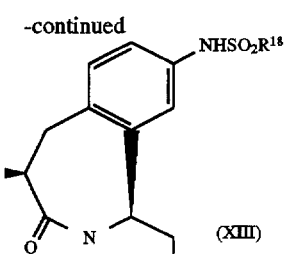

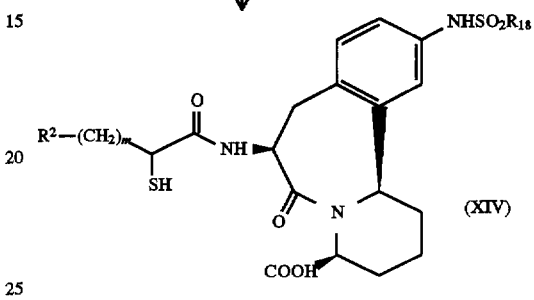

In a series of formulas described above, $R^{1a}, R^2, R^{3a}, R^{18}$ and m have each the same meaning as the one defined above.

(Step 1)

This is a step which comprises condensing a publicly known α-hydroxy carboxylic acid derivative (XI) or an α-hydroxy carboxylic acid derivative (XI) obtained by a publicly known method with the amine compound (VIII) obtained in the above Production process D-1, step 5 to thereby give an amide derivative (XII).

In the above condensation, similar to the above Production process D-1, step 8, the compounds (XI) and (VIII) are reacted in an inert solvent such as methylene chloride and tetrahydrofuran in the presence of a condensing reagent such as EEDQ (1-ethoxycarbonyl-2-ethoxy-1,2-dihydroquinoline), DCC (1,8-dichlorohexylcarbodiimide hydrochloride), DEC or diethyl cyanophosphonate. Thus, the amide derivative (XII) can be obtained.

(Step 2)

This is a process which comprises thioesterifying the hydroxyl group of the amide derivative (XII) obtained in the step 1 to thereby give an acetylthio derivative (XIII). The compound (XIII) can be synthesized in accordance with a method commonly employed for thioesterification of hydroxyl group. For example, the compound (XII) is treated by a Mitsunobu type reaction in an inert solvent such as methylene chloride and tetrahydrofuran with the use of triphenylphosphine and an azodicarboxylic acid ester such as DIAD (diisopropyl azodicarboxylate). Thus, the acetylthio derivative (XIII) can be obtained.

(Step 3)

This is a step which comprises deprotecting either or both of the ester group and thioacyl group of the amide derivative (XIII) obtained in the above step 2 to thereby give a carboxylic acid derivative (XIV). The carboxylic acid derivative (XIV) can be synthesized by the same method as the one in the above Production process D-1, step 7.

Production process E-1

A compound represented by the following general formula (E) can be produced by the following process:

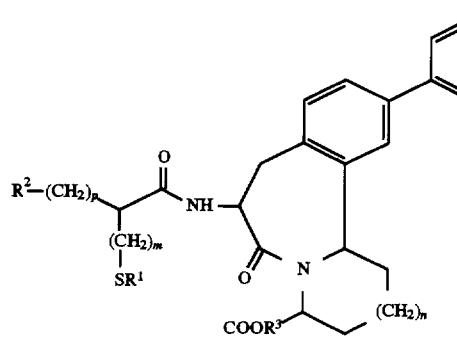
(E)

wherein $R^1$ represents a hydrogen atom or an acyl group;

$R^2$ represents a hydrogen atom, a lower alkyl group, a heteroaryl group which may be substituted or an arylalkyl group which may be substituted;

$R^3$ represents a hydrogen atom, a lower alkyl group or an arylalkyl group;

$R^{19}$ represents a hydrogen atom, a lower alkyl group, a lower alkoxy group, a hydroxyl group or a halogen atom; and p, m and n represent each independently an integer of 0, 1 or 2;

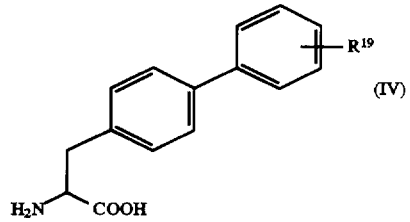
(IV)

Step 1 | phthalimidation

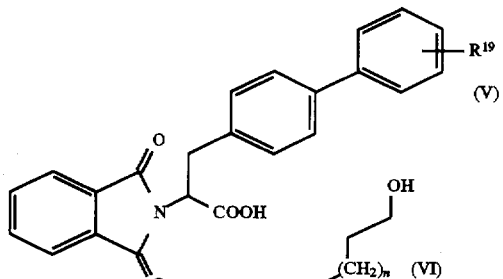
(V)

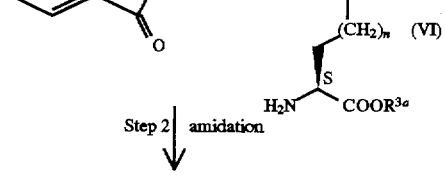
(VI)

Step 2 | amidation

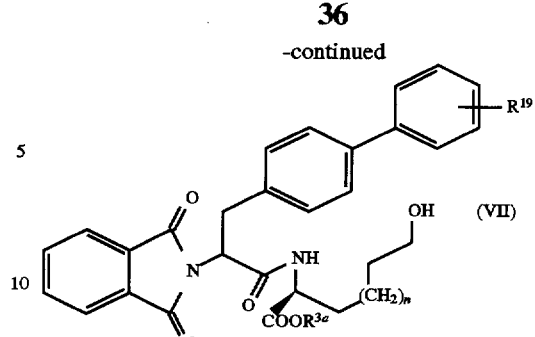
(VII)

Step 3 | oxidation

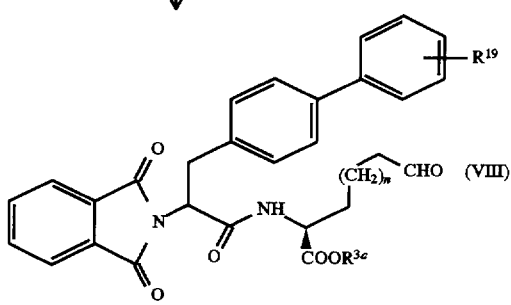
(VIII)

Step 4 | cyclization

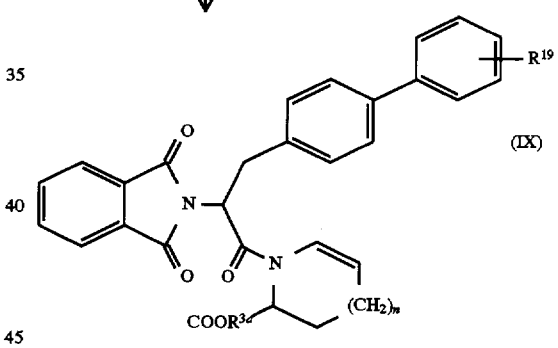
(IX)

Step 5 | cyclization

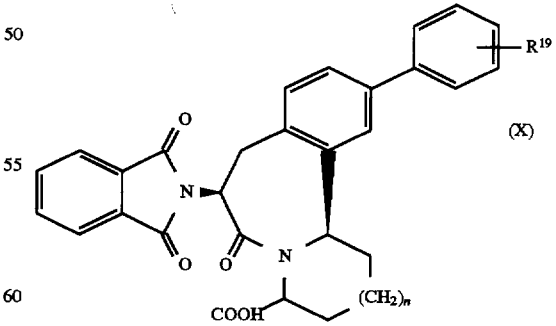
(X)

Step 6 | esterification

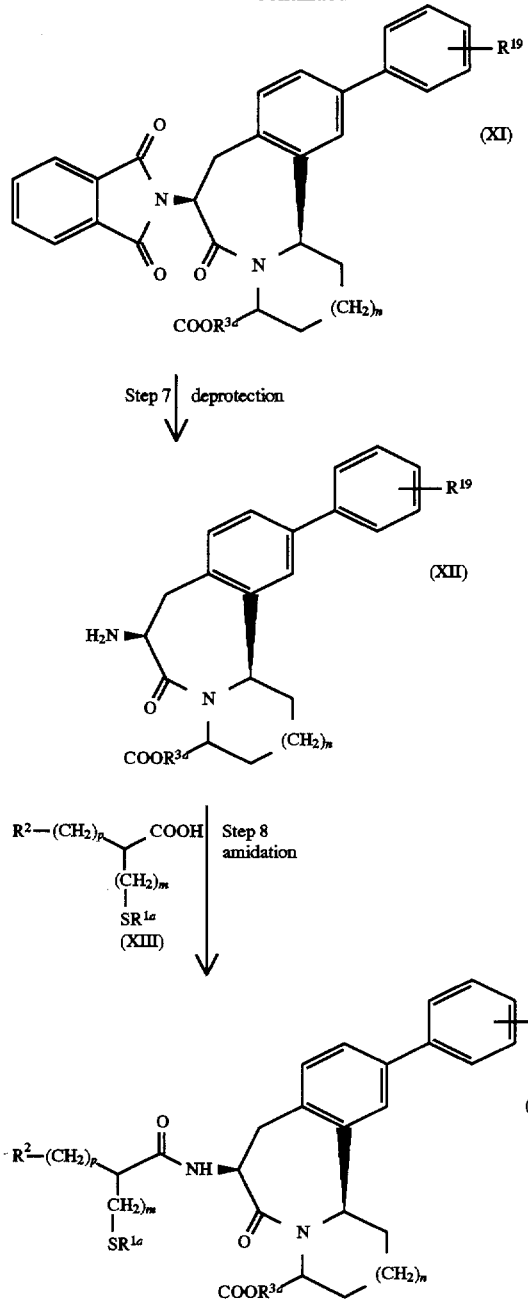

In a series of formulas described above, $R^2$, $R^{19}$, p, n and m have each the same meaning as the one defined above;
$R^{1a}$ represents a group selected from among those given in the definition of $R^1$ except a hydrogen atom; and
$R^{3a}$ represents a group selected from among those given in the definition of $R^3$ except a hydrogen atom.

(Step 1)

This step is one wherein the amino group of a biphenylamino acid derivative represented by the general formula (IV) is protected through phthalimidation to thereby give a phthalimide carboxylic acid derivative (V). The phthalimidation can be effected by a method commonly employed in the art. For example, the phthalimide carboxylic acid derivative (V) can be obtained by heating phthalic anhydride together with the compound (IV) in an inert solvent such as dimethylformamide and dioxane or without using any solvent. Alternatively, it can be obtained by reacting a phthalimidation agent such as ethoxycarbonylphthalimide with the compound (IV) in the presence of a base such as sodium carbonate and sodium hydrogencarbonate.

(Step 2)

This step is one wherein the phthalimide carboxylic acid derivative (V) obtained in the step 1 or an active derivative thereof such as an acid halide thereof is condensed with an amino acid ester derivative represented by the general formula (VI) by the conventional manner to thereby give an amide derivative (VII). The condensation may be effected by a method commonly employed in the art. For example, the compounds (V) and (VI) are reacted in an inert solvent represented by methylene chloride, tetrahydrofuran and so on in the presence of a commonly employed condensing reagent such as EEDQ (1-ethoxycarbonyl-2-ethoxy-1,2-dihydroquinoline), DCC (1,3-dicyclohexylcarbodiimide), DEC [1-(3-dimethylaminopropyl)-3-ethylcarbodiimide hydrochloride] or diethyl cyanophosphonate. Thus, the compound (VII) can be obtained. When the condensation is carried out via an acid chloride of the compound (V), the compound (V) is converted into an acid chloride in an appropriate inert solvent with a commonly employed chlorinating agent such as thionyl chloride and oxalyl chloride, and then the acid chloride thus obtained is reacted with the amine compound (VI) to thereby give the compound (VII).

(Step 3)

This step is one wherein the hydroxyl group of the amide derivative (VII) obtained in the step 2 is oxidized to thereby give an aldehyde derivative (VIII). The compound (VIII) can be obtained by a method commonly used for the oxidation of alkyl alcohols. For example, the aldehyde derivative (VIII) can be obtained by effecting the Swann oxidation with the use of oxalyl chloride and dimethyl sulfoxide or an oxidation with the use of pyridinium chlorochromate or manganese dioxide in an appropriate aprotic solvent such as dichloromethane and chloroform.

(Step 4)

This step is one wherein the aldehyde derivative (VIII) obtained in the step 3 is cyclized by the conventional manner to thereby give an enamine compound (IX). The enamine compound (IX) can be obtained by, for example, treating the aldehyde derivative (VIII) with trifluoroacetic acid in an appropriate aprotic solvent such as dichloromethane and chloroform.

(Step 5)

This step is one wherein the enamine compound (IX) obtained in the step 4 is subjected to the Friedel-Crafts reaction to thereby give the corresponding tricyclic derivative (X). This reaction can be made to proceed in accordance with a method commonly employed in the art. For example, the tricyclic derivative (X) can be obtained by treating the compound (IX) with a mixture of trifluoromethanesulfonic acid and trifluoroacetic anhydride or trifluoromethanesulfonic acid alone in an appropriate aprotic solvent such as dichloromethane and chloroform.

(Step 6)

This step is one wherein the functional carboxylic acid group of the tricyclic derivative (X) obtained in the step 5 is protected through esterification to thereby give an ester derivative (XI). As the ester group, a general alkyl group, a branched alkyl group or a group which can be selectively deprotected under such reaction conditions that the acylthio group of the compound (XIV) to be synthesized in the step 8 is not hydrolyzed may be introduced. The esterification is effected by a method commonly employed in the art. For example, the compound (X) is reacted with an alcohol in the presence of a mineral acid such as hydrochloric acid and sulfuric acid. Alternatively, the compound (X) is reacted with, for example, diphenylbromomethane, triphenylbromomethane or trimethylsilylethanol in an inert solvent such as dimethylformamide and tetrahydrofuran in the presence of a base such as cesium carbonate and potassium carbonate. Thus, the ester derivative (XI) can be obtained.

(Step 7)

This step is one wherein the phthalimide group of the tricyclic derivative (XI) obtained in the step 6 is deprotected to thereby give an amine compound (XII). This reaction can be effected by the conventional manner. For example, the compound (XI) is treated with hydrazine in a solvent such as water, an alcohol and tetrahydrofuran to thereby deprotect the phthalimide. Thus, the amine compound (XII) can be obtained.

(Step 8)

This step is one wherein the carboxylic acid derivative represented by the general formula (XIII) or an active derivative thereof, such as an acid halide thereof, is condensed with the amine derivative (XII) obtained in the step 7 to thereby give an amide derivative (XIV). This reaction is effected by the conventional manner. For example, the carboxylic acid derivative (XIII) is reacted with the amine derivative (XII) in an inert solvent such as methylene chloride and tetrahydrofuran in the presence of a commonly employed condensing reagent such as EEDQ, DCC, DEC or diethyl cyanophosphonate. Thus, the amide derivative (XIV) can be obtained. When the reaction is carried out via an acid chloride of the carboxylic acid derivative (XIII), the carboxylic acid derivative (XIII) is converted into an acid halogenide in an appropriate inert solvent with a halogenating agent commonly employed in the art, such as thionyl chloride and oxalyl chloride, and then the obtained acid halogenide is reacted with the amine derivative (XII) to thereby give the amide derivative (XIV).

Production process E-2

When $R^3$ in the above general formula (E) is a hydrogen atom, the compound can be produced by the following process:

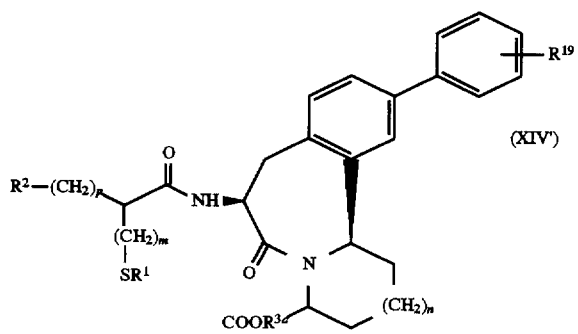

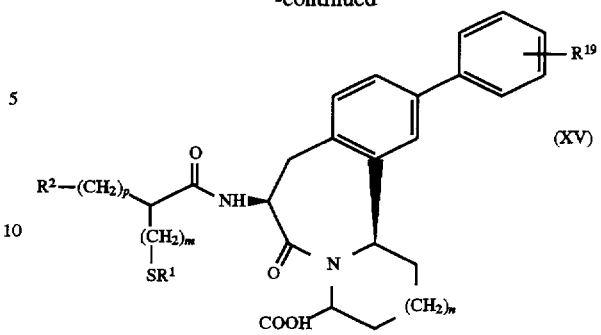

In a series of formulas, $R^1$, $R^2$, $R^{3a}$, $R^{19}$, p, n and m have each the same meaning as the one defined above.

Namely, this is a method which comprises deprotecting an amide derivative represented by the general formula (XIV') by the conventional manner to thereby give a carboxylic acid derivative represented by the general formula (XV).

The deprotection is effected by a method commonly employed in the art. For example, when $R^1$ in the target carboxylic acid derivative (XV) is an acyl group, an acid derivative wherein $R^{2a}$ is, for example, a t-butyl group or an arylalkyl group is selected as the starting compound, and then the starting compound is deprotected under such reaction conditions that the acrylthio group remains stable, for example, by catalytically hydrogenating or treating with trifluoroacetic acid. Thus, the target compound (XV) can be obtained.

When $R^1$ of the carboxylic acid derivative (XV), i.e., the target compound, is a hydrogen atom, an amide derivative wherein $R^{2a}$ is a lower alkyl is selected as the starting compound and hydrolyzed in a dilute aqueous solution of an alkali such as sodium hydroxide and lithium hydroxide or in a dilute aqueous solution of a mineral acid to thereby give the target compound (XV).

Production process E-3

When $R^1$ and $R^2$ in the above general formula (E) are each a hydrogen atom, the compound (XV') can be also produced by the following process:

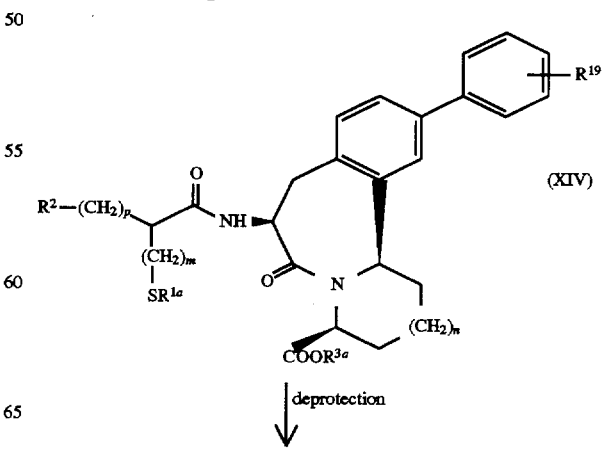

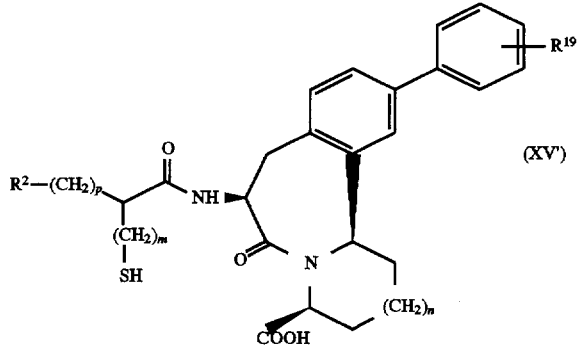

In a series of formulas, $R^{1a}$, $R^2$, $R^{3a}$, $R^{19}$, p, n and m have each the same meaning as the one defined above.

Namely, this is a reaction which comprises hydrolyzing a carboxylic acid derivative represented by the general formula (XIV) by the conventional manner to thereby give a mercapto carboxylic acid derivative (XVI).

The hydrolysis can be effected by a method commonly employed in the art. For example, the starting compound may be hydrolyzed in a dilute aqueous solution of an alkali such as sodium hydroxide and lithium hydroxide or in a dilute aqueous solution of a mineral acid.

Production process E-4

When m in the above general formula (E) is 0, the compound (XIV') can be also synthesized by the following process:

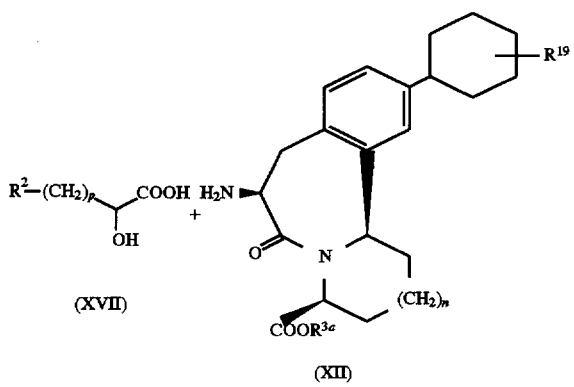

Step 1 | amidation

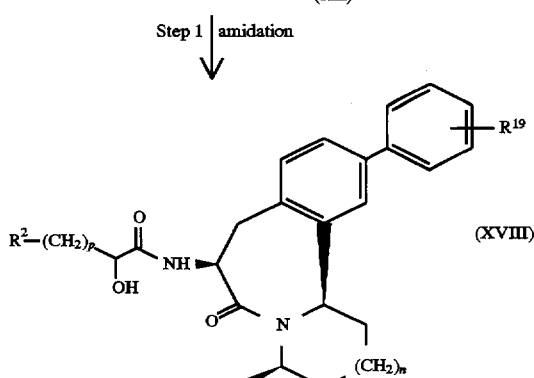

Step 2 | thioesterification

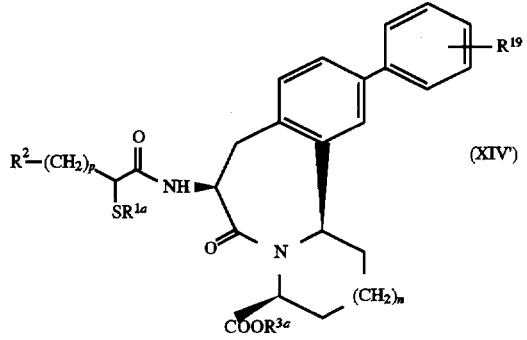

In a series of formulas, $R^{1a}$, $R^2$, $R^{3a}$, $R^{19}$, p and n have each the same meaning as the one defined above.

(Step 1)

This step is one wherein an α-hydroxy carboxylic acid derivative (XVII) is condensed with the amine compound (XII) obtained in the above Production process E-1, step 7 to thereby give an α-hydroxy carboxylic acid amide derivative (XVIII). Similar to the above Production process 1, step 8, the compounds (XII) and (XVII) are reacted in an inert solvent such as methylene chloride and tetrahydrofuran in the presence of a condensing reagent commonly employed in the art, such as EEDQ, DCC, DEC or diethyl cyanophosphonate. Thus, the amide derivative (XVIII) can be obtained.

(Step 2)

This step is one wherein the hydroxyl group of the amide derivative (XVIII) obtained in the step 1 is converted into an acylthio group to thereby give an acylthio derivative (XIV'). The compound (XIV') can be synthesized in accordance with a method commonly employed for the conversion of a hydroxyl group into an acylthio group. For example, the compound (XVIII) is treated by a Mitsunobu type reaction in an inert solvent such as methylene chloride and tetrahydrofuran with the use of triphenylphosphine and an azodicarboxylic acid ester such as DIAD (diisopropyl azodicarboxylate). Thus, the acylthio derivative (XIV') can be obtained.

Production process F-1

Among compounds represented by the following general formula (F), compounds other than those wherein $R^1$ and $R^3$ are each a hydrogen atom can be produced by the following process:

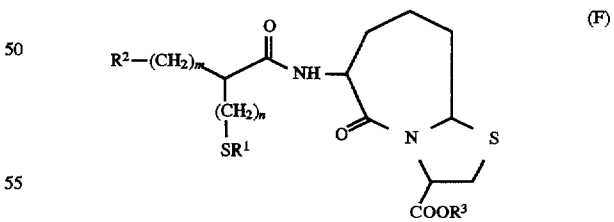

wherein $R^1$ represents a hydrogen atom or an acyl group;
$R^2$ represents a hydrogen atom, a lower alkyl group, an aryl group which may be substituted, a heteroaryl group which may be substituted, an arylalkyl group which may be substituted, a heteroarylalkyl group which may be substituted or a lower alkoxy group;
$R^3$ represents a hydrogen atom or a carboxyl-protecting group; and
m and n represent each independently an integer of 0, 1 or 2;

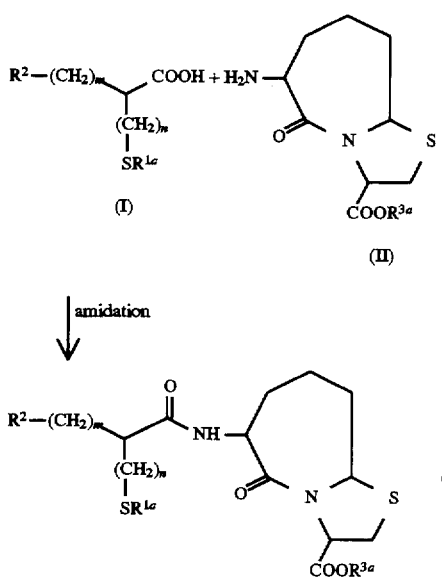

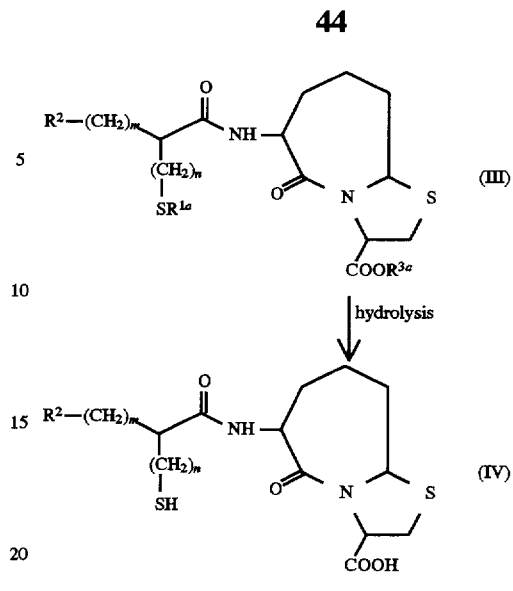

In a series of formulas, R², m and n have each the same meaning as the one defined above; R^(1a) represents a group selected from among those given in the definition of R¹ except a hydrogen atom; and R^(3a) represents a group selected from among those given in the definition of R³ except a hydrogen atom.

Namely, this is a method which comprises condensing a carboxylic acid derivative represented by the general formula (I) or an active derivative thereof, such as an acid halide thereof, with an amine derivative represented by the general formula (II) to thereby give an amide derivative (III).

The condensation may be effected by the conventional manner. For example, a condensation in the presence of a commonly employed condensing reagent such as 1-ethoxycarbonyl-2-ethoxy-1,2-dihydroquinoline (hereinafter referred to EEDQ), 1,3-dichlorohexylcarbodiimide hydrochloride (hereinafter referred to DEC) or diethyl cyanophosphonate may be usually cited.

As the reaction solvent, every organic solvent which remains inert during the reaction may be used. Examples thereof include methylene chloride, tetrahydrofuran and so on.

When the condensation is carried out via an acid chloride of the carboxylic acid derivative (I), the carboxylic acid derivative (I) is converted into an acid chloride in an appropriate inert solvent with a commonly employed chlorinating agent such as thionyl chloride and oxalyl chloride, and then the acid chloride thus obtained is reacted with the amine derivative (II) to thereby give the compound (III).

Production process F-2

Among compounds represented by the above general formula (F), those wherein R¹ and R³ are each a hydrogen atom can be also produced by the following process:

In a series of formulas, R², m, n, R^(1a) and R^(3a) have each the same meaning as the one defined above.

Namely, this is a reaction which comprises hydrolyzing an amide compound of the general formula (III) by the conventional manner to thereby give a mercapto carboxylic acid derivative (IV). To effect the hydrolysis, a method commonly employed in the art may be employed. For example, a method which comprises reacting the amide compound (III) in a dilute aqueous solution of an alkali such as sodium hydroxide and lithium hydroxide or in a dilute aqueous solution of a mineral acid and others may be cited.

Production process F-3

Among compounds represented by the above general formula (F), those wherein n is 0 can be also produced by the following process:

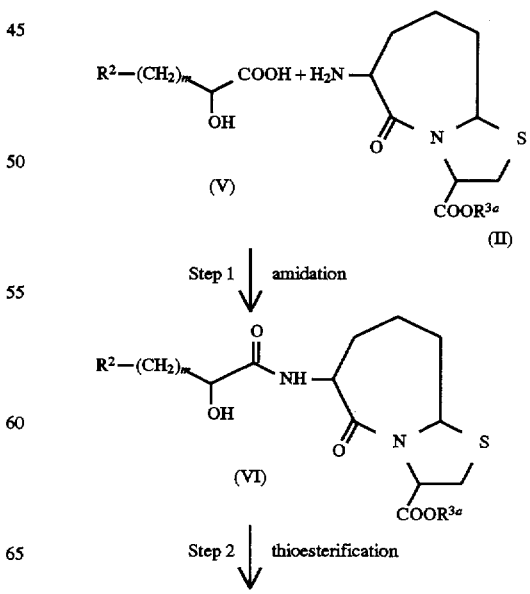

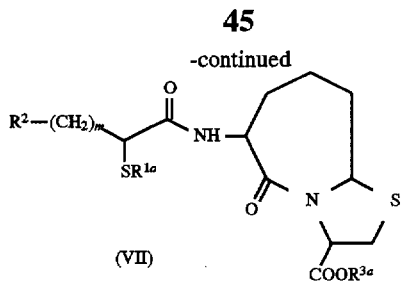

(VII)

In a series of formulas, $R^2$, m, $R^{1a}$ and $R^{3a}$ have each the same meaning as the one defined above.

(Step 1)

Namely, this is a step which comprises condensing a lactic acid derivative represented by the general formula (V) or a reactive derivative thereof, such as an acid halide thereof, with an amine derivative (II) to thereby give an amide derivative (VI). Similar to the above-mentioned Production process F-1, the compounds (V) and (II) are reacted in an inert solvent such as methylene chloride and tetrahydrofuran in the presence of a condensing reagent such as EEDQ or diethyl cyanophosphonate. Thus, the amide derivative (VI) can be obtained.

(Step 2)

Namely, this is a step wherein the hydroxyl group of the amide derivative (VI) obtained in the step 1 is thioesterified in the conventional manner to thereby give an acetylthio derivative (VII).

An example of the method for thioesterifying the hydroxyl group includes one which comprises treating the compound (VI) by a Mitsunobu type reaction in an inert solvent such as methylene chloride and tetrahydrofuran with the use of triphenylphosphine and an azodicarboxylic acid ester such as diisopropyl azodicarboxylate (hereinafter referred to as DIAD) to thereby give the target compound (VII).

Further, among compounds represented by the general formula (F), one wherein $R^2$ and $R^3$ are each hydrogen can be obtained by effecting hydrolysis in the same manner as the one described in the Production process F-2.

Now, main methods for synthesizing the starting compounds used in the Production processes F-1 and F-3 will be described.

Production process F-4

Among compounds represented by %he above general formula (V) used in the Production process F-3 and the compounds represented by the above general formula (I) used in the Production process F-1, those wherein n is can be synthesized by the following process:

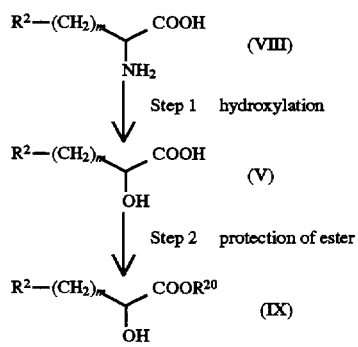

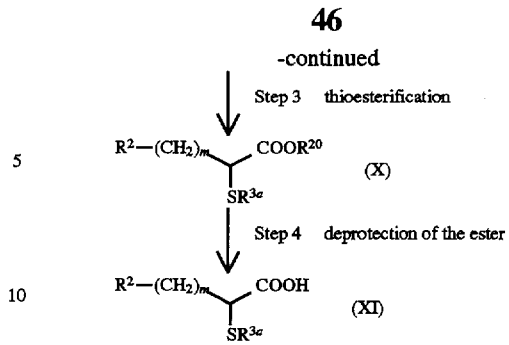

In a series of formulas, $R^2$, m and $R^{3a}$ have each the same meaning as the one defined above; and $R^{20}$ represents a group represented by the formula: —$CHPh_2$ (wherein Ph represents a phenyl group), a group represented by the formula: —$CPh_3$ or a group represented by the formula: —$(CH_2)_2$—$Si(CH_3)_3$.

(Step 1)

Namely, this is a step which comprises hydroxylating an amino acid derivative represented by the general formula (VIII) to thereby give a lactic acid derivative (V) which is a starting material in the Production process F-3.

The above-mentioned lactic acid derivative (V) can be synthesized through the hydroxylation for a common amino acid. The lactic acid derivative (V) can be synthesized by, for example, treating the amino acid derivative (VIII) and an azidating agent such as sodium nitrite and silver nitrite in an aqueous acidic solution such as dilute hydrochloric acid or dilute sulfuric acid.

(Step 2)

Namely, this is a step which comprises protecting the functional carboxylic acid group of the lactic acid derivative (V) obtained in the step 1 through esterification to thereby give an ester derivative (IX).

As an appropriate protecting group, one which can be selectively deprotected under such reaction conditions that the acylthio group of the compound (X) to be synthesized in the subsequent step 3 is not hydrolyzed is introduced. For example, the lactic acid derivative (V) is reacted with diphenylbromomethane, triphenylbromomethane or trimethylsilylethyl bromide in an inert solvent commonly employed in the art such as dimethylformamide and tetrahydrofuran in the presence of a base such as cesium carbonate and potassium carbonate. Thus, the lactate derivative (IX) can be obtained.

(Step 3)

Namely, this is a step which comprises thioesterifying the hydroxyl group of the lactate derivative (IX) obtained in the step 2.

This step can be effected in the same manner as the one described in the Production process F-3, step 2.

(Step 4)

Namely, this is a step which comprises deprotecting the ester group of the acylthio derivative (X) obtained in the step 3 to thereby give a carboxylic acid derivative (XI). When the ester-protecting group $R^4$ is an arylalkyl group such as diphenylmethyl and triphenylmethyl, the acylthio derivative (X) is treated with trifluoroacetic acid and anisole to thereby give the carboxylic acid derivative (XI). When the ester-protecting group $R^4$ is a silylalkyl group such as trimethylsilylethyl, the acylthio derivative (X) is treated with a fluorine compound such as potassium fluoride and tetrabutylammonium fluoride to thereby give the carboxylic acid derivative (XI).

The compounds according to the present invention can be obtained by processes commonly employed in the art or by combining these processes. Major production processes will now be described.

Production process 1

Among compounds represented by the general formula (I), one (X) wherein $R^1$ is a group other than a hydrogen atom can be obtained by the following process:

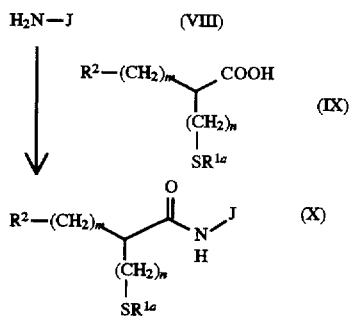

In a series of formulas, $R^{1a}$ represents an acyl group; $R^2$ represents a hydrogen atom, a lower alkyl group, a cycloalkyl group, an aryl group which may have a substituent, a heteroaryl group which may have a substituent, an arylalkyl group which may have a substituent or a heteroarylalkyl group which may have a substituent; m and n represent each independently an integer of 0, 1 or 2; and J represents a cyclic group having an angiotensin I-converting enzyme inhibition activity.

Namely, this is a step which comprises condensing an amino acid derivative represented by the general formula (VIII) with a carboxylic acid derivative represented by the general formula (IX) or an active derivative thereof, such as an acid halide thereof, by the conventional manner to thereby give an amide derivative represented by the general formula (X).

The condensation may be effected by a method commonly employed in the art. For example, the amino acid derivative (VIII) is reacted with the carboxylic acid derivative (IX) in an inert solvent represented by methylene chloride or tetrahydrofuran in the presence of a commonly employed condensing reagent such as EEDQ (1-ethoxycarbonyl-2-ethoxy-1,2-dihydroquinoline), DCC (1,3-dicyclohexylcarbodiimide), DEC (1-(3-dimethylaminopropyl)-3-ethylcarbodiimide hydrochloride) or diethyl cyanophosphonate. Thus, the amide derivative (X) can be obtained.

When the condensation is carried out via an acid chloride of the carboxylic acid derivative (IX), the carboxylic acid derivative (IX) is converted into an acid chloride in an appropriate inert solvent with the use of a commonly employed chlorinating agent such as thionyl chloride and oxalyl chloride, and then the acid chloride thus obtained is reacted with the amino acid derivative (VIII) to thereby give the amide acid derivative (X) as the target compound.

Production process 2

When $R^1$ is a hydrogen atom, the compound (XI) can also be produced by the following precess;

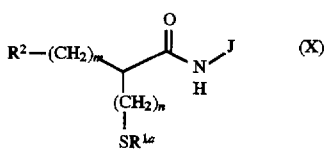

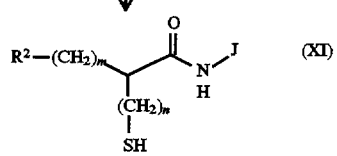

In a series of formulas, $R^{1a}$, $R^2$, J, n and m have each the same meaning as the one defined above.

Namely, this is a process which comprises deprotecting the ester group and the acylthio group of the amide derivative (X) obtained by the Production process 1 by the conventional manner to thereby give an amino acid derivative, i.e., the target compound (XI).

The deprotection may be effected by a method commonly employed in the art. Namely, it is effected by hydrolyzing the amide derivative (X) in a dilute aqueous solution of an alkali such as sodium hydroxide and lithium hydroxide or in a dilute aqueous solution of a mineral acid.

Production process 3

Among compounds represented by the general formula (I), one (XIV) wherein n is 0 can also be produced by the following method:

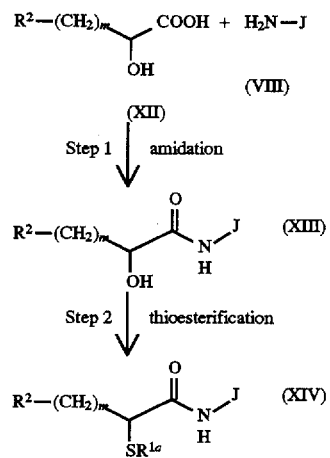

In a series of formulas, $R^{1a}$, $R^2$, m and J have each the same meaning as the one defined above.

(Step 1)

Namely, this is a step which comprises condensing a lactic acid derivative represented by the general formula (XII) or a reactive derivative thereof, such as an acid halide thereof, with an amine derivative represented by the general formula (VIII) to thereby give an amide derivative (XIII). Similar to the above-mentioned Production process 1, the compounds (XII) and (VIII) are reacted in an inert solvent such as methylene chloride and tetrahydrofuran in the presence of a condensing reagent such as EEDQ or diethyl cyanophosphonate. Thus, the amide derivative (XIII) can be obtained.

(Step 2)

Namely, this is a step which comprises thioesterifying the hydroxyl group of the amide derivative (XIII) obtained in the step 1 in the conventional manner to thereby give the target compound represented by the general formula (XIV).

An example of the method for thioesterifying the hydroxyl group includes one which comprises treating the amide derivative (XIII) by a Mitsunobu type reaction in an inert solvent such as methylene chloride and tetrahydrofuran with the use of triphenylphosphine and an azodicarboxylic acid ester such as diisopropyl azodicarboxylate (hereinafter referred to as DIAD) to thereby give the target compound (XIV).

Production process 4

The compound represented by the general formula (VII) can also be obtained by the following process:

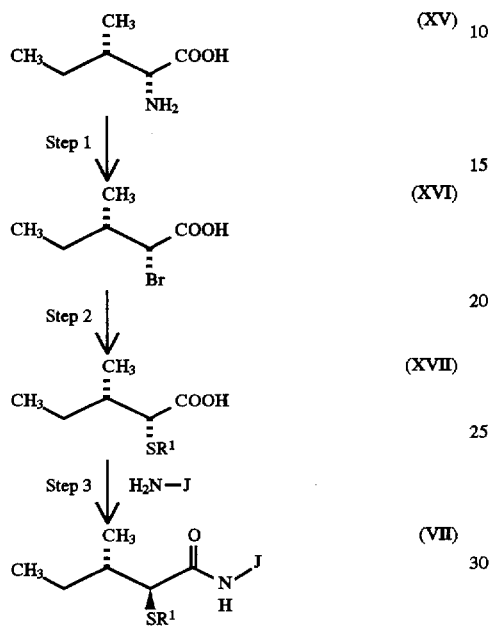

In a series of formulas, $R^1$ and J have each the same meaning as the one defined above.

(Step 1)

Namely, this step is one which comprises brominating the amino group of D-allo-isoleucine (XV) to thereby give a bromide (XVI). The compound (XVI) can be obtained in accordance with a method commonly employed in the art for stereoselective bromination. For example, the compound (XV) is treated with a nitrite such as sodium nitrite or silver nitrite in an aqueous hydrogen bromide. Thus, the bromide (XVI) can be obtained.

(Step 2)

Namely, this step is one which comprises converting the bromine group of the bromide (XVI) obtained in the step 1 into an acylthio group to thereby give an acylthiopentanoic acid derivative (XVII). This reaction is effected in accordance with the conventional manner. For example, the bromide (XVI) is reacted with a thiocarboxylate such as potassium thioacetate and sodium thioacetate in a polar solvent such as acetonitrile and acetone. Alternatively, the bromide (XVI) is reacted with a thiocarboxylic acid such as thioacetic acid and thiobenzoic acid in the presence of a base such as potassium carbonate and cesium carbonate. Thus, the acylthiopentanoic acid derivative (XVII) can be obtained.

(Step 3)

Namely, this step is one which comprises condensing the acylthiopentanoic acid derivative (XVII) obtained in the step 2 or an active derivative thereof, such as an acid halide thereof, with an amino acid ester derivative, which is a publicly known compound or one obtained by a publicly known method, to thereby give the target compound (VII). For example, the acylthio derivative (XVII) is reacted with the amino acid ester derivative in an inert solvent such as methylene chloride and tetrahydrofuran in the presence of a commonly employed condensing reagent such as EEDQ (1-ethoxycarbonyl-2-ethoxy-1,2-dihydroquinoline), DCC (1,3-dicyclohexylcarbodiimide). DEC [1-(3-dimethylaminopropyl)-3-ethylcarbodiimide hydrochloride] or diethyl cyanophosphonate. Thus, the compound (VII) can be obtained. When the condensation is carried out via an acid chloride of the acylthio derivative (XVII), the acylthio derivative (XVII) is converted into an acid chloride in an appropriate inert solvent with the use of a chlorinating agent such as thionyl chloride and oxalyl chloride, and then the acid chloride thus obtained is reacted with the amino acid ester derivative to thereby give the target compound (VII).

Production Process 5

The compound represented by the general formula (VII) can also be obtained by the following process:

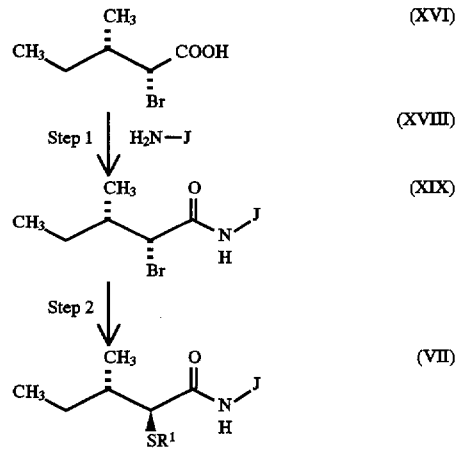

In a series of formulas, $R^1$ represents a hydrogen atom or an acyl group; and J has the same meaning as the one defined above.

(Step 1)

Namely, this step is one which comprises condensing the bromo carboxylic acid derivative (XVI) obtained in the Production process 4, step 1 or an active derivative thereof, such as an acid halide thereof, with an amino acid ester derivative (XVIII) by the conventional manner to thereby give an amide derivative (XIX). The amide derivative (XIX) can be obtained by the same treatment as the one described in the Production process 4, step 3.

(Step 2)

Namely, this step is one which comprises converting the bromine group of the amide derivative (XIX) obtained in the step 1 into an acylthio group to thereby give the target compound. The target compound (VII) can be obtained by the same treatment as the one described in the Production process, step 2.

To illustrate the effects of the compounds according to the present invention, Pharmacological Experiment Examples will now be given.

PHARMACOLOGICAL EXPERIMENT
EXAMPLE A-1

Determination of NEP Inhibition Activity of Medicament by Using Rat Renal Cortex 1. Experimental method The NEP activity was determined by using a membrane fraction prepared from rat renal cortex in accordance with the method of Booth and Kenny (A Rapid Metod for the Purificaton of Microvilli from Rabbit Kidney., Andrew G. Booth and A. John Kenny, Biochem j., 1974, 142, 578–881.).

The NEP activity was determined by the following manner in accordance with the method of Orlowsky and Wilk (Purification and Specificity of a Membrane-Bound Metalloendopeptidase from Bovine Pituitaries., Marian Orlowsky and Shrwin Wilk, Biochemistry, 1981, 20, 4942–4950.).

As a substrate, benzoyl-glycyl-arginyl-arginyl-2-naphthylamide (benzoyl-Gly-Arg-Arg-2-naphthylamide (Nova Biochem, Switzerland)) was used. In the presence of an NEP enzyme preparation and excessive leucine aminopeptidase (sigma chemical Co., U.S.A.), the liberated naphthylamine was made to undergo color development with first garnet (Sigma chemical Co., U.S.A.), followed by the measurement of the absorbance at a wavelength of 540 nm.

With respect to the NEP inhibition activity, the inhibitor was added to the experimental system as described above in such a manner as to give the final concentrations of 1, 3, 10, 30, 100, 300 and 1000 nM, an inhibition curve was prepared, and then the concentration at which 50% inhibition was achieved was taken as $IC_{50}$.

2. Results of the experiment

Table A-1 shows the results of the above experiment together with the results of the following Pharmacological Experiment Example A-2.

PHARMACOLOGICAL EXPERIMENT EXAMPLE A-2

Determination of ACE Inhibition Activity of Medicament by Using Rat Lung

1. Experimental method

The ACE inhibition activity was determined by using a membrane fraction prepared from rat lung in accordance with the method of Wu-Wong et al. (Characterization of Endthelin Converting Enzyme in Rat Lung., Junshyum R. Wu-Wong, Gerald, P. Budzik, Edward M. Devine and Terry J. Opgenorth, Biochem. Biophys. Res. Commun., 1990, 171, 1291–1296.).

The ACE activity was determined with the use of a modification (modified to a borate buffer, pH 8.3) of the method of Cushman and Cheung (Spectrophotometric Assay and Properties of the Angiotensin-Converting Enzyme of Rabbit Lung., Cushman, D. W. and Cheung H. S., 1971, 20, 1637–1648.).

In the presence of ACE, the hippurate liberated from hippuryl-histidyl-leucine (Hippuryl-His-Leu (PeptideInstitute Inc., Japan)) was extracted with ethyl acetate and then the absorbance was measured at a wavelength of 228 nm.

With respect to the ACE inhibition activity, the inhibitor was added to the experimental system as described above in such a manner as to give the final concentrations of 1, 3, 10, 30, 100, 300 and 1000 nM, an inhibition curve was prepared, and then the concentration at which 50% inhibition was achieved was taken as $IC_{50}$.

2. Results of the experiment

The following Table A-1 shows the results of the experiment effected according to the above-mentioned experimental method.

TABLE A-1

| | NEP inhibition activity $IC_{50}$ (nM) | ACE inhibition activity $IC_{50}$ (nM) |
|---|---|---|
| Cpd. of Ex. A-3 | 90 | 50 |
| Cpd. of Ex. A-5 | 160 | 50 |
| Cpd. of Ex. A-7 | 8.2 | 10 |
| Cpd. of Ex. A-9 | 13 | 13 |
| Cpd. of Ex. A-11 | 6.2 | 11 |

PHARMACOLOGICAL EXPERIMENT EXAMPLE B-1

Determination of NEP Inhibition Activity of Medicament by Using Rat Renal Cortex 1. Experimental method The NEP activity was determined by using a membrane fraction prepared from rat renal cortex in accordance with the method of Booth and Kenay (A Rapid Metod for the Purificaton of Microvilli from Rabbit Kidney., Andrew G. Booth and A. John Kenny, Biochem j., 1974, 142, 575–581.).

The NEP activity was determined by the following manner in accordance with the method of Orlowsky and Wilk (Purification and Specificity of a Membrane-Bound Metalloendpeptldase from Bovine Pituitaries., Marian Orlowsky and Shrwin Wilk, Biochemistry, 1981, 20, 4942–4950.).

As a substrate, benzoyl-glycine-arginine-arginine-2-naphthylamide (benzoyl-Gly-Arg-Arg-2-naphthylamide (Nova Biochem, Switzerland)) was used. In the presence of an NEP enzyme preparation and excessive leucine aminopeptidase (sigma chemical Co., U.S.A.), the liberated naphthylamine was made to undergo color development with first garnet (Sigma chemical Co., U.S.A.), followed by the measurement of the absorbance at a wavelength of 540 nm.

With respect to the NEP inhibition activity, the inhibitor was added to the reaction system as described above in such a manner as to give the final concentrations of 1, 3, 10, 30, 100, 300 and 1000 nM, an inhibition curve was prepared, and then the concentration at which 50% inhibition was achieved was taken as $IC_{50}$.

2. Results of the experiment

Table B-1, which will be described below, shows the results of the above experiment together with the results of the following Pharmacological Experiment Example B-2.

PHARMACOLOGICAL EXPERIMENT EXAMPLE B-2

Determination of ACE Inhibition Activity of Medicament by Using Rat Lung

1. Experimental method

The ACE inhibition activity was determined by using a membrane fraction prepared from rat lung in accordance with the method of Wu-Wong et al. (Characterization of Endthelin Converting Enzyme in Rat Lung., Junshyum R. Wu-Wong, Gerald, P. Budzik, Edward M. Devine and Terry J. Opgenorth, Biochem. Biophys. Res. Commun., 1990, 171, 1291–1296.).

The ACE activity was determined with the use of a modification (modified to a borate buffer, p11 8.3) of the method of Cushman and Cheung (Spectrophotometric Assay and Properties of the Angiotensin-Converting Enzyme of Rabbit Lung., Cushman, D. W. and Cheung H. S., 1971, 20, 1687–1648.).

In the presence of ACE, the hippurate liberated from hippuryl-histidine-leucine (Hippuryl-His-Leu (PeptideInstitute Inc., Japan)) was extracted with ethyl acetate and then the absorbance was measured at a wavelength of 228 nm.

With respect to the ACE inhibition activity, the inhibitor was added to the reaction system as described above in such a manner as to give the final concentrations of 1, 3, 10, 30, 100, 300 and 1000 nM, an inhibition curve was prepared, and then the concentration at which 50% inhibition was achieved was taken as $IC_{50}$.

2. Results of the experiment

The following Table B-1 shows the results of the experiment effected according to the above-mentioned experimental method.

TABLE B-1

|  | NEP inhibition activity $IC_{50}$ (nM) | ACE inhibition activity $IC_{50}$ (nM) |
|---|---|---|
| Cpd. of Ex. B-3 | 8.6 | 16 |
| Cpd. of Ex. B-7 | 55 | 60 |
| Cpd. of Ex. B-8 | 72 | 90 |

PHARMACOLOGICAL EXPERIMENT EXAMPLE C-1

1. Experimental method

The NEP activity was determined by the following manner in accordance with the method of Orlowsky and Wilk (Purification and Specificity of a Membrane-Bound Metalloendpeptidase from Bovine Pituitaries., Marian Orlowsky and Shrwin Wilk, Biochemistry, 1981, 20, 4942–4950.).

As a substrate, benzoyl-glycyl-arginyl-arginyl-2-naphthylamide (benzoyl-Gly-Arg-Arg-2-naphthylamide (Nova Biochem, Switzerland)) was used. In the presence of an NEP enzyme preparation and excessive leucine aminopeptidase (sigma chemical Co., U.S.A.), the liberated naphthylamine was made to undergo color development with first garnet (Sigma chemical Co., U.S.A.), followed by the measurement of the absorbance at a wavelength of 540 nm.

With respect to the NEP inhibition activity, the test compound was added to the experimental system as described above in such a manner as to give the final concentrations of 1, 3, 10, 30, 100, 300 and 1000 nM, an inhibition curve was prepared, and then the concentration at which 50% inhibition was achieved was taken as $IC_{50}$. As a comparative compound, [4S-[4α,7α(R*),12bβ]]-7-[(1-oxo-2-(S)-thio-3-phenyl-propyl)amino]-1,2,3,4,6,7,8,12b-octahydro-6-oxopyrido-[2,1-a][2]benzazepine-4-carboxylic acid was used.

2. Results of the experiment

Table C-1, which will be described below, shows the results of the above experiment together with the results of the Pharmacological Experiment Example C-2.

PHARMACOLOGICAL EXPERIMENT EXAMPLE C-2

Determination of ACE Inhibition Activity of Medicament by Using Rat Lung

1. Experimental method

The ACE inhibition activity was determined by using a membrane fraction prepared from rat lung in accordance with the method of Wu-Wong et al. (Characterization of Endthelin Converting Enzyme in Rat Lung., Junshyum R. Wu-Wong, Gerald P. Budzik, Edward M. Devine and Terry J. Opgenorth, Biochem. Biophys. Res. Commun., 1990, 171, 1291–1296.).

The ACE activity was determined with the use of a modification (modified to a borate buffer, pH 8.3) of the method of Cushman and Cheung (Spectrophotometric Assay and Properties of the Angiotensin-Converting Enzyme of Rabbit Lung., Cushman D. W. and Cheung H. S., 1971, 20, 1637–1648.).

In the presence of ACE, the hippurate liberated from hippuryl-histidyl-leucine (Hippuryl-His-Leu (PeptideInstitute Inc., Japan)) was extracted with ethyl acetate and then the absorbance was measured at a wavelength of 228 nm.

With respect to the ACE inhibition activity, the test compound was added to the reaction system as described above in such a manner as to give the final concentrations of 1, 3, 10, 30, 100, 300 and 1000 nM, an inhibition curve was prepared, and then the concentration at which 50% inhibition was achieved was taken as $IC_{50}$. As a comparative compound, [4S-[4α,7α(R*),12bβ]]-7-[(1-oxo-2-(S)-thio-3-phenyl-propyl)amino]-1,2,3,4,6,7,8,12b-octahydro-6-oxopyrido-[2,1-a][2]benzazepine-4-carboxylic acid was used.

2. Results of the experiment

The following Table C-1 shows the results of the experiment effected according to the above-mentioned experimental method.

TABLE C-1

| Test compound | NEP inhibition activity $IC_{50}$ (nM) | ACE inhibition activity $IC_{50}$ (nM) |
|---|---|---|
| Ex. C-8 | 13.4 (n = 3) | 5.3 (n = 3) |
| Ex. C-10 | 12.5 (n = 2) | 13.0 (n = 2) |
| Ex. C-11 | 6.2 (n = 1) | 11.0 (n = 1) |
| Ex. C-12 | 15.1 (n = 2) | 12.5 (n = 2) |
| Ex. C-14 | 17.8 (n = 6) | 12.3 (n = 6) |
| Ex. C-15 | 6.6 (n = 2) | 12.5 (n = 2) |
| Comparative Cpd. | 27.0 (n = 4) | 9.0 (n = 4) |

PHARMACOLOGICAL EXPERIMENT EXAMPLE C-3

Hypotensive Effect on 2K-1C-Goldblatt Hypertensive Rat

1. Experimental method

A silver clip with a slit of 0.25 mm in width was fitted into the left renal artery of each of male Sprague Dawley rats (aged 6 to 7 weeks) and, after three weeks, rats showing a systolic blood pressure of 180 mmHg or above were employed. One to several drops of a 1N aqueous solution of sodium hydroxide were dropped into purified water and each test compound was dissolved or emulsified therein to prepare it at a dose of 5 ml/kg, followed by orally administration. After keeping the rats in an incubator at 45° C. for 5 to 10 minutes, the systolic blood pressure was measured by the indirect method of tail artery plethysmography. As a comparative compound, [4S-[4α,7α(R*),12bβ]]-7-[(1-oxo-2-(S)-thio-3-phenyl-propyl)amino[-1,2,3,4,6,7,8,12b-octahydro-6-oxo-pyrido[2,1-a][2]benzazepine-4-carboxylic acid was used.

2. Results of the experiment

The following Table C-2 shows the results of the experiment effected according to the above-mentioned method.

TABLE C-2

| Compound examined (dose) | Decrease (%) in blood pressure after 1–3 hrs. | Decrease (%) in blood pressure after 6 hrs. |
|---|---|---|
| Ex. C-8 (1 mg/kg) | 28.4 (after 2 hrs) | 25.3 |
| Ex. C-10 (1 mg/kg) | 17.3 (after 2 hrs) | 20.8 |
| Ex. C-14 (1 mg/kg) | 13.4 (after 3 hrs) | 12.7 |
| Ex. C-14 (3 mg/kg) | 25.9 (after 3 hrs) | 22.2 |
| Comp. compound (3 mg/kg) | 15.4 (after 1 hr) | 12.9 |
| Comp. compound (10 mg/kg) | 14.2 (after 1 hr) | 19.1 |

As described above, the hypotensive effect according to the present invention was excellent about three or more times that of the comparative compound.

PHARMACOLOGICAL EXPERIMENT
EXAMPLE C-4

Diuretic Effect on ANP-treated SHR

1. Experimental method 50 ng/kg/min of rat Atrial natriuretic peptide (r-ANP) was intravenously injected into Spontaneously hypertensive male rats (aged 14 to 16 weeks). When the hematogenic dynamics and the blood r-ANP level became stable 1 hour after the injection, the diuretic effect of each test compound was examined. The diuretic effect was determined by intravenously injecting the test compound and measuring an increase (% rate of change) in urinary accumulation within 20 minutes. As a comparative compound, [4S-[4α,7α(R*), 12bβ]]-7-[(1-oxo-2(S)-thio-3-phenylpropyl)amino[-1,2,3,4, 6,7,8,12b-octahydro-6-oxopyrido[2,1-a][2]benzazepine-4-carboxylic acid was used.

2. Results of the experiment

The following Table C-3 shows the results obtained by the above experiment.

TABLE C-3

| Test cpd. | 0.01 mg/kg i.v. | 0.03 mg/kg i.v. | 0.1 mg/kg i.v. | 0.3 mg/kg i.v. |
|---|---|---|---|---|
| Ex. C-8 | 200% | 280% | 340% | — |
| Ex. C-11 | 220% | 390% | 460% | — |
| Ex. C-14 | — | 240% | 420% | 470% |
| Comp. cpd. | — | 220% | 370% | 360% |

As these results show, the activities of the test compounds in the diuretic effects were about three times that of the comparative compound.

PHARMACOLOGICAL EXPERIMENT
EXAMPLE C-5

Hypotensive Effect on SHR

SHRs aged 15 to 20 weeks were anesthetized by intraperitoneally administering thiopental sodium (50 mg/kg). The depth of anesthesia was maintained by optionally effecting supplemental anesthesia (5 mg/kg, i.v.). Catheters were inserted into the left common carotid artery and the vein respectively for the measurement of blood pressure and for the administration of a medicament. The cardiac rate was counted by using blood pressure as a trigger.

When the blood pressure became stable after the completion of the operation, the comparative compound was intravenously administered in 0.1, 0.3 and 1.0 mg/kg and changes in blood pressure and cardiac rate were measured. Following the administration, the measurement was effected for 10 minutes in the cases of 0.1 and 0.3 mg/kg or for 30 minutes in the case of 1.0 mg/kg. The invention compound was intravenously administered in 0.03, 0.1 and 0.3 mg/kg and the measurement was effected for 10 minutes after the administration in the cases of 0.03 and 0.1 mg/kg or for 30 minutes after the administration in the case of 0.3 mg/kg.

The comparative compound showed a continuous decrease in blood pressure of 3 to 4% at the dose of 0.3 mg/kg or above, and 12 to 13% in the case of 1.0 mg/kg, and the blood pressure did not return within 30 minutes after the administration. The cardiac rate tended to gradually decrease.

The compound of the present invention showed an obvious hypotensive effect of about 8% at the dose of 0.03 mg/kg or above, and further showed a continuous hypotensive effect of 13 to 154 at the dose of 0.1 mg/kg and 23% at the dose of 0.3 mg/kg. The cardiac rate showed no change.

Thus, it is considered that the compound of the present invention is about 10 times as active as the comparative compound in the hypotensive effect on SHR.

PHARMACOLOGICAL EXPERIMENT
EXAMPLE C-6

Hypertensive Effect by Oral Administration on SHR

By using Spontaneously hypertensive male rats (aged 16 to 17 weeks), the compound of Example C-8 and a comparative compound [S-(R*,R*)]-2,3,4,5-tetrahydro-3-[(2-mercapto-1-oxohexyl)amino]-2-oxo-1H-benzazepine-1-acetic acid having the following structure each dissolved in 0.5% methylcellulose were orally administered thereto. Hypotensive effects were measured by the tail cuff method and data obtained before the oral administration and 2, 4 and 8 hours after the administration were compared. The hypotensive effect achieved by 1.0 mg/kg of the compound of Example C-8 was comparable to the one achieved by 10 mg/kg of the above comparative compound. Accordingly, the compound of Example C-8 has an activity about 10 times as high as that of the comparative compound.

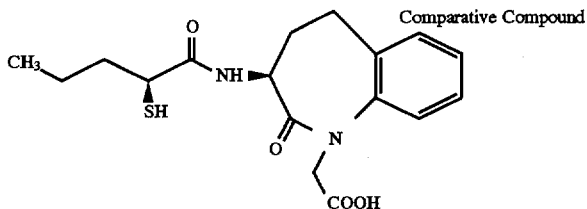

Comparative Compound

PHARMACOLOGICAL EXPERIMENT EXAMPLE D-1

Determination of NEP and ACE Inhibition Activities

1. Experimental method

As a source of the enzyme NEP, a membrane fraction prepared from rat renal cortex in accordance with the method of Booth and Kenny (A Rapid Method for the Purification of Microvilli from Rabbit Kidney., Andrew G. Booth and A. John Kenny, Biochem. j., 1974, 142, 575–581.) was employed. The NEP activity was determined in accordance with the method of Orlowsky and Wilk (Purification and Specificity of a Membrane-Bound Metalloendpeptidase from Bovine Pituitaries., Marian Orlowsky and Shrwin Wilk, Biochemistry, 1981, 20, 4942–4950.). Now the procedure will be briefly described.

As a substrate, benzoyl-glycine-arginine-arginine-2-naphthylamide benzoyl-Gly-Arg-Arg-2-naphthylamide (Nova Biochem, Switzerland)) was used. In the presence of an NEP enzyme preparation and excessive leucine aminopeptidase (sigma chemical Co., U.S.A.), the liberated naphthylamine was made to undergo color development with first garnet (Sigma chemical Co., U.S.A.), followed by the measurement of the absorbance at a wavelength of 540 nm.

As a source of the enzyme ACE, a membrane fraction prepared from rat lung in accordance with the method of Wu-Wong et al. (Characterization of Endthelin Converting Enzyme in Rat Lung., Junshyum R. Wu-Wong, Gerald, P. Budzik, Edward M. Devine and Terry J. Opgenorth, Biochem. Biophys. Res. Commun., 1990, 171, 1291–1296.) was used. The ACE activity was determined with the use of a modification (modified to a borate buffer, pH 8.3) of the method of Cushman and Cheung (Spectrophotometric Assay and Properties of the Angiotensin-Converting Enzyme of Rabbit Lung., Cushman D. W. and Cheung H. S., 1971, 20, 1637–1648.). Now the procedure will be briefly described.

In the presence of ACE, the hippurate liberated from hippuryl-histidine-leucine (Hippuryl-His-Leu (Peptide Institute Inc., Japan)) was extracted with ethyl acetate and then the absorbance was measured at a wavelength of 228 nm.

To determine the NEP inhibition activity and the ACE inhibition activity, the inhibitor was added to the assay systems of both enzyme activities as described above in such a manner as to give the final concentrations of 1, 3, 10, 30, 100, 300 and 1000 nM and inhibition curves were prepared. Then the concentration at which 50% inhibition was achieved was taken as $IC_{50}$.

2. Results of the experiment

The following Table D-1 shows the results of the above Experimental Example D-1.

TABLE D-1

| | NEP inhibition activity $IC_{50}$ (nM) | ACE inhibition activity $IC_{50}$ (nM) |
|---|---|---|
| Ex. D-5 | 33 | 17 |
| Ex. D-6 | 38 | 12 |
| Comp. cpd.*[1] | 14 | 11 |

Note)
*[1]Comparative compound: 5(S)-[2-mercapto-3-(4-methoxyphenyl)propylamino]-4-oxo-2,3,4,5,6,10b(R)-hexahydro-1-thia-3a-azabenzo[e]azuleno-3(S)-carboxylic acid.

PHARMACOLOGICAL EXPERIMENT EXAMPLE D-2

1. Experimental method

Spontaneously hypertensive rats (SHR) aged 15 to 20 weeks were anesthetized by intraperitoneally administering thiopental sodium (50 mg/kg). The depth of anesthesia was maintained by optionally effecting supplemental anesthesia (5 mg/kg, i.v.). Catheters were inserted into the left common carotid artery and the vein respectively for the measurement of blood pressure and for the administration of a medicament. The cardiac rate was counted by using blood pressure as a trigger.

When the blood pressure became stable after the completion of the operation, the comparative compound or the compound of Example 9 was intravenously administered in doses of 0.1, 0.3 and 1.0 mg/kg and changes in blood pressure and cardiac rate were measured. Following the administration, the measurement was effected for 10 minutes in the cases of 0.1 and 0.3 mg/kg or for 30 minutes in the case of 1.0 mg/kg.

2. Results of the experiment

The comparative compound showed a continuous decrease in blood pressure of 3 to 4% at the dose of 0.3 mg/kg or above, and 12 to 13% in the case of 1.0 mg/kg, and the blood pressure did not return within 30 minutes after the administration. While, the cardiac rate tended to gradually decrease.

On the other hand, the compound of Example D-6 showed an obvious hypotensive effect (3 to 4%) at the dose of 0.1 mg/kg orr above, and showed a continuous hypotensive effect of 10 to 13% at the dose of 0.3 mg/kg and 25% at the dose of 1.0 mg/kg. While, the cardiac rate tended to gradually decrease.

Accordingly, on the basis of the results of the Experimental Example D-2 described above, it was confirmed that the hypotensive effect of the compound of Example D-6 on SHR was about three times that of the comparative compound.

PHARMACOLOGICAL EXPERIMENT EXAMPLE E-1

(Determination of NEP and ACE Inhibition Activities)

1. Experimental method

As a source of the enzyme NEP, a membrane fraction prepared from rat renal cortex in accordance with the method of Booth and Kenny (A Rapid Method for the Purification of Microvilli from Rabbit Kidney., Andrew G. Booth and A. John Kenny, Biochem. j., 1974, 142,575–581.) was employed. The NEP activity was determined in accordance with the method of Orlowsky and Wilk (Purification and Specificity of a Membrane-Bound Metalloendpeptidase from Bovine Pituitaries., Marian Orlowsky and Shrwin Wilk, Biochemistry, 1981, 20, 4942–4950.). Now the procedure will be briefly described.

As a substrate, benzoyl-glycyl-arginyl-arginyl-2-naphthylamide (benzoyl-Gly-Arg-Arg-2 naphthylamide (Nova Biochem, Switzerland)) was used. In the presence of an NEP enzyme preparation and excessive leucine aminopeptidase (sigma chemical Co., U.S.A.), the liberated naphthylamine was made to undergo color development with first garnet (Sigma chemical Co., U.S.A.), followed by the measurement of the absorbance at a wavelength of 540 nm.

As a source of the enzyme ACE, a membrane fraction prepared from rat lung in accordance with the method of Wu-Wong et al. (Characterization of Endthelin Converting Enzyme in Rat Lung., Jinshyum R. Wu-Wong, Gerald, P. Budzik, Edward M. Devine and Terry J. Opgenorth, Biochem. Biophys. Res. Commun., 1990, 171, 1291–1296.) was used. The ACE activity was determined with the use of a modification (modified to a borate buffer pH 8.3) of the method of Cushman and Cheung (Spectrophotometric Assay and Properties of the Angiotensin-Converting Enzyme of Rabbit Lung., Cushman D. W. and Cheung H. S., 1971, 20, 1637–1648.). Now the procedure will be briefly described.

In the presence of ACE, the hippurate liberated from hippuryl-histidyl-leucine (Hippuryl-His-Leu (PeptideInstitute Inc., Japan)) was extracted with ethyl acetate and then the absorbance was measured at a wavelength of 228 nm.

To determine the NEP inhibition activity and the ACE inhibition activity, the inhibitor was added to the assay systems of both enzyme activities as described above in such a manner as to give the final concentrations of 1, 3, 10, 30, 100, 800 and 1000 nM and inhibition curves were prepared. Then the concentration at which 50% inhibition was achieved was taken as $IC_{50}$.

2. Results of the experiment

The following Table E-1 shows the results of the experiment effected according to the above experimental method.

TABLE E-1

|  | NEP inhibition activity $IC_{50}$ (nM) | ACE inhibition activity $IC_{50}$ (nM) |
| --- | --- | --- |
| cpd. of Ex. E-6 | 28 (n = 3) | 10 (n = 3) |
| cpd. of Ex. E-7 | 45 (n = 3) | 11 (n = 3) |
| cpd. of Ex. E-10 | 8.2 (n = 3) | 10 (n = 3) |
| cpd. of Ex. E-13 | 14 (n = 4) | 11 (n = 4) |
| Comp. cpd. E-1*[1] | 27 (n = 4) | 9 (n = 4) |

Note)
*[1]Comparative compound 1: [4S-[4α,7α(R*),12bβ]]-7-[(1-oxo-2(S)-thio-3-phenylpropyl)-amino]-1,2,3,4,6,7,8,12b-octahydro-6-oxopyrido[2,1-a]-[2]benzazepine-4-carboxylic acid (compound name: MDL-100,173).

PHARMACOLOGICAL EXPERIMENT EXAMPLE E-2

To male Wistar rats aged 11 to 13 weeks was intravenously injected (1 mg/kg) and orally administered (10 mg/kg, 30 mg/kg) the compound of Example E-6 or the comparative compound E-1. Then changes in the blood level of each medicament were monitored with the lapse of time by using liquid chromatography. In the case of the compound of Example E-6, the blood level of the medicament was determined by measuring the UV (257 nm) absorbance. While in the case of the comparative compound E-1, the the blood level of the medicament was determined by the fluorescent labeling method with the use of ABD-F. The bioavailabilities of the compound of Example E-6 calculated from the AUC of the oral administration and the AUC of the intravenous administration were respectively 24.6% (30 mg/kg, p.o.) and 18.8% (10 mg/kg, p.o.). On the other hand, the dynamics in vivo of the comparative compound E-1 were measured by the same method. As a result, the bioavailabilities thereof were 7.8% (30 mg/kg, p.o.) and 4.3% (10 mg/kg, p.o.). Accordingly, the compound of Example E-6 is superior in oral absorbability to the comparative compound E-1.

PHARMACOLOGICAL EXPERIMENT EXAMPLE e-3

V1 and V2 Receptor Binding Assay

Membrane specimens of rat liver (V1) and rat kidney (V2) were used. 100,000 counts (3.69 nM) of [$^3$H]-Arg-vasopressin, 25 µg (1 mg protein/ml) of each membrane specimen and a test medicament ($10^{-7}$ to $10^{-5}$M) were incubated in a total volume of 250 µl of an assay buffer (pH=7.4) containing 10 mM of $MgCl_2$, 2 mM of EGTA and 20 mM of HEPES at 4° C. over day and night. Then, the incubation was washed with 5-ml portions of the buffer 5 times to thereby separate the membrane specimen binding to vasopressin followed by filtration with the use of a glass filter (GF/F). This glass filter was dried for about 3 hours and mixed with a cocktail for liquid scintillation (10 ml, ACSII). After allowing to stand overnight, the amount of the [$^3$H]-Arg-vasopressin binding to the membrane was determined with a liquid scintillation counter and the inhibition ratio was calculated in accordance with the following formula:

Inhibition ratio (%)=100−[(C1−B1)/(C0−B1)]×100 wherein

B1; the amount of [$^3$H]-Arg-vasopressin binding to the membrane in the presence of excessive vasopressin (10 µM)

C0; the amount of [$^3$H]-Arg-vasopressin binding to the membrane in the absence of the test medicament and C1; the amount of [$^3$H]-Arg-vasopressin binding to the membrane in the presence of both the test medicament in a known amount and [$^3$H]-Arg-vasopressin.

The amount of the test medicament giving an inhibition ratio as calculated in accordance with the above formula of 50% was determined and taken as $IC_{50}$.

The $IC_{50}$ of the compound of Example E-10 determined by the above-mentioned method for the vasopressin (V1) receptor was 10µM or above, while that for the vasopressin (V2) receptor was 4.49 µM.

PHARMACOLOGICAL EXPERIMENT EXAMPLE F-1

(Determination of NEP and ACE Inhibition Activities)

1. Experimental method

As a source of the enzyme NEP, a membrane fraction prepared from rat renal cortex in accordance with the method of Booth and Kenny (A Rapid Method for the Purification of Microvilli from Rabbit Kidney., Andrew G. Booth and A. John Kenny, Biochem. j., 1974, 142, 575–581.) was employed. The NEP activity was determined in accordance with the method of Orlowsky and Wilk (Purification and Specificity of a Membrane-Bound Metalloendpeptidase from Bovine Pituitaries., Marian Orlowsky and Shrwin Wilk, Biochemistry, 1981, 20, 4942–4950.). Now the procedure will be briefly described.

As a substrate, benzoyl-glycyl-arginyl-arginyl-2-naphthylamide (benzoyl-Gly-Arg-Arg-2-naphthylamide (Nova Biochem, Switzerland)) was used. In the presence of an NEP enzyme preparation and excessive leucine aminopeptidase (sigma chemical Co., U.S.A.), the liberated naphthylamine was made to undergo color development with first garnet (Sigma chemical Co., U.S.A.), followed by the measurement of the absorbance at a wavelength of 540 nm.

As a source of the enzyme ACE, a membrane fraction prepared from rat lung in accordance with the method of Wu-Wong et al. (Characterization of Endthelin Converting Enzyme in Rat Lung., Jinshyum R. Wu-Wong, Gerald P. Budzik, Edward M, Devine and Terry J. Opgenorth, Biochem. Biophys. Res. Commun., 1990, 171, 1291–1296.) was used. The ACE activity was determined with the use of a modification (modified to a borate buffer pH 8.3) of the method of Cushman and Cheung (Spectrophotometric Assay and Properties of the Angiotensin-Converting Enzyme of Rabbit Lung., Cushman D. W. and Cheung H. S., 1971, 20, 1637–1648.). Now the procedure will be briefly described.

In the presence of ACE, the hippurate liberated from hippuryl-histidyl-leucine (Hippuryl-His-Leu (Peptide Institute Inc., Japan)) was extracted with ethyl acetate and then the absorbance was measured at a wavelength of 228 nm.

With respect to the NEP inhibition activity and the ACE inhibition activity, the inhibitor was added to the assay systems of both enzyme activities as described above in such a manner as to give the final concentrations of 1, 3, 10, 30, 100, 300 and 1000 inhibition curves were prepared, and then the concentration at which 50% inhibition was achieved was taken as $IC_{50}$.

2. Results of the experiment

The following Table 1 shows the results of the experiment effected according to the above experimental method.

TABLE F-1

| | NEP inhibition activity $IC_{50}$ (nM), (case no.) | ACE inhibition activity $IC_{50}$ (nM), (case no.) |
|---|---|---|
| Ex. F-14 | 22.5 (2) | 7.7 (3) |
| Ex. F-15 | 9.2 (1) | 5.2 (1) |
| Ex. F-17 | 11.1 (4) | 13.4 (2) |
| Ex. F-18 | 5.6 (4) | 7.0 (3) |
| Ex. F-19 | 104 (2) | 13.5 (2) |
| Ex. F-20 | 56.5 (2) | 16.0 (2) |
| Ex. F-22 | 9.0 (1) | 13 (1) |
| Ex. F-23 | 120 (1) | 8.0 (1) |
| Ex. F-24 | 8.0 (1) | 13.0 (1) |
| Ex. F-25 | 265 (2) | 9.0 (2) |
| Comp cpd.*[1] F-1 | 17.1 (7) | 48.0 (7) |
| Comp cpd.*[1] F-2 | 13.5 (3) | 10.6 (2) |

Note)
*[1]Comparative compound F-1: Glycoprilat N-[1-oxo-2(S)-mercaptomethyl-3-(3,4-methylenedioxy-phenyl)propyl]glycine
*[2]Comparative compound F-2: [4S-[4α,7α(R*),12bβ]]-7-[(1-oxo-2(S)-thio-3-phenylpropyl)-amino[-1,2,3,4,6,7,8,12b-octahydro-6-oxopyrido[2,1-a]-[2] benzazepine-4-carboxylic acid.

PHARMACOLOGICAL EXPERIMENT EXAMPLE F-2

V1 and V2 Receptor Binding Assay

Membrane specimens of rat liver (V1) and rat kidney (V2) were used. 100,000 counts (3.69 nM) of [$^3$H]-Arg-vasopressin, 25 μg (1 mg protein/ml) of each membrane specimen and a test medicament ($10^{-7}$ to $10^{-5}$M) were incubated in 250 μl in total of an assay buffer (pH=7.4) containing 10 mM of $MgCl_2$, 2 mM of EGTA and 20 mM of HEPES at 4° C. over day and night. Then, the incubation was washed with 5-ml portions of the buffer 5 times to thereby separate the membrane specimen binding to vasopressin followed by filtration with the use of a glass filter (GF/F). This glass filter was dried for about 3 hours and mixed with a cocktail for liquid scintillation (10 ml, ACSII). After allowing to stand overnight, the amount of the [$^3$H]-Arg-vasopressin binding to the membrane was determined with a liquid scintillation counter and the inhibition ratio was calculated in accordance with the following formula:

$$\text{Inhibition ratio } (\%) = 100 - [(C1-B1)/(C0-B1)] \times 100$$

wherein

B1; the amount of [$^3$H]-Arg-vasopressin binding to the membrane in the presence of excessive vasopressin (10 μM)

C0; the amount of [$^3$H]-Arg-vasopressin binding to the membrane in the absence of the test medicament and C1; the amount of [$^3$H]-Arg-vasopressin binding to the membrane in the presence of both the test medicament in a known amount and [$^3$H]-Arg-vasopressin.

The amount of the test medicament giving an inhibition ratio as calculated in accordance with the above formula of 50% was determined and taken as $IC_{50}$.

The $IC_{50}$ of the compound of Example F-17 determined by the above-mentioned method for the vasopressin (V1) receptor was 10 μM or above, while that for the vasopressin (V2) receptor was 1.39 μM.

The results of the pharmacological experiments as described above have clearly indicated that the invention compounds have ACE inhibition effects, NEP inhibition effects or vasopressin antagonist effects. Accordingly, the compounds of the present invention suppress the formation of AT-II, which is an increment factor of heart failure, simultaneously with the enhancement of the action of ANP, which is a compensation mechanism for symptoms of heart failure, and, therefore, are expected to have various therapeutic effects on heart failure, for example, reducing body fluids, relieving preload, relieving postload or the like. In addition, these compounds are usable as an antihypertensive diuretic. Furthermore, the compounds of the present invention are efficacious to diseases which might be therapeutically treated with the use of NEP inhibition action or ACE inhibition action, in particular, cardiovascular disorders such as acute or chronic heart failure, angina pectoris and hypertension, renal failure, edema, salt retention, pulmonary edema, pain, treatment of a specific mental state such as depression, angina, premenstrual syndrome, Meniere disease, hyperaldosteronism, hypercalcinuria, ascites, glaucoma, asthma, gastrointestinal disorders such as diarrhea, irritative intestinal syndrome and hyperacidity, cyclosporin-induced renal failure and the like.

Further, the above Pharmacological Experiment Examples have clearly indicated that the compounds of the present invention are comparable or even superior to the existing and representative ACE- and NEP-double inhibitors in the ACE and NEP inhibition effects and apparently superior thereto in the hypotensive and diuretic effects. In addition to the above-mentioned Pharmacological Experiment Examples, an experiment was separately effected with the use of SHR for examining hypotensive effects through intravenous administration. As the result, in the comparison of the conventionally known double inhibitors (1) [S-(R*, R*)]-2,3,4,5-tetrahydro-3-[(2-mercapto-1-oxohexyl-3-phenylpropyl)amino]-2-oxo-1H-benzazepine-1-acetic acid and (2) [S-(R*,R*)]-2,3,4,5-tetrahydro-3-[(2-mercapto-1-oxo-4-methylpentyl)amino]-2-oxo-1H-benzazepine-1-acetic acid with the compounds of the present invention, Example C-8 and Example C-10, the inhibitors (1) and (2) should be administered each in a dose of 1.0 mg/kg to decrease the blood pressure by 10%, whereas the administration of 0.03 to 0.1 mg/kg of the compound of Example C-8 and the administration of 0.1 to 0.3 mg/kg of the compound of Example C-10 each achieved the same effect.

It has been also clarified that the compounds of the present invention have such an advantage that they are excellent in an efficacy in oral administration. This characteristic of being excellent in oral efficacy is a highly preferable one from a viewpoint that the diseases to which the compounds of the present invention are applied generally require prolonged administration.

The present inventors have also clarified that among the compounds of the present invention, those having a (2S,3S)-3-methyl-2-thiopentanoic acid moiety in the side chain are particularly excellent in oral efficacy.

Since the invention compounds have natures that they are little toxic but highly safe, they are substances each having an extremely excellent value as a medicament.

In addition, the compounds of the present invention also have antagonistic effects on vasopressin receptors. It is considered that vasopressin is one of increment factors in heart failure, hypertension or the like. It is believed that these actions further enhance the efficacy of the compounds of the present invention on the above-mentioned diseases.

When the compound of the present invention is employed as a preventive or therapeutic medicament against the above-mentioned diseases, it can be administered either orally or parenterally. The dose thereof is not particularly restricted but varies depending on, for example, the levels of the conditions, age, sex and sensitivity to medicaments of a patient, administration route, administration time, administration intervals, properties of the medicinal preparation, type of the medicinal preparation and kind of the active ingredient. It is generally appropriate to administer from about 0.1 to 1000 mg/day to an adult once to several times.

The compounds of the present invention can be formulated into a medicinal preparation in the convectional manner with the use of fillers for medicinal preparations commonly employed in the art.

Namely, when a solid oral preparation is prepared, fillers for the principal agent and, if necessary, binders, disintegrating agents, lubricants, coloring agents, corrigents, antioxidants, etc., are added thereto, and then the mixture is formulated into tablets, coated tablets, granules, powders, capsules, etc., by the conventional manner.

As the above-mentioned fillers, for example, lactose, corn starch, sucrose, glucose, sorbitol, crystalline cellulose and silicon dioxide are usable.

As the binders, for example, polyvinyl alcohol, polyvinyl ether, ethylcellulose, methylcellulose, gum arabic, tragacanth, gelatin, shellac, hydroxypropylcellulose, hydroxypropylmethylcellulose, calcium citrate, dextrin, pectin and the like are usable. As the lubricants, for example, magnesium stearate, talc, polyethylene glycol, silica, hardened vegetable oils and the like are usable.

As the coloring agents, those which are approved to add to medicines may be used. As the corrigents, cocoa powder, mentha herb, aromatic powders, mentha oil, borneol, powdered cinnamon bark and the like are usable. As the antioxidants, those which are approved to added to medicines, such as ascorbic acid (vitamin C) and α-tocopherol (vitamin E), may be used. As a matter of course, these tablets and granules may be subjected to an appropriate coating treatment, such as sugar coating, gelatin coating and others, at need.

On the other hand, when an injection is prepared, pH regulators, buffers, suspending agents, dissolution aids, stabilizers, isotonic agents, antioxidants, preservatives and the like are added to the principal agent at need. Thus, an intravenous, subcutaneous or intramuscular injection can be prepared. The injection may also be formulated into a freeze-dried preparation, at need.

Examples of the above-mentioned suspending agent include methylcellulose, Polysorbate 80, hydroxyethylcellulose, gum arabic, tragacanth powder, carboxymethylcellulose sodium, polyoxyethylene sorbitan monolaurate and the like.

Examples of the dissolution aids include polyoxyethylene hardened castor oil, Polysorbate 80, nicotinamide, polyoxyethylene sorbitan monolaurate, Macrogol, castor oil fatty acid ethyl ester and the like.

As the stabilizers, for examples, sodium sulfite, sodium metasulfite, ether and the like are usable. Examples of the preservatives include methyl parahydroxybenzoate, ethyl parahydroxybenzoate, sorbic acid, phenol, cresol, chlorocresol and the like.

EXAMPLES

To further promote the understanding of the present invention, Examples will be given hereinafter. However it is needless to say that the present invention is not restricted to them only.

Synthesis examples for the starting compounds in the present invention will also be described hereinafter, prior to Examples.

Synthesis Example A-1

7-Trifluoromethanesulfonyloxy-3,4-dihydro-1(2H)-naphthalenone

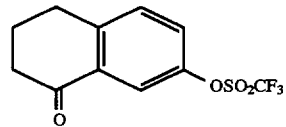

Into 100 ml of a solution of 9.94 g (61.29 mmol) of 7-hydroxy-3,4-dihydro-1(2H)-naphthalenone and 24.8 ml (306 mmol) of pyridine in dichloromethane being stirred at 0° C. was dropped 11.86 ml of trifluoromethanesulfonic anhydride in portions while maintaining the temperature so as not to exceed 5° C. After stirring at the same temperature for 10 minutes and then at room temperature for 30 minutes, water was added to the reaction mixture. The dichloromethane layer was collected, washed with 1 N hydrochloric acid, water and a saturated aqueous solution of sodium chloride and dried over anhydrous magnesium sulfate. After distilling off the solvent under reduced pressure, the residue was subjected to silica gel column chromatography. After successively eluting with hexane:ethyl acetate in a ratio ranging from 10:1 (v/v) to 8:1 (v/v), 15.33 g of the title compound was obtained as a pale yellow, oily product. Yield 85%.

$^1$H-NMR (400 MHz, CDCl$_3$) δ: 7.91(1H, t, J=1 Hz) 7.37(2H, d, J=1 Hz), 3.00(2H, t, J=6 Hz) 2.70(1H, d, J=6 Hz), 2.68(1H, d, J=6 Hz) 2.18(2H, quint, J=6 Hz).

Synthesis Example A-2

7-Phenyl-3,4-dihydro-1(2H)-naphthalenone

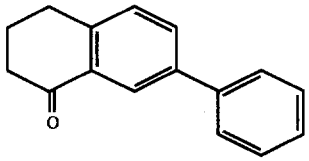

While stirring a mixture comprising 15.32 g (52.06 mmol) of 7-trifluoromethanesulfonyloxy-3,4-dihydro-1(2H)-naphthalenone obtained in the Synthesis Example A-1, 12.7 g (104.12 mmol) of phenylboric acid, 10.8 g (78.09 mmol) of potassium carbonate and 450 ml of toluene at room temperature, nitrogen gas was bubbled thereinto for 30 minutes. Next, 1.81 g (1.57 mmol) of tetrakistriphenylphosphine palladium was added thereto. The mixture was slowly heated to thereby maintain the bulk temperature at about 90° C. After stirring at this temperature for 90 minutes, the reaction mixture was cooled and water was added thereto. The insoluble matters were filtered through celite and thoroughly washed with ethyl acetate. The organic phase was collected, washed successively with a saturated aqueous solution of sodium hydrogencarbonate, water, 1N hydrochloric acid, water and a saturated aqueous solution of sodium chloride and dried over anhydrous magnesium sulfate. After distilling off the solvent under reduced pressure, the residue was subjected to silica gel column chromatography. After successively eluting with hexane:ethyl acetate in a ratio ranging from 20:1 (v/v) to 12:1 (v/v), 9.53 g of the title compound was obtained as white crystals. Yield 82%.

$^1$H-NMR (400 MHz, CDCl$_3$) δ: 8.28(1H, d, J=2 Hz) 7.72(2H, dd, J=8.2 Hz), 7.64~7.33(8H, m) 3.01(2H, t, J=6 Hz), 2.71(1H, d, J=6 Hz) 2.69(1H, d, J=6 Hz), 2.18(2H, quint, J=6 Hz).

Synthesis Example A-3

8Phenyl-2,3,4,5-tetrahydro-1H-[1]-benzazepin-2-one

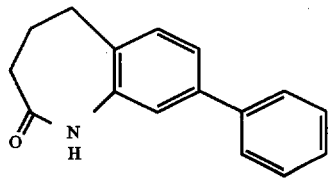

A mixture of 9.19 g (41.34 mmol) of 7-phenyl-3,4-dihydro-1(2H)-naphthalenone obtained in the Synthesis Example A-2 with 150 g of polyphosphoric acid was stirred at 50° to 60° C. and 2.96 g (45.47 mmol) of sodium azide was added in portions thereto in the form of a solid as such. After stirring at this temperature for additional 90 minutes, the reaction mixture was added to ice water. The crystals thus precipitated were collected by filtration, washed with water and n-hexane and hot-air dried at 70° C. overnight. Thus, 9.3 g of the title compound was obtained. Yield 95%.

$^1$H-NMR (400 MHz, DMSO-d$_6$) δ: 9.60(1H, s) 7.58(2H, d, J=8 Hz) 7.44(2H, t, J=8 Hz), 7.35–7.29(3H, m) 7.22(1H, d, J=2 Hz), 2.69(2H, t, J=7 Hz) 2.17(2H, t, J=7 Hz), 2.09(2H, quint, J=7 Hz).

Synthesis Example A-4

3,3-Dichloro-8-phenyl-2,3,4,5-tetrahydro-1H-[1]benzazepin-2-one

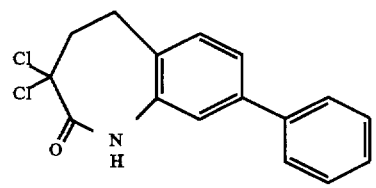

To a mixture of 8.94 g (37.67 mmol) of 8-phenyl-2,3,4,5-tetrahydro-1H-[1]benzazepin-2-one obtained in the Synthesis Example A-3 with 180 ml of xylene was added 23.53 g (113 mmol) of phosphorus pentachloride and the mixture was slowly heated. After stirring at about 90° C. for 30 minutes, water was added to the reaction mixture, followed by neutralization with a saturated aqueous solution of sodium hydrogen-carbonate. After extracting with dichloromethane, the dichloromethane phase was washed with saturated aqueous solution of sodium chloride and dried over anhydrous magnesium sulfate. After distilling off the solvent under reduced pressure, the oily residue was crystallized by adding ethyl acetate thereto. Thus, 2.60 g of the title compound was obtained. The mother liquor was subjected to silica gel column chromatography. After successively eluting with hexane:ethyl acetate in a ratio ranging up to 20:1 (v/v), 0.38 g of the title compound was further obtained. By combining with the one obtained above, 2.98 g of the title compound was obtained in total. Yield 26%.

$^1$H-NMR (400 MHz, CDCl$_3$) δ: 7.70(1H, d, J=2 Hz) 7.61~7.35(6H, m), 7.21(1H, d, J=6 Hz) 3.09~3.01(4H, m).

Synthesis Example A-5

3-Chloro-8-phenyl-2,3,4,5-tetrahydro-1H-[1]benzazepin-2-one

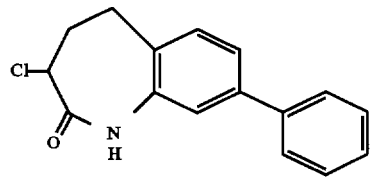

A mixture comprising 2.88 g (9.4 mmol) of 3,3-dichloro-8-phenyl-2,3,4,5-tetrahydro-1H-[1]benzazepin-2-one obtained in the Synthesis Example A-4, 0.89 g (11.89 mmol) of sodium acetate, 0.2 g of 10% palladium-carbon and 40 ml of acetic acid was catalytically hydrogenated at room temperature under 3 atm for 2 hours. After filtering off the insoluble matters, the filtrate was concentrated. Then, dichloromethane was added to the residue, followed by neutralization with a saturated aqueous solution of sodium hydrogencarbonate. The dichloromethane phase was separated, washed with a saturated aqueous solution of sodium chloride and dried over anhydrous magnesium sulfate. After distilling off the solvent under reduced pressure, a small amount of dichloromethane was added to the residue, followed by collection of crystals by filtration. Thus, 0.53 g of the title compound was obtained. The mother liquor was subjected to silica gel column chromatography. After successively eluting with hexane:ethyl acetate in a ratio ranging from 6:1 (v/v) to 3:1 (v/v) and then with dichloromethane:methanol in a ratio of 200:1 (v/v), 0.4 g of the title compound was further obtained. By combining with the one obtained above, 0.93 g of the title compound was obtained in total. Yield 36%.

¹H-NMR (400 MHz, CDCl₃) δ: 7.55~7.21(8H, m) 4.55 (1H, dd, J=11.7 Hz), 3.09~2.51(4H, m).

Synthesis Example A-6

3-Azido-8-phenyl-2,3,4,5-tetrahydro-1H-[1]benzazepin-2-one

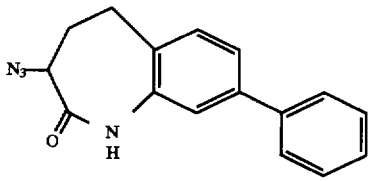

A mixture comprising 0.93 g (3.42 mmol) of 3-chloro-8-phenyl-2,3,4,5-tetrahydro-1H-[1]benzazepin-2-one obtained in the Synthesis Example A-5, 0.27 g (4.18 mmol) of sodium azide and 15 ml of dimethyl sulfoxide was stirred at 80° C. for 3 hours. After further adding 0.05 g of sodium azide and stirring for 30 minutes, the reaction mixture was added to ice water. The crystals were collected by filtration and dried under reduced pressure to thereby give 0.77 g of the title compound. Yield 81%.

¹H-NMR (400 MHz, DMSO-d₆) δ: 7.60~7.33(7H, m) 7.24(1H, d, J=2 Hz), 3.97(1H, dd, J=11.7 Hz) 2.81~2.69(2H, m), 2.40(1H, m) 2.10(1H, m).

Synthesis Example A-7

3-Azido-1-ethoxycarbonylmethyl-8-phenyl-2,3,4,5-tetrahydro-1H-[1]benzazepin-2-one

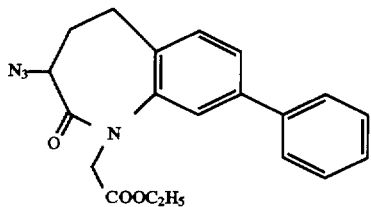

While stirring 30 ml of a mixture of 0.75 g (2.70 mmol) of 3-azido-8-phenyl-2,3,4,5-tetrahydro-1H-[1]benzazepin-2-one obtained in the Synthesis Example A-6, 0.093 g (0.288 mmol) of tetra-n-butylammonium bromide, 0.17 g (3.03 mmol) of powdery potassium carbonate and tetrahydrofuran at room temperature, 0.35 ml (3.16 mmol) of ethyl bromoacetate was added thereto, followed by stirring for 2 hours. After adding ethyl acetate to the reaction mixture, the obtained mixture was washed with water and a saturated aqueous solution of sodium chloride and dried over anhydrous magnesium sulfate. After distilling off the solvent under reduced pressure, the residue was subjected to silica gel column chromatography. After eluting with hexane:ethyl acetate in a ratio of 15:1 (v/v), 0.8 g of the title compound was obtained as a pale yellow, oily product. Yield 81%.

¹H-NMR (400 MHz, CDCl₃) δ: 7.55~7.34(7H, m) 7.31 (1H, d, J=8 Hz), 4.78(1H, d, J=17 Hz) 4.47(1H, d, J=17 Hz), 4.20(2H, dq, J=7.3 Hz) 3.87(1H, brt, J=9 Hz), 3.40(1H, m) 2.74(1H, m) 2.52~2.33(2H, m), 1.26(3H, t, J=7 Hz).

Synthesis Example B-1

(S)-2-(1,3-Dihydro-1,3-dioxo-2H-isoindol-2-yl)-3-(2-thienyl)propanoic acid

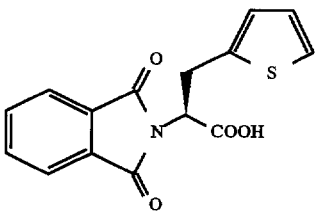

To 29.3 g (171 mmol) of L-(S)-3-(2-thienyl)alanine were added 257 ml of dioxane, 86 ml of water, 25.9 g (175 mmol) of phthalic anhydride and 23.9 ml (171 mmol) of triethylamine. While stirring the mixture at room temperature for 1 hour, 23.9 ml of triethylamine was slowly added thereto. 342 ml of dioxane was added and the mixture was heated under reflux. When the pH of the liquid distilled off showed no basicity any more, heating was ceased and the reaction mixture was concentrated under reduced pressure. 10 ml of diethyl ether and 684 ml of 0.5N hydrochloric acid were added thereto and the mixture was vigorously stirred. The crystals thus precipitated were collected by filtration, washed with a small amount of water and dried by passing a dry nitrogen gas therethrough. 40.7 g of the title compound was obtained as yellow crystals (yield 79%).

MASS m/e (FAB); 302(MH⁺)

m.p.; 172°~173° C.

¹H-NMR (400 MHz, CDCl₃, Me₄Si) δ; 3.76(1H, dd, J=4.8, 15.3 Hz), 3.89(1H, dd, J=11.6, 15.3 Hz), 5.19(1H, dd, J=4.8, 11.6 Hz) 6.81–6.84(2H, m), 7.08(1H, dd, J=1.6, 4.8 Hz) 7.70–7.74(2H, m), 7.80–7.85(2H, m).

Synthesis Example B-2

N-[(S)-2-(1,3-Dihydro-1,3-dioxo-2H-isoindol-2-yl)-3-(2-thienyl)propanoyl]-6-hydroxynorleucine ethyl ester

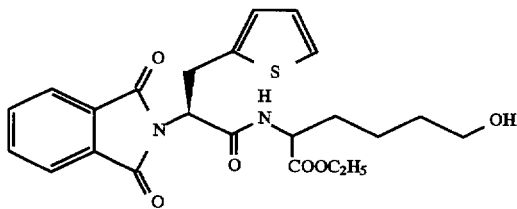

To 21.8 g (102.9 mmol) of 6-hydroxy-DL-norleucine ethyl ester hydrochloride were added 686 ml of dichloromethane and 17.0 ml (154 mmol) of N-methylmorpholine at 0° C. to thereby give a homogeneous solution. Then, 31.0 g (102.9 mmol) of the compound obtained in the Synthesis Example B-1 and 38.2 g (154 mmol) of EEDQ were added thereto and the obtained mixture was stirred overnight while slowly heating to room temperature. The reaction mixture was washed with 1000 ml of 1N hydrochloric acid, an aqueous sodium hydrogencarbonate and an aqueous sodium chloride and dried over sodium sulfate. After filtering, the filtrate was concentrated under reduced pressure. The residue thus obtained was purified by silica gel column chromatography (dichloromethane/ethyl acetate=3→2). Thus, 22.8 g of the title compound was obtained as a pale yellow solid (yield 48%).

MASS m/e (FAB); 459(MH⁺)

m.p.; 102°–104° C.

$^1$H-NMR (400 MHz, CDCl$_3$, Me$_4$Si) δ; 1.22–1.27(3H, m) 1.28–1.96(7H, m), 3.57–3.65(2H, m) 3.74–3.87(2H, m), 4.09–4.20(2H, m) 4.58–4.66(1H, m), 5.07–5.13(1H, m) 6.60–6.71(total 1H, each brd), 6.78–6.83(2H, m) 7.05–7.09 (1H, m), 7.70–7.75(2H, m) 7.81–7.85(2H, m).

Synthesis Example B-3

Ethyl [5S-(5α,8α(R*),11αβ]]-5-(1,3-dihydro-1,3-dioxo-2H-isoindol-2-yl)-6-oxo-4,5,6,8,9,10,11,11a-octahydropyrido[1,2-a]thieno[3,2-c]azepine-8-carboxylate

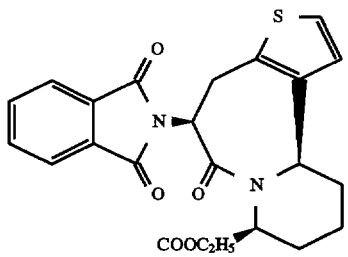

Under a nitrogen gas stream, 93 ml of dichloromethane was cooled to –65° C. and 1.71 ml (19.6 mmol) of oxalyl chloride was added thereto. After dropping 1.53 ml (21.3 mmol) of dimethyl sulfoxide thereinto, the mixture was stirred for 30 minutes. A solution of 3.00 g (6.54 mmol) of the compound obtained in the Synthesis Example B-2 in dichloromethane (24 ml) was dropped thereinto and the resulting mixture was stirred for 30 minutes. Further, 9.1 ml (65 mmol) of triethylamine was dropped thereinto and the mixture was slowly heated to 0° C. Three hours thereafter, a solution of 12.2 g of potassium peroxymonophosphate (OXONE®) in water (50 ml) was dropped thereinto at 0° C. and the mixture was vigorously stirred. After 10 minutes, the organic phase was separated, washed with a saturated aqueous solution of sodium chloride. After drying over magnesium sulfate, the solution was concentrated to a volume of about 65 ml at 20° C. or below. 6.5 ml of trifluoroacetic acid was dropped thereinto at 0° C. and the obtained mixture was heated to room temperature and stirred for 14 hours. The reaction mixture was concentrated under reduced pressure at a low temperature and 100 ml of ethyl acetate was added. At 0° C., a saturated aqueous sodium hydrogencarbonate and solid sodium hydrogencarbonate were slowly added thereto and the mixture was vigorously stirred. The organic phase was separated, washed with water and a saturated aqueous sodium chloride, dried over magnesium sulfate, and then concentrated. The crude product (3.27 g) was purified by silica gel column chromatography (hexane/ethyl acetate=3) to thereby give 540 mg (yield: 19%) of the title compound as white crystals.

m.p.; 140°–150° C.

$^1$H-NMR (400 MHz, CDCl$_3$, Me$_4$Si) δ; 0.94(3H, t, J=7.2 Hz) 1.62–1.95(3H, m), 2.14–2.20(2H, m) 2.41–2.49(1H, m), 3.44(1H, ddd, J=1.6, 4.0, 16.8 Hz), 3.72–3.80(1H, m) 3.87–3.95(1H, m), 4.58(1H, m like t) 5.32(1H, dd, J=1.6, 7.6 Hz), 5.36(1H, brt) 6.06(1H, dd, J=4.0, 13.6 Hz), 6.83(1H, d, J=5.4 Hz) 7.09(1H, d, J=5.4 Hz), 7.07–7.76(2H, m) 7.86–7.92(2H, m).

Synthesis Example B-4

2-(1,3-Dihydro-1,3-dioxo-2H-isoindol-2-yl)-3-(3-thienyl)propanoic acid

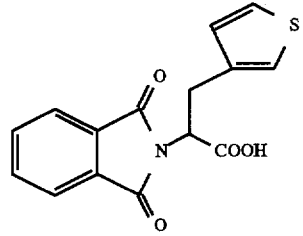

56.0 g (269.6 mmol) of DL-3-(3-thienyl)alanine was reacted in the same manner as that of the Synthesis Example B-1. Thus, 68.4 g of the title compound was obtained as pale yellow crystals (yield 84%).

MASS m/e (FAB); 302(MH⁺)

m.p.; 162°–165° C.

$^1$H-NMR (400 MHz, CDCl$_3$, Me$_4$Si) δ; 3.55(1H, dd, J=4.8, 15.0 Hz), 3.72(1H, dd, J=11.6, 15.0 Hz), 5.21(1H, dd, J=4.8, 11.6 Hz) 6.91–6.93(1H, m), 6.97(1H, m like brs) 7.18(1H, dd, J=3.2, 4.8 Hz), 7.69–7.72(2H, m) 7.78–7.81 (2H, m).

Synthesis Example B-5

N-[2-(1,3-dihydro-1,3-dioxo-2H-isoindo]-2-yl)-3-(3-thienyl)propanoyl]-6-hydroxynorleucine ethyl ester 23.0 g (108.7 mmol) of 6-hydroxy-DL-norleucine ethyl ester hydrochloride and 32.74 g (108.7 mmol) of the compound obtained in the Synthesis Example B-4 were reacted in the same manner as that of the Synthesis Example B-2. Thus, 25.9 g of the title compound was obtained as pale yellow crystals (yield 52%).

MASS m/e (FAB); 458(MH⁺)

m.p.; 80°–85° C.

$^1$H-NMR (400 MHz, CDCl$_3$, Me$_4$Si) δ; 1.23–1.30(3H, m) 1.31–1.96(6H, m), 3.54–3.67(4H, m) 4.09–4.24(2H, m), 4.58–4.68(1H, m) 5.11–5.17(1H, m), 6.68–6.77(total 1H, each brd) 6.93–7.01(2H, m), 7.17–7.22(1H, m) 7.70–7.74 (2H, m), 7.79–7.84(2H, m).

Synthesis Example B-6

Ethyl 5-(1,3-dihydro-1,3-dioxo-2H-isoindol-2-yl)-6-oxo-4,5,6,8,9,10,11,11a-octahydropyrido[1,2-a]thieno-[2,3-c]azepin-8-carboxylate

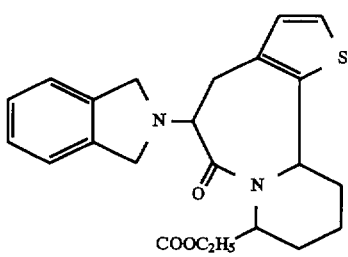

2 g (4.36 mmol) of the compound obtained in the Synthesis Example B-5 was reacted in the same manner as that of the Synthesis Example B-3. Thus, the title compound was obtained as white crystals and as a mixture of two diastereomers (1.25 g, 67%).

¹H-NMR (400 MHz, CDCl₃, Me₄Si) δ; 0.92 and 1.25 (total 3H, each t, each J=7.2 Hz) 1.65–2.50(6H, m) 8.20 and 3.30(total 1H, each ddd, each J=1.6, 4.0, 16.8 Hz) 3.76–7.23 (total 2H, m) 4.28–4.45(total 1H, m) d 5.30(total 1H, each m) 5.54–5.61(total 1H, m) 5.83 and 6.03(total 1H, each dd, each J=4.0, 13.6 Hz, J=4.0, 14.0 Hz) 6.84 and 6.87(total 1H, each d, each J=5.2 Hz and J=5.6 Hz) 7.13–7.16(total 1H, m) 7.72–7.75(2H, m) 7.85–7.90(2H, m).

Synthesis Example C-1

(2R,3S)-2-Bromo-3-methylpentanoic acid

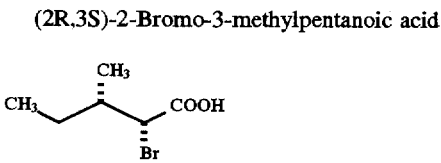

1.50 g (11.43 mmol) of D-allo-isoleucine[(2R,3S)-2-amino-3-methylpentanoic acid] was dissolved in a mixed solution of 12.7 ml of a 47% aqueous solution of hydrogen bromide with 12.7 ml of water, followed by cooling to 0° C. A solution of 1.20 g of sodium nitrite in 3.0 ml of water was slowly dropped thereinto at such a rate that the reaction temperature did not exceed 5° C. Next, the mixture was stirred at 0° C. for 30 minutes and then at room temperature for 3 hours. After distilling off the excessive nitric acid gas under reduced pressure, ether extraction was effected. The organic phase was washed with water and a saturated aqueous sodium chloride, dried over anhydrous magnesium sulfate and concentrated. Thus, 2.11 g of the title compound was obtained as a yellow oil. Yield 95%.

¹H-NMR (400 MHz, CDCl₃) δ; 4.29(1H, d, J=7 Hz) 2.01(1H, m) 1.52(1H, m), 1.33(1H, m) 1.08(3H, d, J=7 Hz) 0.95(3H, t, J=7 Hz).

Synthesis Example C-2

(2R,3S)-2-Acetylthio-3-methylpentanoic acid

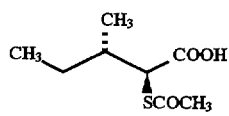

2.11 g (10.8 mmol) of (2R,3S)-2-bromo-3-methylpentanoic acid obtained in the Synthesis Example C-1 was dissolved in 43 ml of acetonitrile and 1.42 g of potassium thioacetate was added thereto at 0° C. The mixture was stirred at 0° C. for 30 minutes and then at room temperature for 5 hours. After filtering off the insoluble matters, the filtrate was concentrated. To the residue were added ether and a saturated aqueous solution of sodium hydrogencarbonate, followed by separation. The aqueous phase was acidified by adding a 2N aqueous solution of hydrochloric acid at a low temperature and then extracted with ether. The ether phase was washed with a saturated aqueous sodium chloride, dried over anhydrous magnesium sulfate and concentrated. Thus, 1.68 g of the title compound was obtained as a colorless oil (yield 82%).

¹H-NMR (400 MHz, CDCl₃) δ; 4.21(1H, d, J=7 Hz) 2.39(3H, s) 2.02(1H, m), 1.58(1H, m) 1.22(1H, m) 1.03(3H, d, J=7 Hz), 0.92(3H, t, J=7 Hz).

Synthesis Example C-3

α-(1,3-Dihydro-1,3-dioxo-2H-isoindol-2-yl-(1,1'-biphenyl)-4-propanoic acid

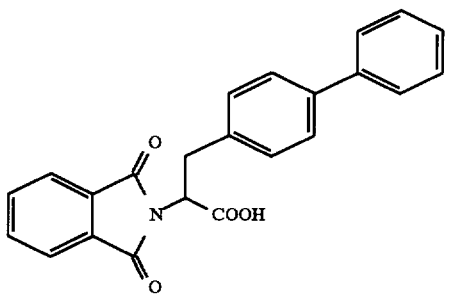

43.70 g (181.3 mmol) of α-amino-(1,1'-biphenyl)-4-propanoic acid and 26.80 g (181.3 mmol) of anhydrous fumaric acid were suspended in 100 ml of dimethylformamide, followed by heating at 120° C. for 2 hours and half. Then, the transparent solution thus obtained was poured into 1.2 l of ice water, followed by vigorously stirring. Thus, white crystals were precipitated. These crystals were collected by filtration, washed with water and hexane and hot-air dried. Thus, 65.5 g of the title compound was obtained as white crystals (yield 73%).

¹H-NMR (400 MHz, DMSO-d₆) δ; 7.83(4H, s) 7.58(2H, d, J=8 Hz) 7.51(2H, d, J=8 Hz), 7.40(2H, t, J=8 Hz) 7.31(1H, t, J=8 Hz), 7.26(2H, d, J=8 Hz) 5.16(1H, dd).

Synthesis Example C-4

(S)-N-[α-(1,3-Dihydro-1,3-dioxo-2H-isoindol-2-yl)-(1,1'-biphenyl)-4-propionyl]-6-hydroxynorleucine methyl ester

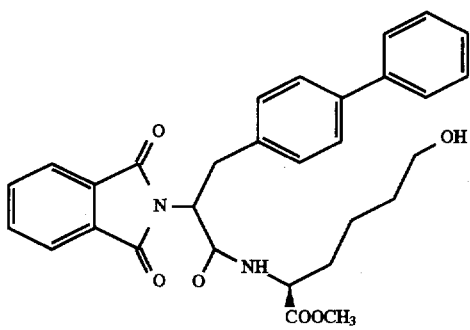

To a mixed solution of 28.53 g (76.90 mmol) of α-(1,3-dihydro-1,3-dioxo-2H-isoindol-2-yl)-(1,1'-biphenyl)-4-propanoic acid obtained in the Synthesis Example C-3 and 19.10 g (96.70 mmol) of (S)-6-hydroxynorleucine methyl ester hydrochloride in 600 ml of dichloromethane was added 42.47 ml of N-methylmorpholine. After preparing a homogeneous solution therefrom, 1-hydroxybenztriazole hydrate and 28.92 g (150.87 mmol) of 1-(3-dimethylaminopropyl)-3-ethylcarbodiimide hydrochloride were added thereto at 0° C. The reaction mixture was stirred at 0° C. for 30 minutes and then at room temperature overnight and washed with a 2N aqueous solution of hydrochloric acid, water, a saturated aqueous solution of sodium hydrogencarbonate and a saturated aqueous sodium chloride. The dichloromethane phase was dried over magnesium sulfate and concentrated. The residue was purified by silica gel column chromatography (eluent; chloroform:methanol=99:1). Thus, 24.80 g of the title compound was obtained as a colorless amorphous product (yield 63%).

$^1$H-NMR (400 MHz, CDCl$_3$) δ; 7.79(2H, m) 7.69(2H, m) 7.52~7.22(9H, m), 6.77 and 6.68(total 1H, each brd, J=8 Hz), 5.19(1H, m) 4.63(1H, m), 3.72 and 3.71(total 3H, each s) 3.68~3.52(4H, m), 1.97~1.30(6H, m).

Synthesis Example C-5

(S)-N-[α-(1,3-Dihydro-1,3-dioxo-2H-isoindol-2-yl)-(1,1'-biphenyl)-4-propionyl]-6-oxonorleucine methyl ester

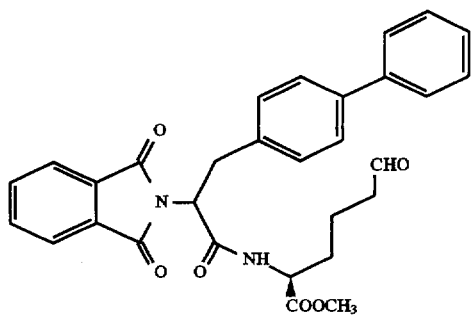

A solution of 9.82 ml (115.35 mmol) of oxalyl chloride in 330 ml of dichloromethane was cooled to −70° C. and a solution of 8.18 ml (115.35 mmol) of dimethyl sulfoxide in dicloromethane (70 ml) was slowly dropped thereinto within 15 minutes. This reaction mixture was stirred at −70° C. for 15 minutes. Then, a solution of 24.80 g (48.20 mmol) of (S)-N-[α-(1,3-dihydro-1,3-dioxo-2H-isoindol-2-yl)-(1,1'-biphenyl)-4-propionyl]-6-hydroxynorleucine methyl ester obtained in the Synthesis Example C-4 in dicloromethane (130 ml) was slowly dropped thereinto at −70° C. to −60° C. within about 40 minutes. After stirring the reaction mixture at −70° C. for 20 minutes, 52.66 ml of triethylamine was slowly dropped thereinto within 20 minutes. The reaction mixture was stirred at 0° C. for 1 hour and a solution of 70.18 g of potassium peroxymonosulfate (OXONE®) in water (830 ml) was dropped thereinto at 0° to 5° C., followed by extraction with dichloromethane. The dichloromethane phase was washed with water and a saturated aqueous sodium chloride, dried over anhydrous magnesium sulfate and concentrated. Thus, the title compound was obtained as a brown oil. This aldehyde was not purified but employed in the subsequent reaction (Synthesis Example C-6).

$^1$H-NMR (400 MHz, CDCl$_3$) δ; 9.71 and 9.70 (total 1H, m) 7.78(2H, m), 7.68(2H, m) 7.50~7.20(9H, m), 6.82 and 6.78 (total 1H, each brd, J=8 Hz), 5.20(1H, m) 4.61(1H, m) 3.91(3H, s), 3.75~3.52(4H, m) 2.50~1.30(total 6H, m).

Synthesis Example C-6

Methyl (S)-1-[α-(1,3-dihydro-1,3-dioxo-2H-isoindol-2-yl)-(1,1'-biphenyl)-4-propionyl]-1,2,3,4-tetrahydro-2-pyridinecarboxylate

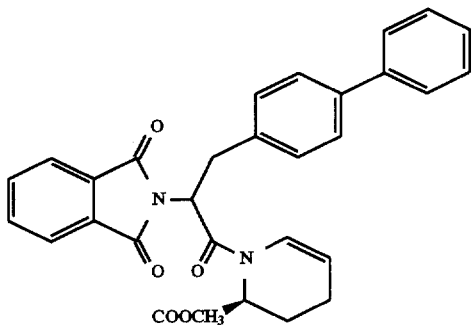

To (S)-N-[α-(1,3-dihydro-1,3-dioxo-2H-isoindol-2-yl)-(1,1'-biphenyl)-4-propionyl]-6-oxonorleucine methyl ester obtained in the Synthesis Example C-5 (crude product, 48.2 mmol) was added 60 ml of trifluoroacetic acid at once at 0° C. The solution thus formed was stirred at room temperature for 2 hours. The mixture was concentrated and the residual oil was subjected to azeotropic distillation with benzene. The brown, oily residue was partitioned into dichloromethane and water and washed with a saturated aqueous solution of sodium hydrogencarbonate, water and a saturated aqueous sodium chloride. The dichloromethane phase was dried over magnesium sulfate and then concentrated. The residual oil was purified by silica gel column chromatography (eluent; dichloromethane). Thus, 8.70 g of the title compound was obtained as a colorless amorphous product (yield from the Synthesis Example C-4 37%).

$^1$H-NMR (400 MHz, CDCl$_3$) δ; 7.84~7.74(2H, m) 7.69 (2H, m) 7.53~7.20(9H, m), 6.73 and 6.51(total 1H, each brd, J=8 Hz), 5.52 and 5.42(total 1H, each dd, J=12.7 Hz), 5.29 and 5.24(total 1H, each dtlike), 5.03 and 4.88(total 1H, each m) 3.87~3.47(2H, m), 3.75 and 3.65(total 3H, each s) 2.39(1H, m), 2.10~1.75(3H, m).

Synthesis Example C-7

[4S-[4α,7α(R*),12bβ]]-7-(1,3-Dihydro-1,3-dioxo-2H-isoindol-2-yl)-6-oxo-11-phenyl-1,2,3,4,6,7,8,12b-octahydropyrido[2,1-a][2]benzazepine-4-carboxylic acid

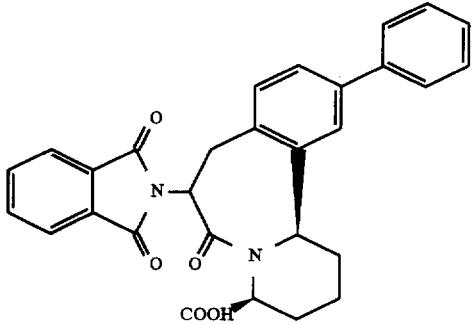

A solution of methyl (S)-1-[α-(1,3-dihydro-1,3-dioxo-2H-isoindol-2-yl)-(1,1'-biphenyl)-4-propionyl]- 1,2,3,4-tetrahydro-2-pyridinecarboxylate (8.70 g, 17.61 mmol, a 1:1 mixture of diastereomers) obtained in the Synthesis Example C-6 in dichloromethane (58 ml) was dropped into a mixed solution of 10.82 ml (2 mmol) of trifluoromethanesulfonic acid and trifluoroacetic anhydride (TFAA, 2.75 ml, 19.51 mmol) at 0° C. After the mixture was stirred under a nitrogen atmosphere at room temperature for 30 hours, the mixture was poured into ice water, followed by extraction with ethyl acetate. The ethyl acetate phase was washed with water and a saturated aqueous sodium chloride, dried over magnesium sulfate and concentrated. The amorphous residue was purified by silica gel column chromatography (eluent; trichloromethane:methanol=99:1). Thus, 1.80 g of the title compound was obtained as an amorphous product (yield 42%).

$^1$H-NMR (400 MHz, CDCl$_3$) δ; 7.78(2H, dd, J=8.4 Hz) 7.66(2H, dd, J=8.4 Hz), 7.49(2H, dd, J=8.2 Hz) 7.43(1H, d, J=2 Hz), 7.37(3H, m) 7.28(1H, tt, J=7.2 Hz), 7.14(1H, d, J=8 Hz) 5.78(1H, dd, J=10.6 Hz), 5.30(1H, t, J=6 Hz) 5.14(1H, dd, J=8.4 Hz), 4.05(1H, dd, J=16.10 Hz) 3.44(1H, dd, J=16.6 Hz), 2 52~2.32(2H, m) 2.10~1.97(2H, m), 1.88~1.66(2H, m).

Synthesis Example C-8

Diphenylmethyl [4S-[4α,7α(R*),12bβ]]-7-(1,2-dihydro-1,3-dioxo-2H-isoindol-2-yl)-6-oxo-11-phenyl-1,2,3,4,6,7,8,12b-octahydropyrido[2,1-a][2]benzazepine-4-carboxylate

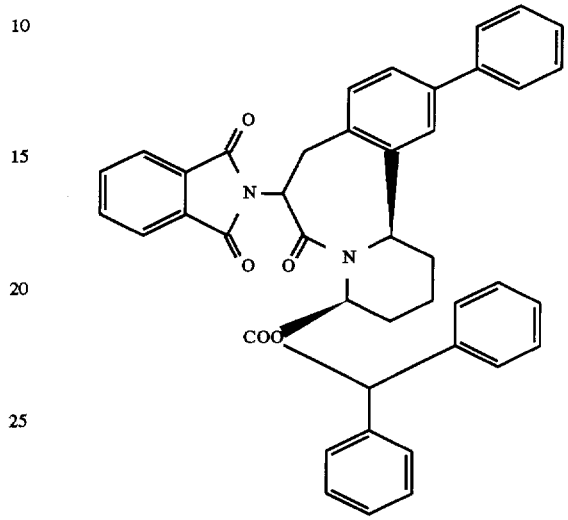

To a solution of 1.80 g (375 mmol) of [4S-[4α,7α(R*), 12bβ]]-7-(1,3-dihydro-1,3-dioxo-2H-isoindol-2-yl)-6-oxo-11-phenyl-1,2,3,4,6,7,8,12b-octahydropyrido[2,1-a][2] benzazepine-4-carboxylic acid obtained in the Synthesis Example C-7 in dimethylformamide (40 ml) was added 1.34 g (4.21 mmol) of cesium carbonate. The obtained mixture was stirred for 30 minutes. 1.30 g (5.25 mmol) of promo-diphenylmethane was added thereto and the mixture was stirred at room temperature for 5 hours. It was partitioned into ethyl acetate and water. The ethyl acetate phase was washed with water and a saturated aqueous sodium chloride, dried over magnesium sulfate and concentrated. The amorphous residue was purified by silica gel column chromatography (eluent; chloroform:hexane=4:1). Thus, 2.03 g of the title compound was obtained as a colorless amorphous product (yield 84%).

$^1$H-NMR (400 MHz, CDCl$_3$) δ; 7.85(2H, brs) 7.69(2H, dd, J=8.4 Hz), 7.44~6.98(7H, m) 6.58(1H, d, J=8 Hz) 6.18(1H, s), 6.03(1H, dd, J=10.6 Hz) 5.42(1H, t, J=6 Hz), 5.14(1H, dd, J=8.4 Hz) 4.35(1H, dd, J=16.10 Hz), 3.22(1H, dd, J=16.6 Hz) 2.37(2H, m) 2.05(1H, m), 1.80~1.63(3H, m).

Synthesis Example C-9

Diphenylmethyl [4S-[4α,7α(R*),12bβ]]-7-amino-6-oxo-11-phenyl-1,2,3,4,6,7,8,12b-octahydropyrido-[2,1-a][2]benzazepine-4-carboxylate

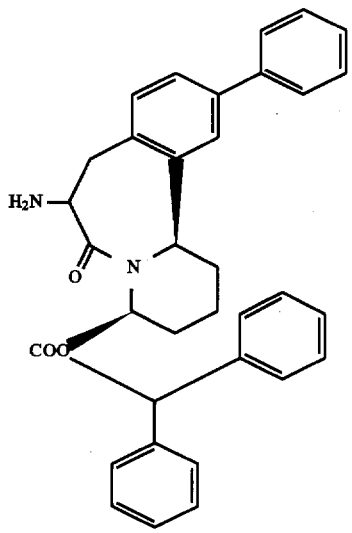

2.03 g (3.14 mmol) of diphenylmethyl [4S-[4α,7α(R*),12β]]-7-(1,3-dihydro-1,3-dioxo-2H-isoindol-2-yl)-6-oxo-11-phenyl-1,2,3,4,6,7,8,12b-octahydropyrido[2,1-a][2]benzazepine-4-carboxylate obtained in the Synthesis Example C-8 was dissolved in a mixed solution of 40 ml of methanol with 20 ml of tetrahydrofuran. 0.34 ml (7.10 mmol) of hydrazine monohydrate was added thereto, followed by heating under reflux for 3 hours. The reaction mixture was concentrated, the residual solid was dissolved in dichloromethane and the insoluble solid matters were removed by filteration. The filtrate was concentrated, and the sticky residue was purified by silica gel column chromatography (eluent; chloroform:methanol:aqueous ammonia= 98:2:0.2). Thus, 1.20 g of the title compound was obtained as a colorless amorphous product (yield 74%).

$^1$H-NMR (400 MHz, CDCl$_3$) δ; 7.40(4H, m) 7.31(1H, tt, J=7.2 Hz), 7.24(1H, d, J=2 Hz) 7.15(1H, dd, J=8.2 Hz), 6.99(2H, dd, J=8.4 Hz) 6.87(2H, dd, J=8.2 Hz), 6.63(1H, d, J=8 Hz) 6.20(1H, s) 5.42~5.33(2H, m), 4.53(1H, dd, J=10.6 Hz) 3.17(1H, dd, J=16.6 Hz), 2.58(1H, dd, J=16.10 Hz) 2.40(2H, m) 1.94(1H, m), 1.85~1.58(3H, m).

Synthesis Example C-10

[4S-[4α,7α(R*),12bβ]]-7-(1,3-Dioxo-1,3-dihydroisoindol-2-yl)-9-nitro-6-oxo-1,2,3,4,6,7,8,12b-octahydropyrido[2,1-a][2]benzazepine-4-carboxylic acid and

[4S-[4α,7α(R*),12bβ]]-7-(1,3-Dioxo-1,3-dihydroisoindol-2-yl)-9-nitro-6-oxo-1,2,3,4,6,7,8,12b-octahydropyrido[2,1-a][2]benzazepine-4-carboxylic acid 8.30 g (20.5 mmol) of [4S-[4α,7α(R*),12bβ]]-7-(1,3-dioxo-1,3-dihydroisoindol-2-yl)-6-oxo-1,2,3,4,6,7,8,12b-octahydropyrido[2,1-a][2]benzazepine-4-carboxylic acid was dissolved in 110 ml of methylene chloride, followed by cooling to −60° C. Next, a solution obtained by dissolving nitronium tetrafluoroborate (0.5M solution in sulfolane 148 ml, 74 mmol) in 90 ml of methylene chlorine was dropped Thereinto. Then the mixture was slowly heated to 2° C. within 10 hours and then stirred at 2° C. for 5 hours. Then, it was partitioned into 500 ml of methylene chloride and 1200 ml of water. Further, after the organic phase separated was washed with a saturated aqueous sodium chloride, it was dried over anhydrous magnesium sulfate and the solvent was concentrated under reduced pressure. The residue thus obtained was purified by flash silica gel chromatography (1:1 ethyl acetate/hexane→ethyl acetate containing 5% of acetic acid added). Thus, a mixture of the title compounds was obtained.

Synthesis Example C-11

Methyl [4S-[4α,7α(R*),12bβ]]-7-(1,3-dioxo-1,3-dihydroisoindol-2-yl)-9-nitro-6-oxo-1,2,3,4,6,7,8,12b-octahydropyrido[2,1-a][2]benzazepine-4-carboxylate and methyl [4S-[4α,7α(R*),12bβ]]-7-(1,3-dioxo-1,3-dihydroisoindol-2-yl)-11-nitro-6-oxo-1,2,3,4,6,7,8,12b-octahydropyrido[2,1-a][2]benzazepine-4-carboxylate 5.47 g (12.2 mmol) of a mixture of [4S-[4α,7α(R*),12bβ]]-7-(1,3-dioxo-1,3-dihydroisoindol-2-yl)-9-nitro-6-oxo-1,2,3,4,6,7,8,12b-octahydropyrido-[2,1-a][2]benzazepine-4-carboxylic acid and [4S-[4α,7α(R*),12bβ]]-7-(1,3-dioxo-1,3-dihydroisoindol-2-yl)-11-nitro-6-oxo-1,2,3,4,6,7,8,12b-octahydropyrido[2,1-a][2]benzazepine-4-carboxylic acid obtained in the above Synthesis Example C-10 was dissolved in 80 ml of dimethylformamide. To this solution was added 4.76 g (14.6 mmol) of cesium carbonate at room temperature. The mixture thus obtained was stirred under a nitrogen atmosphere for 30 minutes and then 2.42 g (17.0 mmol) of methyl iodide was added thereto. The resulting mixture was stirred for 11 hours. Next, the solution stirred was partitioned into 300 ml of water and two 250-ml portions of ethyl acetate. Further, after the organic phase separated was washed with a saturated aqueous sodium chloride, it was dried over anhydrous magnesium sulfate and the solvent was concentrated under reduced pressure. After the completion of the concentration, the residue thus obtained was purified and separated by flash silica gel chromatography (1:1 ethyl acetate/hexane). Thus, 1.62 g (yield: 29%) of the title compound having a nitro group at the 11-position and 1.78 g (yield: 31%) of the title compound having a nitro group at the 9-position were obtained.

Synthesis Example C-12

Methyl [4S-[4α,7α(R*),12bβ]]-11-amino-7-(1,3-dioxo-1,3-dihydroisoindol-2-yl]-6-oxo-1,2,3,4,6,7,8,12b-octahydropyrido[2,1-a][2]benzazepine-4-carboxylate

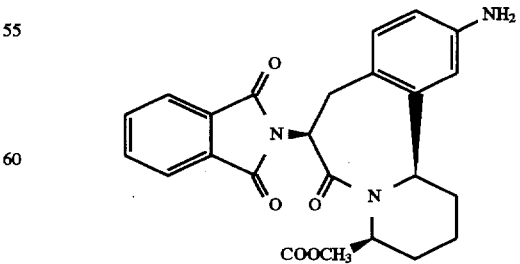

1.62 g (32.5 mmol) of methyl [4S-[4α,7α(R*),12bβ]]-7-(1,3-dioxo-1,3-dihydroisoindol-2-yl)-11-nitro-6-oxo-1,2,3, 4,6,7,8,12b-octahydropyrido[2,1-a][2]benzazepine-4-carboxylate obtained in the above Synthesis Example C-11 was dissolved in 5 ml of acetic acid and 60 ml of dimethylformamide. Then, 230 g of 10% palladium/carbon was added to this solution, followed by shaking at room temperature for 2 hours. 150 ml of methanol was further added to the solution shaken, followed by filtration. The filtrate was concentrated under reduced pressure to thereby give 1.50 g of the title compound.

$^1$H-NMR (400 MHz, CDCl$_3$, Me$_4$Si) δ; 1.70–2.45(6H, m) 3.20(3H, s), 3.30(1H, dd, J=16.6, 6.7 Hz), 4.26(1H, dd, J=16.6, 12.1 Hz) 5.19(1H, m), 5.34(1H, m) 5.98(1H, dd, J=12.1, 6.7 Hz), 6.56(2H, m) 6.98(1H, d, J=8.8 Hz) 7.70–7.90(4H, m).

Synthesis Example C-13

Methyl [4S-[4α,7α(R*),12bβ]]-11-methylsulfonylamino-7-(1,3-dioxo-1,3-dihydroisoindol-2-yl)-6-oxo-1,2,3,4,6,7,8,12b-octahydropyrido[2,1-a][2benzazepine-4-carboxylate

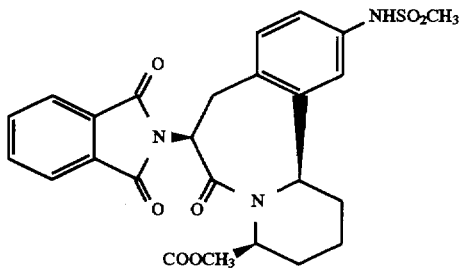

1.50 g (3.5 mmol) of methyl [4S-[4α,7α(R*),12bβ]]-11-amino-7-(1,3-dioxo-1,3-dihydroisoindol-2-yl)-6-oxo-1,2,3,4,6,7,8,12b-octahydropyrido[2,1-a][2]benzazepine-4-carboxylate obtained in the above Synthesis Example C-12 was dissolved in 50 ml of methylene chloride. Next, to this solution were added 3 ml of pyridine and 440 mg (3.8 mmol) of methanesulfonyl chloride under cooling with ice. Then, the mixture was stirred at room temperature under a nitrogen atmosphere for 2 hours. After 100 ml of a 1N aqueous solution of hydrochloric acid was further added to the solution stirred under cooling with ice, it was extracted with methylene chloride. After drying over anhydrous magnesium sulfate, it was concentrated under reduced pressure. Next, the residue was purified by silica gel column chromatography (3:1 methylene chloride/ethyl acetate). Thus, 1.14 g of the title compound was obtained (yield: 64%).

$^1$H-NMR (400 MHz, CDCl$_3$, Me$_4$Si) δ; 1.60–2.46(6H, m) 3.00(3H, s) 3.23(3H, s), 3.42(1H, dd, J=17.1, 7.0 Hz), 4.46(1H, dd, J=17.1, 11.9 Hz) 5.21(1H, m), 5.44(1H, m) 6.04(1H, dd, J=11.9, 7.0 Hz), 6.65(1H, s) 7.05(1H, dd, J=8.2, 2.2 Hz), 7.19(1H, d, J=8.2 Hz) 7.24(1H, d, J=2.2 Hz), 7.74–7.90(4H, m).

Synthesis Example C-14

Methyl [4S-[4α,7α(R*),12bβ]]-11-methylsulfonylamino-7-amino-6-oxo-1,2,3,4,6,7,8,12b-octahydropyrido[2,1-a][2benzazepine-4-carboxylate

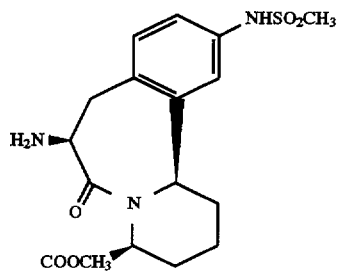

1.14 g (2.23 mmol) of methyl [4S-[4α,7α(R*),12bβ]]-11-methylsulfonylamino-7-(1,3-dioxo-1,3-dihydroisoindol-2-yl)-6-oxo-1,2,3,4,6,7,8,12b-octahydropyrido[2,1-a][2]-benzazepine-4-carboxylate obtained in the above Synthesis Example C-13 was dissolved in 49 ml of methanol. Next, to this solution was added 123 mg (2.46 mmol) of hydrazine hydrate. Then, the mixture was stirred under an argon atmosphere at room temperature for 66 hours. The solution stirred was concentrated under reduced pressure. Further, methylene chloride was added to the concentrate. After removing out the insoluble matters by filtration, ethyl acetate was added to the filtrate. Thus, 0.50 g (yield: 59%) of the title compound was obtained as white crystals.

$^1$H-NMR (400 MHz, CD$_3$OD/CDCl$_3$, Me$_4$Si) δ; 1.60–2.45(6H, m) 2.87(1H, dd, J=17.6, 12.7 Hz) 2.94(3H, s) 3.13(3H, s), 3.40(1H, dd, J=17.6, 6.0 Hz), 4.65(1H, dd, J=12.7, 6.0 Hz) 5.30(1H, m), 5.43(1H, m) 7.02(1H, dd, J=8.2, 2.2 Hz), 7.11(1H, d, J=8.2 Hz) 7.16(1H, d, J=2.4 Hz).

Synthesis Example D-1

[4S-[4α,7α(R*),12bβ]]-7-(1,3-Dioxo-]1,3-dihydroisoindol-2-yl)-9-nitro-6-oxo-1,2,3,4,6,7,8,12b-octahydropyrido[2,1-a][2]benzazepine-4-carboxylic acid and

[4S-[4α,7α(R*),12bβ]]-7-(1,3-Dioxo-]1,3-dihydroisoindol-2-yl)-11-nitro-6-oxo-1,2,3,4,6,7,8,12b-octahydropyrido[2,1-a][2]benzazepine-4-carboxylic acid

[4S-[4α,7α(R),12bβ]]-7-(1,3-dioxo-1,3-dihydroisoindol-2-yl) 6-oxo-1,2,3,4,6,7,8,12b-octahydropyrido[2,1-a][2]benzazepine-4-carboxylic acid (8.30 g, 20.5 mmol) was dissolved in methylene chloride (110 ml), followed by cooling to −60° C. Next, a solution obtained by dissolving nitronium tetrafluoroborate (0.5M solution in sulfolane 148 ml, 74 mmol) in methylene chloride (90 ml) was dropped thereinto. Thereafter, the mixture was slowly heated to 2° C. within 10 hours and then stirred at 2° C. for 5 hours. Next, it was partitioned into methylene chloride (500 ml) and water (1200 ml). Further, after the organic phase separated was washed with a saturated aqueous sodium chloride, it was dried over (MgSO$_4$ was used) and the solvent was concentrated under reduced pressure. The residue thus obtained was purified by flash silica gel chromatography (1:1 ethyl acetate/hexane→ethyl acetate containing 5% of acetic acid added). Thus, a mixture of the title compounds was obtained.

Synthesis Example d-2

Methyl [4S-[4α,7α(R*),12bβ]]-7-(1,3-dioxo-1,3-dihydroisoindol-2-yl)-9-nitro-6-oxo-1,2,3,4,6,7,8,12b-octahydropyrido[2,1-a][2]benzazepine-4-carboxylate and methyl [4S-[4α,7α(R*),12bβ]]-7-(1,3-dioxo-1,3-dihydroisoindol-2-yl)-11-nitro-6-oxo-1,2,3,4,6,7,8,12b-octahydropyrido(2,1-a][2]benzazepine-4-carboxylate A mixture (5.47 g, 12.2 mmol) of [4S-[4α,7α(R*),12bβ]]-7-(1,3-dioxo-1,3-dihydroisoindol-2-yl)-9-nitro-6-oxo-1,2,3,4,6,7,8,12b-octahydropyrido-[2,1-a][2]benzazepine-4-carboxylic acid and [4S-[4α,7α(R*),12bβ]]-7-(1,3-dioxo-1,3-dihydroisoindol-2-yl)-11-nitro-6-oxo-1,2,3,4,6,7,8,12b-octahydropyrido[2,1-a][2]benzazepine-4-carboxylic acid obtained in the above Synthesis Example D-1 was dissolved in dimethylformamide (80 ml). To this solution was added cesium carbonate (4.76 g, 14.6 mmol) at room temperature. The mixture thus obtained was stirred under a nitrogen atmosphere for 30 minutes and then 2.42 g (17.0 mmol) of methyl iodide was added thereto. The resulting mixture was stirred for 11 hours. Next, the solution stirred was partitioned into water (300 ml) and ethyl acetate (250 ml×2). Further, after the organic phase separated was washed with a saturated aqueous sodium chloride, it was dried over (MgSO₄ was used) and the solvent was concentrated under reduced pressure. After the completion of concentration, the residue thus obtained was purified and separated by flash silica gel chromatography (1:1 ethyl acetate/hexane). Thus, the title 11-nitro compound (1.62 g, 29%) and the title 9-nitro compound (1.78 g, 31%) were obtained.

Synthesis Example d-3

Methyl [4S-[4α,7α(R*),12bβ]]-11-amino-7-(1,3-dioxo-1,3-dihydroisoindol-2-yl)-6-oxo-1,2,3,4,6,7,8,12b-octahydropyrido(2,1-a][2]benzazepine-4-carboxylate

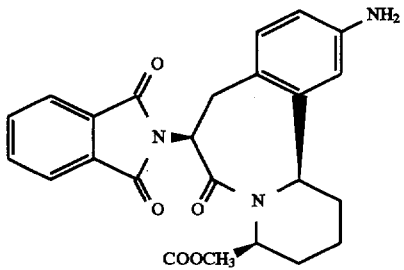

Methyl [4S-[4α,7α(R*),12bβ]]-7-(1,3-dioxo-1,3-dihydroisoindol-2-yl)-11-nitro-6-oxo-1,2,3,4,6,7,8,12b-octahydropyrido[2,1-a][2]benzazepine-4-carboxylate (1.62 g, 3.5 mmol) obtained in the above Synthesis Example D-2 was dissolved in acetic acid (5 ml) and dimethylformamide (60 ml). Next, 10% palladium/carbon (230 mg) was added to this solution, followed by shaking at room temperature for 2 hours. After methanol (150 ml) was further added to the solution shaken, it was filtered and the filtrate was concentrated under reduced pressure. Thus, the title compound (1.50 g) was obtained.

¹H-NMR (400 MHz, CDCl₃, Me₄Si) δ; 1.70~2.45(6H, m), 3.20(3H, s), 8.30(1H, dd, J=16.6, 6.7 Hz), 4.26(1H, dd, J=16.6, 12.1 Hz), 5.19(1H, m), 5.34(1H, m), 5.98(1H, dd, J=12.1, 6.7 Hz), 6.56(2H, m), 6.98(1H, d, J=8.8 Hz), 7.70~7.90(4H, m).

Synthesis Example E-1

α-(1,3-Dihydro-1,3-dioxo-2H-isoindol-2-yl-(1,1'-biphenyl)-4-propanoic acid

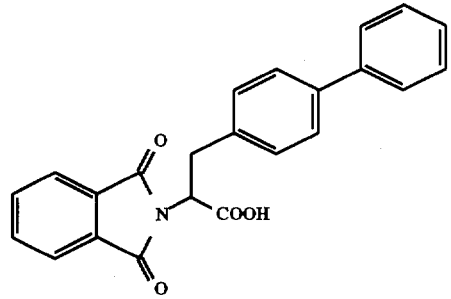

α-Amino-(1,1'-biphenyl)-4-propanoic acid (43.70 g, 181.3 mmol) and anhydrous fumaric acid (26.80 g, 181.3 mmol) were suspended in 100 ml of dimethylformamide (DMF), followed by heating at 120° C. for 2 hours and half. Next, the transparent solution thus obtained was poured into ice water (1.2 l), followed by vigorously stirring. Thus, white crystals were precipitated. These crystals were collected by filtration, (washed with water and hexane) and hot-air dried. Thus, the title compound was obtained as white crystals (65.5 g, yield 73%).

¹H-NMR (400 MHz, DMSO-d₆) δ; 7.83(4H, s), 7.58(2H, d, J=8 Hz), 7.51(2H, d, J=8 Hz), 7.40(2H, t, J=8 Hz), 7.31(1H, t, J=8 Hz), 7.26(2H, d, J=8 Hz), 5.16(1H, dd).

Synthesis Example E-2

(S)-N-[α-(1,3-Dihydro-1,3-dioxo-2H-isoindol-2-yl)-(1,1'-biphenyl)-4-propionyl]-6-hydroxynorleucine methyl ester

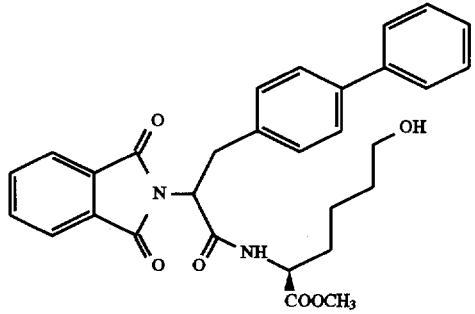

To a mixed solution of α-(1,3-dihydro-1,3-dioxo-2H-isoindol-2-yl)-(1,1'-biphenyl)-4-propanoic acid (28.53 g, 76.90 mmol) obtained in Synthesis Example E-1 with (S)-6-hydroxynorleucine methyl ester hydrochloride (19.10 g, 96.70 mmol) in 600 ml of dichloromethane (CH₂Cl₂) was added 42.47 ml of N-methylmorpholine (NMM). After preparing a homogeneous solution therefrom, 1-hydroxybenztriazole hydrate (HOBT) and 1-(3-dimethylaminopropyl)-3-ethylcarbodiimide hydrochloride (DEC) (28.92 g, 150.87 mmol) were added thereto at 0° C. After the reaction mixture was stirred at 0° C. for 30 minutes and then at room temperature overnight, it was washed with a 2N aqueous solution of hydrochloric acid, water, a saturated aqueous solution of sodium hydrogencarbonate and a saturated aqueous sodium chloride. The CH₂Cl₂ phase was dried over anhydrous magnesium sulfate and concentrated. The residual oil was purified by silica gel column chromatography (eluent; chloroform (CHCl₃) : methanol (MeOH) =99:1). Thus, the title compound was obtained as a colorless amorphous product (24.80 g, yield 63%).

¹H-NMR (400 MHz, CDCl₃) δ; 7.79(2H, m), 7.69(2H, m), 7.52~7.22(9H, m), 6.77 and 6.68 (total 1H, each brd, J=8 Hz), 5.19(1H, m), 4.63(1H, m), 3.72 and 3.71(total 3H, each s), 3.68~3.52(4H, m), 1.97~1.30(6H, m).

Synthesis Example E-3

(S)-N-[α-(1,3-Dihydro-1,3-dioxo-2H-isoindol-2-yl)-(1,1'-biphenyl)-4-propionyl]-6-oxonorleucine methyl ester

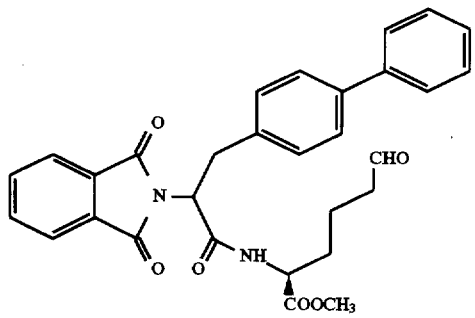

A solution of oxalyl chloride (9.82 ml, 115.35 mmol) in CH₂Cl₂ (330 ml) was cooled to −70° C. and a solution of dimethyl sulfoxide (DMSO, 8.18 ml, 115.35 mmol) in CH₂Cl₂ (70 ml) was slowly dropped thereinto within 15 minutes. This reaction mixture was stirred at −70° C. for 15 minutes. Then, a solution of (S)-N-[α-(1,3-dihydro-1,3-dioxo-2H-isoindol-2-yl)-(1,1'-biphenyl)-4-propionyl]-6-hydroxynorleucine methyl ester (24.80 g, 48.20 mmol) obtained in the Synthesis Example E-2 in CH₂Cl₂ (130 ml) was slowly dropped thereinto at −70° C. to −60° C. within about 40 minutes. After stirring the reaction mixture at −70° C. for 20 minutes, triethylamine (TEA, 52.66 ml) was slowly dropped thereinto within 20 minutes. The reaction mixture was stirred at 0° C. for 1 hour and then a solution of potassium peroxymonosulfate (OXONE, 70.18 g) in water (830 ml) was dropped thereinto at 0° to 5° C., followed by extraction with CH₂Cl₂. The CH₂Cl₂ layer was washed with water and a saturated aqueous sodium chloride, dried over magnesium sulfate and then concentrated. Thus, the title compound was obtained as a brown oil. This aldehyde was not purified but employed in the subsequent reaction (Synthesis Example E-4).

¹H-NMR (400 MHz, CDCl₃) δ; 9.71 and 9.70(total 1H, m), 7.78(2H, m), 7.68(2H, m), 7.50~7.20(9H, m), 6.82 and 6.78(total 1H, each brd, J=8 Hz), 5.20(1H, m), 4.61(1H, m), 3.91(3H, s), 3.75~3.52(4H, m), 2.50~1.30(total 6H, m).

Synthesis Example E-4

Methyl (S)-1-[α-(1,3-dihydro-1,3-dioxo-2H-isoindol-2-yl)-(1,1'-biphenyl)-4-propionyl]1,2,3,4-tetrahydro-2-pyridinecarboxylate

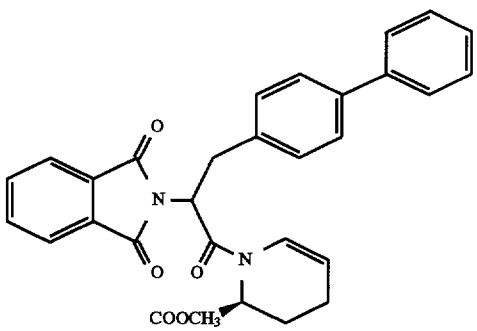

To (S)-N-[α-(1,3-dihydro-1,3-dioxo-2H-isoindol-2-yl)-(1,1'-biphenyl)-4-propionyl]-6-oxonorleucine methyl ester obtained in the Synthesis Example E-3 (crude product, 48.2 mmol) was added to trifluoroacetic acid (TFA, 60 ml) at once at 0° C. The solution thus formed was stirred at room temperature for 2 hours. The mixture was concentrated and the residual oil was subjected to azeotropic distillation with benzene. The brown, oily residue was partitioned into CH₂Cl₂ and water, and the CH₂Cl₂ phase was washed with a saturated aqueous solution of sodium hydrogen-carbonate, water and a saturated aqueous sodium chloride. The CH₂Cl₂ phase was dried over magnesium sulfate and then concentrated. The residual oil was purified by silica gel column chromatography (eluent; dichloromethane). Thus, the title compound was obtained as a colorless amorphous product (8.70 g, yield from Synthesis Example E-2 37%).

¹H-NMR (400 MHz, CDCl₃) δ; 7.84~7.74(2H, m), 7.69 (2H, m), 7.53~7.20(9H, m), 6.73 and 6.51(total 1H, each brd, J=8 Hz), 5.52 and 5.42(total 1H, each dd, J=12, 7 Hz), 5.29 and 5.24(total 1H, each dt like), 5.03 and 4.88(total 1H, each m), 3.87~3.47(2H, m), 3.75 and 3.65(total 3H, each s), 2.39(1H, m), 2.10~1.75(3H, m).

Synthesis Example E-5

[4S-[4α,7α(R*), 12bβ]]-7-(1,3-Dihydro-1,3-dioxo-2H-isoindol-2-yl )-6-oxo-11-phenyl-1,2,3,4,6,7,8,12b-octahydropyrido[2,1-a][2]benzazepine-4-carboxylic acid

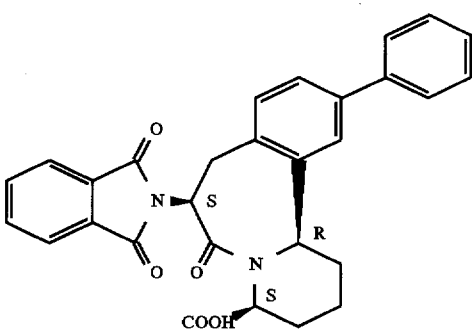

A solution of methyl (S)-1-[α-(1,3-dihydro-1,3-dioxo-2H-isoindol-2-yl)-(1,1'-biphenyl)-4-propionyl]-1,2,3,4-tetrahydro-2-pyridinecarboxylate (8.70 g, 17.61 mmol, a 1:1 mixture of diastereomers) obtained in the Synthesis Example E-4 in CH$_2$Cl$_2$ (58 ml) was dropped into a mixed solution of trifluoromethanesulfonic acid (10.82 ml, 122 mmol) and trifluoroacetic anhydride (TFAA, 2.75 ml, 19.51 mmol) at 0° C. The mixture was stirred under a nitrogen atmosphere at room temperature for 30 hours, and then poured into ice water. The mixture thus obtained was extracted with ethyl acetate. The ethyl acetate phase was washed with water and a saturated aqueous sodium chloride, dried over magnesium sulfate and concentrated. The amorphous residue was purified by silica gel column chromatography (eluent; CHCl$_3$: MeOH=99:1). Thus, the title compound was obtained as an amorphous product (1.80 g, yield 42%).

$^1$H-NMR (400 MHz, CDCl$_3$) δ; 7.78(2H, dd, J=8, 4 Hz), 7.66(2H, dd, J=8, 4 Hz), 7.49(2H, dd, J=8, 2 Hz), 7.43(1H, d, J=2 Hz), 7.37(3H, m), 7.28(1H, tt, J=7, 2 Hz), 7.14(1H, d, J=8 Hz), 5.78(1H, dd, J=10, 6 Hz), 5.30(1H, t, J=6 Hz), 5.14(1H, dd, J=8, 4 Hz), 4.05(1H, dd, J=16, 10 Hz), 3.44 (1H, dd, J=16, 6 Hz), 2.52~2.32(2H, m), 2.10~1.97(2H, m), 1.88~1.66(2H, m).

Synthesis Example E-6

Diphenylmethyl [4S-[4α,7α(R*),12bβ]]-7-(1,3-dihydro-1,3-dioxo-2H-isoindol-2-yl)-6-oxo-11-phenyl-1,2,3,4,6,7,8,12b-octahydropyrido[2,1-a][2]benzazepine-4-carboxylate

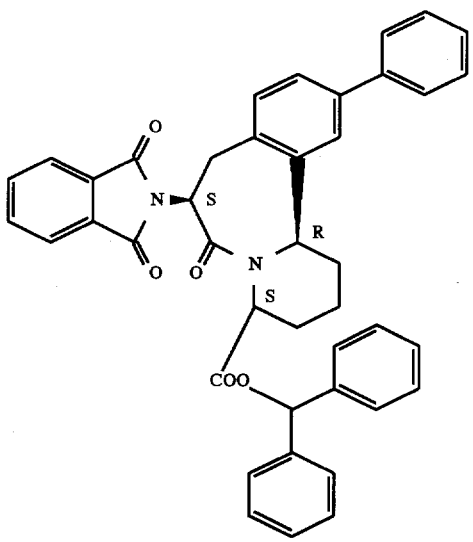

To a solution of [4S-[4α,7α(R*),12bβ]]-7-(1,3-dihydro-1,3-dioxo-2H-isoindol-2-yl)-6-oxo-11-phenyl-1,2,3,4,6,7,8,12b-octahydropyrido[2,1-a][2]benzazepine-4-carboxylic acid (1.80 g, 375 mmol) obtained in the Synthesis Example E-5 in DMF (40 ml) was added cesium carbonate (1.34 g, 4.21 mmol). The mixture was stirred for 30 minutes. Bromodiphenylmethane (1.30 g, 5.25 mmol) was added to the obtained mixture and the mixture was stirred at room temperature for 5 hours. The obtained reaction mixture was partitioned into ethyl acetate and water. After the ethyl acetate phase was washed with water and a saturated aqueous sodium chloride, it was dried over magnesium sulfate and concentrated. The amorphous residue was purified by silica gel column chromatography (eluent; CHCl$_3$:hexane (Hex)=4:1). Thus, the title compound was obtained as a colorless amorphous product (2.03 g, yield 84).

$^1$H-NMR (400 MHz, CDCl$_3$) δ; 7.85(2H, brs), 7.69(2H, dd, J=8, 4 Hz), 7.44~6.98(7H, m), 6.58(1H, d, J=8 Hz), 6.18(1H, s), 6.03(1H, dd, J=10, 6 Hz), 5.42(1H, t, J=6 Hz), 5.14(1H, dd, J=8, 4 Hz), 4.35(1H, dd, J=16, 10 Hz), 3.22 (1H, dd, J=16, 6 Hz), 2.37(2H, m), 2.05(1H, m), 1.80~1.63 (3H, m).

Synthesis Example F-1

Preparation of diphenylmethyl 3-(4-fluorophenyl) lactate

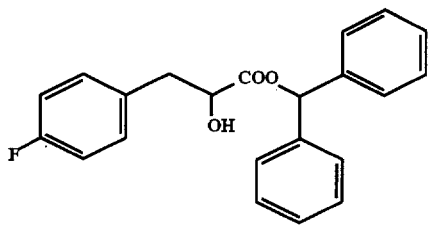

To 4-fluorophenylalanine (4.99 g, 27.2 mmol) was added a 0.5N aqueous solution of HCl (123 ml). The obtained mixture was cooled to 0° C. under cooling with ice and silver nitrite (5.6 g, 36.2 mmol) was further added thereto in several portions within 1 hour under vigorous stirring. Six hours thereafter, the obtained mixture was heated to room temperature and further stirred for 1 day. The silver chloride thus precipitated was removed out by filtration and the filtrate was extracted with diethyl ether (200 ml×4). The diethyl ether phase was dried over (MgSO$_4$ was used). The diethyl ether phase filtered was concentrated under reduced pressure. Thus, a crude product (4.69 g) of 3-(4-fluorophenyl)lactic acid was obtained. Next, this crude product (4.69 g) was dissolved in dry dimethylformamide (80 ml) and cesium carbonate (8.58 g, 26.8 mmol) was added thereto. The mixture thus obtained was stirred at room temperature for 40 minutes and subsequently bromodiphenylmethane (11.8 g, 47.8 mmol) was added thereto. The resulting mixture was stirred at room temperature for a day and water (300 ml) was then added thereto. The mixture thus obtained was extracted with ethyl acetate (100 ml×3). Next, the organic phase was washed with a saturated aqueous solution of sodium hydrogencarbonate (100 ml) and a saturated aqueous sodium chloride (100 ml) and dried over magnesium sulfate. After filtering thereof, the residue (13.4 g), which was obtained by concentrating the filtrate under reduced pressure, was purified by silica gel column chromatography (hexane: ethyl acetate=90:10). As a result, the title compound (4.2 g, 44%) was obtained as white crystals.

$^1$H-NMR (400 MHz, CDCl$_3$) δ; 2.74(1H, d, J=6.2 Hz), 2.98(1H, dd, J=6.2, 14.1 Hz), 3.13(1H, dd, J=4.8, 14.1 Hz), 4.55(1H, q, J=5.4 Hz), 6.85(2H, t, J=8.4 Hz), 6.94(1H, s), 6.99(2H, dd, J=5,6, 8.4 Hz), 7.28~7.38(10H, m).

MASS m/e (FAB); 373(MNa$^+$)

m.p.; 52°~54° C.

Synthesis Example F-2

Preparation of diphenylmethyl 2-acetylthio-3-(4-fluorophenyl)propionate

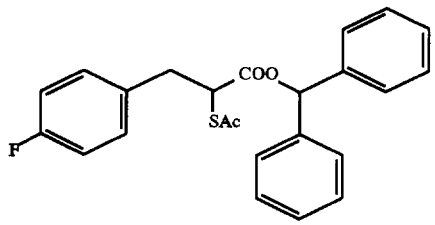

Triphenylphosphine (3.99 g, 15.2 mmol) was dissolved in dry tetrahydrofuran (78 ml), followed by cooling to 0° C. under cooling with ice. Further, diisopropyl azodicarboxylate (DIAD (2.99 ml, 15.2 mmol)) was dropped thereinto under stirring. Thirty minutes thereafter, a solution of a mixture of thioacetic acid (1.25 ml, 17.8 mmol) with diphenylmethyl 3-(4-fluorophenyl)lactate (4.0 g, 11.4 mmol) obtained in the Synthesis Example F-1 in dry tetrahydrofuran (45 ml) was dropped thereinto. The mixture was allowed to react at 0° C. for 3 hours. Then the ice bath was removed and the reaction mixture was warmed to room temperature and allowed to react at this temperature overnight. Next, this reaction mixture was concentrated under reduced pressure. The residue thus obtained was separated by silica gel column chromatography (hexane:ethyl acetate=6:1) to thereby give a crude product (4.7 g). This crude product was recrystallized from diisopropyl ether and hexane (20 ml–30 ml). The solid thus precipitated was removed by filtration and the filtrate was concentrated under reduced pressure to thereby give the title compound (3.54 g, 76%) as an oily product.

$^1$H-NMR (400 MHz, CDCl$_3$) δ; 2.33(3H, s), 3.01(1H, dd, J=6.6, 14.0 Hz), 3.19(1H, dd, J=8.8, 14.0 Hz), 4.52 (1H, t, J=8.2 Hz), 6.81 (1H, s), 6.85(2H, t, J=8.6 Hz), 7.05(2H, dd, J=5.8, 7.8 Hz), 7.14~7.17(2H, m), 7.26~7.36(8H, m).

Synthesis Example F-3

Preparation of 2-acetylthio-3-(4-fluorophenyl)propionic acid

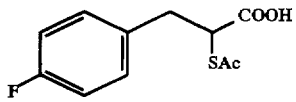

Diphenylmethyl 2-acetylthio-3-(4-fluorophenyl)propionate (3.38 g, 8.27 mmol) was dissolved in anisole (9.0 ml), followed by cooling to −10° C. Into this solution was further dropped trifluoroacetic acid (51.0 ml). Next, this solution was heated to 0° C. About 1 hour thereafter, it was concentrated under reduced pressure. To the concentrate was added diethyl ether (80 ml) and the resulting solution was extracted with a saturated aqueous solution of sodium hydrogencarbonate (100 ml×2). To the alkaline aqueous solution thus obtained was added a 2N aqueous solution of hydrochloric acid until the solution became acidic. Further, it was extracted with methylene chloride (100 ml×3). The organic phase was washed with a saturated aqueous sodium chloride (100 ml) and dried over magnesium sulfate. After drying, the filtrate obtained by filtering thereof was concentrated under reduced pressure. Thus, the title compound (1.96 g, 98%) was obtained as colorless crystals.

$^1$H-NMR (400 MHz, CDCl$_3$) δ; 2.35(3H, s), 3.00(1H, dd, J=7.4, 14.2 Hz), 3.26(1H, dd, J=7.8, 14.2 Hz), 4.40(1H, t, J=7.6 Hz), 6.99(2H, t, J=8.6 Hz), 7.20(2H, dd, J=5.6, 8.4 Hz).

MASS m/e (FAB); 243(MH$^+$)

m.p.; 44°~46° C.

Synthesis Examples F-4 to F-6

In accordance with the processes of the Synthesis Examples F-1 to F-3, the following compounds were obtained.

Synthesis Example F-4

(S)-2-Acetylthio-3-phenylpropionic acid

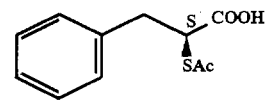

By using D-phenylalanine as the starting material, it was synthesized in accordance with the processes of the Synthesis Examples F-1 to F-3.

$^1$H-NMR (400 MHz, CDCl$_3$) δ; 2.34(3H, s), 3.02(1H, dd, J=7.6, 14.0 Hz), 3.30(1H, dd, J=7.6, 14.0 Hz), 4.44(1H, t, J=7.6 Hz), 7.21~7.33(5H, m).

MASS m/e (FAB); 225(MH$^+$)

m.p.; 59°~61° C.

Synthesis Example F-5

2-Acetylthio-3(1,4-biphenyl)propionic acid

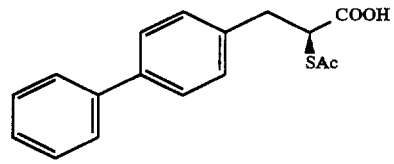

$^1$H-NMR (400 MHz, CDCl$_3$) δ; 2.36(3H, s), 3.07(1H, dd, J=7.6, 14.4 Hz), 3.34(1H, dd, J=7.6, 14.4 Hz), 4.48(1H, t, J=7.6 Hz), 7.29~7.59(9H, m).

MASS m/e (FAB); 301(MH$^+$)

m.p.; 122°~123° C.

Synthesis Example F-6

(S)-2-Acethylthio-3-(4-methoxyphenyl)propionic acid

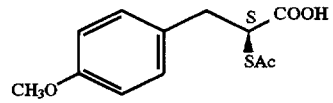

$^1$H-NMR (400 MHz, CDCl$_3$) δ; 2.34(3H, s), 2.97(1H, dd, J=7.6, 14.4 Hz), 3.23(1H, dd, J=7.6, 14.4 Hz), 3.79(3H, s), 4.39(1H, t, J=7.6 Hz), 6.81~6.86(2H, m), 7.12~7.17(2H, m).

MASS m/e (FAB); 255(MH$^+$)

m.p.; 95°~98° C.

Example A-1

3-Amino-1-ethoxycarbonylmethyl-8-phenyl-2,3,4,5-tetrahydro-1H-[1]benzazepin-2-one

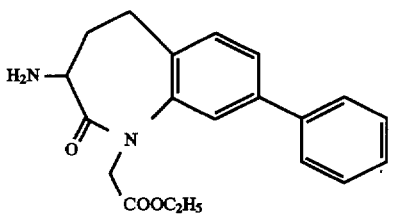

A mixture comprising 0.785 g (2.15 mmol) of 3-azido-1-ethoxycarbonylmethyl-8-phenyl-2,3,4,5-tetrahydro-1H-[1]benzazepin-2-one obtained in the Synthesis Example A-7, 0.05 g of 10% palladium-carbon and 20 ml of ethanol was catalytically hydrogenated at room temperature under 4 atm for 1 hour. After filtering off the catalyst, the filtrate was concentrated. Thus, 0.73 g of the title compound was obtained as a pale yellow oily product. Yield 100%.

$^1$H-NMR (400 MHz, CDCl$_3$) δ: 7.56~7.35(6H, m) 7.33 (1H, d, J=2 Hz), 7.30(1H, d, J=8 Hz) 4.69(1H, d, J=17 Hz), 4.51(1H, d, J=17 Hz) 4.21(2H, dq, J=7.1 Hz), 3.53(1H, dd, J=11.8 Hz) 3.28(1H, dr, J=13.8 Hz), 2.65(1H, dd, J=14.7 Hz) 2.46(1H, m) 1.96(1H, m).

Example A-2

3-[(S)-Acetylthio-3-phenylpropionylamino]-1-ethoxycarbonylmethyl-8-phenyl-1H-[1]benzazepin-2-one

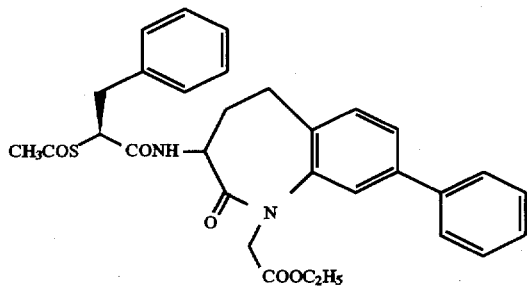

341 mg (1 mmol) of 3-amino-1-ethoxycarbonylmethyl-8-phenyl-2,3,4,5-tetrahydro-1H-[1]benzazepin-2-one obtained in the Example A-1 and 247 mg (1.1 mmol) of (S)-2-acetylthio-3-phenylpropionic acid were dissolved in 20 ml of dichloromethane. 300 mg (1.21 mmol) of EEDQ was added thereto and the obtained mixed solution was stirred overnight. The reaction mixture was washed with 1N hydrochloric acid, water and a saturated aqueous sodium chloride and dried over anhydrous magnesium sulfate. The solvent was distilled off under reduced pressure, and the residue was subjected to silica gel column chromatography. After successively eluting with hexane: ethyl acetate in a ratio ranging from 15:1 (v/v) to 3:1 (v/v), 329 mg of the title compound was obtained as a colorless amorphous product. Yield 72%.

$^1$H-NMR (400 MHz, CDCl$_3$) δ: 7.55~7.15(13H, m), 7.04 and 6.88(total 1H, each br), 4.82 and 4.78(total 1H, each d, J=17 Hz), 4.50(1H, m), 4.39 and 4.34(total 1H, each d, J=17 Hz), 4.27~4.12(3H, m) 3.42~3.22(2H, m) 2.94(1H, m), 2.77~2.49(2H, m) 2.34 and 2.33(total 3H, each s), 1.24(3H, q, J=7 Hz).

Example A-3

1-Carboxymethyl-3-[(S)-2-mercapto-3-phenylpropionylamino]-8-phenyl-1H-[1]benzazepin-2-one

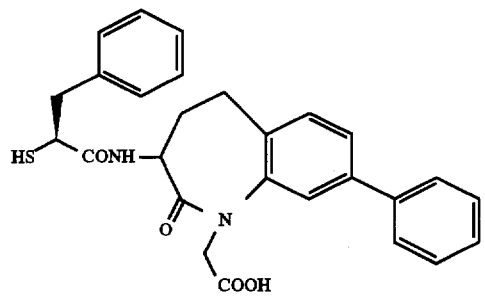

To a mixture of 358 mg (0.657 mmol) of 3-[(S)-2-acetylthio-3-phenylpropionylamino]-1-ethoxycarbonylmethyl-8-phenyl-1H-[1]benzazepin-2-one obtained in the Example A-2 with 10 ml of degassed ethanol was added 3.3 ml of a degassed 1N aqueous solution of sodium hydroxide at 0° C. under a nitrogen atmosphere under stirring. The mixture thus obtained was stirred at room temperature for 2 hours and half. The reaction mixture was cooled and acidified with 1N hydrochloric acid and water was further added thereto. The white crystals thus precipitated were collected by filtration, washed with water and n-hexane and dried under reduced pressure. Thus, 267 mg of the title compound was obtained. Yield 86%.

$^1$H-NMR (400 MHz, CDCl$_3$) δ: 7.54~7.14(18H, m), 4.74 and 4.73(total 1H, each d, J=17 Hz), 4.54(1H, m), 4.47 and 4.45(total 1H, each d, J=17 Hz), 3.56 and 3.42(total 1H, each m) 3.3~3.16(2H, m), 3.06(1H, dd, J=14.7 Hz) 2.98(1H, dd, J=14.7 Hz), 2.74~2.52(2H, m), 2.08 and 1.97(total 1H, each d, J=9 Hz).

Example A-4

3-[(S)-Acetylthio-3-methylbutyrylamino]-1-ethoxycarbonylmethyl-8-phenyl-1H-[1]benzazepin-2-one

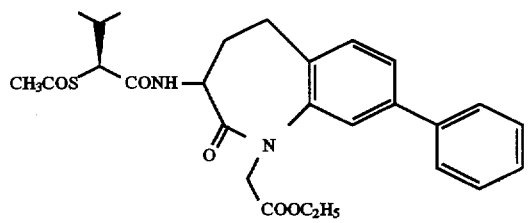

352 mg (1.04 mmol) of 3-amino-1-ethoxycarbonylmethyl-8-phenyl-2,3,4,5-tatrahydro-1H-[1]benzazepin-2-one obtained in the Example A-1 and 202 mg (1.14 mmol) of (S)-2-acetylthio-3-methylbutanoic acid were reacted in the same manner as that of Example A-2. Thus, 396 mg of the title compound was obtained as a colorless amorphous product. Yield 77%.

$^1$H-NMR (400 MHz, CDCl$_3$) δ: 7.55~7.29(8H, m), 7.10 and 7.03 (total 1H, each brd, J=7 Hz), 4.86 and 4.83 (total 1H, each d, J=17 Hz), 4.61~4.54(1H, m), 4.39 and 4.37(total 1H, each d, J=17 Hz), 4.24~4.13(3H, m), 3.85 and 3.84(total 1H, each d, J=7 Hz), 3.40(1H, m) 2.80~2.60(2H, m) 2.37 (3H, s), 2.26 and 2.95(total 1H, each m), 1.25(3H, q, J=7 Hz), 0.99 and 0.96(total 6H, each d, dd, each J=7 Hz, J=7.2 Hz).

Example A-5

1-Carboxymethyl-3-[(S)-2-mercapto-3-methylbutyrylamino]-8-phenyl-1H-[1]benzazepin-2-one

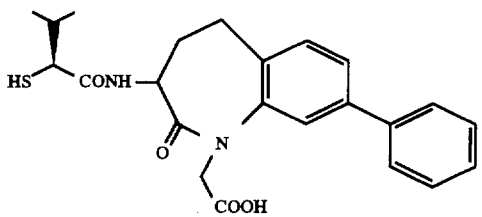

347 mg (0.7 mmol) of 3-[(S)-2-acetylthio-3-methylbutyrylamino]-1-ethoxycarbonylmethyl-8-phenyl-1H-[1]benzazepin-2-one obtained in the Example A-4 was hydrolyzed in the same manner as that of Example A-3. Thus, 243 mg of the title compound was obtained as white crystals. Yield 81%.

$^1$H-NMR (400 MHz, CDCl$_3$) δ: 7.55~7.29(8H, m), 4.80 and 4.78(total 1H, each d, J=17 Hz), 4.60(1H, m), 4.48 and 4.46(total 1H, each d, J=17 Hz), 3.33(1H, m) 3.11(1H, m) 2.78~2.62(2H, m), 2.18(1H, m) 2.01(1H, m), 1.84 and 1.83(total 1H, each d, J=9 Hz), 0.99~0.94(6H, m).

Example A-6

3-[(S)-Acetylthio-3-phenylpropionylamino]-1-ethoxycarbonylmethyl-1H-[1]benzazepin-2-one

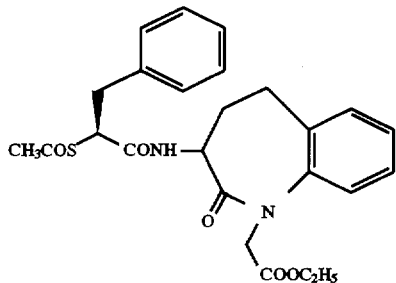

To a mixed solution comprising 0.76 g (2.9 mmol) of 3-amino-1-ethoxycarbonylmethyl-1H-[1]benzazepin-2-one, 0.65 g (2.9 mmol) of (S)-2-acetylthio-3-phenylpropionic acid and 30 ml of tetrahydrofuran were added 0.61 g (3.18 mmol) of DEC, 0.35 ml (3.18 mmol) of N-methylmorpholine and 0.43 g (3.18 mmol) of 1-hydroxybenztriazole. The mixture thus obtained was stirred at room temperature for 5 hours. After adding water to the reaction mixture, it was extracted with ethyl acetate. The organic phase was washed with water, 1N hydrochloric acid and water and dried over anhydrous magnesium sulfate. The solvent of the organic phase was distilled off under reduced pressure, and the residue was subjected to silica gel column chromatography. After eluting with toluene:ethyl acetate in a ratio of 7:1 (v/v), 0.95 g of the title compound was obtained as a colorless amorphous product. Yield 70%.

$^1$H-NMR (400 MHz, CDCl$_3$) δ: 7.30~7.08(9H, m), 7.04 and 6.88(total 1H, each brd, J=7 Hz), 4.77 and 4.72(total 1H, each d, J=17 Hz), 4.42(1H, m), 4.33 and 4.28(total 1H, each d, J=17 Hz), 4.24~4.08(3H, m) 3.38~3.21(2H, m) 2.93(1H, m), 2.75~2.46(2H, m) 2.33 and 2.32(total 3H, each s), 1.83 and 1.66(total 1H, each m).

Example A-7

1-Carboxymethyl-3-[(S)-2-mercapto-3-phenylpropionylamino]1H-[1]benzazepin-2-one

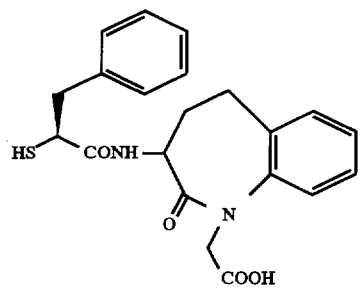

To a mixed solution of 0.65 mg (1.39 mmol) of 8-[(S)-2-acetylthio-3-phenylpropionylamino]-1-ethoxycarbonylmethyl-1H-[1]benzazepin-2-one obtained in the Example A-6 with 10 ml of degassed ethanol was added 7 ml of a degassed 1N aqueous solution of sodium hydroxide at 0° C. under a nitrogen atmosphere with stirring. The mixture thus obtained was stirred at room temperature for 3 hours. After the reaction mixture was cooled and acidified with 1N hydrochloric acid, it was extracted with dichloromethane. The dichloromethane phase was washed with a saturated aqueous sodium chloride and dried over anhydrous sodium sulfate. The solvent of the organic phase was distilled off under reduced pressure. Thus, 0.53 g of the title compound was obtained as a colorless amorphous product. Yield 96%.

$^1$H-NMR (400 MHz, CDCl$_3$) δ: 7.31~7.11(9H, m), 4.68 and 4.65(total 1H, each d, J=17 Hz), 4.51~4.88(2H, m) 3.55 and 3.42(total 1H, each m), 3.28~3.14(2H, m), 3.05 and 2.97(total 1H, each dd, J=14.7 Hz), 2.72~2.48(2H, m), 2.07 and 1.96(total 1H, each d, J=9 Hz), 1.88 and 1.64(total 1H, each m).

Example A-8

3-[(2S, 3S)-2-Acetylthio-3-methylvalerylamino]-1-ethoxycarbonylmethyl-1H-[1]benzazepin-2-one

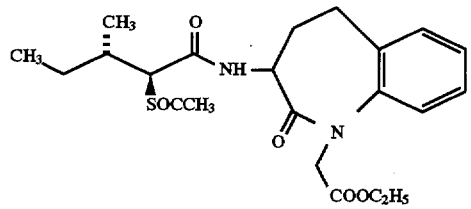

0.525 g (2 mmol) of 3-amino-1-ethoxycarbonylmethyl-1H-[1]benzazepin-2-one and 0.418 g (2.2 mmol) of (2S,3S)-2-acetylthio-3-methylvaleric acid were reacted in the same manner as that of Example A-2. Thus, 0.42 g of the title compound was obtained as a colorless amorphous product. Yield 48%.

$^1$H-NMR (400 MHz, CDCl$_3$)δ: 7.31~7.00(5H, m), 4.81 and 4.78(total 1H, each d, J=17 Hz), 4.53~4.45(1H, m), 4.33 and 4.31(total 1H, each d, J=17 Hz), 4.22~4.12(2H, m), 3.91 and 3.89(total 1H, each d, J=7 Hz), 3.44~3.33(1H, m) 2.78~2.56(2H, m) 2.37(3H, s), 2.07~1.87(2H, m) 1.59~1.50 (1H, m), 1.28~1.22(3H, m), 0.96 and 0.95(total 3H, each d, J=7 Hz), 0.85(total 3H, each t, J=7 Hz).

Example A-9

1-Carboxymethyl-3-[(2S,3S)-2-mercapto-3-methylvarelylamino]-1H-[1]benzazepin-2-one

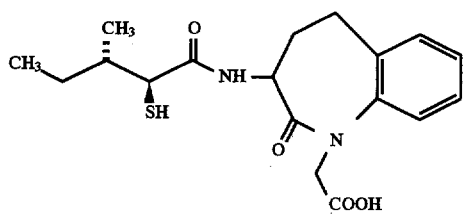

A mixed solution of 0.385 g (0.89 mmol) of 3-[(2S,3S)-2-acetylthio-3-methylvalerylamino]-1-ethoxycarbonylmethyl-1H-[1]benzazepin-2-one obtained in the Example A-8 with 15 ml of degassed ethanol was acidified with degassed 1N hydrochloric acid under stirring at 0° C. under a nitrogen atmosphere. It was extracted with ethyl acetate. The organic phase was washed with water and dried over anhydrous magnesium sulfate. The solvent of the organic phase was distilled off under reduced pressure. Thus, 0.34 g of the title compound was obtained as a colorless amorphous product (yield quantitative).

$^1$H-NMR (400 MHz, CDCl$_3$) δ: 7.39~7.14(5H, m), 4.74 and 4.71(total 1H, each d, J=17 Hz), 4.57~4.50(1H, m), 4.44 and 4.43(total 1H, each d, J=17 Hz), 3.34~3.10(2H, m) 2.77~2.58(2H, m), 2.03~1.87(2H, m), 1.85 and 1.84(total 1H, each d, J=9 Hz), 1.64~1.50(1H, m) 1.22~1.15(1H, m), 0.95(3H, d, J=7 Hz) 0.86(3H, t, J=7 Hz).

Example A-10

(S)-3-[(2S,3S)-2-Acetylthio-3-methylvarelylamino]-1-ethoxycarbonylmethyl-2,3,4,5-tetrahydro-1H-[1]benzazepin-2-one

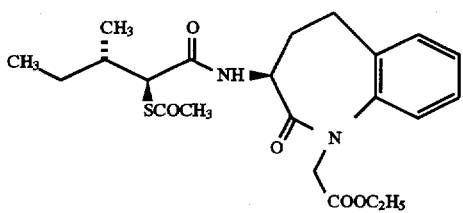

0.55 g (2.1 mmol) of (S)-3-amino-1-ethoxycarbonylmethyl-2,3,4,5-tetrahydro-1H-[1]benzazepin-2-one and 0.434 g (2.3 mmol) of (2S,3S)-2-acetylthio-3-methylvaleric acid were reacted in the same manner as that of Example A-2. Thus, 0.614 g of the title compound was obtained as a colorless amorphous product. Yield 67%.

$^1$H-NMR (400 MHz, CDCl$_3$) δ: 7.31~7.17(3H, m) 7.12 (1H, dd, J=8.1 Hz), 7.01(1H, brd, J=7 Hz) 4.78(1H, d, J=17 Hz), 4.49(1H, dt, J=11.8 Hz) 4.33(1H, d, J=17 Hz), 4.24~4.12(2H, m) 3.89(1H, d, J=7 Hz) 3.38(1H, m), 2.74~2.56(2H, m) 2.37(3H, s) 2.04~1~87(2H, m), 1.56(1H, m) 1.25(3H, t, J=7 Hz) 1.14(1H, m), 0.96(3H, d, J=7 Hz) 0.88(3H, t, J=6 Hz).

Example A-11

(S)-3-[(2S,3S)-2-Mercapto-3-methylvarelylamino]-1-carboxymethyl-2,3,4,5-tetrahydro-1H-[1]benzazepin-2-one

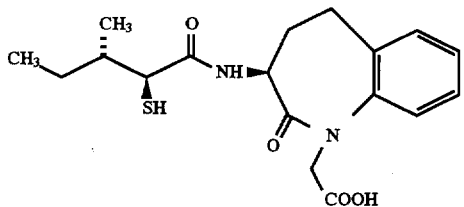

0.6 g (1.38 mmol) of (S)-3-[(2S,3S)-2-acetylthio-3-methylvarelylamino]-1-ethoxycarbonylmethyl-2,3,4,5-tetrahydro-1H-[1]benzazepin-2-one obtained in the Example A-10 was hydrolyzed in the same manner as that of Example A-9. Thus, 0.49 g of the title compound was obtained as a colorless amorphous product. Yield 97%.

$^1$H-NMR (400 MHz, CDCl$_3$) δ: 7.40(1H, brd, J=7 Hz) 7.33~7.14(4H, m), 4.71(1H, d, J=17 Hz) 4.54(1H, dr, J=11, 7 Hz), 4.44(1H, d, J=17 Hz) 3.29(1H, m), 3.17(1H, dd, J=9.7 Hz) 2.74~2.59(2H, m), 2.04~1.89(2H, m) 1.84(1H, d, J=9 Hz) 1.55(1H, m), 1.17(1H, m) 0.95(3H, d, J=7 Hz) 0.86(3H, t, J=7 Hz).

Example B-1

Ethyl [5S-(5α,8α(R*),11αβ)]-5-amino-6-oxo-4,5,6,8,9,10,11,11a-octahydropyrido[1,2-a]thieno[3,2-c]azepine-8-carboxylate

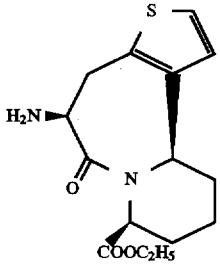

540 mg (1.23 mmol) of the compound obtained in the Synthesis Example B-3 was dissolved in 31 ml of ethanol and 0.072 ml (1.48 mmol) of hydrazine monohydrate was added thereto. The mixture thus obtained was stirred at room temperature for a week. The reaction mixture was concentrated as such under reduced pressure and dichloromethane was added thereto. The filtrate obtained by filtering it was concentrated again. The residue was purified by silica gel column chromatography (dicloromethane/methanol/aqueous ammonia=98/2/0.3) to thereby give 332 mg of the title compound (yield 88%).

MASS m/e (FAB); 309(MH$^+$)

m.p.; 92°~97° C.

$^1$H-NMR (400 MHz, CDCl$_3$, Me$_4$Si) δ; 0.881(3H, t, J=7.2 Hz) 1.57~1.94(5H, m), 2.03–2.21(2H, m) 2.40–2.47(1H, m), 2.95(1H, m like t), 3.32(1H, ddd, J=1.6, 4.8, 16.8 Hz), 3.67–3.75(1H, m) 3.81–3.88(1H, m), 4.61(1H, dd, J=4.8, 13.2 Hz) 5.1(1H, brt, J=6.4 Hz), 5.30(1H, dd, J=1.6, 8.0 Hz) 6.78(1H, d, J=5.0 Hz), 7.04(1H, d, J=5.0 Hz).

Example B-2

Ethyl [5S-(5α,8α(R*),11αβ)]-5-[[(S)-2-acetylthio-1-oxo-3-phenylpropyl]amino-6-oxo-4,5,6,8,9,10,11,11a-octahydropyrido[1,2-a]thieno[3,2-c]azepine-8-carboxylate

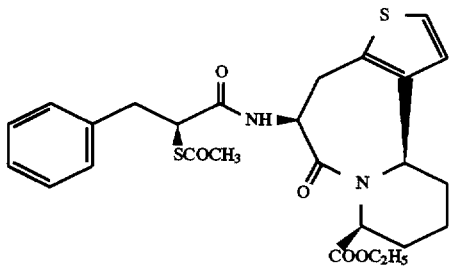

150 mg (0.49 mmol) of the compound obtained in the Example B-1 was dissolved in 12 ml of dichloromethane. 120 mg (0.54 mmol) of 2(S)-acetylthio-3-phenylpropionic acid and 144 mg (0.58 mmol) of EEDQ were added thereto at 0° C. The mixture thus obtained was stirred at room temperature overnight and then concentrated under reduced pressure. The residue was purified by silica gel column chromatography (hexane/ethyl acetate=3) to thereby give 168 mg (yield: 67%) of the title compound as an amorphous product.

$^1$H-NMR (400 MHz, CDCl$_3$, Me$_4$Si) δ; 0.87(3H, t, J=7.2 Hz) 1.60–1.91(3H, m), 2.01–2.20(2H, m) 2.36(3H, s) 2.39–2.48(1H, m), 2.81(1H, m like dd) 3.04(1H, dd, J=7.6, 14.0 Hz), 3.34(1H, dd, J=7.6, 14.0 Hz) 3.51(1H, m like dd), 3.68–3.88(2H, m) 4.33(1H, t, J=7.6 Hz), 5.19–5.25(2H, m) 5.50–5.57(1H, m), 6.75(1H, d, J=5.2 Hz) 7.04(1H, d, J=5.2 Hz), 7.21–7.33(5H, m) 7.50(1H, brd).

Example B-3

[5S-[5α,8α(R*),11αβ]]-5-[[(S)-2-Mercapto-1-oxo-3-phenylpropyl]amino]-6-oxo-4,5,6,8,9,10,11,11a-octahydropyrido[1,2-a]thieno[3,2-c]azepine-8-carboxylic acid

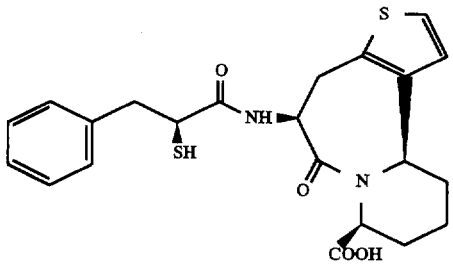

To 163 mg (0.32 mmol) of the compound obtained in the Example B-2 was added 12.7 ml of degassed methanol. Further, 3.8 ml of degassed 1N sodium hydroxide was added thereto. The mixture thus obtained was stirred at 40° C. Seven hours thereafter, it was cooled to 0° C. To the reaction mixture was added 5.7 ml of 2N hydrochloric acid. Then, the mixture was concentrated to a certain extent under reduced pressure. The crystals precipitated by adding a small amount of water thereto were collected by filtration and dried over phosphorus pentaoxide under reduced pressure. Thus, 92 mg of a mixture of the title compound with its epimer at a ratio of 4:3 was obtained (yield 60%).

$^1$H-NMR (400 MHz, CDCl$_3$, Me$_4$Si) δ; 1.63–2.43(6H, m) 2.54–4.30(5H, m), 5.16 and 5.24(total 1H, each m), 5.31 and 5.40(total 1H, each m), 5.62 and 5.79(total 1H, each m), 6.73–6.78(total 1H, m) 6.90–7.04(total 1H, m), 7.19–7.91 (total 6H, m).

Example B-4

Ethyl [5S-[5α,8α(R*),11αβ]]-5-[[(S)-2-acetylthio-3-methyl-1-oxobutyl]amino]-6-oxo-4,5,6,8,9,10,11,11a-octahydropyrido[1,2-a]thieno[3,2-c]azepine-8-carboxylate

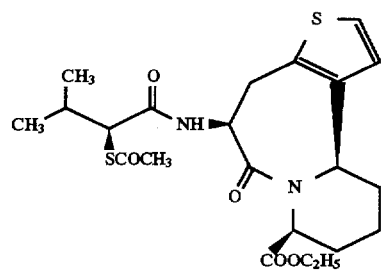

170 ml (0.55 mmol) of the compound obtained in the Example B-1 and (S)-2-acetylthio-3-methylbutanoic acid (107 mg, 0.61 mmol) were reacted in the same manner as that of Example B-2. Thus, 203 mg of a stereoisomeric mixture of the title compound with its epimer was obtained (yield 79%).

$^1$H-NMR (400 MHz, CDCl$_3$, Me$_4$Si) δ; 0.88 and 0.89 (total 3H, each t, each J=7.2 Hz), 1.00 and 1.01(total 3H, each d, each J=6.8 Hz), 1.05 and 1.06(total 3H, each d, each J=6.4 Hz), 1.59–2.24(total 5H, m) 2.32–2.48(total 2H, m), 2.40 and 2.42(total 3H, each s), 2.84–2.98(total 1H, m) 3.49–3.58(total 1H, m), 3.68–3.96(total 3H, m) 5.23–5.29 (total 2H, m), 5.58–5.66(total 1H, m) 6.76(total 1H, m), 7.04(total 1H, m) 7.52–7.59(total 1H, m).

Example B-5

[5S-[5α,8α(R*),11αβ]]-5-[[(S)-2-Mercapto-8-methyl-1-oxobutyl]amino]-6-oxo-4,5,6,8,9,10,11,11a-octahydropyrido[1,2a]thieno[3,2c]azepine-8-carboxylic acid

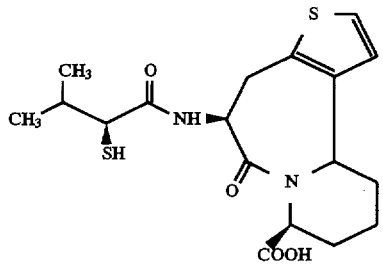

200 mg of ethyl [5S-[5α,8α(R*),11αβ]]-5-[[(S)-2-acetylthio-3-methyl-1-oxobutyl]amino]-6-oxo-4,5,6,8,9,10,11,11a-octahydropyrido[1,2-a]thieno-[3,2-c]azepine-8-carboxylate obtained in the Example B-4 was reacted in the same manner as that of Example B-3. Thus, a stereoisomeric mixture of the title compound was obtained as a white solid (127 mg, 74%).

$^1$H-NMR (400 MHz, CDCl$_3$, Me$_4$SO$_4$) δ; 1.01–1.06(total 6H, m) 1.66–2.42(total 8H, m), 2.85–3.60(total 3H, m)

5.19–5.24(total 1H, m), 5.32–5.40(total 1H, m) 5.64–5.79 (total 1H, m), 6.74–6.79(total 1H, m) 7.00–7.05(total 1H, m), 7.87–8.23(total 1H, m).

Example B-6

Ethyl 5-amino-6-oxo-4,5,6,8,9,10,11,11a-octahydropyrido[1,2-a]thieno[2,3-c]azepine-8-carboxylate

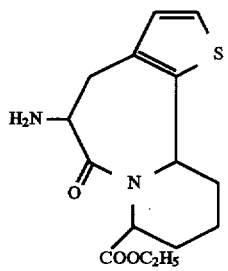

1.28 g (2.92 mmol) of the compound obtained in the Synthesis Example B-6 was reacted in the same manner as that of Example B-1. Thus, 581 mg of a mixture of two diastereomers of the title compound was obtained as a racemic modification (65%).

MASS m/e (FAB); 3.09(MH$^+$)

$^1$H-NMR (400 MHz, CDCl$_3$, Me$_4$Si) δ; 0.87 and 1.30 (total 3H, each t, each J=7.2 Hz), 1.60–2.48(total 8H, m) 2.77(total H, m like q), 3.13–3.21(total 1H, m) 3.71–3.91 and 4.24(total 2H, each m and q, each J=7.2 Hz) 4.47 and 4.57(total 1H, each dd, each J=4.8, 12.8 Hz), 4.76 and 5.28(total 1H, each t and dd, each J=5.0 Hz and J=1.6, 7.6 Hz) 5.43 and 5.49(total 1H, each brt and brs), 6.77–6.81 (total 1H, m) 7.07–7.11(total 1H, m).

Example B-7

Ethyl 5-[(S)-2-acetylthio-1-oxo-3-phenylpropyl]amino-6-oxo-4,5,6,8,9,10,11,11a-octahydropyrido[1,2-a]thieno[2,3-c]azepine-8-carboxylate

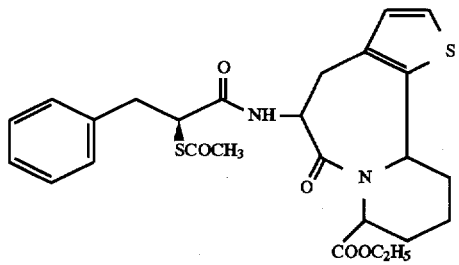

581 ml (1.88 mmol) of the compound obtained in the Example B-4 and (S)-2-acetylthio-3-phenylpropionic acid (423 mg, 1.88 mmol) were reacted in the same manner as that of Example B-2. After purifying by silica gel column chromatography (hexane/ethyl acetate=3), 232 mg (yield 24%) of a 7:3 mixture of two diastereomers was obtained from the former fraction. Further, from the latter fraction, 324 mg (yield 33%) of a 1:1 mixture of two diastereomers different from those contained in the former fraction was obtained.

Former fraction $^1$H-NMR (400 MHz, CDCl$_3$, Me$_4$Si) δ; 0.86 and 1.29 (total 3H, each t, each J=7.2 Hz), 1.62–2.48(total 6H, m), 2.34 and 2.36(total 3H, each s), 2.58–2.70(total 1H, m like q), 2.96–3.06(total 1H, m) 3.30–3.42(total 2H, m), 3.72–3.88 and 4.23(total 2H, each m and q, each J=7.2 Hz) 4.28–4.35(total 1H, m), 4.80 and 5.19–5.23(total 1H, each brt and m), 5.34–5.54(total 2H, m) 6.74–6.77(total 1H, m), 7.06–7.10(total 1H, m) 7.20–7.47(total 6H, m).

Latter fraction $^1$H-NMR (400 MHz, CDCl$_3$, Me$_4$Si) δ; 0.85 and 1.29 (total 3H, each t, each J=7.2 Hz), 1.60–2.44(total 6H, m), 2.34 and 2.40(total 3H, each s), 2.44–3.37(total 4H, m), 3.69–3.88 and 4.18–4.30(total 3H, m), 4.78 and 5.22(total 1H, each brt and m), 5.35–5.55(total 2H, m) 6.71(total 1H, t, J=5.2 Hz), 7.08(total 1H, dd, J=5.2, 8.4 Hz) 7.21–7.36 (total 6H, m).

Example B-8

5-[(S)-2-Mercapto-1-oxo-3-phenylpropyl]amino-6-oxo-4,5,6,8,9,10,11,11a-octahydro[1,2-a]thieno-[2,3-c]azepine-8-carboxylic acid

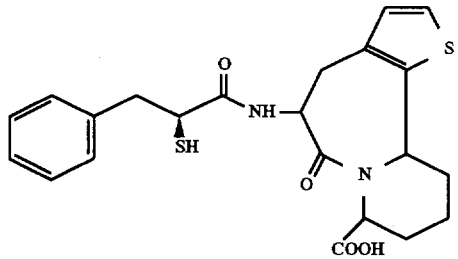

227 mg (0.44 mmol) of the compound obtained from the former fraction in the Example B-7 was reacted in the same manner as that of Synthesis Example B-3. Thus, 143 mg of the title compound, which was a mixture of two diastereomers at a ratio of 7:3, was obtained as white crystals (yield 67%).

$^1$H-NMR (400 MHz, CDCl$_3$, Me$_4$Si) δ; 1.72–2.48(total 7H, m), 2.64–2.78(total 1H, m like q), 3.06–3.15(total 1H, m) 3.25–3.41(total 2H, m), 3.58–3.65(total 1H, m) 4.80 and 5.20(total 1H, each dd and m like d, each J=3.8, 5.0 Hz), 5.40–5.63(total 2H, m) 6.71–6.79(total 1H, m), 7.05–7.14 (total 1H, m) 7.21–7.61(total 6H, m).

Example B-9

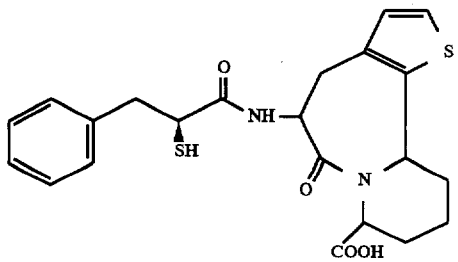

320 mg (0.82 mmol) of the compound obtained from the latter fraction in the Example B-7 was reacted in the same manner as that of Synthesis Example B-3. Thus, 189 mg of the title compound, which was a mixture of two diastereomers at a ratio of 1:1, was obtained as white crystals (yield 63%).

$^1$H-NMR (400 MHz, CDCl$_3$, Me$_4$Si) δ; 1.68–2.52(total 7H, m) 2.84–3.83(total 5H, m), 4.76 and 5.17–5.21(total 1H, each brt and m like brd, each J=4.6 Hz) 5.39–5.63(total 2H, m), 6.67 and 6.71(total 1H, each d and d, each J=5.2 Hz and J=5.2 Hz) 7.03 and 7.11(total 1H, each d, and d, each J=5.2 Hz and J=4.8 Hz) 7.20–7.33(total 6H, m).

¹H-NMR (400 MHz, CDCl₃, Me₄Si) δ; 1.60–2.42(6H, m) 2.15(1H, d, J=9.2 Hz), 2.61(1H, m like dd, J=12.8, 16.0 Hz), 3.07(1H, dd, J=6.4, 13.6 Hz) 3.24–3.32(2H, m), 3.45–3.51 (1H, m) 5.21(1H, dd, J=2.0, 7.6 Hz), 5.29–5.34(1H, m) 5.59–5.66(1H, m), 6.76(1H, d, J=5.2 Hz) 7.01(1H, d, J=5.2 Hz), 7.20–7.34(6H, m).

Example C-1

Methyl [3R-[3α, 6α(S*),9aβ]]-6-[[(2S,3S)-2-acetyl-thio-3-methyl-1-oxopentyl]amino]octahydro-5-oxo-thiazol[3,2-a]azepine-3-carboxylate

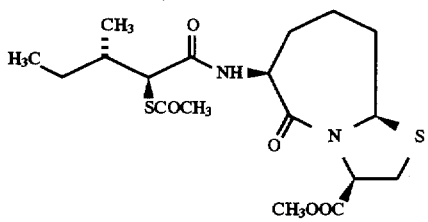

A solution of 225 mg (0.92 mmol) of methyl [3R-[3α,6α (S*),9aβ]]-6-aminooctahydro-5-oxothiazol[3,2-a]-azepine-3-carboxylate in methylene chloride (17 ml) was cooled to 0° C. under cooling with ice. Next, to this solution were continuously added a solution of 193 mg (1.01 mmol) of (2S,3S)-2-acetylthio-3-methylpentanoic acid in methylene chloride (6 ml) and 296 mg (1.20 mmol) of EEDQ. Then, the ice bath was removed, and the obtained mixture was stirred at room temperature overnight under nitrogen. Then, it was concentrated on an evaporator to a ceratin extent. Next, this residue was dissolved in ethyl acetate. The mixture thus obtained was successively washed with a 1N aqueous solution of hydrochloric acid, a saturated aqueous solution of sodium hydrogencarbonate and a saturated aqueous sodium chloride and then dried over anhydrous magnesium sulfate. The residue, which was obtained by filtering it and concentrating the filtrate under reduced pressure, was purified by a column chromatography (hexane:ethyl acetate=3). Thus, 206 mg of the title compound was obtained as an amorphous product (yield: 54%).

¹H-NMR (400 MHz, CDCl₃) δ; 0.88(3H, t, J=7.6 Hz) 0.99(3H, d, J=6.8 Hz), 1.10–1.22(1H, m) 1.51–1.70(2H, m), 1.82–2.14(6H, m) 2.38(3H, s), 3.20(1H, dd, J=6.4, 11.8 Hz), 3.28(1H, dd, J=2.4, 11.8 Hz) 3.79(3H, s), 3.98(1H, d, J=6.8 Hz) 4.54(1H, dd, J=6.4, 10.4 Hz), 5.02(1H, d, J=8.8 Hz) 5.28(1H, dd, J=2.4, 6.4 Hz), 7.41(1H, d, J=6.0 Hz).

Example D-C2

Methyl [3R-[3α, 6α(S*),9aβ]]-6-[[(2S,3S)-2-acetyl-thio-3-methyl-1-oxopentyl]amino]-2,2-dimethyl-5-oxo-octahydrothiazol [3,2-a]azepine-3-carboxylate

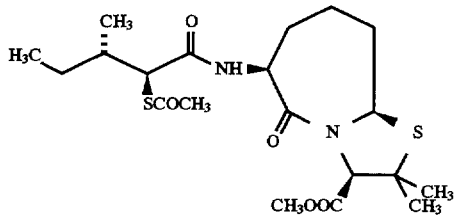

In the same manner as that of Example C-1 and starting with 170 mg (0.62 mmol) of methyl [3R-[3α,6α(S*), 9aβ] ]-6-amino-2,2-dimethyl-5-oxo-octahydrothiazol[3,2-a] azepine-3-carboxylate and 131 mg (0.69 mmol) of (2S,3S) -2-acetylthio-3-methylpentanoic acid obtained in the Synthesis Example C-2, 136 mg of the title compound was obtained as a colorless amorphous product (yield: 49%).

¹H-NMR (400 MHz, CDCl₃) δ; 0.88(3H, t, J=7 Hz) 0.99(3H, d, J=7 Hz), 1.10–1.21(1H, m) 1.41(3H, s) 1.55(3H, s), 1.50–1.62(2H, m) 1.84–2.32(6H, m) 2.38(3H, s), 3.79 (3H, s) 3.98(1H, d, J=7 Hz) 4.52–4.57(1H, m), 4.77(1H, s) 5.11(1H, d, J=10 Hz), 7.43(1H, d, J=6 Hz).

Example C-3

3-[[(2S,3S)-2-Acetylthio-3methyl-1-oxopentyl] amino]-1-ethoxycarbonylmethyl-2,3,4,5-tetrahydro-1H-[1]benzazepin-2-one

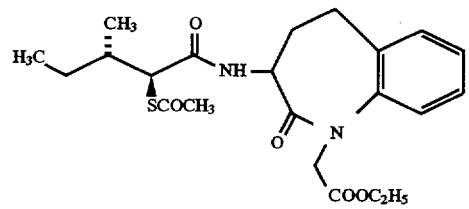

By using 0.525 g (2.00 mmol) of 3-amino-1-ethoxycarbonylmethyl-2,3,4,5-tetrahydro-1H-[1]-benzazepin-2-one and 0.418 g (2.20 mmol) of (2S,3S)-2-acetylthio-3-methylpentanoic acid obtained in the Synthesis Example C-2, the treatment of Example C-1 was repeated. Thus, 0.420 g of the title compound was obtained as a colorless amorphous product (yield 48%).

¹H-NMR (400 MHz, CDCl₃) δ; 7.31–7.00(5H, m), 4.81 and 4.78(total 1H, each d, J=17 Hz), 4.53–4.45(1H, m), 4.33 and 4.31(total 1H, each d, J=17 Hz), 4.22–4.12(2H, m), 3.91 and 3.89(total 1H, each d, J=7 Hz), 3.44–3.33(1H, m) 2.78–2.56(2H, m) 2.37(3H, s), 2.07–1.87(2H, m) 1.59–1.50 (1H, m), 1.28–1.22(3H, m), 0.96 and 0.95(total 3H, each d, J=7 Hz), 0.85(total 3H, each t, J=7 Hz).

Example C-b 4

(S)3-[[(2S,3S)-2-Acetylthio-3-methyl-1-oxopentyl]
amino]-1-ethoxycarbonylmethyl-2,3,4,5-tetrahydro-
1H-[1]benzazepin-2-one

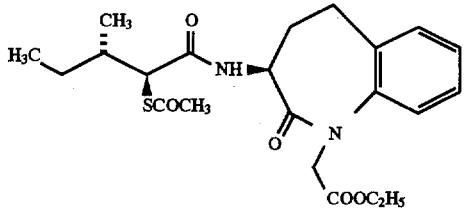

0.550 g (2.10 mmol) of (S)-3-amino-1-ethoxy-
carbonylmethyl-2,3,4,5-tetrahydro-1H-[1]benzazepin-2-one
and 0.434 mg (2.30 mmol) of (2S,3S)-2-acetylthio-3-
methylpentanoic acid were treated in the same manner as
that of Example C-1. Thus, 0.614 g of the title compound
was obtained as a colorless amorphous product (yield 67%).

$^1$H-NMR (400 MHz, CDCl$_3$) δ; 7.31~7.17(3H, m) 7.12
(1H, dd, J=8.1 Hz), 7.01(1H, brd, J=7 Hz) 4.78(1H, d, J=17
Hz), 4.49(1H, dt, J=11.8 Hz) 4.33(1H, d, J=17 Hz),
4.24~4.12(2H, m) 3.89(1H, d, J=7 Hz) 3.38(1H, m),
2.74~2.56(2H, m) 2.37(3H, s) 2.04~1.87(2H, m), 1.56(1H,
m) 1.25(3H, t, J=6 Hz) 1.14(1H, m), 0.96(3H, d, J=7 Hz)
0.86(3H, t, J=8 Hz).

Example C-5

(R)-3-[[(2S,3S)-2-Acethylthio-3-methyl-1-
oxopentyl]amino]-5-ethoxycarbonylmethyl-2,3-
dihydro-1,5-benzothiazepin-4(5H)-one

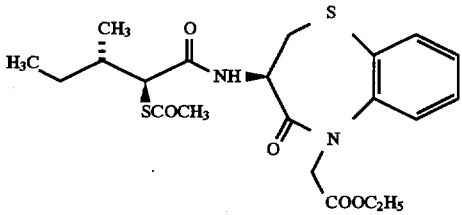

0.208 g (2.74 mmol) of (R)-3-amino-5-
ethoxycarbonylmethyl-2,3-dihydro-1,5-benzothiazepin-4
(5H)-one and 0.166 g (0.872 mmol) of (2S,3S)-2-acetylthio-
3-methylpentanoic acid obtained in the Synthesis Example
C-2 were treated in the same manner as that of Example C-1.
Thus, 0.200 g of the title compound was obtained as a
colorless amorphous product (yield 60%).

$^1$H-NMR (400 MHz, CDCl$_3$) δ; 7.64(1H, dd, J=8.2 Hz)
7.43(1H, dt, J=8.2 Hz), 7.33(1H, dd, J=8.2 Hz) 7.25(1H, dt,
J=8.2 Hz), 7.08(1H, brd, J=7 Hz) 4.81(1H, d, J=17 Hz),
4.67(1H, dt, J=11.7 Hz) 4.25(2H, q, J=7 Hz), 4.15(1H, d,
J=17 Hz) 3.87(1H, d, J=8 Hz), 3.83(1H, dd, J=11.7 Hz)
2.77(1H, t, J=11 Hz), 2.37(3H, s) 2.00(1H, m) 1.54(1H, m),
1.29(3H, t, J=7 Hz) 1.33(1H, m) 0.94(3H, d, J=7 Hz),
0.85(3H, t, J=7 Hz).

Example C-6

Diphenylmethyl [4S-[4α,7α(R*),12bβ]]-7-[[(2S,3S)
-2-acetylthio-3-methyl-1-oxopentyl]amino]-6-oxo-
11-phenyl-1,2,3,4,6,7,8,12b-octahydropyrido[2,1-a]
[2]-benzazepine-4-carboxylate

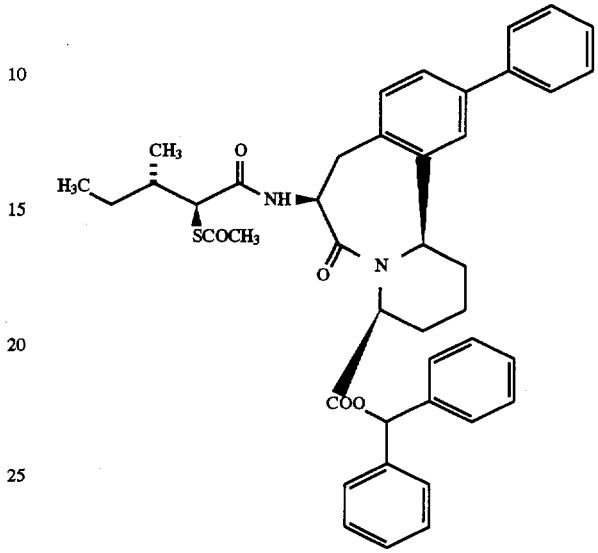

In the same manner as that of Example C-1 and starting
with 1.23 g (2.38 mmol of diphenylmethyl [4S-[4α,7α(R*)
,12bβ]]-7-amino-6-oxo-11-phenyl-1,2,3,4,6,7,8,12b-
octahydropyrido[2,1-a][2]-benzazepine-4-carboxylate
obtained in the Synthesis Example C-9 and 0.52 g (2.74
mmol) of (2S,3S)-2-acetylthio-3-methylpentanoic acid
obtained in the Synthesis Example C-2, 1.22 g of the title
compound was obtained as a colorless amorphous product
(yield 74).

$^1$H-NMR (400 MHz, CDCl$_3$) δ; 7.55~6.91(17H, m) 6.67
(1H, d, J=8 Hz) 6.27(1H, s), 5.65(1H, quint, J=6 Hz)
5.47(1H, d like), 5.41(1H, d like) 4.05(1H, d, J=7 Hz),
3.42(1H, dd, J=16, 6 Hz) 2.61~2.40(2H, m), 2.14(1H, m)
2.00(1H, m) 1.92~1.58(5H, m), 1.24(1H, m) 1.05(3H, d, J=7
Hz) 0.94(3H, t, J=7 Hz).

Example C-7

Methyl [4S-[4α,7α(R*),12bβ]]-11-methylsulfonylamino-
7-[[(2S,3S)2-acetylthio-3-methyl-1-oxopentyl]amino]-
6oxo-1,2,3,4,6,7,8,12b-octahydropyrido[2,1-a]-[2]
benzazepine-4carboxylate

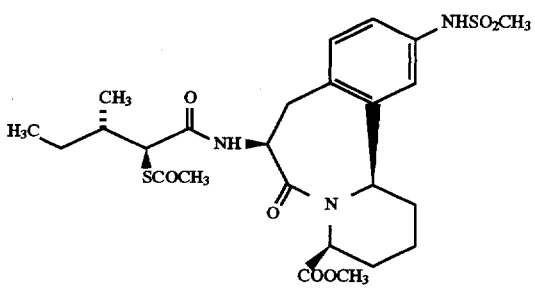

140 mg (0.367 mmol) of methyl [4S-[4α,7α(R*), 12bβ]
]-11-methylsulfonylamino-7-amino-6-oxo-1,2,3,4,6,7,8,
12b-octahydropyrido[2,1-a][2]benzazepine-4-carboxylate obtained in the Synthesis Example C-14 and 77 mg (0.405 mmol) of (2S,3S)-2-acetylthio-3-methylpentanoic acid were dissolved in 10 ml of methylene chloride and 10 ml of ethanol. To this solution was added 118 mg (0.477 mmol) of N-ethoxycarbonyl-2-ethoxy-1,2-dihydroquinoline (EEDQ) at room temperature. Then, the mixture thus obtained was stirred for 19 hours under a nitrogen atmosphere and concentrated under reduced pressure. 1N hydrochloric acid was added to the residue, followed by extraction with dichloromethane. The organic phase was washed with a saturated aqueous sodium chloride, dried over anhydrous magnesium sulfate and then concentrated under reduced pressure. The residue thus obtained was purified by silica gel column chromatography (2:98, ethanol:dichloromethane) to thereby give 198 mg (yield: 98%) of the title compound.

¹H-NMR (400 MHz, CDCl₃, Me₄Si) δ; 0.92(3H, t, J=8 Hz) 1.04(3H, d, J=7 Hz), 1.10~1.15(2H, m) 1.60~2.12(6H, m) 2.39(3H, m), 2.41(3H, s) 2.81(1H, dd, J=17.2, 12.8 Hz), 2.93(3H, s) 3.09(3H, s), 3.48(1H, dd, J=17.2, 5.9 Hz) 4.03(1H, d, J=7 Hz), 5.26(1H, m) 5.36(1H, m) 5.68(1H, m), 6.94~7.68(5H, m).

Example C-8

[3R-[3α,6α,(S*),9aβ]]-6-[[(2S,3S)-3-methyl-1-oxo-2-thiopentyl]amino]-octahydro-5-oxothiazol[3,2-a]-azepine-3-carboxylic acid

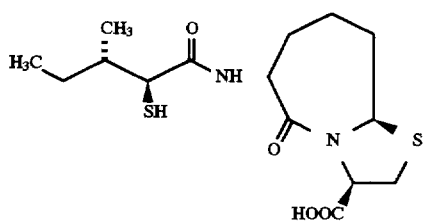

200 mg (0.48 mmol) of methyl [3R-[3α,6α(S*),9aβ]]-6-[[(2S,3S)-2-acetylthio-3-methyl-1-oxopentyl]amino]-octahydro-5-oxothiazol[3,2-a]azepine-3-carboxylate obtained in the Example C-1 was introduced into a flask and 8 ml of degassed ethanol was added thereto, followed by cooling to 0° C. under a nitrogen atmosphere. 3.8 ml of a degassed 1N aqueous solution of lithium hydroxide was added thereto, and the obtained mixture was stirred at room temperature for 50 minutes. The reaction mixture thus obtained was acidified by adding 2.9 ml of a 2N aqueous solution of hydrochloric acid at 0° C. and then extracted with dichloromethane. After the organic phase was washed with a saturated aqueous sodium chloride, it was dried over anhydrous magnesium sulfate and concentrated. The solid residue was recrystallized from hexanedichloromethane. Thus, 150 mg of the title compound was obtained as white crystals (87%).

¹H-NMR (400 MHz, CDCl₃) δ; 0.90(3H, t, J=7 Hz) 1.00(3H, d, J=7 Hz) 1.24(1H, m), 1.55~1.74(2H, m) 1.87 (1H, d, J=8 Hz), 1.90~2.10(6H, m) 3.20(1H, dd, J=6, 12 Hz), 3.24(1H, d, J=7 Hz) 3.36(1H, d, J=2, 12 Hz), 4.62(1H, dd, J=6, 10 Hz) 5.07(1H, t like, J=6 Hz), 5.29(1H, dd, J=2, 6 Hz) 7.69(1H, d, J=6 Hz).

Example C-9

[3R-[3α,6α(S*), 9aβ]]-6-[[(2S,3S)-3-Methyl-1-oxo-2-thiopentyl]amino]-2,2-dimethyl-5-oxo-octahydrothiazal-[3,2-a]azepine-3-carboxylic acid

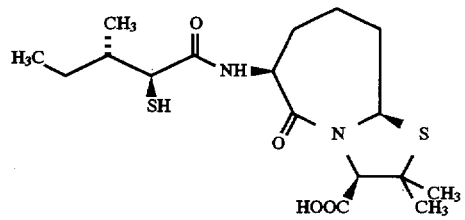

130 mg (0.29 mmol) of methyl [3R-[3α,6α(S*),9aβ]]-6-[[(2S,3S)-2-acetylthio-3-methyl-1-oxopentyl]amino]-2,2-dimethyl-5-oxooctahydrothiazol[3,2-a]azepine-3-carboxylate obtained in the Example C-2 was introduced into a flask and 5.8 ml of degassed methanol was added thereto. To the obtained mixture was added a degassed 1N aqueous solution of sodium hydroxide (2.3 ml) under a nitrogen atmosphere. The obtained mixture was stirred at 45° C. for 8 hours. To the reaction mixture thus obtained was added 1.8 ml of 2N hydrochloric acid, and it was concentrated under reduced pressure to a certain extent. Water (50 ml) was added to the concentrate. The crystals thus precipitated were collected by filtration and air-dried for a while. Thus, 80 mg of the title compound was obtained (yield:71%).

¹H-NMR (400 MHz, CDCl₃) δ; 0.90(3H, t, J=7 Hz) 1.01(3H, d, J=7 Hz), 1.17~1.29(1H, m) 1.53(3H, s) 1.56(3H, s), 1.52~1.68(2H, m) 1.86(1H, d, J=9 Hz), 1.88~2.28(6H, m) 3.27(1H, dd, J=6, 9 Hz), 4.58~4.66(1H, m) 4.79(1H, s) 5.15(1H, d, J=10 Hz), 7.84(1H, d, J=6 Hz).

Example C-10

1-Carboxymethyl-3-[[(2S,3S)-3-methyl-3-oxo-2-thiopentyl]amino]-2,3,4,5-tetrahydro-1H-[1]benzazepin-2-one

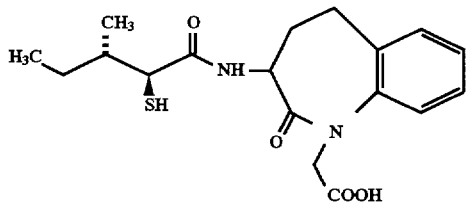

To a mixed solution of 0.385 g (0.89 mmol) of 3-[[(2S, 3S)-2-acetylthio-3-methyl-1-oxopentyl]-amino]-1-ethoxycarbonyl-1H-[1]benzazepin-2-one obtained in the Example C-3 with 15 ml of degassed ethanol was added 4.4 ml of a degassed 1N aqueous solution of sodium hydroxide at 0° C. under a nitrogen atmosphere with stirring. The mixture thus obtained was stirred at room temperature for 1 hour. The reaction mixture was cooled, acidified with 1N hydrochloric acid and extracted with ethyl acetate. The organic phase was washed with water and dried over anhydrous magnesium sulfate. After distilling off the solvent of the organic phase, 0.34 g of the title compound was obtained as a colorless amorphous product (quantitative).

¹H-NMR (400 MHz, CDCl₃) δ; 7.39~7.14(5H, m), 4.7 and 4.71(total 1H, each d, J=17 Hz), 4.57~4.50(1H, m), 4.44 and 4.43(total 1H, each d, J=17 Hz), 3.34~3.10(2H, m) 2.77~2.58(2H, m), 2.03~1.87(2H, m), 1.85 and 1.84(total 1H, each d, J=9 Hz), 1.64~1.50(1H, m) 1.22~1.15(1H, m), 0.95(3H, d, J=7 Hz) 0.86(3H, t, J=7 Hz).

Example C-11

(S)-1-Carboxymethyl-3-[[(2S,3S)-3-methyl-1-oxo-2-thiopentyl]amino]-2,3,4,5-tetrahydro-1H-[1]benzazepin-2-one

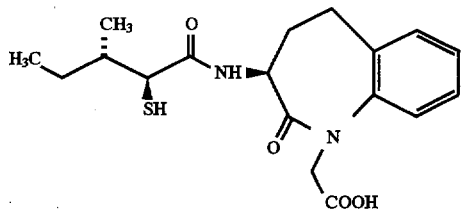

0.600 g (1.38 mmol) of (S)-3-[[(2S,3S)-2-acetylthio-3-methyl-1-oxopentyl]amino]-1-ethoxycarbonylmethyl-2,3,4,5-tetrahydro-1H-[1]benzazepin-2-one obtained in the Example C-4 was hydrolyzed in the same manner as that of Example C-10. Thus, 0.490 g of the title compound was obtained as a colorless amorphous product (yield 97%).

¹H-NMR (400 MHz, CDCl₃) δ; 7.40(1H, brd, J=7 Hz) 7.33~7.14(4H, m), 4.71(1H, d, J=17 Hz) 4.54(1H, dt, J=11, 7 Hz), 4.44(1H, d, J=17 Hz) 3.29(1H, m), 3.17(1H, dd, J=9, 7 Hz) 2.74~2.59(2H, m), 2.04~1.89(2H, m) 1.84(1H, d, J=9 Hz) 1.55(1H, m), 1.17(1H, m) 0.95(3H, d, J=7 Hz) 0.86(3H, t, J=7 Hz).

Example C-12

(R)-3-[[(2S,3S)-3-Methyl-1-oxo-2-thiopentyl]amino]-5-carboxymethyl-2,3-dihydro-1,5-benzothiazepin-4(5H)-one

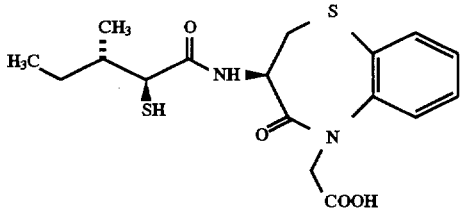

0.187 g (0.43 mmol) of (R)-3-[[(2S,3S)-2-acetylthio-3-methyl-1-oxopentyl]amino]-5-ethoxycarbonylmethyl-2,3-dihydro-1,5-benzothiazepin-4(5H)-one obtained in the Example C-5 was treated in the same manner as that of Example C-10. Thus, 126 mg of the title compound was obtained as white crystals (yield 77%).

¹H-NMR (400 MHz, CDCl₃) δ; 7.67(1H, dd, J=8.1 Hz) 7.53(1H, d, J=7 Hz), 7.46(1H, dt, J=8, 2 Hz) 7.36(1H, dt, J=8, 2 Hz), 7.29(1H, dt, J=8, 1 Hz) 4.91(1H, d, J=18 Hz), 4.72(1H, dt, J=11, 7 Hz) 4.16(1H, d, J=18 Hz), 3.83(1H, dd, J=11, 7 Hz) 3.19(1H, dd, J=9, 6 Hz), 2.88(1H, t, J=11 Hz) 1.94(1H, m), 1.85(1H, d, J=9Hz) 1.54(1H, m) 1.20(1H, m), 0.95(3H, d, J=7 Hz) 0.86(3H, t, J=7 Hz).

Example C-13

[4S-[4α,7α(R*),12bβ]]-7-[[(2S,3S)-2-Acetylthio-3-methyl-1-oxopentyl]amino]-6-oxo-11-phenyl-1,2,3,4,6,7,8,12b-octahydropyrido[2,1-a][2]benzazepine-4-carboxylic acid

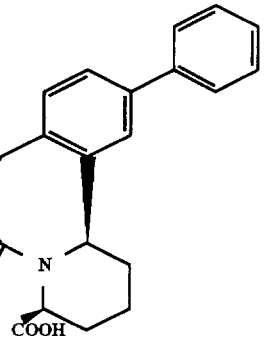

Into a mixed solution of 1.22 g (1.773 mmol) of diphenylmethyl [4S-[4α,7α(R*),12bβ]]-7-[[(2S,3S)-2-acetylthio-3-methyl-1-oxopentyl]amino]-6-oxo-11-phenyl-1,2,3,4,6,7,8,12b-octahydropyrido[2,1-a][2]-benzazepine-4-carboxylate obtained in the Example C-6 with 1.92 ml of anisole was dropped 11.01 ml of trifluoromethanesulfonic acid at 0° C. After stirring the reaction mixture at 0° C. for 40 minutes, it was concentrated at a temperature not exceeding 40° C. The residual oil was subjected to azeotropic distillation with toluene twice. The residual oil was purified by silica gel column chromatography (eluent; chloroform:hexane=4:1 and chloroform:methanol=98.5:1.5, successively). Thus, the title compound was obtained as a colorless amorphous product (0.897 g, yield 97%).

¹H-NMR (400 MHz, CDCl₃) δ; 7.52~7.31(8H, m) 7.04 (1H, d, J=8 Hz), 5.69(1H, quint, J=6 Hz) 5.48(1H, m) 5.18(1H, m), 4.02(1H, d, J=7 Hz) 3.54(1H, m), 2.86(1H, dd, J=16, 12 Hz) 2.51(1H, m) 2.40(3H, s), 2.28(1H, m) 2.11(1H, m) 2.04~1.56(5H, m), 1.20(1H, m) 1.02(3H, d, J=7 Hz) 0.91(3H, t, J=7 Hz).

Example C-14

[4S-[4α,7α(R*),12bβ]]-7-[[(2S,3S)-3-Methyl-1-oxo-2-thiopentyl]amino]-6-oxo-11-phenyl-1,2,3,4,6,7,8,12b-octahydropyrido[2,1-a][2]benzazepine-4-carboxylic acid

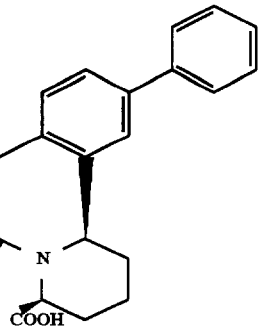

0.780 g (1.492 mmol) of [4S-[4α,7α(R*),12bβ]]-7-[[(2S,3S)-2-acetylthio-3-methyl-1-oxopentyl]amino]-6-oxo-11-phenyl-1,2,3,4,6,7,8,12b-octahydropyrido-[2,1-a][2]benzazepine-4-carboxylic acid obtained in the Example C-13 was dissolved in 20 ml of degassed ethanol and 4.48 ml of a 1.0N aqueous solution of lithium hydroxide was added thereto at 0° C. The mixed solution was stirred under a nitrogen atmosphere for 40 minutes.

The reaction mixture was acidified by adding 20.0 ml of water and 2.0N hydrochloric acid. The white solid thus precipitated was collected by filtration and washed with water. Thus, 0.622 g of the title compound was obtained (yield: 87%).

$^1$H-NMR (400 MHz, CDCl$_3$) δ; 7.66(1H, d, J=7 Hz) 7.58~7.32(7H, m), 7.08(1H, d, J=8 Hz) 5.72(1H, qunit, J=6 Hz), 5.52(1H, m) 5.25(1H, m) 3.60(1H, dd, J=17.6 Hz), 3.23(1H, dd, J=9, 7 Hz) 2.93(1H, dd, J=17, 13 Hz), 2.55(1H, m) 2.34(1H, m) 2.00(2H, m), 1.92(1H, d, J=8 Hz) 1.98~1.61 (4H, m) 1.25(1H, m), 1.03(3H, d, J=7 Hz) 0.93(3H, t, J=7 Hz).

Example C-15

[4S-[4α,7α(R*),12bβ]]-11-Methylsulfonylamino-7-[[(2S,3S)-3-methyl-1-oxo-2-thiopentyl]amino]-6-oxo-1,2,3,4,6,7,8,12b-octahydropyrido[2,1-a][2]benzazepine-4-carboxylic acid

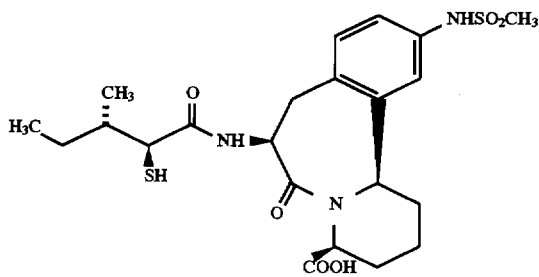

198 mg (0.158 mmol) of methyl [4S-[4α,7α(R*),12bβ]]-11-methylsulfonylamino-7-[[(2S,3S)-2-acetylthio-3-methyl-1-oxopentyl]amino]-6-oxo-1,2,3,4,6,7,8,12b-octahydropyrido[2,1-a][2]-benzazepine-4-carboxylate obtained in the above Example C-7 was introduced into a flask, followed by sufficient purging with nitrogen. Next, 5 ml of degassed ethanol was added thereto and the flask was cooled in an ice bath. Then, 3.6 ml of a degassed 1N aqueous solution of sodium hydroxide was added thereto. After removing the flask from the ice bath, it was slowly warmed to room temperature and the contents thereof were stirred for 1 hour and 40 minutes. 10 ml of a 1N aqueous solution of hydrochloric acid was added to the reaction system, and then it was extracted with dichloromethane. The organic phase was dried over anhydrous magnesium sulfate. The organic phase dried was concentrated under reduced pressure and the residue was crystallized from dichloromethane. Thus, 84 mg (yield: 47%) of the title compound was obtained.

$^1$H-NMR (400 MHz, CDCl$_3$/cD$_3$OD, Me$_4$Si) δ; 0.93(3H, t, J=8 Hz) 1.04(8H, d, J=7 Hz), 1.22~1.35(2H, m) 1.65~2.10 (6H, m) 2.41(2H, m), 2.90(1H, m) 2.91(3H, s) 3.23(1H, d, J=8 Hz), 3.56(1H, dd, J=17.3, 6.1 Hz) 5.23(1H, m), 5.48(1H, m) 5.71(1H, m) 7.01~7.16(3H, m), 7.82(1H, d, J=6.6 Hz).

Example D-1

Preparation of methyl [4S-[4α,7α(R*),12bβ]]-11-methylsulfonylamino-7-(1,3-dioxo-1,3-dihydroisoindol-2-yl)-6-oxo-1,2,3,4,6,7,8,12b-octahydropyrido[2,1-a][2]benzazepine-4-carboxylate

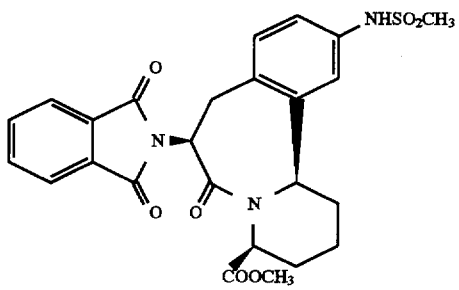

Methyl [4S-[4α,7α(R*),12bβ]]-11-amino-7-(1,3-dioxo-1,3-dihydroisoindol-2-yl)-6-oxo-1,2,3,4,6,7,8,12b-octahydropyrido[2,1-a][2]benzazepine-4-carboxylate (1.50 g, 3.5 mmol) obtained in the above Synthesis Example D-3 was dissolved in methylene chloride (50 ml). Next, to this solution were added pyridine (3 ml) and methanesulfonyl chloride (440 mg, 3.8 mmol) under cooling with ice. The obtained mixture was stirred under a nitrogen atmosphere at room temperature for 2 hours. Further, a 1N aqueous solution of hydrochloric acid (100 ml) was added to the solution stirred under cooling with ice, followed by extraction with methylene chloride. The methylene chloride phase was dried over (MgSO$_4$ was used) and then concentrated under reduced pressure. Next, the residue was purified by silica gel column chromatography (3:1 methylene chloride/ethyl acetate) to thereby give the title compound (1.14 g, 64%).

$^1$H-NMR (400 MHz, CDCl$_3$, Me$_4$Si) δ; 1.60~2.46(6H, m), 3.00(3H, s), 3.23(3H, s), 3.42(1H, dd, J=17.1, 7.0 Hz), 4.46(1H, dd, J=17.1, 11.9 Hz), 5.21(1H, m), 5.44(1H, m), 6.04(1H, dd, J=11.9, 7.0 Hz), 6.65(1H, s), 7.05(1H, dd, J=8.2, 2.2 Hz), 7.19(1H, d, J=8.2 Hz), 7.24(1H, d, J=2.2 Hz), 7.74~7.90(4H, m).

Example D-2

Methyl [4S-[4α,7α(R*),12bβ]]11-methylsulfonylamino-7-amino-6-oxo-1,2,3,4,6,7,8,12b-octahydropyrido-[2,1-a][2]benzazepine-4-carboxylate

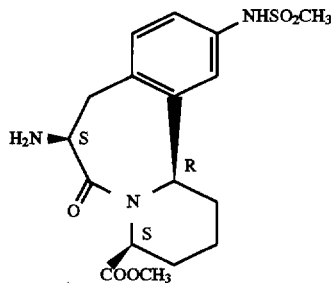

Methyl [4S-[4α,7α(R*),12bβ]]-11-methylsulfonylamino-7-(1,3-dioxo-1,3-dihydroisoindol-2-yl)-6-oxo-1,2,3,4,6,7,8,12b-octahydropyrido[2,1-a][2]benzazepine-4-carboxylate (1.14 g, 2.23 mmol) obtained in the above Example D-1 was dissolved in methanol (49 ml). Next, to this solution was added hydrazine hydrate (123 mg, 2.46 mmol). Then, the obtained mixture was stirred at room temperature under an argon atmosphere for 66 hours. The solution stirred was concentrated under reduced pressure. Further, methylene chloride was added to the concentrate and the insoluble matters were removed out by filtration. Then, ethyl acetate was added to the filtrate. Thus, the title compound was obtained as white crystals (0.50 g, 59%).

$^1$H-NMR (400 MHz, $CD_3OD/CDCl_3$, $Me_4Si$) δ; 1.60~2.45(6H, m), 2.87(1H, dd, J=17.6 12.7 Hz), 2.94(3H, s),3.13(3H, s), 3.40(1H, dd, J=17.6, 6.0 Hz), 4.65(1H, dd, J=12.7, 6.0 Hz), 5.30(1H, m), 5.43(1H, m), 7.02(1H, dd, J=8.2, 2.2 Hz), 7.11(1H, d, J=8.2 Hz), 7.16(1H, d, J=2.4 Hz).

Example D-3

Methyl [4S-[4α,7α(R*), 12bβ]]-11-methylsulfonylamino-7-[[(S)-2-acetylthio-3-phenyl-1-oxopropyl]amino-6-oxo-1,2,3,4,6,7,8,12b-octahydropyrido[2,1-a]-[2benzazepine-4-carboxylate

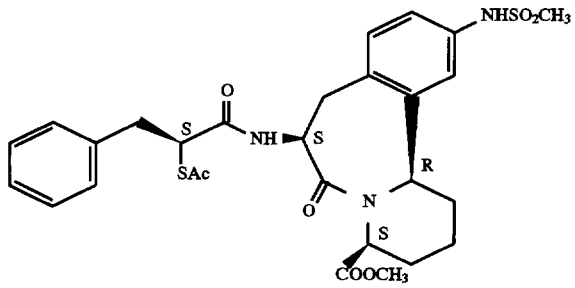

Methyl [4S-[4α,7α(R*),12bβ]]-11-methylsulfonylamino-7-amino-6-oxo-1,2,3,4,6,7,8,12b-octahydropyrido[2,1-a][2] benzazepine-4-carboxylate(310 mg, 0.81 mmol) obtained in the above Example D-2 and (S)-acetylthio-3-phenylpropionic acid (183 mg, 0.81 mmol) were dissolved in methylene chloride (16 ml) and tetrahydrofuran (32 ml). Next, to this solution was added N-ethoxycarbonyl-2-ethoxy-1,2-dihydroquinoline (EEDQ, 221 mg, 0.89 mmol). Then, the mixture thus obtained was stirred under a nitrogen atmosphere for 20 hours and the solution stirred was concentrated under reduced pressure. Further, a 1N aqueous solution of hydrochloric acid was added to theconcentrate, followed by extraction with methylene chloride. Next, after the organic phase was washed with a 1N aqueous solution of hydrochloric acid, water and a saturated aqueous sodium chloride, it was dried over ($MgSO_4$ was used) and concentrated under reduced pressure. The obtained residue was purified by silica gel chromatography (1:1 hexane/ethyl acetate) to thereby give the title compound (240 mg, 50%).

$^1$H-NMR (400 MHz, $CDCl_3$, $Me_4Si$) δ; 1.66~2.40(6H, m), 2.36(3H, s), 2.72(1H, dd, J=17.4, 12.7 Hz), 2.93(3H, s), 3.06(1H, dd, J=14.1, 7.9 Hz), 3.10(3H, s), 3.35(1H, dd, J=14.1, 7.1 Hz), 3.46(1H, m), 4.36(1H, t, J=7.4 Hz), 5.23 (1H, m), 5.33(1H, m), 5.58(1H, m), 6.93~7.56(10H, m).

Example D-4

Methyl [4S-[4α,7α(R*),12bβ]]-11-methylsulfonylamino-7-[[(S)-2-acetylthio-3-(4-methoxyphenyl)-1-oxopropyl]amino]-6-oxo-1,2,3,4,6,7,8,12b-octahydropyrido-[2,1-a][2]benzazepine-4-carboxylate

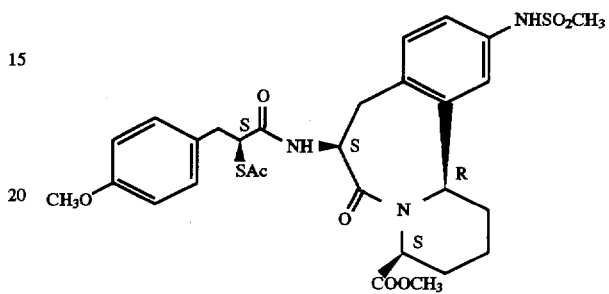

Methyl [4S-[4α,7α(R*),12bβ]]-11-methylsulfonylamino-7-amino-6-oxo-1,2,3,4,6,7,8,12b-octahydropyrido-[2,1-a][2]benzazepine-4-carboxylate (188 mg, 0.49 mmol) obtained in the above Example D-2 and 2(S)-acetylthio-3-(4-methoxyphenyl)-propionic acid (125 mg, 0.49 mmol) were dissolved in methylene chloride (10 ml), tetrahydrofuran (20 ml) and ethanol (40 ml). Next, to this solution was added 405 mg (1.64 mmol) of EEDQ at room temperature. Then, the mixture thus obtained was stirred under a nitrogen atmosphere for 5 hours and the solution stirred was concentrated under reduced pressure. Further, a 1N aqueous solution of hydrochloric acid was added to the concentrate, followed by extraction with methylene chloride. Next, the organic phase was washed with a 1N aqueous solution of hydrochloric acid, water and a saturated aqueous sodium chloride, and then it was dried over ($MgSO_4$ was used) and concentrated under reduced pressure. The obtained residue was purified by silica gel chromatography (1:1 hexane/ethyl acetate) to thereby give the title compound (133 mg, 44%).

$^1$H-NMR (400 MHz, $CDCl_3$, $Me_4Si$) δ; 1.66~2.05(6H, m), 2.37(3H, s), 2.72(1H, dd, J=17.3, 12.7 Hz), 2.94(3H, s), 3.00(1H, dd, J=14.3, 7.7 Hz), 3.11(3H, s), 3.28(1H, dd, J=14.3, 7.7 Hz), 3.48(1H, dd, J=17.3, 5.7 Hz), 3.79(3H, s), 4.30(1H, t, J=7.7 Hz), 5.23(1H, brd), 5.33(1H, brd), 5.57 (1H, quint, J=6.2 Hz), 6.83(2H, d, J=8.7 Hz), 6.97(1H, d, J=8.2 Hz), 7.01(1H, dd, J=8.2, 2.0 Hz), 7.24(1H, s), 7.16 (2H, d, J=8.7 Hz), 7.50(1H, d, J=6.2 Hz).

Example D-5

[4S-[4α,7α(R*),12bβ]]-11-methylsulfonylamino7-[[(S)-2-mercapto-3-phenyl-1-oxopropyl)amino-6-oxo-1,2,3,4,6,7,8,12b-octahydropyrido-[2,1-a][2]benzazepine-4-carboxylic acid

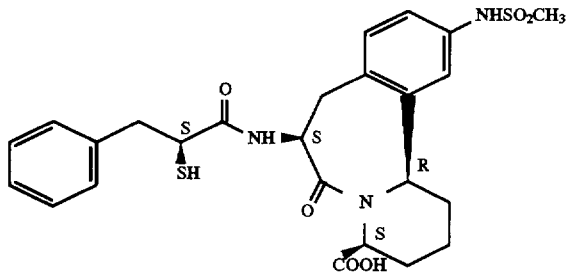

Methyl [4S-[4α,7α(R*),12bβ]]-11-methylsulfonylamino7-[[(S)-2-acetylthio-3-phenyl-1-oxopropyl]amino-6-oxo-1,2,3,4,6,7,8,12b-octahydropyrido-[2,1-a][2]benzazepine-4-carboxylate (228 mg, 0.39 mmol) obtained in the above Example D-3 was introduced into a flask, followed by sufficient purging with nitrogen. Next, degassed tetrahydrofuran (1 ml) and methanol (6.2 ml) were added in the flask, and the flask was cooled in an ice bath. A degassed 1N lithium hydroxide solution (3.3 ml) was added to the obtained solution. After removing the flask from the ice bath, the flask was slowly warmed to room temperature and the obtained mixture was stirred for 5 hours. Next, the solution stirred was concentrated under reduced pressure and the concentrate was extracted with methylene chloride. Then, the aqueous phase was separated and the pH, thereof was adjusted to 1 with a 1N aqueous solution of hydrochloric acid. The concentrate was extracted with methylene chloride. Next, the organic phase was dried over (MgSO$_4$ was used) and then concentrated under reduced pressure. To the concentrate, diisopropyl ether was added, followed by trituration. Thus, the title compound (110 mg, 53%) was obtained.

$^1$H-NMR (400 MHz, CDCl$_3$/CD$_3$OD, Me$_4$Si) δ; 1.70~2.50(6H, m), 2.85(1H, dd, J=17.4, 12.7 Hz), 2.90(3H, s), 3.12(1H, dd, J=13.8, 7.5 Hz), 3.29(1H, dd, J=13.8, 6.6 Hz), 3.52(1H, m), 3.67(1H, m), 5.19(1H, m), 5.47(1H, m), 5.65(1H, m), 7.03~7.80(10H, m).

Example D-6

[4S-[4α,7α(R*),12bβ]]-11-methylsulfonylamino-7-[[(S)-2-mercapto-3-(4-methoxyphenyl)-1-oxopropyl]amino-6-oxo-1,2,3,4,6,7,8,12b-octahydropyrido-[2,1-a][2]benzazepine-4-carboxylic acid

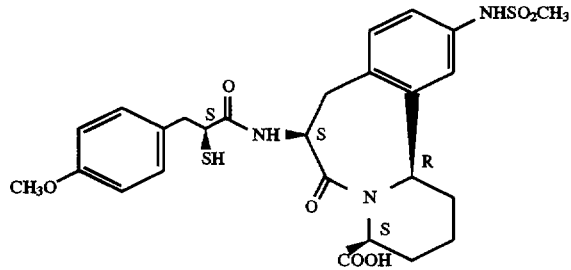

Methyl [4S-[4α,7α(R*),12bβ]]-11-methylsulfonylamino-7-[[(S)-2-acetylthio-3-(4-methoxyphenyl)-1-oxopropyl]amino-6-oxo-1,2,3,4,6,7,8,12b-octahydropyrido-[2,1-a][2]benzazepine-4-carboxylate (133 mg, 0.22 mmol) obtained in the above Example D-4 was introduced into a flask, followed by sufficient purging with nitrogen. Next, degassed ethanol (20 ml) was added into the flask and then a degassed 1N aqueous solution of sodium hydroxide (5 ml) was further added into the flask. The obtained mixture was stirred at room temperature for 3 hours. Next, a 1N aqueous solution of hydrochloric acid (10 ml) was added to the solution stirred, followed by concentration under reduced pressure. To the concentrate were added methylene chloride and water, followed by extraction with methylene chloride. Further, the organic phase separated was dried over (MgSO$_4$ was used) and concentrated under reduced pressure to thereby give the title compound (80 mg, 65%).

$^1$H-NMR (400 MHz, CDCl$_3$/CD$_3$OD, Me$_4$Si) δ; 1.74~1.86(3H, m), 1.92~2.07(1H, m), 2.37~2.49(2H, m), 2.83(3H, s), 2.83(1H, m), 3.11(1H, dd, J=14.0, 6.9 Hz), 3.23(1H, dd, J=13.8, 6.5 Hz), 3.55~3.66(2H, m), 3.80(3H, s), 5.26(1H, brd), 5.43(1H, brd), 5.62(1H, quint, J=6.0 Hz), 6.57(1H, d, J=6.1 Hz), 6.86(2H, d, J=8.7 Hz), 6.96(1H, d, J=6.1 Hz), 7.13~7.19(3H, m), 7.54(1H, s), 7.65(1H, d, J=6.2 Hz).

Example E-1

Diphenylmethyl [4S-[4α,7α(R*),12bβ]]-7-amino-6-oxo-11-phenyl-1,2,3,4,6,7,8,12b-octahydropyrido[2,1-a][2]benzazepine-4-carboxylate

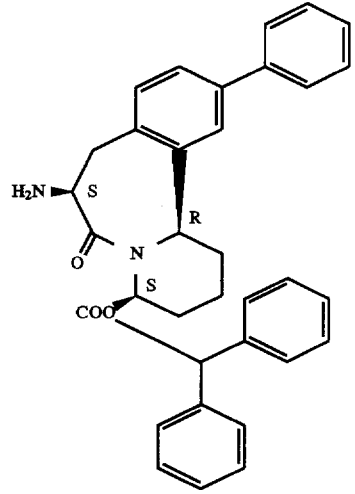

Diphenylmethyl [4S-[4α,7α(R*),12bβ]]-7-(1,3-dihydro-1,3-dioxo-2H-isoindol-2-yl)-6-oxo-11-phenyl-1,2,3,4,6,7,8,12b-octahydropyrido[2,1-a][2]benzazepine-4-carboxylate (2.03 g, 3.14 mmol) obtained in the Synthesis Example E-6 was dissolved in a mixed solution of methanol (40 ml) with tetrahydrofuran (THF, 20 ml), followed by addition thereto of hydrazine monohydrate (0.34 ml, 7.10 mmol). The mixture thus obtained was heated under reflux for 3 hours. The reaction mixture was concentrated and the residue was dissolved in CH$_2$Cl$_2$, and the insoluble matters were removed out by filtration. The filtrate was concentrated and the sticky residue was purified by silica Eel column chromatography (eluent; CHCl$_3$:MeOH: aqueous ammonia (NH$_4$OH)=98:2:0.2). Thus, the title compound was obtained as a colorless amorphous product (1.20 g, yield 74%).

$^1$H-NMR (400 MHz, CDCl$_3$) δ; 7.40(4H, m), 7.31(1H, tt, J=7, 2 Hz), 7.24(1H, d, J=2 Hz), 7.15(1H, dd, J=8, 2 Hz), 6.99(2H, dd, J=8, 4 Hz), 6.87(2H, dd, J=8, 2 Hz), 6.33(1H, d, J=8 Hz), 6.20(1H, s), 5.42~5.33(2H, m), 4.53(1H, dd, J=10, 6 Hz), 3.17(1H, dd, J=16, 6 Hz), 2.58(1H, dd, J=16, 10 Hz), 2.40(2H, m), 1.94(1H, m), 1.85~1.58(3H, m).

Example E-2

Diphenylmethyl [4S-[4α,7α(R*),12bβ]]-7-[(S)-2-acetylthio-3-phenylpropionylamino]-6-oxo-11-phenyl-1,2,3,4,6,7,8,12b-octahydropyrido[2,1-a]-[2]benzazepine-4-carboxylate

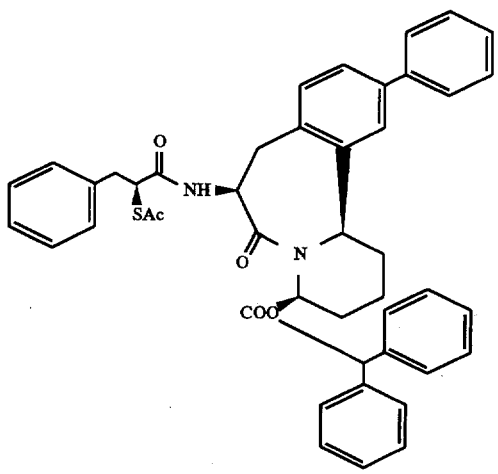

Diphenylmethyl [4S-[4α,7α(R*),12bβ]]-7-amino-6-oxo-11-phenyl-1,2,3,4,6,7,8,12b-octahydropyrido[2,1-a][2]benzazepine-4-carboxylate (0.59 g, 1.14 mmol) obtained in the Example E-1 and (S)-2-acetylthio-3-phenylpropionic acid (0.27 g, 1.20 mmol) were dissolved in $CH_2Cl_2$ (30 ml), and EEDQ (0.37 g, 1.48 mmol) was added thereto. The mixed solution was stirred at room temperature overnight. The reaction mixture was partitioned into $CH_2Cl_2$ and water, and the $CH_2Cl_2$ phase was washed with water, a saturated aqueous solution of sodium hydrogencarbonate and a saturated aqueous sodium chloride. The $CH_2Cl_2$ phase was dried over magnesium sulfate and then concentrated. Thus, the title compound was obtained as a colorless amorphous product (0.89 g, yield 109%). This product was not purified but used in the subsequent reaction as such.

$^1$H-NMR (400 MHz, $CDCl_3$) δ; 7.52~7.41(4H, m), 7.40~7.12(15H, m), 7.04(2H, dd, J=8.4 Hz), 6.93(2H, dd, J=8, 2 Hz), 6.67(1H, d, J=8 Hz), 6.26(1H, s), 5.59(1H, quint, J=6 Hz), 5.44(1H, m), 5.38(1H, d, J=6 Hz), 4.39(1H, t, J=7 Hz), 3.41(1H, dd, J=16, 6 Hz), 3.36(1H, dd, J=14, 7 Hz), 3.07(1H, dd, J=14, 7 Hz), 2.54(1H, dd, J=16, 10 Hz), 2.47(2H, m), 2.40(3H, s), 2.00(1H, m), 1.87~1.70($^{3H}$, m).

Example E-3

Diphenylmethyl [4S-[4α,7α(R*),12bβ]]-7-[(S)-2-acetylthio-3-(4-methoxyphenyl)propionylamino]-6-oxo-11-phenyl-1,2,3,4,6,7,8,12b-octahydropyrido[2,1-a][2]benzazepine-4-carboxylate

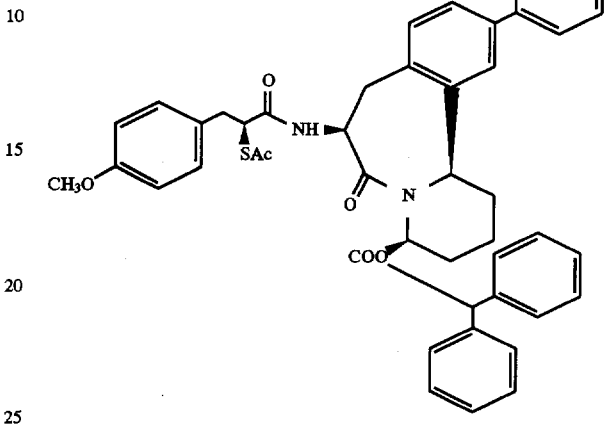

In the same manner as that of Example E-2 and starting with of diphenylmethyl [4S-[4α,7α(R*),12bβ]]-7-amino-6-oxo-11-phenyl-1,2,3,4,6,7,8,12b-octahydropyrido[2,1-a][2]benzazepine-4-carboxylate (0.59 g, 1.14 mmol) obtained in the Example E-1 and (S)-2-acetylthio-3-(4-methoxyphenyl) propionic acid (0.31 g, 1.20 mmol), the title compound was obtained as a colorless amorphous product (0.81 g, yield 95%).

$^1$H-NMR (400 MHz, $CDCl_3$) δ; 7.42~7.34(4H, m), 7.31 (1H, m), 7.24~7.04(10H, m), 6.96(2H, dd, J=8, 4 Hz), 6.86(2H, dd, J=8, 2 Hz), 6.77(2H, d, J=8 Hz), 6.59(1H, d, J=8 Hz), 6.19(1H, s), 5.51(1H, quint, J=6 Hz), 5.37(1H, m), 5.31(1H, d, J=6 Hz), 4.31(1H, t, J=7 Hz), 3.72(3H, s), 3.34(1H, dd, J=16, 6 Hz), 3.20(1H, dd, J=14, 7 Hz), 2.94 (1H, dd, J=14, 7 Hz), 2.47(1H, dd, J=16, 10 Hz), 2.40(2H, m), 2.33(3H, s), 1.92(1H, m), 1.81~1.62(3H, m).

Example E-4

[4S-[4α,7α(R*),12bβ]]-7-[(S)-2-Acetylthio-3-phenylpropionylamino]-6-oxo-11-phenyl-1,2,3,4,6,7,8,12b-octahydropyrido[2,1-a][2]benzazepine-4-carboxylic acid

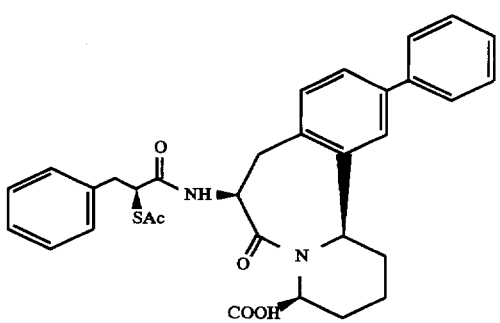

Into a mixed solution of diphenylmethyl [4S-[4α,7α(R*),12bβ]]-7-[(S)-2-acetylthio-3-phenylpropionylamino]-6-oxo-11-phenyl-1,2,3,4,6,7,8,12b-octahydropyrido[2,1-a][2]

benzazepine-4-carboxylate (0.89 g, about 1.14 mmol) obtained in the Example E-2 with anisole (1.24 ml) was dropped trifluoromethanesulfonic acid (TFA, 7.08 ml) at 0° C. After stirring the reaction mixture at 0° C. for 20 minutes, it was concentrated at a temperature not exceeding 40° C. The residual oil was subjected to azeotropic distillation with benzene twice. The residual oil was purified by silica gel column chromatography (eluent; $CH_2Cl_2$: Hex=1:2 and $CH_2Cl_2$:MeOH=99:1, successively). Thus, the title compound was obtained as a colorless amorphous product (0.64 g, yield 100% 2 steps from Example E-1).

$^1$H-NMR (400 MHz, $CDCl_3$) δ; 7.38~7.14(12H, m), 7.00 (1H, d, J=8 Hz), 5.57(1H, quint, J=6 Hz), 5.41(1H, m), 5.14(1H, d, J=6 Hz), 4.29(1H, t, J=7 Hz), 3.51(1H, dd, J=16, 6 Hz), 3.28(1H, dd, J=14, 7 Hz), 2.99(1H, dd, J=14, 7 Hz), 2.73(1H, dd, J=16, 10 Hz), 2.46(1H, m), 2.29(3H, s), 2.26 (1H, m), 2.00~1.60(4H, m).

Example E-5

[4S-[4α,7α(R*),12bβ]]-7-[(S)-2-Acetylthio-3-(4-methoxyphenyl)propionylamino]-6-oxo-11-phenyl-1,2,3,4,6,7,8,12b-octahydropyrido[2,1-a][2]benzazepine-4-carboxylic acid

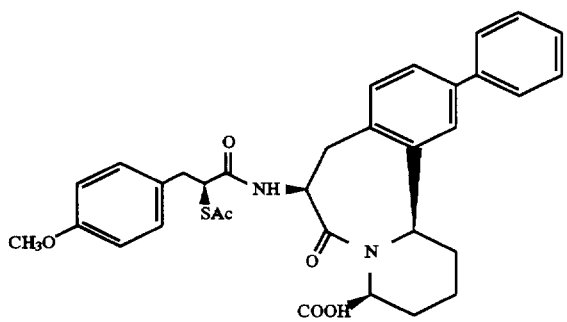

In the same manner as that of Example E-4 and starting with diphenylmethyl [4S-[4α,7α(R*),12bβ]]-7-[(S)-2-acetylthio-3-(4-methoxyphenyl)propionylamino]-6-oxo-11-phenyl-1,2,3,4,6,7,8,12b-octahydropyrido[2,1-a][2]benzazepine-4-carboxylate (0.81 g, 1.08 mmol) obtained in the Example E-3, the title compound was obtained as a colorless amorphous product (0.52 g, yield 81%).

$^1$H-NMR (400 MHz, $CDCl_3$) δ; 7.45~7.32(5H, m), 7.29~7.24(3H, m), 7.08(2H, d, J=8 Hz), 6.96(1H, d, J=8 Hz), 6.76(2H, d, J=8 Hz), 5.53(1H, quint, J=6 Hz), 5.38(1H, brd), 5.09(1H, brd, J=6 Hz), 4.22(1H, t, J=7 Hz), 3.72(3H, s), 3.47(1H, dd, J=16, 6 Hz), 3.19(1H, dd, J=14, 7 Hz), 2.92 (1H, dd, J=14, 7 Hz), 2.71(1H, dd, J=16, 10 Hz), 2.43(1H, m), 2.28(3H, s), 2.22(1H, m), 1.97~1.59(4H, m).

Example E-6

[4S-[4α,7α(R*),12bβ]]-7-[(S)-2-Mercapto-3-phenylpropionylamino]-6-oxo-11-phenyl-1,2,3,4,6,7,8,12b-octahydropyrido[2,1-a][2]benzazepine-4-carboxylic acid

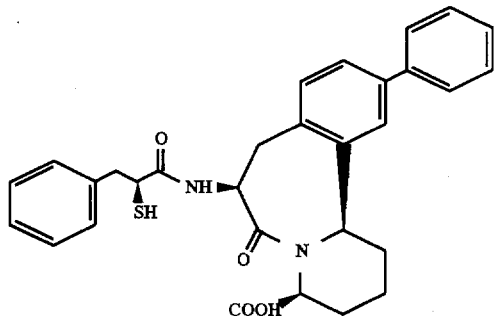

[4S-[4α,7α(R*),12bβ]]-7-[(S)-2-acetylthio-3-phenylpropionylamino]-6-oxo-11-phenyl-1,2,3,4,6,7,8,12b-octahydropyrido[2,1-a][2]benzazepine-4-carboxylic acid (0.55 g, 1.00 mmol) obtained in the Example E-4 was dissolved in degassed THF (2.0 ml) and methanol (10 ml). To this solution was added a 1.0N aqueous solution of lithium hydroxide (4.00 ml). The mixture was stirred at room temperature under a nitrogen atmosphere for 45 minutes. A 2.0N aqueous solution of hydrochloric acid (3.00 ml) was dropped into the mixture, and then water was added thereto. The obtained mixture was vigorously stirred. The white crystals thus precipitated were collected by filtration, washed with water and dried under reduced pressure. Thus, the title compound was obtained (0.45 g, yield 87%).

$^1$H-NMR (400 MHz, $CDCl_3$) δ; 7.75(1H, d, J=7 Hz), 7.66(2H, d, J=8 Hz), 7.59(2H, t, J=8 Hz), 7.55~7.37(7H, m), 7.22(1H, d, J=8 Hz), 5.81(1H, quint, J=6 Hz), 5.65(1H, m), 5.36(1H, d, J=6 Hz), 3.82~3.68(2H, m), 3.45(1H, dd, J=14, 7 Hz), 3.30(1H, dd, J=14, 7 Hz), 2.99(1H, dd, J=17, 12 Hz), 2.70(1H, m), 2.50(1H, m), 2.21(1H, d, J=9 Hz), 2.23~1.85 (4H, m).

Example E-7

[4S-[4α,7α(R*),12bβ]]-7-[(S)-2-Mercapto-3-(4-methoxyphenyl)propionylamino]-6-oxo-11-phenyl-1,2,3,4,6,7,8,12b-octahydropyrido[2,1-a][2]benzazepine-4-carboxylic acid

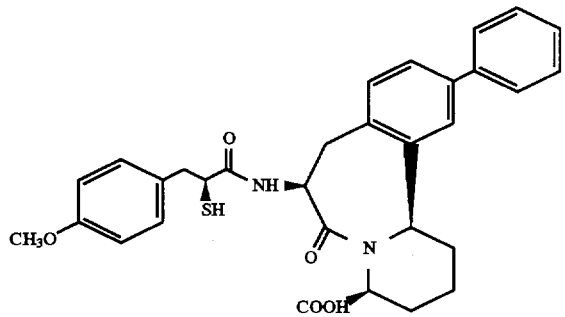

In the same manner as that of Example E-6 and starting with [4S-[4α,7α(R*),12bβ]]-7-[(S)-2-acetylthio-3-(4-methoxyphenyl)propionylamino]-6-oxo-11-phenyl-1,2,3,4,6,7,8,12b-octahydropyrido[2,1-a][2]-benzazepine-4- carboxylic acid (0.42 g, 0.708 mmol) obtained in the Example E-5, the title compound was obtained as white crystals (0.37 g, yield 95%).

¹H-NMR (400 MHz, CDCl₃) δ; 7.51(1H, d, J=7 Hz), 7.43(2H, d, J=8 Hz), 7.36(2H, t, J=8 Hz), 7.28(2H, m), 7.08(2H, d, J=8 Hz), 6.99(1H, d, J=8 Hz), 6.78(2H, d, J=8 Hz), 5.57(1H, quint, J=6 Hz), 5.42(1H, m), 5.13(1H, d like, J=6 Hz), 3.73(3H, s), 3.50(2H, m), 3.14(1H, dd, J=14, 7 Hz), 3.03(1H, dd, J=14, 7 Hz), 2.76(1H, dd, J=17, 12 Hz), 2.47(1H, m), 2.28(1H, m), 1.97(1H, d, J=6 Hz), 2.00~1.63 (4H, m).

Example E-8

Diphenylmethyl [4S-[4α,7α(R*),12bβ]]-7-[(S)-2-acetylthio-3-methylbutyrylamino]-6-oxo-11-phenyl-1,2,3,4,6,7,8,12b-octahydropyrido[2,1-a][2]benzazepine-4-carboxylate

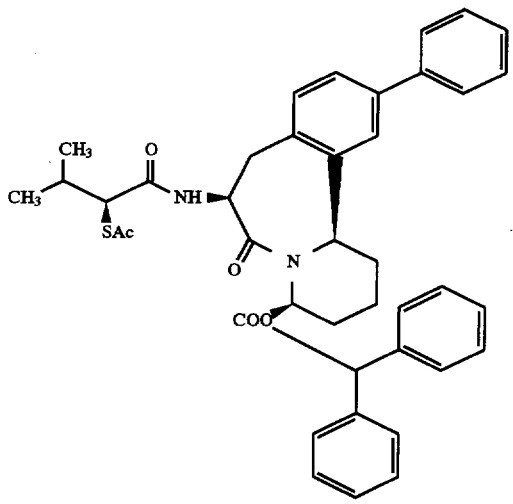

In the same manner as that of Example E-2 and starting with diphenylmethyl [4S-[4α,7α(R*),12bβ]]-7-amino-6-oxo-11-phenyl-1,2,3,4,6,7,8,12b-octahydropyrido[2,1-a][2] benzazepine-4-carboxylate (0.4 g, 0.774 mmol) obtained In the Example E-1 and (S)-2-acetylthio-3-methylbutanoic acid (0.136 g, 0.774 mmol), the title compound was obtained as a colorless amorphous product (0.36 g, yield 69%).

¹H-NMR (400 MHz, CDCl₃) δ; 7.54~6.92(17H, m), 6.68 (1H, d, J=8 Hz), 6.28(1H, s), 5.65(1H, quint, J=6 Hz), 5.49~5.40(2H, m), 4.00(1H, d, J=7 Hz), 3.42(1H, dd, J=16, 6 Hz), 2.60~2.37(7H, m), 2.02(1H, m), 1.88~1.72(3H, m), 1.08(3H, d, J=7 Hz), 1.04(3H, d, J=7 Hz).

Example E-9

[4S-[4α,7α(R*),12bβ]]-7-[(2)-2-Acetylthio-3-methylbutyrylamino]-6-oxo-11-phenyl-1,2,3,4,6,7,8, 12b-octahydropyrido[2,1-a][2]benzazepine-4-carboxylic acid

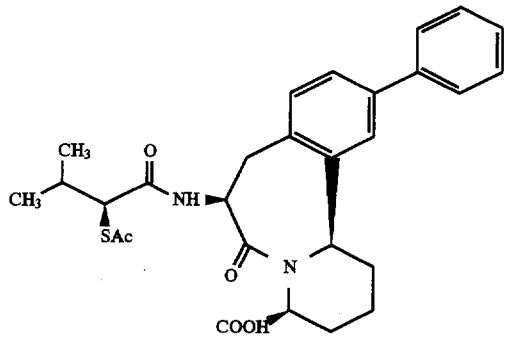

In the same manner as that of Example E-4 and starting with diphenylmethyl [4S-[4α,7α(R*),12bβ]]-7-[(S)-2-acetylthio-3-methylbutyrylamino]-6-oxo-11-phenyl-1,2,3,4, 6,7,8,12b-octahydropyrido[2,1-a][2]-benzazepine-4-carboxylate (0.36 g, 0.533 mmol) obtained in the Example E-8, the title compound was obtained as a colorless amorphous product (0.157 g, yield 58%).

¹H-NMR (400 MHz, CDCl₃) δ; 7.55~7.28(8H, m), 7.03 (1H, brs), 5.69(1H, quint, J=6 Hz), 5.46(1H, m), 3.97(1H, d, J=7 Hz), 3.51(1H, m), 2.96~2.82(2H, m), 2.56~2.20(7H, m), 2.00~1.60(4H, m), 1.05(3H, d, J=7 Hz), 1.01(3H, d, J=7 Hz).

Example E-10

[4S-[4α,7α(R*),12bβ]]-7-[(S)-2-Mercapto-3-methylbutyrylamino]-6-oxo-11-phenyl-1,2,3,4,6,7,8, 12b-octahydropyrido[2,1-a][2]benzazepine-4-carboxylic acid

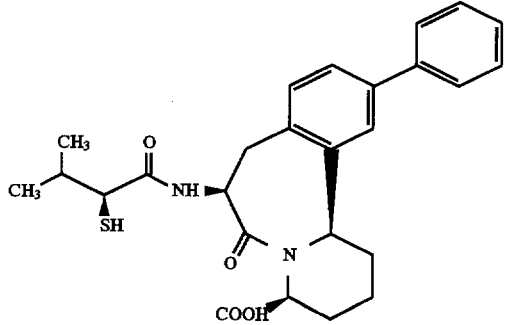

4S-[4α,7α(R*),12bβ]]-7-[(S)-2-acetylthio-3--methylbutyrylamino]-6-oxo-11-phenyl-1,2,3,4,6,7,8,12b-octahydropyrido[2,1-a][2]benzazepine-4-carboxylic acid (0.147 g, 0.289 mmol) obtained in the Example E-9 was dissolved in degassed ethanol (5 ml). To this solution was added a 1.0N aqueous solution of lithium hydroxide (0.9 ml). The mixture was stirred under a nitrogen atmosphere at room temperature for 1 hour. The reaction mixture was acidified by adding a 1.0N aqueous solution of hydrochloric acid under cooling with ice and stirring, followed by extraction with dichloromethane. The organic phase was washed with a saturated aqueous sodium chloride and dried over anhydrous magnesium sulfate. After distilling off the solvent of the organic phase, the obtained residue was crystallized from dichloromethane-hexane. Further, the mother liquor was evaporated to dryness and then treated with isopropyl ether-hexane. Thus, 0.103 g (yield 76%) of the title compound was obtained.

¹H-NMR (400 MHz, CDCl₃) δ; 7.68(1H, d, J=7 Hz), 7.51(2H, d, J=6 Hz), 7.44(2H, d, J=8 Hz), 7.39~7.33(3H, m), 7.08(1H, d, J=8 Hz), 5.73(1H, quint, J=6 Hz), 5.53(1H, m), 5.26(1H, m), 3.61(1H, dd, J=17, 6 Hz), 3.19(1H, dd, J=9, 7 Hz), 2.93(1H, dd, J=17, 13 Hz), 2.60~2.22(3H, m), 2.08~1.70(4H, m), 1.05(6H, d, J=7 Hz).

Example E-11

Diphenylmethyl [4S-[4α,7α(R*),12bβ]]-7-[(2S,3S)-2-acetylthio-3-methylvalerylamino]-6-oxo-11-phenyl-1,2,3,4,6,7,8,12b-octahydropyrido[2,1-a][2]benzazepine-4-carboxylate

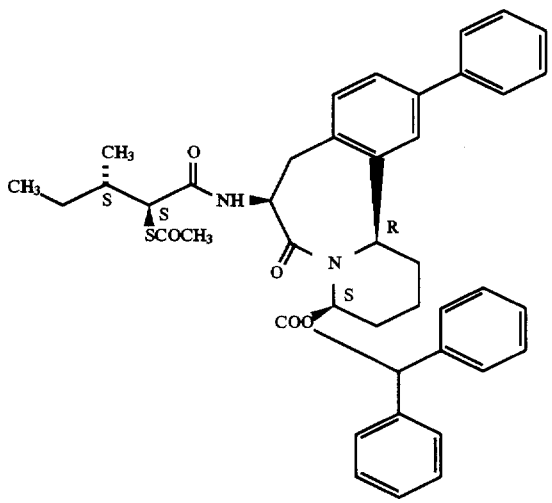

In the same manner as that of Example E-2 and starting with diphenylmethyl [4S-[4α,7α(R*),12bβ]]-7-amino-6-oxo-11-phenyl-1,2,3,4,6,7,8,12b-octahydropyrido[2,1-a][2]benzazepine-4-carboxylate (1.23 g, 2.38 mmol) obtained in the Example E-1 and (2S,3S)-2-acetylthio-3-methylvaleric acid (0.52 g, 2.74 mmol), the title compound was obtained as a colorless amorphous product (1.22 g, yield 74%).

¹H-NMR (400 MHz, CDCl₃) δ; 7.55~6.91(17H, m), 6.67 (1H, d, J=8 Hz), 6.27(1H, s), 5.65(1H, quint, J=6 Hz), 5.47(1H, d like), 5.41(1H, d like), 4.05(1H, d, J=7 Hz), 3.42(1H, dd, J=16, 6 Hz), 2.61~2.40(2H, m), 2.45(3H, s), 2.14(1H, m), 2.00(1H, m), 1.92~1.58(5H, m), 1.24(1H, m), 1.05(3H, d, J=7 Hz), 0.94(3H, t, J=7 Hz).

Example E-12

[4S-[4α,7α(R*),12bβ]]-7-[(2S,3S)-2-Acetylthio-3-methylvalerylamino]-6-oxo-11-phenyl-1,2,3,4,6,7,8,12b-octahydropyrido[2,1-a][2]benzazepine-4-carboxylic acid

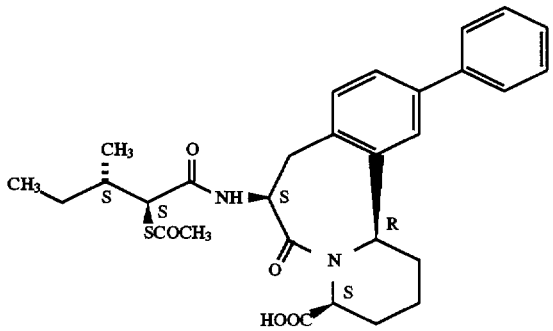

In the same manner as that of Example E-4 and starting with diphenylmethyl [4S-[4α,7α(R*),12bβ]]-7-[(2S,3S)-2-acetylthio-3-methylvalerylamino]-6-oxo-11-phenyl-1,2,3,4,6,7,8,12b-octahydropyrido[2,1-a][2]-benzazepine-4-carboxylate (1.22 g, 1.773 mmol) obtained in the Example E-11, the title compound was obtained as a colorless amorphous product (0.897 g, yield 97%).

¹H-NMR (400 MHz, CDCl₃) δ; 7.52~7.31(8H, m), 7.04 (1H, d, J=8 Hz), 5.69(1H, quint, J=6 Hz), 5.48(1H, m), 5.18(1H, m), 4.02(1H, d, J=7 Hz), 3.54(1H, m), 2.86(1H, dd, J=16, 12 Hz), 2.51(1H, m), 2.40(3H, s), 2.28(1H, m), 2.11(1H, m), 2.04~1.56(5H, m), 1.20(1H, m), 1.02(3H, d, J=7 Hz), 0.91(3H, t, J=7 Hz).

Example E-13

[4S-[4α,7α(R*),12bβ]]-7-[(2S,3S)-2-Mercapto-3-methylvalerylamino]-6-oxo-11-phenyl-1,2,3,4,6,7,8,12b-octahydropyrido[2,1-a][2]benzazepine-4-carboxylic acid

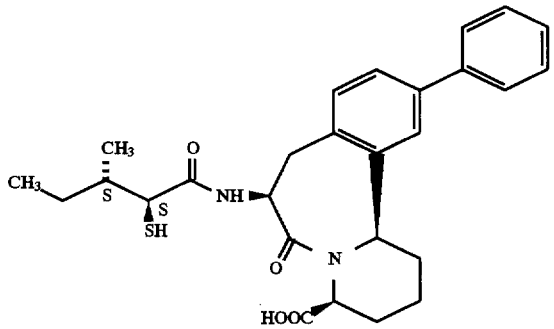

[4S-[4α,7α(R*),12bβ]]-7-[(2S, 3S)-2-acetylthio-3-methylvalerylamino]-6-oxo-11-phenyl-1,2,3,4,6,7,8,12b-octahydropyrido[2,1-a][2]benzazepine-4-carboxylic acid (0.780 g, 1.429 mmol) obtained in the Example E-12 was dissolved in degassed ethanol (20 ml). To this solution was added a 1.0N aqueous solution of lithium hydroxide (4.48 ml) at 0° C. The mixed solution thus obtained was stirred under a nitrogen atmosphere for 40 minutes.

The mixed solution was acidified by adding water (20.0 ml) and a 2.0N aqueous hydrochloric acid. The white solid thus precipitated was collected by filtration (washed with H₂O) to thereby give the title compound (0.622 g, yield 87%).

¹H-NMR (400 MHz, CDCl₃) δ; 7.66(1H, d, J=7 Hz), 7.53~7.32(7H, m), 7.08(1H, d, J=8 Hz), 5.72(1H, quint, J=6 Hz), 5.52(1H m), 5.25(1H, m), 3.60(1H, dd, J=17, 6 Hz), 3.23(1H, dd, J=9, 7 Hz), 2.93(1H, dd, J=17, 13 Hz), 2.55(1H m), 2.34(1H, m), 2.00(2H, m), 1.92(1H, d, J=8 Hz), 1.98~1.61(4H, m), 1.25(1H m), 1.03(3H, d, J=7 Hz), 0.93 (3H, t, J=7 Hz).

Example F-1

Methyl [3R-[3α,6α(S*),9aβ]]-6-[[(S)-1-oxo-2-acetylthio-3-(4-fluorophenyl)propyl]amino]-octahydro-5-oxothiazol[3,2-a]azepine-3-carboxylate

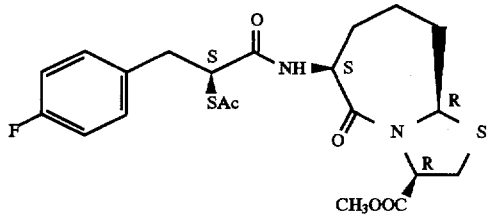

To methyl [3R-[3α,6α(S*),9aβ]]-6-amino-octahydro-5-oxothiazol[3,2-a]azepine-3-carboxylate (681 mg, 2.79 mmol) was added a solution of 2-acetylthio-3-(4-fluorophenyl)propionic acid (743 mg, 3.07 mmol) obtained in the Synthesis Example F-3 in methylene chloride (28 ml). The obtained mixture was cooled to 0° C. under cooling with ice. After adding N-ethoxycarbonyl-2-ethoxy-1,2-dihydroquinoline (EEDQ, 793 mg, 3.21 mmol) thereto, the ice bath was taken away. The obtained mixture was stirred under a nitrogen atmosphere at room temperature for 3 hours. The obtained mixture was washed with a 0.5N aqueous solution of hydrochloric acid (15 ml×2), water (10 ml), a saturated aqueous solution of sodium hydrogencarbonate (15 ml×2) and a saturated aqueous sodium chloride (15 ml), dried over magnesium sulfate and filtered. Next, the filtrate was concentrated under reduced pressure to thereby give a crude product mixture of epimers (1.39 g). This crude product mixture was separated and purified by silica gel column chromatography (hexane:ethyl acetate= 3:1). As a result, the title compound (500 mg, 38%) was obtained as a first epimer from the first fraction.

¹H-NMR (400 MHz, CDCl₃) δ; 1.55~2.02(6H, m), 2.34 (3H, s), 2.97(1H, dd, J=7.2, 14.2 Hz), 3.18(1H, dd, J=6.6, 11.6 Hz), 3.27(1H, dd, J=2.4, 11.6 Hz), 3.27(1H, dd, J=7.6, 14.2 Hz), 3.78(3H, s), 4.24(1H, t, J=7.4 Hz), 4.44(1H, dd, J=6.0, 11.2 Hz), 4.99(1H, d, J=9.2 Hz), 5.25(1H, dd, J=2.4, 6.6 Hz), 6.95(2H, t, J=8.6 Hz), 7.18(2H, dd, J=5.2, 8.4 Hz), 7.31(1H, d, J=3.2 Hz).

MASS m/e (FAB); 469(MH⁺)

m.p.; 53°~57° C.

Example F-2

Methyl [3R-[3α,6α(S*),9aβ]]-6-[[(R)-1-oxo-2-acetylthio-3-(4-fluorophenyl)propyl]amino] octahydro-5-oxothiazol[3,2-a]azepine-3-carboxylate

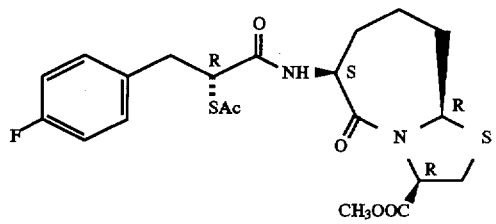

Following the first epimer obtained in the Example F-1, the title compound (486 mg, 37%) was obtained from the column as a second epimer.

¹H-NMR (400 MHz, CDCl₃) δ; 1.45~2.02(6ᴴ, m), 2.33 (3H, s), 2.93(1H, dd, J=6.8, 13.6 Hz), 3.16(1H, dd, J=6.8, 12.0 Hz), 3.26(1H, dd, J=2.4, 12.0 Hz), 3.28(1H, dd, J=8.8, 13.6 Hz), 3.77(3H, s), 4.19(1H, dd, J=6.8, 8.8 Hz), 4.45(1H, dd, J=6.2, 11.2 Hz), 4.97(1H, dd, J=8.8 Hz), 5.26(1H, dd, J=2.4, 6.8 Hz), 6.96(2H, t, J=8.8 Hz), 7.19(2H, dd, J=5.6, 8.0 Hz), 7.32(1H, d, J=5.6 Hz).

MASS m/e (FAB); 469(MH⁺)

m.p.; 55°~60° C.

Example F-3

Methyl [3R-[3α,6α(S*),9aβ]]-6-[[(2S)-1-oxo-2-acetylthio-3-phenylpropyl]amino]-octahydro-5-oxo-thiazol[3,2-a]azepine-3-carboxylate

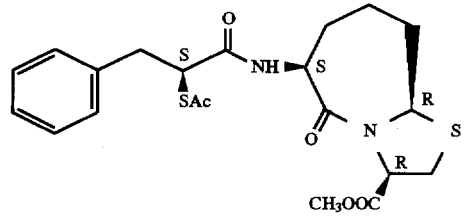

A solution of methyl [3R-[3α,6α(S*),9aβ]]-6-amino-octahydro-5-oxothiazol[3,2-a]azepine-3-carboxylate (430 mg, 1.76 mmol) in methylene chloride (17.6 ml) was cooled to 0° C. under cooling with ice. Next, to this solution were successively added (S)-2-acetylthio-3-phenylpropionic acid (395 mg, 1.76 mmol) obtained in the Synthesis Example F-4 and N-ethoxycarbonyl-2-ethoxy-1,2-dihydroquinoline (EEDQ, 479 mg, 1.94 mmol). Then, the ice bath was raked away, and the mixture thus obtained was stirred under a nitrogen atmosphere at room temperature for 6 hours. Then, the mixture was washed with a 0.5N aqueous solution of hydrochloric acid (10 ml×2), water (10 ml), a saturated aqueous solution of sodium hydrogencarbonate (10 ml×2) and a saturated aqueous sodium chloride (10 ml), and dried over magnesium sulfate. Next, the filtrate, which was obtained by filtering it, was concentrated under reduced pressure. The residue thus obtained was purified by column chromatography (methylene chloride:ethyl acetate=20:1). Thus, the title compound as an amorphous product (563 mg, 71%) was obtained.

¹H-NMR (400 MHz, CDCl₃) δ; 1.50~2.03(6H, m), 2.32 (3H, s), 2.99(1H, dd, J=7.6, 14.0 Hz), 3.17(1H, dd, J=6.4, 12.0 Hz), 3.26(1H, dd, J=2.4, 12.0 Hz), 3.31(1H, dd, J=7.6, 14.0 Hz), 3.78(3H, s), 4.29(1H, t, J=7.6 Hz), 4.46(1H, dd, J=6.4, 10.4 Hz), 4.99(1H, d, J=8.8 Hz), 5.24(1H, dd, J=2.4, 6.4 Hz), 7.18~7.36(6H, m).

MASS m/e (FAB); 451(MH⁺)

m.p.; indeterminable owing to the amorphous form.

Example F-4

Methyl [3R-[3α,6α(S*),9aβ]]-6-[[(S)-1-oxo-2-acetylthiomethyl-3-phenylpropyl]amino]-octahydro-5-oxothiazol[3,2-a]azepine-3-carboxylate

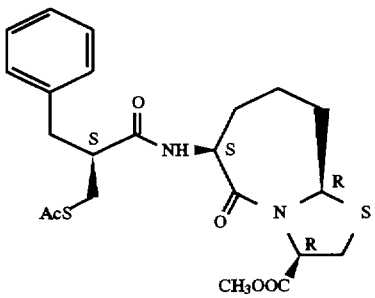

A solution of methyl [3R-[3α,6α(S*), 9aβ]]-6-aminooctahydro-5-oxothiazol[3,2-a]azepine-3-carboxylate (375 mg, 1.53 mmol) in methylene chloride (15.3 ml) was cooled to 0° C. under cooling with ice. Next, (S)-2-acetylthiomethyl-3-phenylpropionic acid (365.8 mg, 1.54 mmol) and N-ethoxycarbonyl-2-ethoxy-1,2-dihydroquinoline (EEDQ, 418 mg, 1.69 mmol) were successively added to this solution. Then, the ice bath was taken away, and the mixture thus obtained was stirred under a nitrogen atmosphere at room temperature for 6 hours. Then, it was washed with a 0.5N aqueous HCl solution (10 ml×2), water (10 ml), a saturated aqueous NaHCO3 solution (10 ml×2) and a saturated aqueous sodium chloride (10 ml), and dried over (MgSO₄ was used). Next, the filtrate, which was obtained by filtering it, was concentrated under reduced pressure. The residue thus obtained was purified by column chromatography (methylene chloride:ethyl acetate=20:1). Thus, the title compound as a sticky solid (435 mg, 61%) was obtained.

¹H-NMR (400 MHz, CDCl₃) δ; 1.55~2.11(6H, m), 2.32 (3H, s), 2.62~2.70(1H, m), 2.82(1H, dd, J=6.8, 14.0 Hz), 2.97(1H, dd, J=8.4, 14.0 Hz), 3.03(1H, dd, J=8.8, 13.6 Hz), 3.11(1H, dd, J=5.2, 13.6 Hz), 3.17(1H, dd, J=6.8, 11.6 Hz), 3.27(1H, dd, J=2.8, 11.6 Hz) 3.78(3H, s), 4.40~4.44(1H, m like q), 4.98(1H, d, J=8.8 Hz), 5.20(1H, dd, J=2.8, 6.8 Hz), 6.79(1H, d, J=6.0 Hz), 7.15~7.28(5H, m).

MASS m/e (FAB); 465(MH⁺)

m.p.; indeterminable owing to the amorphous form.

Example F-5

Methyl [3R-[3α,6α(S*),9aβ]]-6-[[(2S,3S)-1-oxo-2-acetylthio-3-methylpentyl]amino]octahydro-5-oxothiazol [3,2-a]azepine-3-carboxylate

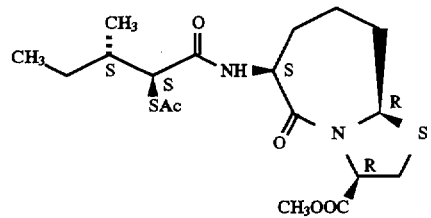

A solution of methyl [3R-[3α,6α(S*), 9aβ]]-6-aminooctahydro-5-oxothiazol[3,2-a]azepine-3-carboxylate (225 mg, 0.92 mmol) in methylene chloride (17 ml) was cooled to 0° C. under cooling with ice. Next, a solution of (2S, 3S)-2-acetylthio-3-methylpentanoic acid (193 mg, 1.01 mmol) in methylene chloride (6 ml) and EEDQ (296 mg, 1.20 mmol) were successively added to this solution. Then, the ice bath was taken away, and the mixture thus obtained was further stirred under a nitrogen atmosphere at room temperature overnight. Then, the mixture was concentrated to a certain extent with an evaporator. Next, the residue was dissolved in ethyl acetate, and the resulting solution was washed with a 1N aqueous HCl solution, a saturated aqueous NaHCO₃ solution and a saturated aqueous sodium chloride and then dried over (MgSO₄ was used). The filtrate, which was obtained by filtering it, was concentrated under reduced pressure. The residue thus obtained was purified by column chromatography (hexane:ethyl acetate=3:1). Thus, the title compound as an amorphous product (206 mg, 54%) was obtained.

¹H-NMR (400 MHz, CDCl₃) δ; 0.88(3H, t, J=7.6 Hz), 0.99(3H, d, J=6.8 Hz), 1.10~1.22(1H, m), 1.51~1.70(2H, m), 1.82~2.14(6H, m), 2.38(3H, s), 3.20(1H, dd, J=6.4, 11.8 Hz), 3.28(1H, dd, J=2.4, 11.8 Hz), 3.79(3H, s), 3.98(1H, d, J=6.8 Hz), 4.54(1H, dd, J=6.4, 10.4 Hz), 5.02(1H, d, J=8.8 Hz), 5.28(1H, dd, J=2.4, 6.4 Hz), 7.41(1H, d, J=6.0 Hz).

Examples F-6 to 7–13

Compounds of Examples F-6 to F-13 as will be shown hereinafter were obtained by the same procedures as those of Examples F-1 to F-5.

Example F-6

Methyl [3R-[3α,6α(S*),9aβ]]-6-[[(S)-1-oxo-2-acetylthio-3-(4-methoxyphenyl)propyl]amino] octahydro-5-oxothiazol[3,2-a]azepine-3-carboxylate

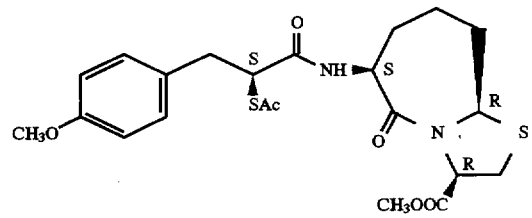

¹H-NMR (400 MHz, CDCl₃) δ; 1.55~2.04(6H, m), 2.33 (3H, s), 2.94(1H, dd, J=7.6, 14.4 Hz), 3.18(1H, dd, J=6.8, 11.6 Hz), 3.24(1H, dd, J=7.2, 14.4 Hz), 3.27(1H, dd, J=2.4, 11.6 Hz), 3.78(6H, s), 4.24(1H, t, J=7.6 Hz), 4.45(1H, dd, J=6.0, 10.8 Hz), 4.99(d, J=8.8 Hz), 5.24(1H, dd, J=2.4, 6.8 Hz), 6.80(2H, d, J=8.8 Hz), 7.13(2H, d, J=8.4 Hz), 7.32(1H, d, J=6.4 Hz).

MASS m/e (FAB); 481(MH$^+$)

m.p.; indeterminable owing to the amorphous form.

Example F-7

Methyl [3R-[3α,6α(S*),9aβ]]-6-[[(S)-1-oxo-2-acetylthio-3-(1,4-biphenyl)propyl]amino]-octahydro-5-oxothiazol[3,2-a]azepine-3-carboxylate

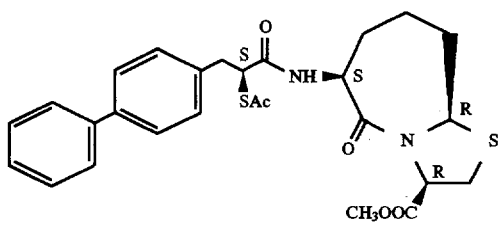

$^1$H-NMR (400 MHz, CDCl$_3$) δ; 1.50~2.05(6H, m), 2.35 (3H, s), 3.05(1H, dd, J=7.6, 14.4 Hz), 3.11(1H, dd, J=6.6, 12.0 Hz), 3.23(1H, dd, J=2.4, 12.0 Hz), 3.34(1H, dd, J=7.6, 14.4 Hz), 3.77(3H, s), 4.32(1H, t, J=7.6 Hz), 4.45(1H, dd, J=6.4, 11.6 Hz), 4.98(1H, d, J=8.4 Hz), 5.21(1H, dd, J=2.4, 6.6 Hz), 7.26~7.60(10H, m).

MASS m/e (FAB); 527(MH$^+$)

m.p.; 68°~72° C.

Example F-8

Methyl [3R-[3α,6α(S*),9aβ]]-6-[[(R)-1-oxo-2-acetylthio-3-(1,4-biphenyl)propyl]amino]-octahydro-5-oxothiazol[3,2-a]azepine-3-carboxylate

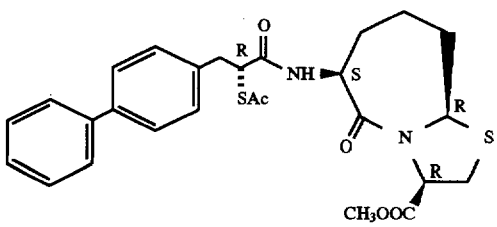

$^1$H-NMR (400 MHz, CDCl$_3$) δ; 1.46~2.00(6H, m), 2.34 (3H, s), 3.01(1H, dd, J=7.2, 14.0 Hz), 3.15(1H, dd, J=6.4, 12.0 Hz), 3.25(1H, dd J=2.4, 12.0 Hz), 3.36(1H, dd, J=8.8, 14.0 Hz), 3.76(3H, s), 4.28(1H, dd, J=7.2, 8.8 Hz), 4.45~4.49(1H, m like q), 4.97~4.99(1H, m like d), 5.26(1H, dd, J=2.4, 6.4 Hz), 7.29~7.59(10H, m)

MASS m/e (FAB); 527(MH$^+$).

m.p.; 77°~80° C.

Example F-9

Methyl [3R-[3α,6α(S*),9aβ]]-6-[[(S)-1-oxo-2-acetylthio-3-(2-thienyl)propyl]amino]-octahydro-5-oxothiazol[3,2-a]azepine-3-carboxylate

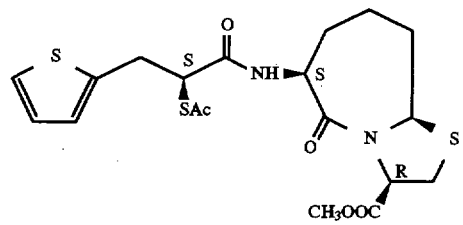

$^1$H-NMR (400 MHz, CDCl$_3$) δ; 1.50~1.70(2H, m), 1.86~2.08(4H, m), 2.36(3H, s), 3.18(1H, dd, J=6, 12 Hz), 3.27(1H, dd, J=2, 12 Hz), 3.29(1H, dd, J=7, 14 Hz), 3.49 (1H, dd, J=7, 14 Hz), 3.78(3H, s), 4.30(1H, d, J=7 Hz), 4.49(1H, dd, J=6, 10 Hz), 5.00(1H, d, J=9 Hz), 5.26(1H, dd, J=2, 6 Hz), 6.86(1H, brd, J=4 Hz), 6.90(1H, dd, J=3, 5 Hz), 7.14(1H, dd, J=2, 5 Hz), 7.40(1H, d, J=6 Hz).

Example F-10

Methyl [3R-[3α,6α(S*),9aβ]]-6-[[(2S,3R)-1-oxo2-acetylthio-3-methylpentyl]amino]-octahydro-5-oxothiazol[3,2-a]azepine-3-carboxylate

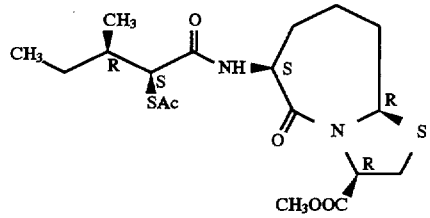

$^1$H-NMR (400 MHz, CDCl$_3$) δ; 0.91(3H, t, J=7 Hz), 0.92(3H, d, J=7 Hz), 1.27(1H, m), 1.44(1H, m), 1.64(1H, m), 1.88~2.06(5H, m), 2.07(1H, quint, J=7 Hz), 2.40(3H, s), 3.19(1H, dd, J=6, 12 Hz), 3.28(1H, dd, J=2, 12 Hz), 3.80 (3H, s), 4.07(1H, d, J=7 Hz), 4.53(1H, dd, J=6, 10 Hz), 5.02(1H, d, J=9 Hz), 5.28(1H, dd, J=2, 6 Hz), 7.51(1H, d, J=6 Hz).

Example F-11

Methyl [3R-[3α,6α(S*),9aβ]]-6-[[(S)-1-oxo-2-acetylthiobutyl]amino]-octahydro-5-oxothiazol[3,2-a]azepine-3-carboxylate

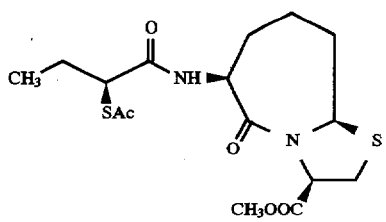

$^1$H-NMR (400 MHz, CDCl$_3$) δ; 0.98(3H, t, J=7 Hz), 1.67(1H, m), 1.77(1H, m), 1.86~2.06(6H, m), 2.37(3H, s), 3.19(1H, dd, J=6, 12 Hz), 3.27(1H, dd, J=2, 12 Hz), 3.79 (3H, s), 3.96(1H, t, J=6 Hz), 4.54(1H, dd, J=6, 10 Hz), 5.02(1H, d, J=9 Hz), 5.28(1H, dd, J=2, 6 Hz), 7.35(1H, d, J=6 Hz).

Example F-12

Methyl [3R-[3α,6α(S*),9aβ]]-6-[[(S)-1-oxo-2-acetylthio-3-methylbutyl]amino]-octahydro-5-oxo-thiazol[3,2-a]azepine-3-carboxylate

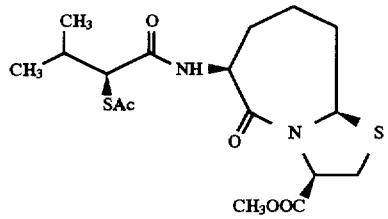

$^1$H-NMR (400 MHz, CDCl$_3$) δ; 0.97(3H, d, J=7 Hz), 1.02(3H, d, J=7 Hz), 1.65(1H, m), 1.88~2.06(4H, m), 2.35 (1H, m), 2.39(3H, s), 3.20(1H, dd, J=6, 12 Hz), 3.28(1H, dd, J=2, 12 Hz), 3.80(3H, s), 3.91(1H, d, J=7 Hz), 4.54(1H, dd, J=6, 10 Hz), 5.02(1H, d, J=9 Hz), 5.28(1H, dd, J=2, 6 Hz), 7.40(1H, d, J=6 Hz).

Example F-13

Methyl [3R-[3α,6α(S*),9aβ]]-6-[[(S)-1-oxo-2-acetylthio-3,3-dimethylbutyl]amino]-octahydro-5-oxothiazol[3,2-a[azepine-3-carboxylate

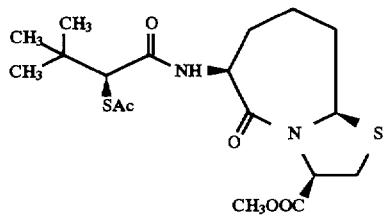

$^1$H-NMR (400 MHz, CDCl$_3$) δ; 1.02(9H, s), 1.63(1H, m), 1.88~2.09(5H, m), 2.17(3H, s), 3.20(1H, dd, J=6, 12 Hz), 3.28(1H, dd, J=2, 12 Hz), 3.77(1H, s), 3.80(3H, s), 4.57(1H, dd, J=6, 10 Hz), 5.03(1H, d, J=9 Hz), 5.28(1H, dd, J=2, 6 Hz), 7.20(1H, d, J=6 Hz).

Example F-14

[3R-[3α,6α(S*),9aβ]]-6[[(S)-1-Oxo-2-thio-3-(4-fluorophenyl)propyl]amino]-octahydro-5-oxothiazol[3,2-a]azepine-3-carboxylic acid

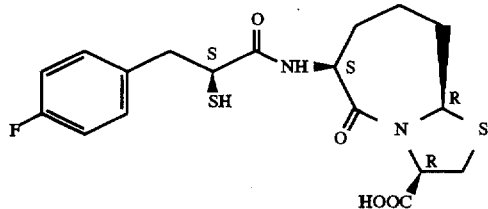

Methyl [3R-[3α,6α(S*), 9aβ]]-6-[(S)-1-oxo-2-acetylthio-3-(4-fluorophenyl)propylamino]-octahydro-5-oxothiazol[3,2-a]azepine-3-carboxylate (384 mg, 0.82 mmol) obtained in the Example F-1 was introduced into a flask, followed by sufficient purging with nitrogen. After adding degassed tetrahydrofuran (1.95 ml) and methanol (11.7 ml) thereto, the flask was cooled to 0° C. To the mixture thus obtained was added a degassed 1N aqueous solution of lithium hydroxide (6.6 ml). The obtained mixture was returned to room temperature and stirred for 2 hours. After cooling the mixture to 0° C. again, a 1N aqueous solution of hydrochloric acid (10 ml) was added thereto. The obtained mixture was extracted with chloroform (50 ml×2). The organic phase was washed with a saturated aqueous sodium chloride (30 ml) and then dried over magnesium sulfate. Then, the organic phase was filtered and the filtrate was concentrated under reduced pressure to a certain extent. Toluene (50 ml) was added to the concentrate, followed by concentration, again. Further, the residue was dissolved in a small amount (about 1 ml) of chloroform and diisopropyl ether (about 1 ml) and recrystallized. To the crystals thus obtained was added hexane (3 ml). After grinding and filtering, the solid was dried under reduced pressure. Thus, the title compound (362 mg, 107%) was obtained as white crystals.

$^1$H-NMR (400 MHz, CDCl$_3$) δ; 1.55~1.68(1H, m), 1.90~2.06(6H, m), 3.09(1H, dd, J=6.8, 14.0 Hz), 3.18~3.25 (2H, m), 3.34(1H, dd, J=2.4, 12.0 Hz), 3.51~3.56(1H, m like q), 4.52(1H, dd, J=6,4, 11.2 Hz), 5.03(1H, t, J=5.2 Hz), 5.26(1H, dd, J=2.4, 6.4 Hz), 6.97(2H, t, J=8.8 Hz), 7.17(2H, dd, J=5.8, 8.2 Hz), 7.52(1H, d, J=6.0 Hz).

MASS m/e (FAB); 413(MH$^+$)

m.p.; 209°~211° C.

Example F-15

[3R-[3α,6α(S*),9aβ]]-6-[[(S,3S)-1-Oxo-2-thio-3-methylpentyl]amino]octahydro-5-oxothiazol[3,2-a]-azepine-3-carboxylic acid

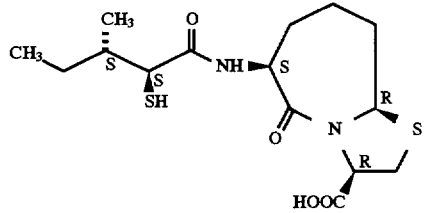

Methyl [3R-[3α,6α(S*),9aβ]]-6-[(2S,3S)-1-oxo-2-acetylthio-3-methylpentylamino]-octahydro-5-oxo-thiazol [3,2-a]azepine-3-carboxylate (200 mg, 0.48 mmol) obtained in the Example F-5 was introduced into a flask, followed by addition of degassed ethanol (8 ml). The flask was cooled to 0° C. under a nitrogen atmosphere. A degassed 1N aqueous solution of lithium hydroxide (3.8 ml) was added to the obtained mixture. The resulting mixture was stirred at room temperature for 50 minutes. The obtained mixture was acidified by adding a 2N aqueous solution of hydrochloric acid (2.9 ml) at 0° C. The obtained mixture was extracted with methylene chloride. After the organic phase was washed with a saturated aqueous sodium chloride, it was dried over magnesium sulfate and concentrated. The residual solid was recrystallized from hexane-methylene chloride. Thus, the title compound (150 mg, 87%) was obtained as white crystals.

$^1$H-NMR (400 MHz, CDCl$_3$) δ; 0.90(3H, t, J=7 Hz), 1.00(3H, d, J=7 Hz), 1.24(1H, m), 1.55~1.74(2H, m), 1.87 (1H, d, J=8 Hz), 1.90~2.10(8H, m), 3.20(1H, dd, J=6, 12 Hz), 3.24(1H, d, J=7 Hz), 3.36(1H, dd, J=2, 12 Hz), 4.62 (1H, dd, J=6, 10 Hz), 5.07(1H, t like, J=6 Hz), 5.29(1H, dd, J=2, 6 Hz), 7.69(1H, d, J=6 Hz).

Example F-16

[3R-[3α,6α(S*),9aβ]]-6-[[(R)-1-Oxo-2-thio-3-(4-fluorophenyl)propyl]amino]-octahydro-5-oxothiazol-[3,2-a]azepine-3-carboxylic acid

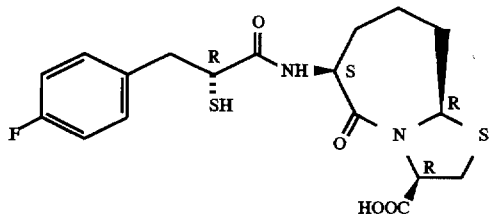

The compound of Example F-2 was treated in the same manner as that of Example F-14 to thereby give the title compound.

$^1$H-NMR (400 MHz, CDCl$_3$) δ; 1.44~1.56(1H, m), 1.82~2.03(5H, m), 2.08(1H, d, J=9.2 Hz), 3.03(1H, dd, J=6.8, 14.0 Hz), 3.20(1H, dd, J=6.8, 11.6 Hz), 3.25(1H, dd, J=8.0, 14.0 Hz), 3.34(1H, dd, J=2.0, 11.6 Hz), 3.45(1H, q, J=8.0 Hz), 4.53(1H, dd, J=6.4, 10.8 Hz), 5.02~5.04(1H, m), 5.27(1H, dd, J=2.0, 6.8 Hz), 6.97(2H, t, J=8.6 Hz), 7.17(2H, dd, J=5.4, 8.6 Hz), 7.34(1H, d, J=6.0 Hz).

MASS m/e (FAB); 413(MH$^+$)

m.p.; 98°~105° C.

Examples F-17 to F-26

Compounds of Examples F-17 to F-26 as will be shown hereinafter were obtained by the same procedures as those of Examples F-14 and F-15 using the compounds of Examples F-3, F-4 and F-6 to F-13.

Example F-17

[3R-[3α,6α(S*),9aβ]]-6-[[(S)-1-Oxo-2-thio-3-phenylpropyl]amino]-octahydro-5-oxothiazol[3,2-a]-azepine-3-carboxylic acid

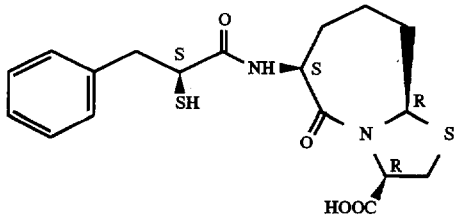

$^1$H-NMR (400 MHz, CDCl$_3$) δ; 1.53~1.68(1H, m), 1.88~2.07(6H, m), 3.10(1H, dd, J=6.8, 13.6 Hz), 3.19(1H, dd, J=6.6, 12.0 Hz), 3.27(1H, dd, J=6.8, 13.6 Hz), 3.34(1H, dd, J=2.4, 12.0 Hz), 3.59(1H, q, J=6.8 Hz), 4.51~4.56(1H, m like dd), 5.02~5.04(1H, m like t), 5.26(1H, dd, J=2.4, 6.6 Hz), 7.17~7.30(5H, m), 7.53(1H, d, J=6.0 Hz).

MASS m/e (FAB); 395(MH$^+$)

m.p.; 232°~235° C.

Example F-18

[3R-[3α,6α(S*),9aβ]]-6-[[(S)-1-Oxo-2-thiomethyl-3-phenylpropyl]amino]-octahydro-5-oxothiazol[3,2-a]-azepine-3-carboxylic acid

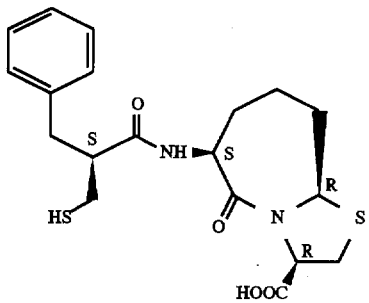

$^1$H-NMR (400 MHz, CDCl$_3$) δ; 1.46(1H, t, J=8.4 Hz), 1.59~1.70(1H, m), 1.84~2.14(5H, m), 2.55~2.68(2H, m), 2.76~2.83(2H, m), 2.97(1H, dd, J=7.0, 13.4 Hz), 3.21(1H, dd, J=6.8, 12.0 Hz), 3.35(1H, dd, J=2.4, 12.0 Hz), 4.54~4.59 (1H, m like q), 5.02~5.05(1H, m like t), 5.24(1H, dd, J=2.4, 6.8 Hz), 6.98(1H, d, J=6.0 Hz), 7.12~7.30(5H, m).

MASS m/e (FAB); 409(MH$^+$)

m.p.; 210°~212° C.

Example F-19

[3R-[3α,6α(S*),9aβ]]-6-[[(S)-1-Oxo-2-thio-3-(4-methoxyphenyl)propyl]amino]-octahydro-5-oxothiazol-[3,2-a]azepine-3-carboxylic acid

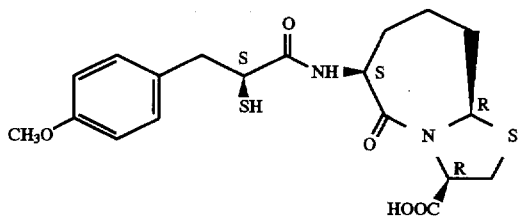

$^1$H-NMR (400 MHz, CDCl$_3$) δ; 1.55~1.68(1H, m), 1.88~2.09(6H, m), 3.07(1H, dd, J=6.8, 14.4 Hz), 3.18(1H, dd, J=6.8, 14.4 Hz), 3.20(1H, dd, J=6.8, 12.0 Hz), 3.34(1H, dd, J=2.4, 12.0 Hz), 3.55(1H, dt, J=8.8, 6.8 Hz), 3.79(3H, s), 4.52~4.56(1H, m like dd), 5.02~5.05(1H, m like t), 5.25(1H, dd, J=2.4, 6.8 Hz), 6.82(2H, d, J=8.4 Hz), 7.12(2H, d, J=8.4 Hz), 7.56(1H, d, J=6.4 Hz).

MASS m/e (FAB); 425(MH$^+$)

m.p.; 182°~183° C.

Example F-20

[3R-[3α,6α(S*),9aβ]]-6-[[(S)-1-Oxo-2-thio-3-(1,4-biphenyl)propyl]amino]-octahydro-5-oxothiazol[3,2-a]azepine3-carboxylic acid

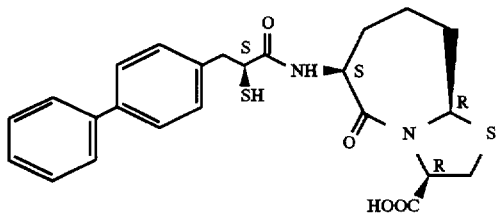

¹H-NMR (400 MHz, CDCl₃) δ; 1.55~1.67(1H, m), 1.88~2.08(5H, m), 2.06(1H, d, J=8.8 Hz), 3.12(1H, dd, J=6.8, 12.0 Hz), 3.16(1H, dd, J=6.8, 14.0 Hz), 3.26~3.31 (2H, m), 3.60(1H, q, J=6.8 Hz), 4.50~4.54(1H, m like q), 5.00~5.03(1H, m), 5.20(1H, dd, J=2.4, 6.8 Hz), 7.28~7.59 (10H, m).

MASS m/e (FAB); 471(MH⁺)
m.p.; 106°~117° C.

Example F-21

[3R-[3α,6α(S*),9aβ]]-6-[[(R)-1-Oxo-2-thio-3-(1,4-biphenyl)propyl]amino]-octahydro-5-oxothiazol[3,2-a]azepine-3-carboxylic acid

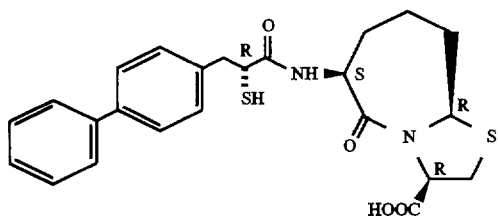

¹H-NMR (400 MHz, CDCl₃) δ; 1.44~1.56(1H, m), 1.84~2.00(5H, m), 2.12(1H, d, J=9.6 Hz), 3.08(1H, dd, J=6.4, 14.0 Hz), 3.16(1H, dd, J=6.8, 12.0 Hz), 3.29~3.50 (2H, m), 3.50~3.55(1H, m like q), 4.52~4.57(1H, m like dd), 5.01~5.04(1H, m), 5.25(1H, dd, J=2.4, 6.8 Hz), 7.26~7.58 (10H, m).

MASS m/e (FAB); 471(MH⁺)
m.p.; 109°~116° C.

Example F-22

[3R-[3α,6α(S*),9aβ]]-6-[[(S)-1-Oxo-2-thio-3-(2-thienyl)propyl]amino]-octahydro-5-oxothiazol-[3,2-a]azepine-3-carboxylic acid

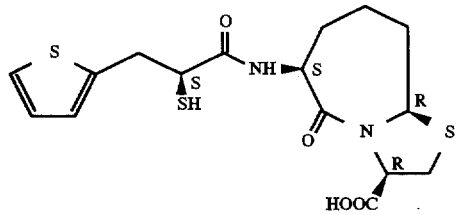

¹H-NMR (400 MHz, CDCl₃) δ; 1.64(1H, m), 1.90~2.12 (5H, m), 2.09(1H, d, J=8 Hz), 3.20(1H, dd, J=6.12 Hz), 3.34(1H, dd, J=2, 12 Hz), 3.44(2H, d, J=6 Hz), 3.58(1H, m), 4.57(1H, dd, J=6, 10 Hz), 5.05(1H, m), 5.26(1H, dd, J=2, 6 Hz), 6.87(1H, brd, J=4 Hz), 6.93(1H, dd, J=3, 5 Hz), 7.17(1H, dd, J=2, 5 Hz), 7.65(1H, d, J=6 Hz).

Example F-23

[3R-[3α,6α(S*),9aβ]]-6-[[(S, 3R)-1-Oxo-2-thio-3-methylpentylamino]-octahydro-5-oxothiazol-[3,2-a]azepine-3-carboxylic acid

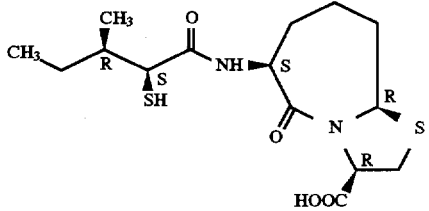

¹H-NMR (400 MHz, CDCl₃) δ: 0.92(3H, t, J=7 Hz), 0.93(3H, d, J=7 Hz), 1.30(1H, m), 1.49(1H, m), 1.70(1H, m), 1.76(1H, d, J=8 Hz), 1.90~2.14(6H, m), 3.22(1H, dd, J=6, 12 Hz), 3.32~3.42(2H, m), 4.62(1H, dd, J=6, 10 Hz), 5.06(1H, m), 5.30(1H, dd, J=2, 6 Hz), 7.94(1H, d, J=6 Hz).

Example F-24

[3R-[3α,6α(S*),9aβ]]-6-[(S)-1-Oxo-2-thiobutylamino]-octahydro-5-oxothiazol[3,2-a]azepine-3-carboxylic acid

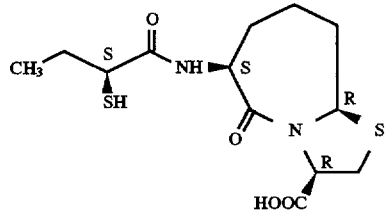

¹H-NMR (400 MHz, CDCl₃) δ; 1.00(3H, t, J=7 Hz), 1.70(1H, m), 1.79(1H, m), 1.90~2.10(7H, m), 3.19~3.30 (2H, m), 3.35(1H, dd, J=2, 12 Hz), 4.62(1H, dd, J=6, 10 Hz), 5.06(1H, m), 5.29(1H, dd, J=2, 6 Hz), 7.61(1H, d, J=6 Hz).

Example F-25

[3R-[3α,6α(S*),9aβ]]-6-[(S)-1-Oxo-2-thio-3-methylbutylamino]-octahydro-5-oxothiazol[3,2-a]azepine-3-carboxylic acid

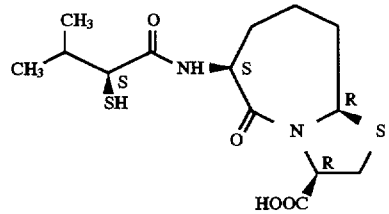

¹H-NMR (400 MHz, CDCl₃) δ; 0.99(3H, d, J=7 Hz), 1.03(3H, d, J=7 Hz), 1.69(1H, m), 1.85(1H, d, J=9 Hz), 1.90~2.10(5H, m), 2.25(1H, septet, J=7 Hz), 3.16~3.26(2H, m), 3.35(1H, dd, J=2, 12 Hz), 4.61(1H, dd, J=6, 10 Hz), 5.06(1H, t like, J=6 Hz), 5.30(1H, dd, J=2, 8 Hz), 7.67(1H, d, J=6 Hz).

Example F-26

[3R-[3α,6α(S*),9aβ]]-6-[(S)-1-Oxo-2-thio-3,3-dimethylbutylamino]-oxtahydro-5-oxothiazol[3,2-a]-azepine-3-carboxylic acid

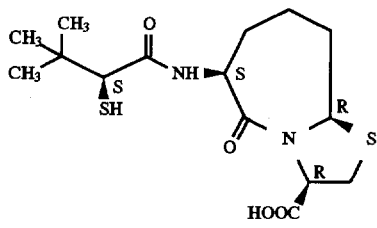

¹H-NMR (400 MHz, CD₃OD) δ: 1.06(9H, s), 1.74(1H, m), 1.85~2.10(5H, m), 3.25~3.35(3H, m), 4.58(1H, m), 5.17~5.25(2H, m).

Example 101

Methyl-{3R-[3α,6α(S*),9aβ]}-6-[[(2S,3S)-2-acetylthio-1-oxo-3-phenylbutyl]amino]octahydro-5-oxothiazol-[3,2-a]azepine-3-carboxylate

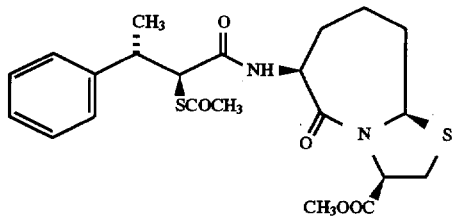

(a) (4S)-3-[(3R)-1-oxo-3-phenylbutyl]-4-phenylmethyl-2-oxazolidinone

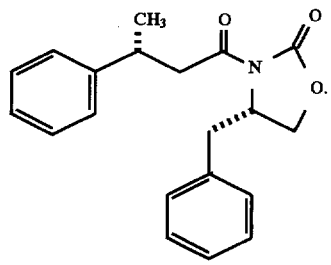

5.96 g of (R)-3-phenylbutanoic acid was dissolved in 90 ml of dichloromethane and several drops of dimethylformamide were added thereinto. Into the mixture thus obtained was dropped 9.5 ml of oxalyl chloride. The obtained mixture was stirred at room temperature for 0.5 hour and then concentrated. The residue was dissolved in 60 ml of tetrahydrofuran. Next, 6.44 g of (S)-4-phenylmethyl-2-oxazolidinone was dissolved in 120 ml of tetrahydrofuran. Into the obtained solution was dropped 14.5 ml of a 2.5M solution of n-butyllithium in hexane under a nitrogen atmosphere at −70° C. The obtained mixture was stirred at the same temperature for 20 minutes and then the solution of the acid chloride in tetrahydrofuran which had been prepared was added thereto. Further, the mixture thus obtained was stirred at −70° C. for 30 minutes and then heated to room temperature. The reaction mixture was concentrated. Ethyl acetate and water were added thereto and the target compound was extracted with ethyl acetate. The extract was washed with a saturated aqueous sodium chloride, and then it was dried over anhydrous magnesium sulfate and concentrated. The concentrate was purified by silica gel column chromatography to thereby give 9.7 g of the title compound (yield 83%).

¹H-NMR (400 MHz, CDCl₃) δ; 7.33–7.18(8H, m) 7.07 (2H, dd, J=2, 8 Hz), 4.63(1H, m) 4.16(1H, dd, J=8, 8 Hz), 4.11(1H, dd, J=9, 3 Hz) 3.45(2H, m) 3.08(2H, m), 2.59(1H, 1H, dd, J=14, 9 Hz) 1.36(3H, d, J=7 Hz).

(b) (4S)-3-[(2S,3S)-2-bromo-1-oxo-3-phenylbutyl]-4-phenylmethyl-2-oxazolidinone

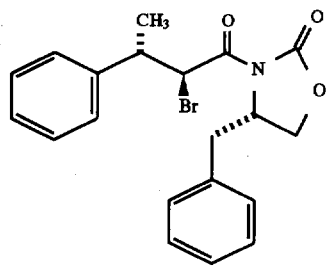

3.25 g of (4S)-3-[(3R)-1-oxo-3-phenylbutyl-4-phenylmethyl]-2-oxazolidinone was dissolved in 50 ml of dicloromethane. To the solution were added 10 ml of diisopropylethylamine and 12.5 ml of di-n-butylborotrifluoromethanesulfonic acid under a nitrogen atmosphere at −70° C. The mixture thus obtained was stirred at the same temperature for 15 minutes and then at 0° C. for 1 hour. The reaction mixture was cooled to −70° C. The one obtained by suspending 3.64 g of N-bromosuccinimide in 20 ml of dichloromethane was prepared in another container and the above-mentioned reaction mixture was added thereto under a nitrogen atmosphere at −70° C. The mixture thus obtained was stirred at the same temperature for 1.25 hours and then poured into a solution comprising 0.5N sodium sulfate and a saturated aqueous sodium chloride. The resulting mixture was extracted with dichloromethane. The organic phase was dried over anhydrous sodium sulfate, concentrated and purified by silica gel column chromatography. Thus, 3.43 g of the target compound was obtained (yield 85%).

¹H-NMR (400 MHz, CDCl₃) δ; 7.38–7.24(10H, m) 5.96 (1H, d, J=10 Hz) 4.76(1H, m), 4.23(2H, m) 3.57(1H, dd, J=10, 7 Hz), 3.34(1H, dd, J=14, 3 Hz) 2.81(1 h, dd, J=14, 10 Hz), 1.38(3H, d, J=7 Hz).

(c) (4S)-3-[(2R,3S)-2-azido-1-oxo-3-phenylbutyl]-4-phenylmethyl-2-oxazolidinone

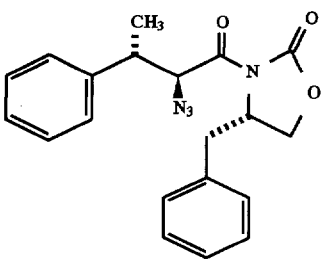

6.43 g of (4S)-3-[(2S,3S)-2-bromo-1-oxo-3-phenylbutyl] -4-phenylmethyl-2-oxazolidinone was dissolved in 80 ml of dicloromethane. To the obtained solution was added a solution of 7.58 g of tetramethylguanidinium azide in 20 ml of dichloromethane at 0° C. The mixture thus obtained was stirred at the same temperature for 1 hour and then at room temperature for 2.5 days. Further, it was heated under reflux for 8 hours. To the reaction mixture thus obtained was added a saturated aqueous solution of sodium hydrogencarbonate. The resulting mixture was extracted with dichloromethane. The organic phase was washed with a saturated aqueous sodium chloride, and then it was dried over anhydrous sodium sulfate and concentrated. After purifying by silica gel column chromatography, 4.33 g of the target compound was obtained (yield 74%).

$^1$H-NMR (400 MHz, CDCl$_3$) δ; 7.37–7.22(8H, m) 6.99 (2H, dd, J=8, 2 Hz), 5.37(1H, d, J=9 Hz) 4.60(1H, m), 4.12(1H, dd, J=9, 9 Hz) 3.45(1H, m), 2.80(1H, dd, J=14, 4 Hz) 1.98(1H, dd, J=14, 10 Hz), 1.50(3H, d, J=7 Hz).

(d) (2R,3S)-2-azido-3-phenylbutanoic acid

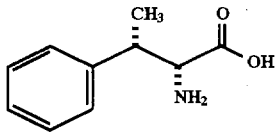

4.32 g of (4S)-3-[(2R,3S)-2-azido-1-oxo-3-phenylbutyl]-4-phenylmethyl-2-oxazolidinone was dissolved in 60 ml of tetrahydrofuran-water (4:1). To the solution thus obtained were added 7.75 ml of a 30% aqueous hydrogen peroxide and an aqueous solution (38 ml) containing 0.73 g of lithium hydroxide at 0° C. The obtained mixture was stirred at 0° C. for 1 hour and then an aqueous solution (57 ml) containing 9.58 g of sodium sulfite was added thereto. The tetrahydrofuran was distilled off from the reaction mixture under reduced pressure. The aqueous phase was washed with dichloromethane, and then the pH, thereof was adjusted to 1 with conc. hydrochloric acid, followed by extraction with ethyl acetate. The ethyl acetate phase was washed with a saturated aqueous sodium chloride, and then it was dried over anhydrous sodium sulfate and concentrated. Thus, 2.80 g of the target compound was obtained (yield 95%).

$^1$H-NMR (400 MHz, CDCl$_3$) δ; 7.37–7.27(5H, m) 4.09 (1H, d, J=6 Hz), 3.39(1H, dq, J=7, 7 Hz) 1.39(3H, d, J=7 Hz).

(e) (2R,3S)-2-amino-3-phenylbutanoic acid

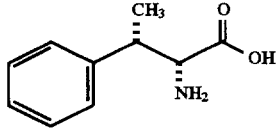

2.20 g of (2R,3S)-2-azido-3-phenylbutanoic acid was dissolved in 40 ml of methanol. To the obtained solution were added 2.71 g of ammonium formate and 0.36 g of 10% palladium carbon (a water-containing preparation), followed by reacting at room temperature for 1.5 hours. After removing out the catalyst by filtration and concentrating the filtrate, 300 ml of a mixed solvent comprising methanol and dichloromethane (1:9) was added to the residue, followed by extraction. After concentrating the extract, 2.43 g of the target compound was obtained (crude product).

$^1$H-NMR (400 MHz, CDCl$_3$) δ; 7.32–7.16(5H, m) 3.78 (1H, d, J=5 Hz) 3.38(1H, m), 1.23(3H, d, J=7 Hz).

(f) (2R,3S)-2-bromo-3-phenylbutanoic acid

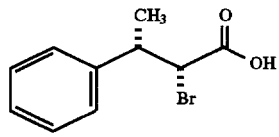

1.70 g of (2R,3S)-2-amino-3-phenylbutanoic acid was dissolved In a mixed solvent comprising 7.2 ml of water and 10.5 ml of 47% hydrobromic acid. To the obtained solution was added 0.98 g of sodium hypochlorite at −10° C. The resulting mixture was stirred at 0° C. for 30 minutes and then at room temperature for 2 hours. Next, water and diethyl ether were added thereto, followed by extraction. The ether phase was washed with water and a saturated aqueous sodium chloride, dried over anhydrous sodium sulfate and then concentrated. Thus, 1.84 g of the target compound was obtained as a crude product.

$^1$H-NMR (400 MHz, CDCl$_3$) δ; 7.38–7.18(5H, m) 4.35 (1H, d, J=10 Hz) 3.36(1H, m), 1.23(3H, d, J=7 Hz).

(g) (2S,3S)-2-acetylthio-3-phenylbutanoic acid

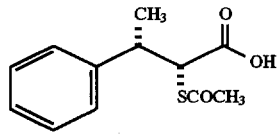

1.80 g (7.35 mmol) of (2R,3S)-2-bromo-3-phenylbutanoic acid was dissolved in 40 ml of acetonitrile. To the obtained solution was added 1.01 g (88.2 mmol) of potassium thioacetate at −10° C. The resulting mixture was stirred at 0° C. for 30 minutes and then at room temperature overnight. The insoluble matters were removed by filtration and the solution was concentrated. Diethyl ether and a saturated aqueous solution of sodium hydrogencarbonate were added to the residue obtained by the concentration, followed by extraction the target compound into the aqueous phase. The pH of the aqueous phase was adjusted to 1 with dilute hydrochloric acid, followed by extraction with diethyl ether. The organic phase was washed with a saturated aqueous sodium chloride, and then it was dried over anhydrous sodium sulfate and concentrated. Thus, 1.52 g of the target crude product was obtained.

$^1$H-NMR (400 MHz, CDCl$_3$) δ; 7.40–7.18(5H, m) 4.42 (1H, d, J=10 Hz) 3.33(1H, m), 2.25(3H, s) 1.43(3H, d, J=7 Hz).

(h) methyl-{3R-[3α,6α(S*),9aβ]}-6-{[(2S,3S)-2-acetylthio-1-oxo-3-phenylbutyl]amino}octahydro-5-oxothiazol[3,2-a]azepine-3-carboxylate

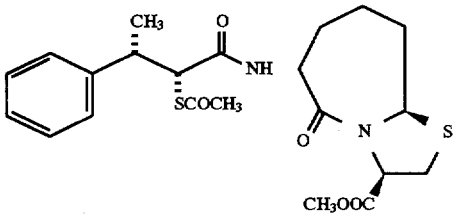

0.3 g (1.23 mmol) of methyl-{3R-[3α,6α(S*),9aβ]}-6-aminooctahydro-5-oxothiazol[3,2-a]-azepine-3-carboxylate was dissolved in 10 ml of dichloromethane. To the obtained solution were successively added a solution of 0.32 g (1.35 mmol) of (2S,3S)-2-acetylthio-3-phenylbutanoic acid in 10 ml of dichloromethane and 0.43 g (1.6 mmol) of EEDQ at 0° C. under a nitrogen atmosphere. The mixture thus obtained was stirred at room temperature overnight. Then, it was successively washed with 1N hydrochloric acid, a saturated aqueous solution of sodium hydrogen-carbonate and a saturated aqueous sodium chloride, dried over anhydrous sodium sulfate, concentrated and purified by silica gel column chromatography. Thus, 0.27 g of the target compound was obtained.

$^1$H-NMR (400 MHz, CDCl$_3$) δ; 7.34–7.15(5H, m) 5.28 (1H, dd, J=6, 2 Hz), 5.02(1H, d, J=9 Hz) 4.56(1H, dd, J=11, 7 Hz), 4.22(1H, d, J=10 Hz) 3.79(3H, s) 3.45(1H, m), 3.28(1H, dd, J=12, 3 Hz) 3.19(1H, dd, J=12, 7 Hz), 2.23(3H, s) 2.04–1.88(6H, m) 1.37(3H, d, D=7 Hz).

Example 102

(3S)-{[(2S,3S)-2-Acetylthio-1-oxo-3-phenylbutyl]-amino}-1-ethoxycarbonylmethyl-2,3,4,5-tetrahydro-1H-[1]benzazepin-2-one

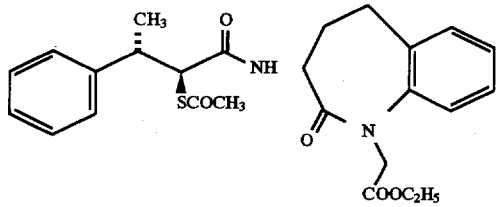

0.40 g (1.53 mmol) of (3S)-amino-1-ethoxycarbonylmethyl-2,3,4,5-tetrahydro-1H-[1]benzazepin-2-one and 0.40 g (1.68 mmol) of (2S,3S)-2-acetylthio-3-phenylbutanoic acid obtained in the Example 101(g) were treated in the same manner as that of Example 101(h). Thus, 0.37 g of the title compound was obtained.

$^1$H-NMR (400 MHz, CDCl$_3$) δ; 7.32–7.10(9H, m) 6.99 (1H, d, J=7 Hz), 4.77(1H, d, J=17 Hz) 4.50(1H, m) 4.34(1H, d, J=17 Hz), 4.22–4.13(3H, m) 3.42–3.30(2H, m), 2.71–2.54 (2h, m) 2.22(3H, s) 1.81(1H, m), 1.33(3H, d, J=7 Hz) 1.25(3H, t, J=7 Hz).

Example 103

{3R-[3α,6α(S*),9aβ]}-6-{[(2S,3S)-1-Oxo-3-phenyl-2-thiobutyl]amino}octahydro-5-oxothiazol[3,2-a]azepine-3-carboxylic acid

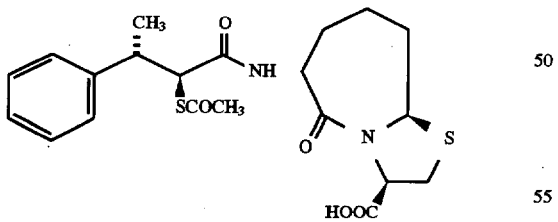

0.25 g (0.539 mmol) of methyl-{3R-[3α,6α(S*),9aβ]}-6-{[(2S,3S)-2-acetylthio-1-oxo-3-phenylbutyl]amino}octahydro-5-oxothiazol[3,2-a]azepine-3-carboxylate obtained in the Example 101 was dissolved in 10 ml of ethanol. To the obtained solution was added 10 ml of a 1N aqueous solution of lithium hydroxide under a nitrogen atmosphere at 0° C. The mixture thus obtained was stirred at room temperature for 1 hour and then cooled to 0° C. again, followed by adjusting the pH, thereof to 1 with dilute hydrochloric acid. Ethanol was distilled off from the reaction mixture under reduced pressure. Water and dichloromethane were added to the residue, followed by extraction. After the organic phase was washed with a saturated aqueous sodium chloride and dried over anhydride sodium sulfate, it was concentrated. Thus, 0.15 g of the target compound was obtained.

$^1$H-NMR (400 MHz, CDCl$_3$) δ; 7.61(1H, d, J=6 Hz) 7.34–7.18(5H, m), 5.29(1 h, dd, J=7, 2 Hz) 5.06(1H, m), 4.62(1H, dd, J=11, 7 Hz) 3.51(1 h, dd, J=8, 7 Hz), 3.45(1H, m) 3.35(1H, dd, J=12, 2 Hz), 3.21(1H, dd, J=12, 7 Hz) 2.10–1.90(6H, m), 1.73(1H, d, J=8 Hz) 1.39(3H, d, J=7 Hz).

Example 104

1-Carboxymethyl-3-{[(2S,3S)-1-oxo-3-phenyl-2-thiobutyl]amino}-1H-[1]benzazepin-2-one

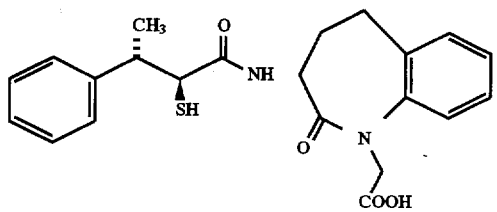

0.35 g (0.726 mmol) of (3S)-{[(2S,3S)-2-acetylthio-1-oxo-3-phenylbutyl]amino}-1-ethoxycarbonylmethyl-2,3,4,5-tetrahydro-1H-[1]benzazepin-2-one obtained in the Example 102 was dissolved in 10 ml of ethanol. To the obtained solution was added 10 ml of a 1N aqueous solution of sodium hydroxide under a nitrogen atmosphere at 0° C. The mixture thus obtained was stirred at room temperature for 1 hour and then the pH, thereof was adjusted to 1 by adding hydrochloric acid at 0° C. Water was added thereto and the crystals thus precipitated were collected by filtration. Thus, 0.25 g of the target compound was obtained.

$^1$H-NMR (400 MHz, CDCl$_3$) δ; 7.34–7.13(9H, m) 4.68(1 h, d, J=17 Hz) 4.52(1H, m), 4.45(1H, d, J=17 Hz) 3.47(1H, dd, J=8, 8 Hz), 3.41(1H, dq, J=8, 7 Hz) 3.23(1H, m), 2.71–2.58(2H, m) 1.83(1H, m) 1.69(1H, d, J=8 Hz), 1.34 (3H, d, J=7 Hz).

Example 105

Methyl [3R-[3α,6α(S*),9aβ]]-6-[[(2S,3S)-2-acetylthio-1-oxo-3,4-dimethylpentyl]amino]-octahydro-5-oxothiazol[3,2-a]azepine-3-carboxylate

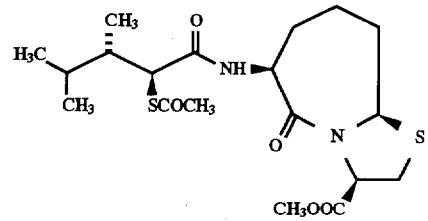

(a) (2S,3S)-2-acetylthio-3,4-dimethylpentanoic acid

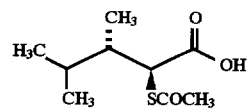

Using 3.70 g (28.2 mmol) of (R)-3,4-dimethylpentanoic acid as the starting material and in the same procedures as those of Example 101(a) to (g), 1.2 g of (2S,3S)-2-acetylthio-3,4-dimethylpentanoic acid was obtained.

¹H-NMR (400 MHz, CDCl₃)δ; 4.21(1H, d, J=8 Hz) 2.38(3H, s) 1.87(1H, m), 1.63(1H, m) 0.97(3H, d, J=7 Hz) 0.93(3H, d, J=7 Hz), 0.80(3H, d, J=7 Hz).

(b) methyl-{3R-[3α,6α(S*),9aβ]}-6-{[(2S,3S)-2-acetylthio-1-oxo-3,4-dimethylpentyl]amino}-octahydro-5-oxothiazol[3,2-a]azepine-3-carboxylate

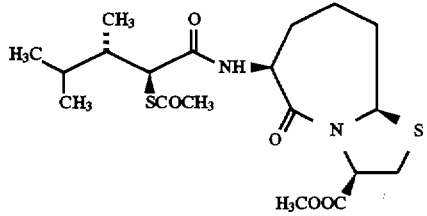

0.275 g (1.35 mmol) of (2S,3S)-2-acetylthio-3,4-dimethylpentanoic acid obtained by the above procedures and 0.300 g (1.23 mmol) of methyl-{3R-[3α,6α(S*),9aβ]}-6-amino-octahydro-5-oxothiazol-[3,2-a]azepine-3-carboxylate used were treated by the same method as that of Example 101(h). Thus, 0.260 g of the target compound was obtained.

¹H-NMR (400 MHz, CDCl₃) δ; 5.28(1H, dd, J=6, 2 Hz) 5.02(1H, d, J=9 Hz), 4.54(1H, m) 3.95(1H, d, J=9 Hz) 3.79(3H, s), 3.28(1H, dd, J=12, 2 Hz) 3.20(1H, dd, J=132, 7 Hz), 2.36(3H, s) 2.10–1.87(6H, m) 1.72–1.60(2H, m), 0.94(3H, d, J=7 Hz) 0.89(3H, d, J=7 Hz), 0.75(3H, d, J=7 Hz).

Example 106

(3S)-[[(2S,3S)-2-Acetylthio-3,4-dimethyl-1-oxopentyl]amino]-1-ethoxycarbonylmethyl-2,3,4,5-tetrahydro-1H-[1]benzazepin-2-one

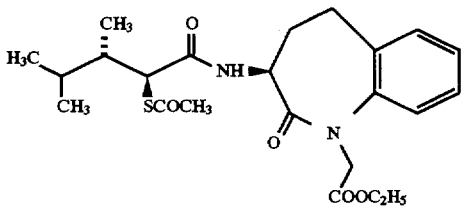

0.500 g (1.91 mmol) of (3S)-amino-1-ethoxycarbonylmethyl-2,3,4,5-tetrahydro-1H-[1] benzazepin-2-one and 0.430 g (2.1 mmol) of (2S,3S)-2-acetylthio- 3,4-dimethylpentanoic acid were treated by the same method as that of Example 101(h). Thus, 0.420 g of the title compound was obtained.

¹H-NMR (400 MHz, CDCl₃) δ; 7.32–7.10(4H, m) 4.78 (1H, d, J=17 Hz) 4.50(1H, m), 4.34(1H, d, J=17 Hz) 4.22–4.14(3H, m), 3.87(1H, d, J=10 Hz) 3.42–3.32(1H, m), 2.75–2.63(1H, m) 2.35(3H, s) 2.02–1.86(3H, m), 1.25(3H, t, J=7 Hz) 0.91(3H, d, J=7 Hz), 0.85(3H, d, J=7 Hz) 0.72(3H, d, J=7 Hz).

Example 107

[3R-[3α,6α(S*),9aβ]]-6-[[(2S,3S)-3,4-Dimethyl-1-oxo-2-thiopentyl]amino]octahydro-5-oxothiazol-[3,2-a]azepine-3-carboxylic acid

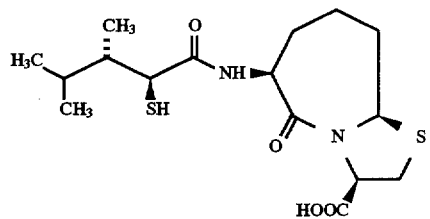

In the same manner as that of Example 104 and starting with 0.200 g (0.465 mmol) of methyl [3R-[3α,6α(S*),9aβ] ]-6-[[(2S,3S)-2-acetylthio-1-oxo-3,4-dimethylpentyl] amino]-octahydro-5-oxothiazol-[3,2-a]azepine-3-carboxylate obtained in the Example 105, 0.150 g of the title compound was obtained.

¹H-NMR (400 MHz, CDCl₃) δ; 7.42(1H, d, J=6 Hz) 5.29(1H, dd, J=6, 2 Hz), 5.07(1H, m) 4.65(1H, dd, J=10, 6 Hz), 3.35(1H, dd, J=12, 2 Hz) 3.23(1H, dd, J=12, 7 Hz), 3.14(1H, dd, J=9, 8 Hz) 2.25–1.92(6H, m), 1.93(1H, d, J=9 Hz) 1.82–1.62(2H, m), 0.95(3H, d, J=7 Hz) 0.84(3H, d, J=7 Hz), 0.77(3H, d, J=7 Hz).

Example 108

1-Carboxymethyl-(3S)-[[(2S,3S)-3,4-dimethyl-1-oxo-2-thiopentyl]amino]-2,3,4,5-tetrahydro-1H-[1]-benzazepin-2-one

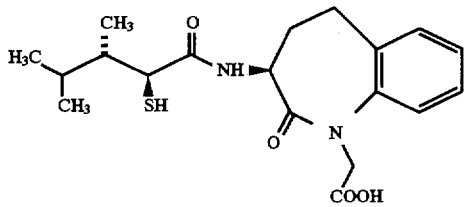

In the same manner as that of Example 104 and starting with 0.300 g (0.67 mmol) of (3S)-[[(2S,3S)-2-acetylthio-3, 4-dimethyl-1-oxopentyl]amino]-1-ethoxycarbonylmethyl-2, 3,4,5-tetrahydro-1H-[1]benzazepin-2-one obtained in the Example 106, 0.200 g of the title compound was obtained.

¹H-NMR (400 MHz, CDCl₃) δ; 7.36–7.13(4H, m) 7.06 (1H, d, J=7 Hz), 4.72(1H, d, J=17 Hz) 4.53(1H, m), 4.43(1H, d, J=17 Hz) 3.28(1H, m), 3.07(1H, t, J=9 Hz) 2.70(1H, m) 2.61(1H, m), 2.15(1H, m) 1.99(1H, m) 1.90(1H, d, J=8 Hz), 1.72(1H, m) 0.91(3H, d, J=7 Hz) 0.79(3H, d, J=7 Hz), 0.72(3H, d, J=7 Hz).

Examples 109 to 138

Compounds which will be described in the Examples 109 to 138 were synthesized in accordance with the processes of the Examples 101 to 108 with the use of appropriate starting materials corresponding thereto.

Example 109

[4S-[4α,7α(R*),12bβ]]-7-[[(2S)-1-Oxo-2-thiopropyl]amino]-6-oxo-11-phenyl-1,2,3,4,6,7,8,12b-octahydropyrido[2,1-a][2]benzazepine-4-carboxylic acid

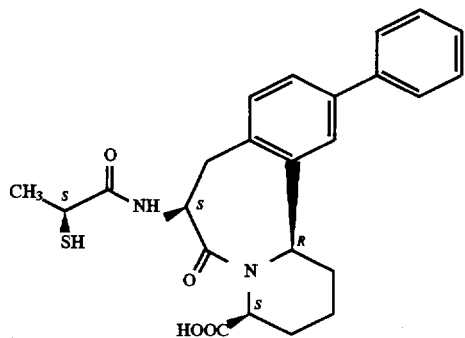

$^1$H-NMR (400 MHz, CDCl$_3$) δ; 7.65(1H, d, J=7 Hz) 7.50(2H, d, J=8 Hz), 7.43(1H, t like, J=8 Hz) 7.38–7.33(3H, m), 7.05(1H, d, J=8 Hz) 5.68(1H, quint, J=6 Hz), 5.50(1H, brd) 5.23(1H, brd), 3.56(1H, dd, J=17, 6 Hz) 3.46(1H, quint, J=7 Hz), 2.90(1H, dd, J=17, 13 Hz) 2.53(1H, m) 2.32(1H, m), 2.14(1H, d, J=10 Hz) 2.05–1.70(4H, m), 1.46(3H, d, J=7 Hz).

Example 110

[4S-[4α,7α(R*),12bβ]]-7-[[(2S)-4-Methyl-1-oxo-2-thiopentyl]amino]-6-oxo-11-phenyl-1,2,3,4,6,7,8,12b-octahydropyrido[2,1-a][2]benzazepine-4-carboxylic acid

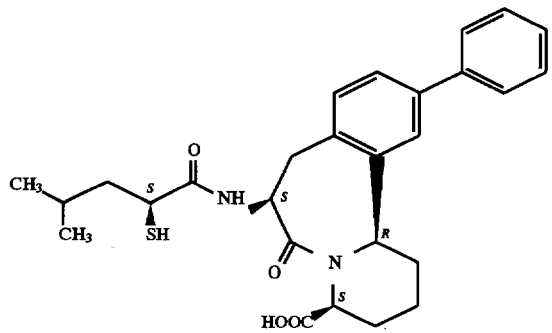

$^1$H-NMR (400 MHz, CDCl$_3$) δ; 7.51(3H, m) 7.44(2H, t like, J=8 Hz), 7.39–7.32(3H, m) 7.08(1H, d, J=8 Hz), 5.71(1H, quint, J=6 Hz) 5.52(1H, m) 5.25(1H, m), 3.60(1H, dd, J=17, 6 Hz) 3.37(1H, q like, J=7 Hz), 2.91(1H, dd, J=17, 13 Hz) 2.55(1H, m) 2.36(1H, m), 2.05–1.72(6H, m) 2.03 (1H, d, J=8 Hz) 1.60(1H, m), 0.96(3H, d, J=7 Hz) 0.92(3H, d, J=7 Hz).

Example 111

[4S-[4α,7α(R*),12bβ]]-7-[[(2S)-1-Oxo-2-thiobutyl]amino]-6-oxo-11-phenyl-1,2,3,4,6,7,8,12b-octahydropyrido[2,1-a][2]benzazepine-4-carboxylic acid

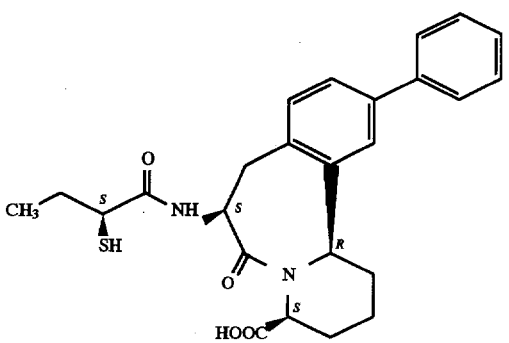

$^1$H-NMR (400 MHz, CDCl$_3$) δ; 7.59(1H, d, J=8 Hz) 7.51(2H, d, J=8 Hz), 7.44(2H, t like, J=8 Hz) 7.39–7.32(3H, m), 7.09(1H, d, J=8 Hz) 5.71(1H, quint, J=6 Hz), 5.54(1H, m) 5.26(1H, m) 3.62(1H, dd, J=17, 6 Hz), 3.27(1H, q like, J=7 Hz) 2.94(1H, dd, J=17, 13 Hz), 2.56(1H, m) 2.37(1H, m) 2.08–1.72(6H, m), 2.04(1H, d, J=8 Hz) 1.04(3H, t, J=7 Hz).

Example 112

[4S-[4α,7α(R*),12bβ]]-7-[(1-Oxo-2-phenyl-2-thioethyl)amino]-6-oxo-11-phenyl-1,2,3,4,6,7,8,12b-octahydropyrido[]2,1-a][2]benzazepine-4-carboxylic acid (isomer A)

A:B = 2:1

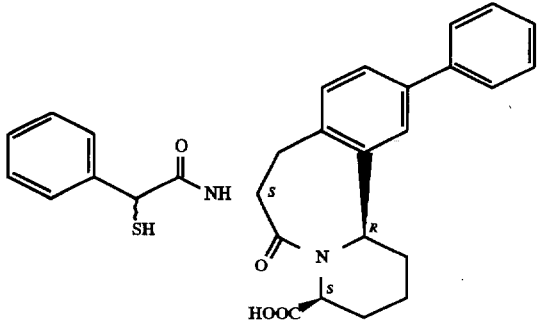

$^1$H-NMR (400 MHz, CD3OD) δ; 7.57–7.26(13H, m) 7.19(1H, d, J=8), 5.78(1H, dd, J=9, 6 Hz) 5.67(1H, m), 5.16(1H, d like) 3.50(1H, dd, J=17, 6 Hz), 3.12(1H, dd, J=17, 13 Hz) 2.58(1H, m) 2.40(1H, m), 2.15–1.76(4H, m).

Example 113

[4S-[4α,7α(R*),12bβ]]-7-[(1-Oxo-2-phenyl-2-thioethyl)amino]-6-oxo-11-phenyl-1,2,3,4,6,7,8,12b-octahydropyrido[2,1-a][2]benzazepine-4-carboxylic acid (isomer B)

A:B = 1:2

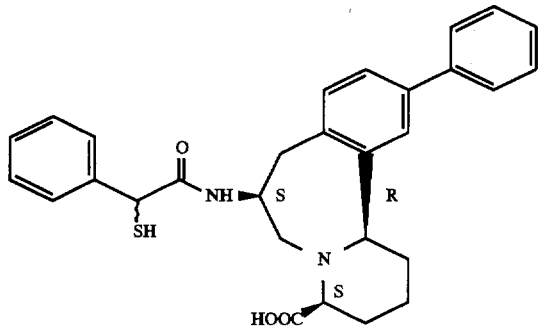

¹H-NMR (400 MHz, CD₃OD) δ: 7.57–7.27(13H, m) 7.08(1H, d, J=8 Hz), 5.77(1H, dd, J=9, 6 Hz) 5.67(1H, m), 5.20(1H, d like) 3.49(1H, dd, J=17, 6 Hz), 3.06(1H, dd, J=17, 13 Hz) 2.60(1H, m) 2.42(1H, m), 2.17–1.75(4H, m).

Example 114

[4S-[4α,7α(R*),12bβ]]-7-[[(2R)-3-Methyl-1-oxo-2-thiobutyl]amino]-6-oxo-11-phenyl-1,2,3,4,6,7,8,12b-octahydropyrido[2,1-a][2]benzazepine-4-carboxylic acid

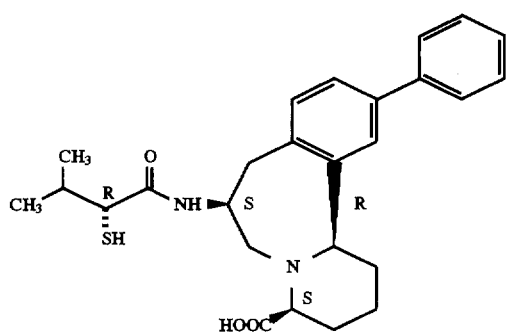

¹H-NMR (400 MHz, CDCl₃) δ; 7.51(1H, d, J=8 Hz) 7.47–7.24(7H, m), 7.03(1H, d, J=8 Hz) 5.67(1H, quint, J=6 Hz), 5.47(1H m) 5.20(1H, d like), 3.57(1H, dd, J=17, 6 Hz) 3.09(1H, t, J=7 Hz), 2.89(1H, dd, J=17, 13 Hz) 2.50(1H, m) 2.31(1H, m), 2.20(1H sextet, J=7 Hz) 2.02–1.50(4H, m), 1.85(1H, d, J=8 Hz) 1.01(3H, d, J=7 Hz), 0.98(3H, d, J=7 Hz).

Example 115

[3R-[3α,6α(S*),9aβ]]-6-[[1-Oxo-3-phenyl-2(S)-thiopropyl]amino]-2,2-dimethyl-5-oxooctahydrothiazol[3,2-a]azepine-3 carboxylic acid

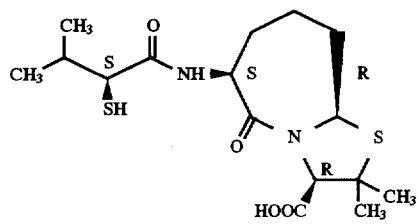

¹H-NMR (400 MHz, CDCl₃) δ; 7.61(1H, d, J=6 Hz) 7.31–7.19(5H, m), 5.12(1H, d, J=10 Hz) 4.74(1H, s), 4.53 (1H, dd like, J=12, 6 Hz), 3.60(1H, dt, J=9, 7 Hz) 3.26(1H, dd, J=14, 6 Hz), 3.12(1H, dd, J=14, 7 Hz) 2.25–2.13(1H, m), 1.99(1H, d, J=9 Hz) 2.07–1.84(4H, m), 1.60–1.50(1H, m) 1.55(3H, s) 1.51(3H, s).

Example 116

[3R-[3α,6α(S*),9aβ]]-6-[[3-methyl-1-oxo-2(S)-thiobutyl]amino]-2,2-dimethyl-5-oxooctahydrothiazol[3,2-a]azepine-3 carboxylic acid

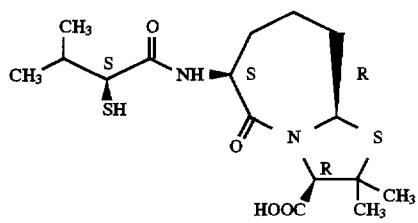

¹H-NMR (400 MHz, CDCl₃) δ; 7.81(1H, d, J=6 Hz) 5.15(1H, d, J=10 Hz), 4.79(1H, s) 4.61(1H, m) 3.21(1H, dt, J=9, 6 Hz), 2.33–1.88(6H, m) 1.83(1H, d, J=9 Hz), 1.69–1.57(1H, m) 1.56(3H, s) 1.52(3H, s), 1.04(3H, d, J=7 Hz) 0.98(3H, d, J=7 Hz).

Example 117

[4S-[4α,7α(R*),12bβ]]-7-[[(2S,3R)-3-Methyl-1-oxo-2-thiopentyl]amino]-6-oxo-11-phenyl-1,2,3,4,6,7,8,12b-octahydropyrido[2,1-a][2]benzazepine-4-carboxylic acid

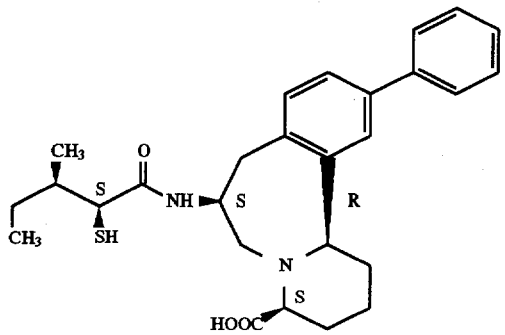

¹H-NMR (400 MHz, CDCl₃) δ; 7.91(1H, d, J=8 Hz) 7.51(2H, d, J=8 Hz), 7.44(2H, t like, J=8 Hz) 7.38–7.32(3H, m), 7.06(1H, d, J=8 Hz) 5.71(1H, quint, J=6 Hz), 5.52(1H, brd) 5.23(1H, m) 3.58(1H, dd, J=17, 6 Hz), 3.39(1H, dd, J=9, 7 Hz) 2.91(1H, dd, J=17, 13 Hz), 2.54(1H, m) 2.32(1H, m) 2.12(1H, septet, J=7 Hz), 2.00(1H, m) 1.87(1H, m) 1.80(1H, d, J=8 Hz), 1.82–1.70(2H, m) 1.51(1H, m) 1.34(1H, m), 0.97(3H, d, J=7 Hz) 0.93(3H, t, J=7 Hz).

Example 118

[3R-[3α,6α(S*),9aβ]]-6-[[3-(4-Methoxyphenyl)-1-oxo-2(S)-thiopropyl]amino]-2,2-dimethyl-5-oxooctahydrothiazol[3,2-a]azepine-3-carboxylic acid

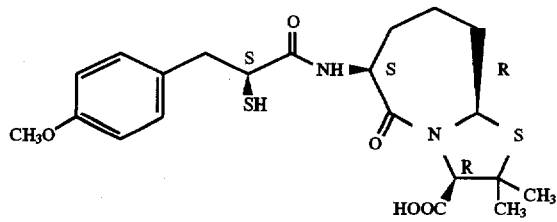

¹H-NMR (400 MHz, CDCl₃) δ; 7.63(1H, d, J=6 Hz) 7.12(2H, d, J=8 Hz), 6.82(2H, d, J=8 Hz) 5.12(1H, d, J=10 Hz), 4.74(1H, s) 4.54(1 h, dd, J=11, 6 Hz) 3.78(3H, s), 3.57(1H, dt, J=9, 7 Hz) 3.18(1H, dd, J=14, 6 Hz), 3.07(1H, dd, J=14, 7 Hz) 2.25–2.14(1H, m), 1.98(1H, d, J=9 Hz) 2.07–1.84(4H, m), 1.60–1.50(1H, m) 1.55(3H, s) 1.51(3H, s).

Example 119

[4S-[4α,7α(R*),12bβ]]-7-[[(2S)-3-(4-Fluorophenyl)-1-oxo-2-thiopropyl]amino]-6-oxo-11-phenyl-1,2,3,4,6,7,8,12b-octahydropyrido[2,1-a][2]benzazepine-4-carboxylic acid

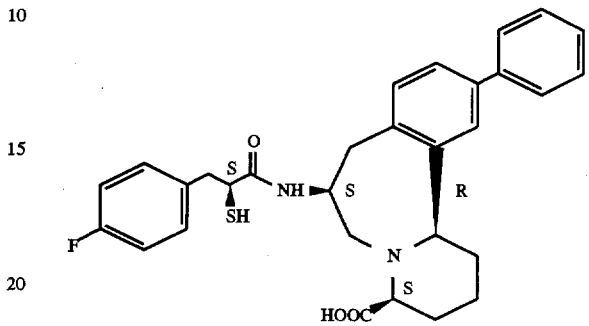

¹H-NMR (400 MHz, DMSO-d6) δ; 8.37(1H, d, J=7 Hz) 7.62(2H, d, J=8 Hz), 7.46(3H, t, J=8 Hz) 7.41(1H, s) 7.35(1H, t, J=8 Hz), 7.29(2H, dd, J=8, 6 Hz) 7.19(1H, d, J=8 Hz), 7.12(2H, t, J=8 Hz) 5.62–5.71(2H, m) 5.05(1H, m), 3.94(1H, m) 3.87(1H, m) 3.19(1H, dd, J=14, 7 Hz), 2.95(1H, dd, J=17, 13 Hz) 2.88–2.80(2H, m), 2.52(1H, m) 2.22(1H, m) 1.96(1H, m), 1.65~1.80(3H, m).

Example 120

[4S-[4α,7α(R*),12bβ]]-7-[[(2R)-3-(4-Fluorophenyl)-1-oxo-2-thiopropyl]amino]-6-oxo-11-phenyl-1,2,3,4,6,7,8,12b-octahydropyrido[2,1-a][2]benzazepine-4-carboxylic acid

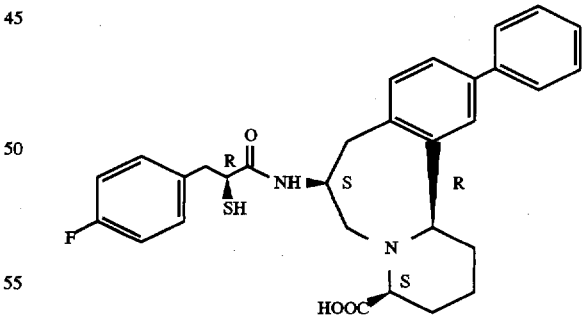

¹H-NMR (400 MHz, DMSO-d6) δ; 8.31(1H, d, J=7 Hz) 7.61(2H, d, J=8 Hz), 7.46(3H, t, J=8 Hz) 7.39(1H, s) 7.35(1H, t, J=8 Hz), 7.30(2H, dd, J=8, 6 Hz) 7.16(2H, t, J=8 Hz), 7.03(1H, d, J=8 Hz) 5.58–5.70(2H, m) 5.06(1H, m), 3.94(1H, m) 3.10(1H, dd, J=14, 9 Hz), 2.98~2.88(2H, m) 2.63(1H, dd, J=17, 12 Hz), 2.49(1H, m) 2.23(1H, m) 1.97(1H, m), 1.78–1.63(3H, m).

Example 121

[4S-[4α,7α(R*),12bβ]]-7-[[(2S)-3-(5-Bromo-2-thienyl)-1-oxo-2-thiopropyl]amino]-6-oxo-11-phenyl-1,2,3,4,6,7,8,12b-octahydropyrido[2,1-a][2]benzazepine-4-carboxylic acid

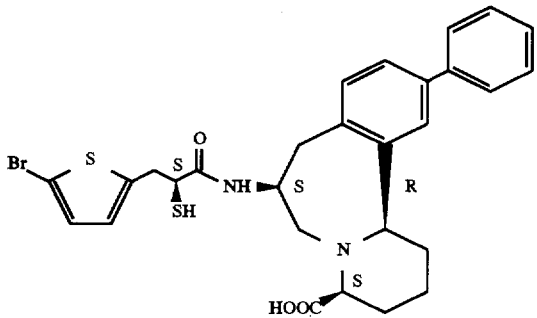

¹H-NMR (400 MHz, CDCl₃) δ; 7.67(1H, d, J=8 Hz) 7.51(2H, d, J=8 Hz), 7.43(2H, t like, J=8 Hz) 7.39-7.32(3H, m), 7.07(1H, d, J=8 Hz) 6.89(1H, d, J=4 Hz), 6.66(1H, d, J=4 Hz) 5.66(1H, quint, J=6 Hz), 5.50(1H, brd) 5.22(1H, m) 3.62-3.49(2H, m), 3.36(2H, d, J=6 Hz) 2.86(1H, dd, J=17, 13 Hz), 2.54(1H, m) 2.34(1H, m) 2.15(1H, d, J=10 Hz) 2.10-1.71(4H, m).

Example 122

[4S-[4α,7α(R*),12bβ]]-7-[[(2S)-3-Phenyl-1-oxo-2-thiomethylpropyl]amino]-6-oxo-11-phenyl-1,2,3,4,6,7,8,12b-octahydropyrido[2,1-a][2]benzazepine-4-carboxylic acid

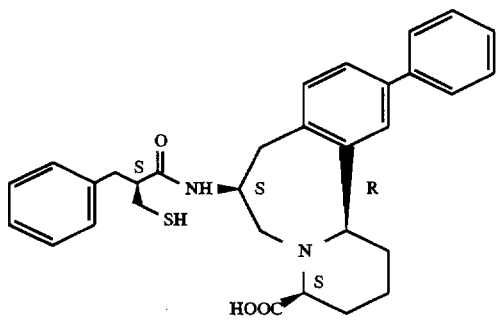

¹H-NMR (400 MHz, DMSO-d6) δ; 8.29(1H, d, J=7 Hz) 7.62(2H, d, J=8 Hz), 7.46(3H, t, J=8 Hz) 7.41(1H, s) 7.38-7.17(7H, m), 5.77-5.66(2H, m) 5.04(1H, d like), 3.07-2.96(2H, m) 2.90(1H, m) 2.73-2.64(2H, m), 2.55(1H, m) 2.43(1H, m) 2.29(1H, m) 2.24(1H, m), 1.99(1H, m) 1.78-1.67(3H, m).

Example 123

[4S-[4α,7α(R*),12bβ]]-7-[[(2S)-1-Oxo-2-thiohexyl]amino]-6-oxo-11-phenyl-1,2,3,4,6,7,8,12b-octahydropyrido[2,1-a][2]benzazepine-4-carboxylic acid

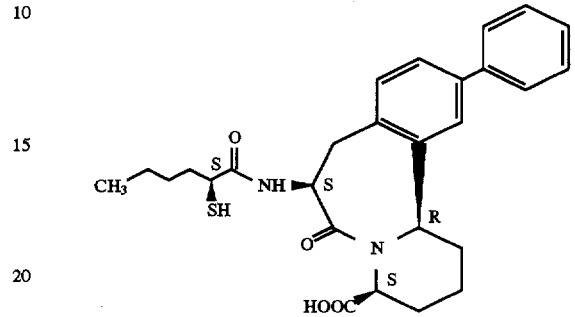

¹H-NMR (400 MHz, CDCl₃S) δ; 7.55(1H, d, J=7 Hz) 7.51(2H, d, J=8 Hz), 7.42(1H, t like, J=8 Hz) 7.40-7.28(3H, m), 7.09(1H, d, J=8 Hz) 5.71(1H, quint, J=6 Hz), 5.52(1H, brd) 5.23(1H, brd), 3.61(1H, dd, J=17, 6 Hz) 3.30(1H, q, J=7 Hz), 2.92(1H, dd, J=17, 13 Hz) 2.57(1H, m) 2.37(1H, m), 2.02(1H, d, J=10 Hz) 2.05-1.70(6H, m), 1.50-1.20(4H, m) 0.91(3H, s).

Example 124

[4S-[4α,7α(R*),12bβ]]-7-[[(2S)-3-(2Thienyl)-1-oxo-2-thiopropyl]amino]-6-oxo-11-phenyl-1,2,3,4,6,7,8,12b-octahydropyrido[2,1-a][2]benzazepine-4-carboxylic acid

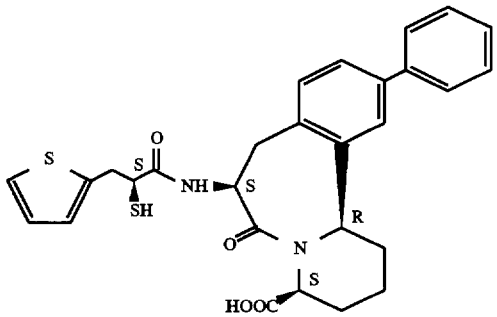

¹H-NMR (400 MHz, CDCl₃) δ; 7.67(1H, d, J=6 Hz) 7.51(2H, d, J=8 Hz), 7.43(2H, t like, J=8 Hz) 7.38-7.82(3H, m), 7.19(1H, d, J=4 Hz) 7.06(1H, d, J=8 Hz), 6.95(1H, d, J=4 Hz) 6.90(1H, d, J=4 Hz), 5.66(1H, quint, J=6 Hz) 5.49(1H, brd) 5.21(1H, m), 3.64-3.54(2H, m) 3.50-3.40 (2H, m), 2.84(1H, dd, J=17, 18 Hz) 2.54(1H, m) 2.33(1H, m), 2.15(1H, d, J=10 Hz) 2.10-1.70(4H, m).

Example 125

[4S-[4α,7α(R*),12bβ]]-7-[[(2S)-1-Oxo-2-thiopentyl]amino]-6-oxo-11-phenyl-1,2,3,4,6,7,8,12b-octahydropyrido[2,1-a][2]benzazepine-4-carboxylic acid

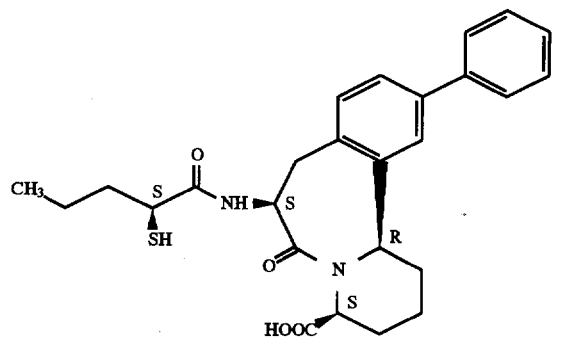

¹H-NMR (400 MHz, CDCl₃) δ; 7.57(1H, d, J=7 Hz) 7.51(2H, d, J=8 Hz), 7.44(1H, t like, J=8 Hz) 7.38–7.32(3H, m), 7.07(1H, d, J=8 Hz) 5.71(1H, quint, J=6 Hz), 5.52(1H, brd) 5.23(1H, brd), 3.58(1H, dd, J=17, 6 Hz) 3.32(1H, q, J=7 Hz), 2.81(1H, dd, J=17, 13 Hz) 2.54(1H, m) 2.33(1H, m), 2.09(1H, d, J=10 Hz) 2.10–1.67(6H, m), 1.55–1.35(2H, m) 0.94(3H, t, J=7 Hz).

Example 126

[4S-[4α,7α(R*),12bβ]]-7-[[(2S)-3-(3-Methylsulfonylaminophenyl)-1-oxo-2-thiopropyl]amino]-6-oxo-11-phenyl-1,2,3,4,6,7,8,12b-octahydropyrido[2,1-a][2]benzazepine-4-carboxylic acid

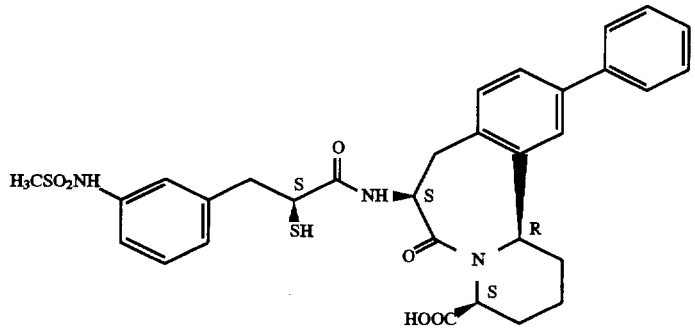

¹H-NMR (400 MHz, CDCl₃) δ; 7.71(1H, d, J=7 Hz) 7.61(1H, brs), 7.47(2H, d, J=8 Hz) 7.40(2H, t like, J=8 Hz), 7.36–7.28(3H, m) 7.22(1H, d, J=8 Hz), 7.16(1H, d, J=8 Hz) 7.03–6.98(3H, m), 5.68(1H, quint, J=6 Hz) 5.45(1H, brd), 5.06(1H, d like) 3.63(1H, m), 3.44(1H, dd, J=17, 6 Hz) 3.24–3.06(2H, m), 2.90(3H, s) 2.82(1H, dd, J=17, 13 Hz) 2.51(1H, m), 2.32(1H, m) 2.20(1H, d, J=10 Hz) 2.05–1.70 (4H, m).

Example 127

[4S-[4α,7α(R*),12bβ]]-7-[[(2S)-3-(3-Thienyl)-1-oxo-2-thiopropyl]amino]-6-oxo-11-phenyl-1,2,3,4,6,7,8,12b-octahydropyrido[2,1-a][2]benzazepine-4-carboxylic acid

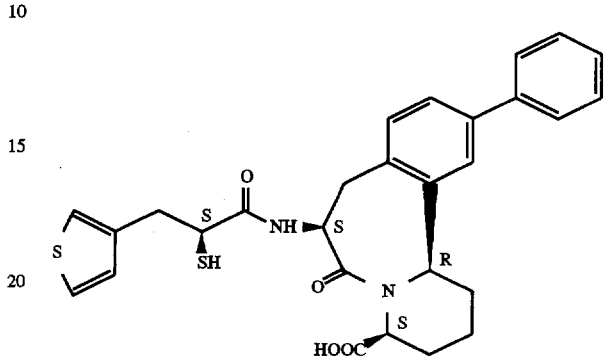

¹H-NMR (400 MHz, CDCl₃) δ; 7.64(1H, d, J=7 Hz) 7.50(2H, d, J=8 Hz), 7.43(2H, t like, J=8 Hz) 7.37–7.32(3H, m), 7.26(1H, d, J=8 Hz) 7.07(1H, m) 7.03(1H, d, J=8 Hz), 6.96(1H, d, J=5 Hz) 5.64(1H, quint, J=6 Hz), 5.47(1H, brd) 5.18(1H, d like) 3.62–3.45(2H, m), 3.30–3.16(2H, m) 2.80 (1H, dd, J=17, 13 Hz), 2.52(1H, m) 2.30(1H, m) 2.09(1H, d, J=10 Hz), 2.04–1.67(4H, m).

Example 128

[4S-[4α,7α(R*),12bβ]]-7-[(2-Methyl-oxo-2-thiopropyl)amino]-6-oxo-11-phenyl-1,2,3,4,6,7,8,12b-octahydropyrido[2,1-a][2]benzazepine]-4-carboxylic acid

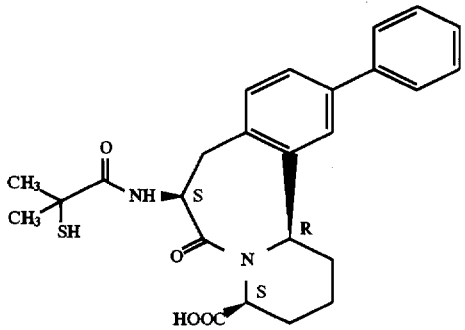

$^1$H-NMR (400 MHz, CDCl$_3$) δ; 8.11(1H, d, J=7 Hz) 7.50(2H, d, J=8 Hz), 7.43(1H, t like, J=8 Hz) 7.38~7.32(3H, m), 7.08(1H, d, J=8 Hz) 5.65(1H, quint, J=6 Hz), 5.52(1H, brd) 5.23(1H, brd), 3.59(1H, dd, J=17, 6 Hz) 2.81(1H, dd, J=17, 13 Hz), 2.53(1H, m) 2.32(1H, m) 2.32(1H, s), 2.06–1.70(4H, m) 1.63(3H, s) 1.64(3H, s).

Example 129

[4S-[4α,7α(R*),12bβ]]-7-[[(2S)-3-(4Methylsulfonylaminophenyl)-1-oxo-2-thiopropyl]amino]-6-oxo-11-phenyl-1,2,3,4,6,7,8,12b-octahydropyrido[2,1-a][2]-benzazepine-4-carboxylic acid $^1$H-NMR (400 MHz, CDCl$_3$) δ; 7.83 and 7.53(total 1H, each brs), 7.60–7.02(total 12H, m), 6.89 and 6.80(total 1H, each d, J=8 Hz), 5.66 and 5.64(total 1H, each quint, J=6 Hz), 5.44(total 1H, m), 5.08 and 4.97(total 1H, each brd), 3.54–3.00(4H, m) 2.83 and 2.82(total 3H, each s), 2.72 and 2.20(total 2H, m), 2.21 and 2.19(total 1H, each d, J=10 Hz), 2.04–1.90(total 4H, m),

Example 130

[4S-[4α,7α(R*),12bβ]]-7-[(2-Cyclohexyl-1-oxo-2-thioethyl)amino]-6-oxo-11-phenyl-1,2,3,4,6,7,8,12b-octahydropyrido[2,1-a][2]benzazepine-4-carboxylic acid (isomer A)

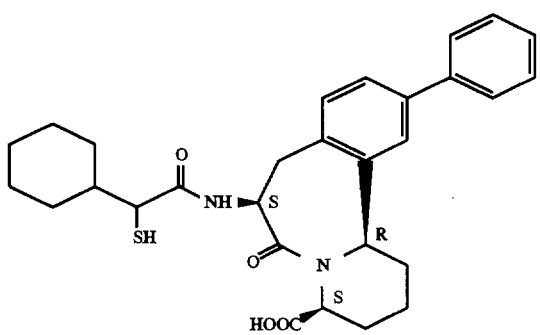

$^1$H-NMR (400 MHz, CDCl$_3$) δ; 7.60(1H, d, J=7 Hz) 7.51(2H, d, J=8 Hz), 7.44(1H, t like, J=8 Hz) 7.38–7.32(3H, m), 7.07(1H, d, J=8 Hz) 5.62(1H, quint, J=6 Hz), 5.43(1H, brd) 5.24(1H, brd), 3.59(1H, dd, J=17, 6 Hz) 3.35(1H, q, J=7 Hz), 2.80(1H, dd, J=17, 13 Hz) 2.53(1H, m) 2.33(1H, m), 2.06–1.63(9H, m) 1.91(1H, d, J=10 Hz), 1.34~1.96(6H, m).

Example 131

[4S-[4α,7α(R*),12bβ]]-7-[(2-Cyclohexyl-1-oxo-2-thioethyl)amino]-6-oxo-11-phenyl-1,2,3,4,6,7,8,12b-octahydropyrido[2,1-a][2]benzazepine-4-carboxylic acid (isomer B)

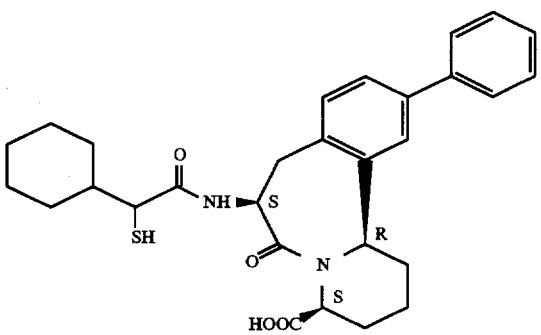

$^1$H-NMR (400 MHz, CDCl$_3$) δ; 7.53(1H, d, J=7 Hz) 7.51(2H, d, J=8 Hz), 7.44(1H, t like, J=8 Hz) 7.38–7.32(3H, m), 7.05(1H, d, J=8 Hz) 5.61(1H, quint, J=6 Hz), 5.51(1H, brd) 5.21(1H, brd), 3.57(1H, dd, J=17, 6 Hz) 3.42(1H, dd, J=7, 6 Hz), 2.90(1H, dd, J=17, 13 Hz) 2.52(1H, m) 2.31(1H, m), 2.04–1.64(9H, m) 1.90(1H, d, J=10 Hz), 1.36–1.95(6H, m).

Example 132

[4S-[4α,7α(R*),12bβ]]-7-[(2-Cyclohexyl-1-oxo-2-thioethyl)amino]-6-oxo-11-phenyl-1,2,3,4,6,7,8,12b-octahydropyrido[2,1-a][2]benzazepine-4-carboxylic acid (isomer A)

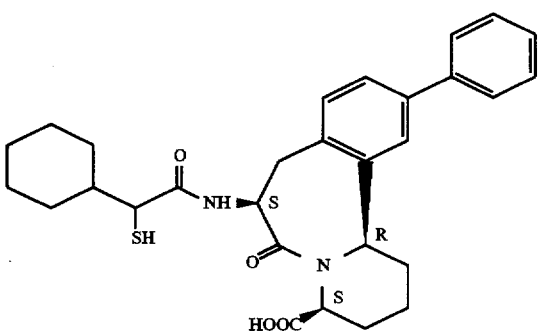

$^1$H-NMR (400 MHz, CDCl$_3$) δ; 7.45(2H, d, J=8 Hz) 7.40–7.25(6H, m), 7.02(1H, d, J=8 Hz) 5.66(1H, quint, J=6 Hz), 5.47(1H, m) 5.17(1H, d like), 3.54(1H, dd, J=17, 6 Hz) 3.13(1H, t, J=7 Hz), 2.85(1H, dd, J=17, 13 Hz) 2.49(1H, m), 2.33–2.20(2H, m) 2.00–1.46(10H, m), 1.97(1H, d, J=8 Hz) 1.37~1.23(2H, m).

Example 133

[4S-[4α,7α(R*),12bβ]]-7-[(2-Cyclohexyl-1-oxo-2-thioethyl)amino]-6-oxo-11-phenyl-1,2,3,4,6,7,8,12b-octahydropyrido[2,1-a][2]benzazepine-4-carboxylic acid (isomer B)

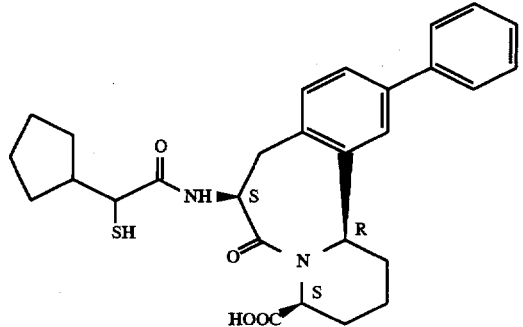

$^1$H-NMR (400 MHz, CDCl$_3$) δ; 7.45(2H, d, J=8 Hz) 7.40–7.24(6H, m), 7.03(1H, d, J=8 Hz) 5.67(1H, quint, J=6 Hz), 5.47(1H, m) 5.19(1H, d like), 3.57(1H, dd, J=17, 6 Hz) 3.31(1H, t, J=7 Hz), 2.88(1H, dd, J=17, 13 Hz) 2.50(1H, m), 2.36–2.22(2H, m) 1.98(1H, d, J=8 Hz), 2.02–1.18(12H, m).

Example 134

[4S-[4α,7α(R*),12bβ]]-7-[[(2R)-3-(3-Thienyl)-1-oxo-2-thiopropyl]amino]-6-oxo-11-phenyl-1,2,3,4,6,7,8,12b-octahydropyrido[2,1-a][2]benzazepine-4-carboxylic acid

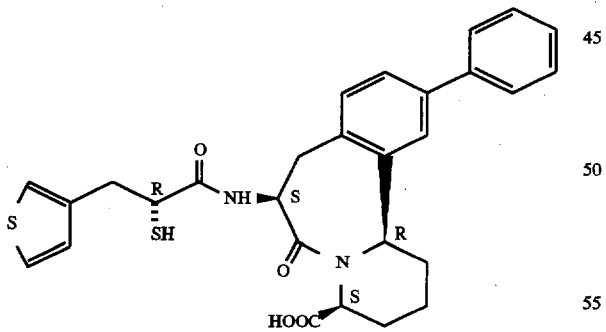

$^1$H-NMR (400 MHz, CDCl$_3$) δ; 7.49(2H, d, J=8 Hz) 7.43(2H, t like, J=8 Hz), 7.39–7.32(4H, m) 7.27(1H, m) 7.08(1H, brd, J=8 Hz), 7.02–6.96(2H, m) 5.64(1H, quint, J=6 Hz), 5.47(1H, brd) 5.18(1H, m) 3.48(1H, m), 3.40–3.25 (2H, m) 3.13(1H, dd, J=17, 6 Hz), 2.65(1H, dd, J=17, 13 Hz) 2.52(1H, m) 2.31(1H, m), 2.15(1H, d, J=10 Hz) 2.04–1.68 (4H, m).

Example 135

[4S-[4α,7α(R*),12bβ]]-7-[(3-Ethyl-1-oxo-2-thiopentyl)amino]-6-oxo-11-phenyl-1,2,3,4,6,7,8,12b-octahydropyrido[2,1-a][2]benzazepine-4-carboxylic acid

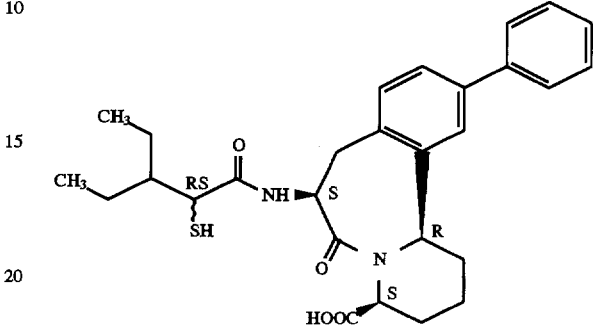

$^1$H-NMR (400 MHz, DMSO-d6) δ; 8.42 and 8.38(total 1H, each d, J=7 Hz), 7.62(2H, d, J=8 Hz) 7.46(3H, t, J=8 Hz) 7.41(1H, s), 7.35(1H, t, J=8 Hz) 7.18(total 1H, each d, J=8 Hz), 5.77–5.65(total 2H, m) 5.06(total 1H, d like), 3.58 and 3.54(total 1H, each t, J=7 Hz), 3.30–3.17(total 1H, m) 2.58–2.47(total 1H, m), 2.23(1H, m) 1.98(1H, m) 1.80–1.60 (8H, m), 0.87(3H, t, J=7 Hz) 0.82(3H, t, J=7 Hz).

Example 136

[4S-[4α,7α(R*),12bβ]]-7-[[(3S)-3-Hydroxy-1-oxo-2-thiobutyl]amino]-6-oxo-11-phenyl-1,2,3,4,6,7,8,12b-octahydropyrido[2,1-a][2]benzazepine-4-carboxylic acid

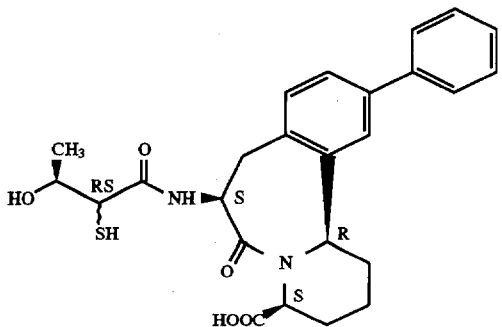

$^1$H-NMR (400 MHz, CDCl$_3$) δ; 7.56–7.92(1H, m) 7.52–7.30(7H, m), 7.10–6.94(1H, m) 5.81–5.66(1H, m), 5.56–5.48(1H, m) 5.26–5.19(1H, m), 3.68–2.85(3H, m) 2.53 (1H, brd) 2.34(1H, brd), 2.08–1.70(5H, m) 2.17(total 1H, each d, J=8 Hz), 2.05 and 2.17(total 1H, each d, J=8 Hz), 1.40 and 1.96(total 3H, each d, J=7 Hz).

Example 137

[4S-[4α,7α(R*),12bβ]]-7-[[(2S,3S)-3-Methoxy-1-oxo-2-thiobutyl]amino]-6-oxo-11-phenyl-1,2,3,4,6,7,8,12b-octahydropyrido[2,1-a][2]benzazepine-4-carboxylic acid

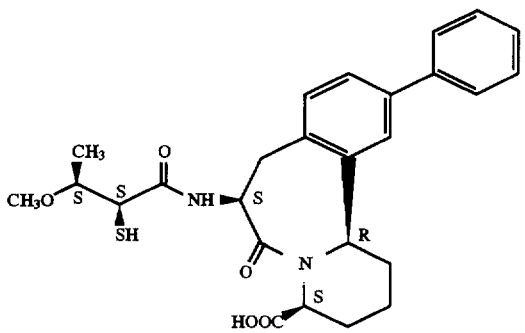

¹H-NMR (400 MHz, CDCl₃) δ; 7.84(1H, d, J=7 Hz) 7.51(2H, d, J=8 Hz), 7.43(2H, t, J=8 Hz) 7.38–7.31(3H, m), 7.09(1H, d, J=8 Hz) 5.61(1H, quint, J=6 Hz), 5.53(1H, m) 5.25(1H, m) 3.70(1H, quint, J=7 Hz), 3.62(1H, dd, J=17, 6 Hz) 3.40(3H, s), 3.39(1H, t, J=7 Hz) 2.94(1H, dd, J=17, 13 Hz), 2.55(1H, m) 2.36(1H, m) 2.27(1H, d, J=8 Hz), 2.08–1.72(4H, m) 1.30(3H, d, J=7 Hz);

Example 138

[4S-[4α,7α(R*),12bβ]]-7-[(3-Methyl-1-oxo-2-thiohexyl)amino]-6-oxo-11-phenyl-1,2,3,4,6,7,8,12b-octahydropyrido[2,1-a][2]benzazepine-4-carboxylic acid

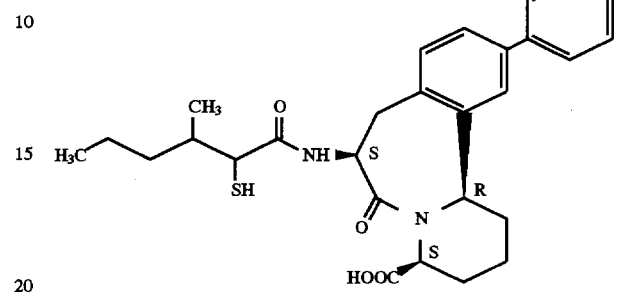

¹H-NMR (400 MHz, CDCl₃) δ; 7.70 and 7.61(total 1H, each d, J=7 Hz), 7.50(2H, d, J=8 Hz) 7.43(2H, t, J=8 Hz) 7.40–7.30(3H, m), 7.07 and 7.06(total 1H, each d, J=8 Hz), 5.71(1H, quint, J=6 Hz) 5.52(1H, m) 5.23(1H, m), 3.59(1H, m) 3.29(1H, dd, J=17, 12 Hz), 2.92(1H, dd, J=17, 12 Hz) 2.54(1H, m) 2.34(1H, m), 2.10–1.94(2H, m) 1.94–1.82(1H, m), 1.80–1.70(1H, m) 1.56(1H, m) 1.41(1H, m), 1.35–1.14 (2H, m), 1.03 and 1.02(total 3H, each d, J=7 Hz), 0.92 and 0.91(total 3H, each t, J=7 Hz).

Example 139

[4S-[4α,7α(R*),12bβ]]-7-[[(2S,3S)-3-Methyl-2-(4-morpholinyl)acetylthio-1-oxopentyl]amino]-6-oxo-11-phenyl-1,2,3,4,6,7,8,12b-octahydropyrido[2,1-a][2]-benzazepine-4-carboxylic acid trifluoroacetate

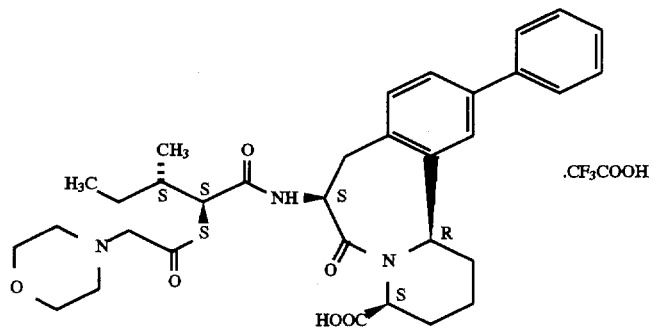

(a) diphenylmethyl [4S-[4α,7α(R*),12bβ]]-7-[[(2S,3S)-3-methyl-1-oxo-2-thiopentyl]amino]-6-oxo-11-phenyl-1,2,3,4,6,7,8,12b-octahydropyrido[2,1-a][2]benzazepine-4-carboxylate

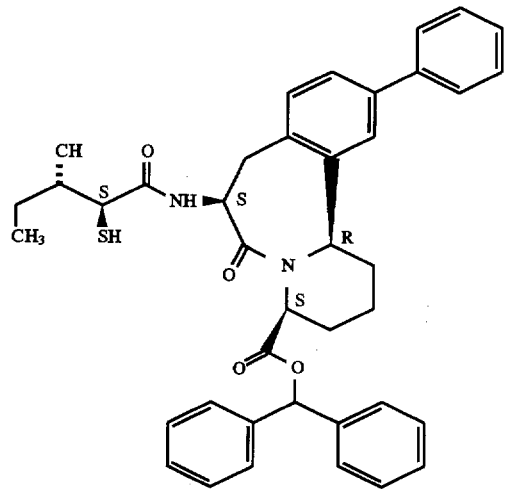
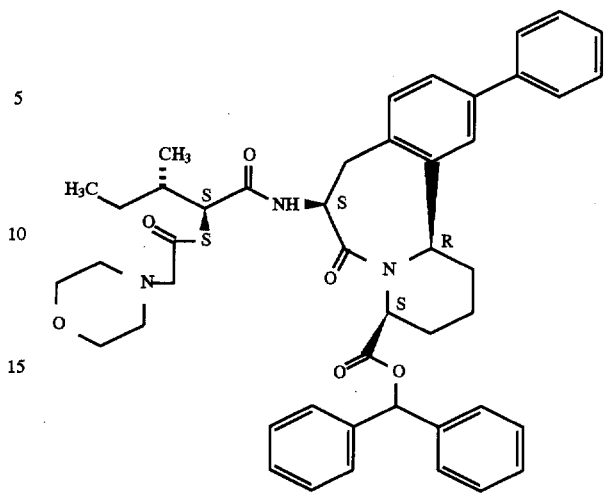

0.500 g (0.730 mmol) of diphenylmethyl [4S-[4α,7α(R*),12bβ]]-7-[[(2S,3S)-2-acetylthio-3-methyl-1-oxopentyl]amino]-6-6-oxo-11-phenyl-1,2,3,4,6,7,8,12b-octahydropyrido[2,1-a][2]benzazepine-4-carboxylate obtained in the Example C-6 was dissolved in 10 ml of dry ethanol. To the solution thus obtained was added 10 ml of a 12% (w/w) ammonia-ethanol solution under cooling with ice. The resulting mixture was stirred at room temperature for 2 hours, concentrated under reduced pressure and diluted with dichloromethane. It was washed with water and a saturated aqueous sodium chloride, dried over anhydrous magnesium sulfate and then concentrated. Thus, 0.468 g of the title compound was obtained as white crystals (yield 99%).

$^1$H-NMR (400 MHz, CDCl$_3$) δ; 7.72(1H, d, J=6 Hz) 7.50–6.92(17H, m), 6.70(1H, d, J=8 Hz) 6.30(1H, s), 5.67 (1H, dt, J=13, 6 Hz) 5.49(1H, m), 5.42(1H, d like, J=4 Hz) 3.45(1H, dd, J=18, 6 Hz), 3.28(1H, dd, J=8, 7 Hz) 2.61(1H, dd, J=18, 13 Hz), 2.55–2.45(2H, m) 1.95(1H, d, J=8 Hz), 1.62–2.08(6H, m) 1.37–1.25(1H, m), 1.06(3H, d, J=7 Hz) 0.96(3H, t, J=7 Hz).

(b) diphenylmethyl [4S-[4α,7α(R*),12bβ]]-7-[[(2S,3S)-3-methyl-2-(4-morpholinyl/acetylthio-1-oxopentyl]amino]-6-oxo-11-phenyl-1,2,3,4,6,7,8,12b-octahydropyrido[2,1-a][2]benzazepine-4-carboxylate 0.262 mg (1.44 mmol) of 4-morpholinylacetic acid hydrochloride was dissolved in 7.2 ml of degassed dry dimethylformamide. To the solution thus obtained was added 0.176 g (1.08 mmol) of carbodinylimidazole under cooling with ice. The resulting mixture was stirred at room temperature for 1.5 hours. The obtained mixture was cooled with ice again and a solution of 0.467 g (0.72 mmol) of diphenylmethyl [4S-[4α,7α(R*), 12bβ]]-7-[[(2S,3S)-3-methyl-1-oxo-2-thiopentyl]amino]-6-oxo-11-phenyl-1,2,3,4,6,7,8,12b-octahydropyrido-[2,1-a][2]benzazepine-4-carboxylate obtained in the above (a) in degassed dry tetrahydrofuran (7.2 ml) was dropped thereinto. The obtained mixture was stirred at room temperature for 1 hour and then concentrated under reduced pressure until the volume of the liquid was reduced to about one-half. Ethyl acetate was added thereto and the resulting mixture was washed with a saturated aqueous solution of sodium hydrogencarbonate and a saturated aqueous sodium chloride, dried over anhydrous magnesium sulfate and then concentrated. Thus, 0.500 g of the target morpholino compound was obtained (yield 90%).

$^1$H-NMR (400 MHz, CDCl$_3$) δ; 7.54(1H, d, J=6 Hz) 7.49–6.92(17H, m), 6.67(1H, d, J=8 Hz) 6.29(1H, s), 5.64 (1H, dt, J=13, 6 Hz) 5.44–5.49(1H, m), 5.40–5.36(1H, m) 3.99(1H, d, J=7 Hz), 3.80(4H, t, J=5 Hz) 3.41(1H, dd, J=16, 7 Hz), 3.35(2H, s) 2.71–2.60(4H, m) 2.60–2.44(2H, m), 2.21–1.59(7H, m) 1.31–1.91(1H, m), 1.06(3H, d, J=7 Hz) 0.94(3H, t, J=7 Hz).

(c) [4S-[4α,7α(R*),12bβ]]-7-[[(2S,3S)-3-methyl-2-(4-morpholinyl)acetylthio-1-oxopentyl]amino]-6-oxo-11- phenyl-1,2,3,4,6,7,8,12b-octahydropyrido[2,1-a][2]-benzazepine-4-carboxylic acid trifluoroacetate 4,6,7,8,12b-octahydropyrido[2,1-a][2]-benzazepine-4-

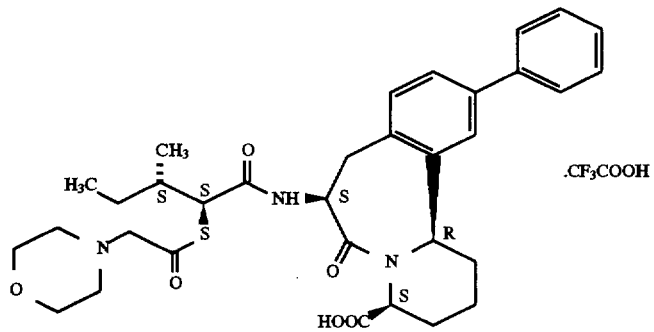

Into a solution of 0.500 g (0.65 mmol) of diphenylmethyl 4S-[4α,7α(R*),12bβ]]-7-[[(2S,3S)-3-methyl-2-(4-morpholinyl)acetylthio-1-oxopentyl]amino]-6-oxo-11-phenyl-1,2,3,4,6,7,8,12b-octahydropyrido-[2,1-a][2]benzazepine-4-carboxylate obtained in the above (b) and 0.54 ml (5.00 mmol) of anisole in dichloromethane (6.2 ml) was dropped 0.95 ml 12.00 mmol) of trifluoroacetic acid at −50° C. The mixture thus obtained was heated to room temperature and stirred for 3 hours. The reaction mixture was concentrated under reduced pressure and the residue was recrystallized from diethyl ether-hexane. Thus, 0.414 g of the title compound was obtained (yield 89%).

$^1$H-NMR (400 MHz, CDCl$_3$) δ; 7.59–7.30(8H, m) 7.09 (1H, d, J=9 Hz), 5.74–5.65(1H, m) 5.54–5.47(1H, m), 5.20–5.14(1H, m) 4.06(1H, d, J=7 Hz) 3.81(4H, m), 3.67 (2H, s) 3.54(1H, dd, J=17, 6 Hz), 3.52–3.30(2H, br) 3.02–2.90(5H, m) 2.55(1H, brd), 2.36(1H, brd) 2.17–1.74 (5H, m) 1.66–1.55(1H, m), 1.26–1.14(1H, m) 1.03(3H, d, J=7 Hz), 0.92(3H, t, J=7 Hz).

Example 140

[4S-[4α,7α(R*),12bβ]]-7-[[(2S,3S)-2-(Diethylamino)acetylthio-3-methyl-1-oxopentyl] amino]-6-oxo-11-phenyl-1,2,3,4,6,7,8,12b-octahydropyrido[2,1-a[2]benzazepine-4-carboxylic acid trifluoroacetate carboxylate, 0.896 g of the title compound was obtained at a yield of 81% through two steps.

$^1$H-NMR (400 MHz, CDCl$_3$) δ; 7.79(1H, d, J=7 Hz) 7.50–7.03(8H, m), 5.75(1H, dt, J=13, 6 Hz) 5.55–5.48(1H, m), 5.18–5.16(1H, m) 4.22(1H, d, J=7 Hz), 4.14–4.04(2H, m) 3.46(1H, dd, J=17, 6 Hz), 3.30–3.20(4H, m) 2.98(1H, dd, J=17, 13 Hz), 2.57(1H, brd, J=12 Hz) 2.40(1H, brd, J=12 Hz), 2.17–1.74(5H, m) 1.67–1.56(1H, m), 1.25(6H, t, J=7 Hz) 1.28–1.16(1H, m), 1.05(3H, d, J=7 Hz) 0.92(3H, t, J=7 Hz).

Example 141

[4S-[4α,7α(R*),12bβ]]-7-[[(2S,3S)-2-(1-Imidazolino)acetylthio-3-methyl-1-oxopentyl] amino]-6-oxo-11-phenyl-1,2,3,4,6,7,8,12b-octahydropyrido-[2,1-a][2]benzazepine-4-carboxylic acid trifluoroacetate

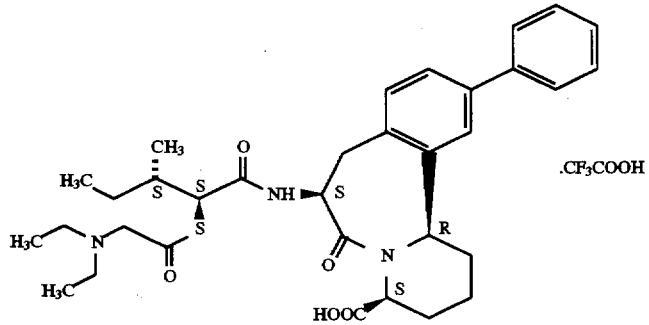

In the same method as that of Example 139 except that 0.526 g (3.14 mmol) of N,N-diethylaminoacetic acid hydrochloride was used in place of 4-morpholinylacetic acid hydrochloride, and starting with 1.1 g (1.57 mmol) of diphenylmethyl 4S-[4α,7α(R*),12bβ]]-7-[[(2S,3S)-3-methyl-1-oxo-2-thiopentyl]amino]-6-oxo-11-phenyl-1,2,3,

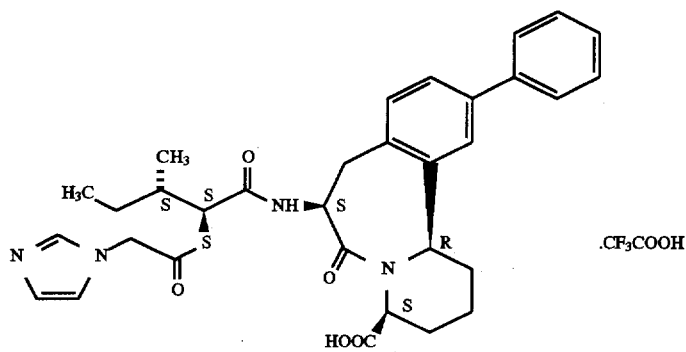

In the same method as that of Example 139 except that 0.287 g (1.76 mmol) of 1-imidazolylacetic acid hydrochloride was used in place of the 4-morpholinylacetic acid hydrochloride, and starting with 0.570 g (0.88 mmol) of diphenylmethyl 4S-[4α,7α(R*),12bβ]]-7-[[(2S,3S)-3-methyl-1-oxo-2-thiopentyl]amino]-6-oxo-11-phenyl-1,2,3,4,6,7,8,12b-octahydropyrido[2,1-a][2]-benzazepine-4-carboxylate, 0.355 g of the title compound was obtained as a white amorphous product at a yield of 57% through two steps.

$^1$H-NMR (400 MHz, CDCl$_3$) δ; 8.37(1H, brs) 7.69(1H, d, J=7 Hz) 7.53–7.25(7H, m), 7.09(1H, brs) 7.03–6.98(2H, m), 5.65(1H, dt, J=13, 6 Hz) 5.48–5.42(1H, m), 5.10–5.04(1H, m) 5.01(1H, d, J=18 Hz), 4.92(1H, d, J=18 Hz) 4.16(1H, d, J=6 Hz), 3.41(1H, dd, J=17, 6 Hz) 2.92(1H, dd, J=17, 13 Hz), 2.55(1H, brd) 2.32(1H, brd) 2.16–2.07(1H, m), 2.04–1.86(2H, m) 1.83–1.72(2H, m), 1.67–1.55(1H, m) 1.23–1.10(1H, m), 1.03(3H, d J=7 Hz) 0.92(3H, t, J=7 Hz).

Example 142

(3S)-[[(2S, 3R)-2-Acetylthio-3-methyl-1-oxo-pentyl]amino]-2,3,4,5-tetrahydro-1H-[1]benzazepin-2-one

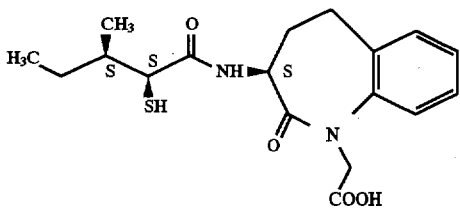

In accordance with the Example 117, the title compound was synthesized.

$^1$H-NMR (400 MHz, CDCl$_3$) δ; 7.60(1H, brd, J=7 Hz) 7.33–7.14(4H, m), 4.70(1H, d, J=17 Hz) 4.53(1H, dt, J=11, 7 Hz), 4.44(1H, d, J=17 Hz) 3.35–3.24(2H, m), 2.74–2.59 (2H, m) 2.06–1.96(2H, m), 1.74(1H, d, J=9 Hz) 1.44(1H, m) 1.26(1H, m), 0.87(6H, m).

Example 143

Ethyl (3S)-[[(2S,3S)-2-acetylthio-3-methyl-1-oxopentyl]amino]-4-oxo-2,3,4,5-tetrahydro-1,5-benzoxazepine-5-acetate

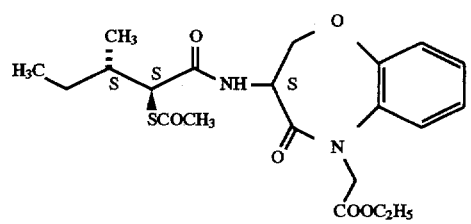

528 mg of ethyl (3S)-amino-4-oxo-2,3,4,5-tetrahydro-1,5-benzoxazepine-5-acetate and 419 mg (1.1 eq.) of (2S,3S)-2-acetylthio-3-methylpentanoic acid were dissolved in 40 ml of methylene chloride. To the solution thus obtained was added 544 mg (1.1 eq.) of EEDQ under cooling with ice. The resulting mixture was further stirred at room temperature for 21 hours. The reaction mixture was made weekly acidic by adding 1N hydrochloric acid under cooling with ice, and the methylene chloride phase was separated. After the methylene chloride phase was washed with an aqueous sodium chloride twice, it was dried over anhydrous magnesium sulfate and concentrated. The obtained residue was purified by silica gel chromatography (ethanol:chloroform= 1.5:98.5–4:96). Thus, 370 mg of the title compound was obtained.

$^1$H-NMR (400 MHz, CDCl$_3$) δ: 7.14–7.25(4H, m) 7.04 (1H, d, J=7 Hz), 4.94(1H, dd, J=10, 7 Hz) 4.69(1H, dd, J=10, 7 Hz), 4.68(1H, d, J=18 Hz) 4.33(1H, d, J=18 Hz), 4.25(2H, q, J=7 Hz) 4.13(1H, t, J=10 Hz), 3.92(1H, d, J=7 Hz) 2.37(3H, s) 2.02(1H, m), 1.56(1H, m) 1.26(3H, t, J=7 Hz) 1.14(1H, m), 0.96(3H, d, J=7 Hz) 0.85(3H, t, J=7 Hz).

Example 144

(3S)-[[(2S,3S)-3-Methyl-1-oxo-2-thiopentyl]-amino]-4-oxo-2,3,4,5-tetrahydro-1,5-benzoxazepine-5-acetic acid

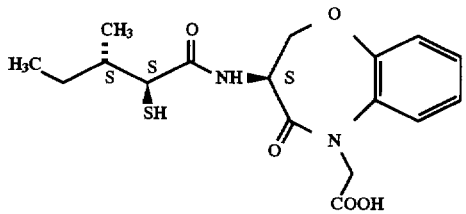

360 mg of ethyl (3S)-[[(2S,3S)-2-acetylthio-3-methyl-1-oxopentyl]amino]-4-oxo-2,3,4,5-tetrahydro-1,5-benzoxazepine-5-acetate obtained in the Example 143 was dissolved in 6 ml of degassed ethanol. To the obtained solution was added a degassed 1N aqueous solution of sodium hydroxide under cooling with ice. The obtained mixture was stirred at room temperature for 30 minutes and then made weakly acidic by adding 1N hydrochloric acid, followed by extraction with chloroform (15 ml×2). The organic phase was washed with water and then dried over anhydrous magnesium sulfate. After distilling off the solvent under reduced pressure, 250 mg (yield 83%) of the title compound was obtained.

$^1$H-NMR (400 MHz, CDCl$_3$) δ: 7.47(1H, d, J=7 Hz) 7.18–7.29(4H, m), 4.90(1H, dt, J=10, 7 Hz) 4.78(1H, d, J=18 Hz), 4.69(1H, dd, J=10, 7 Hz) 4.30(1H, d, J=18 Hz), 4.22(1H, t, J=10 Hz) 3.23(1H, dd, J=9, 6 Hz), 1.94(1H, m) 1.88(1H, d, J=9 Hz) 1.53(1H, m), 1.22(1H, m) 0.96(3H, d, J=6 Hz) 0.87(3H, t, J=7 Hz).

Example 145

[3R-[3α,6α(S*),9aβ]]-6-[[(2R,3S)-3-Methyl-1-oxo-2-thiopentyl]amino]-octahydro-5-oxothiazo[3,2-a]azepine-3-carboxylic acid

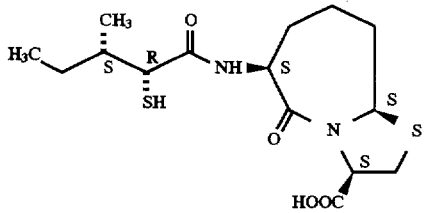

In accordance with Example 144, the title compound was synthesized.

$^1$H-NMR (400 MHz, CDCl$_3$) δ; 7.80(1H, d, J=6 Hz) 5.30(1H, dd, J=7, 2 Hz), 5.08–5.06(1H, m) 4.63(1H, dd, J=11, 6 Hz), 3.37–3.33(2H, m) 3.22(1H, dd, J=12, 7 Hz), 2.14–1.90(6H, m) 1.79(1H, d, J=9 Hz), 1.75–1.64(1H, m) 1.55–1.43(1H, m), 1.36–1.22(1H, m) 0.92(3H, d, J=7 Hz), 0.92(3H, t, J=7 Hz).

Example 146

[3R-[3α,6α(S*),9aβ]]-6-[[(2S,3S)-2-Acetylthiomethyl-3-methyl-1-oxopentyl]amino]-octahydro-5-oxothiazol[3,2-a]azepine-3-carboxylic acid

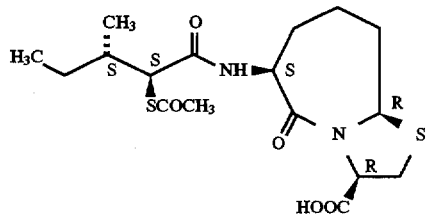

0.200 g (0.550 mmol) of [3R-[3α,6α(S*),9aβ]]-6-[[(2S,3S)-3-methyl-1-oxo-2-thiopentyl]amino]-octahydro-5-oxothiazol[3,2-a]azepine-3-carboxylic acid obtained in the Example C-8 and 0.058 ml (0.610 mmol) of acetic anhydride were dissolved in 6 ml of acetonitrile-tetrahydrofuran (1:1). The obtained solution was dropped into a solution of 0.022 g (0.170 mmol) of cobalt (II) chloride in 5 ml of acetonitrile. After the mixture thus obtained was stirred for 7 hours, it was concentrated under reduced pressure, and water was added thereto, followed by extraction with ethyl acetate. The organic phase was washed with a saturated aqueous sodium chloride, dried over anhydrous magnesium sulfate and then concentrated under reduced pressure. The residual solid was recrystallized from ethyl acetate-diethyl etherhexane. Thus, 0.180 g of the title compound was obtained as white crystals (yield 85%).

$^1$H-NMR (400 MHz, CDCl$_3$) δ: 7.44(1H, d, J=6 Hz) 5.30(1H, dd, J=7, 2 Hz), 5.05(1H, t like, J=5 Hz) 4.60(1H, dd, J=11, 6 Hz), 3.97(1H, d, J=7 Hz) 3.35(1H, dd, J=12, 2 Hz), 3.21(1H, dd, J=12, 7 Hz) 2.38(3H, s), 2.14–1.86(6H, m) 1.72–1.52(2H, m), 1.24–1.10(1H, m) 1.00(3H, d, J=7 Hz), 0.88(3H, t, J=7 Hz).

Example 147

(3S)-[[(2S,3S)-2-Acetylthio-3-methyl-1-oxopentyl]amino]-2,3,4,5-tetrahydro-1H-[1]benzazepin-2-one

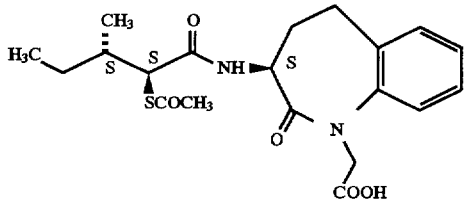

0.547 g (1.5 mmol) of (S)-1-carboxymethyl-3-[[(2S,3S)-3-methyl-1-oxo-2-thiopentyl]amino]-2,3,4,5-tetrahydro-1H-[1]benzazepin-2-one obtained in the Example C-11 and 0.168 ml (1.650 mmol) of acetic anhydride were dissolved in 7 ml of acetonitrile. The obtained solution was dropped into a solution of 0.075 g (0.577 mmol) of cobalt (II) chloride in 10 ml of acetonitrile. After the mixture thus obtained was stirred for 2 hours, it was concentrated under reduced pressure, and water was added thereto, followed by extraction with ethyl acetate. The organic phase was washed with a saturated aqueous sodium chloride, dried over anhydrous magnesium sulfate and then concentrated under reduced pressure. Thus, 0.43 g of the title compound was obtained as a colorless amorphous product.

¹H-NMR (400 MHz, CDCl₃) δ; 7.30–7.09(5H, m) 4.76 (1H, d, J=17 Hz), 4.49(1H, dt, J=11, 7 Hz) 4.39(1H, d, J=17 Hz), 3.88(1H, d, J=7 Hz) 3.30(1H, m) 2.70–2.50(2H, m), 2.35(3H, s) 2.02–1.82(2H, m) 1.53(1H, m), 1.11(1H, m) 0.93(3H, d, J=7 Hz) 0.84(3H, t, J=7 Hz).

Examples 148 to 152

In accordance with the processes of the above Examples 101 to 108, compounds of Examples 148 to 152 were obtained.

Example 148

[4S-[4α,7α(R*),12bβ]]-7-[[(2S,3S)-3-Methyl-1-oxo-2-thiopentyl]amino]-6-oxo-1,2,3,4,6,12b-octahydropyrido[2,1-a][2]benzazepine-4-carboxylic acid

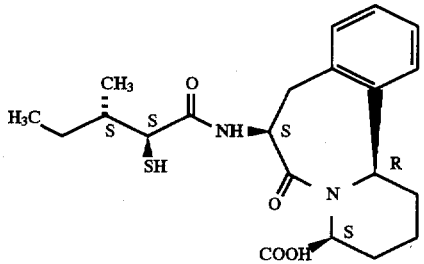

¹H-NMR (400 MHz, CD3OD) δ; 7.69(2H, d, J=8 Hz) 7.17–7.05(3H, m), 7.02(1H, d, J=8 Hz) 5.69(1H, quint, J=6 Hz), 5.48(1H, brd, J=6 Hz) 5.20(1H, m), 3.52(1H, dd, J=17, 6 Hz) 3.21(1H, dd, J=9, 7 Hz), 2.90(1H, dd, J=17, 13 Hz) 2.50(1H, m) 2.35(1H, m), 1.92–2.03(2H, m) 1.92(1H, d, J=8 Hz) 1.27(1H, m), 1.02(3H, d, J=7 Hz) 0.93(3H, t, J=7 Hz).

Example 149

[3R-[3α,6α(S*),9aβ]]-6[[(2S,3S)-3-Methyl-1-oxo-2-thiopentyl]amino]-octahydro-5-oxothiazol[3,2-a]-azepine-3-carboxylic acid

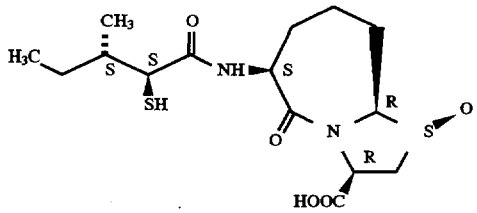

¹H-NMR (400 MHz, CDCl₃) δ; 7.78 and 7.84(total 1H, each d, J=7 Hz), 5.56–4.58(3H, m) 3.82–2.92(3H, m), 2.34–1.45(9H, m) 1.30–1.18(1H, m), 0.88–1.00(6H, m).

Example 150

[3R-[3α,6α(S*),9aβ]]-6[[(S)-4-Methyl-1-oxo-2-thiopentyl]-amino]-octahydro-5-oxothiazol[3,2-a]azepine-3-carboxylic acid

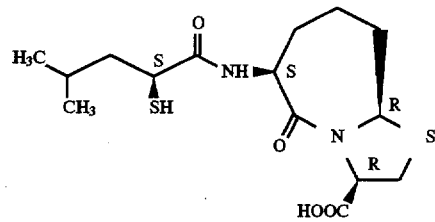

¹H-NMR (400 MHz, CDCl₃) δ; 7.56–7.60(1H, t like) 5.29(1H, dd, J=7, 3 Hz), 5.08–5.06(1H, m) 4.65–4.61(1H, m), 3.40–3.33(2H, m) 3.23(1H, dd, J=12, 7 Hz), 2.08–1.90 (6H, m) 1.88–1.64(3H, m), 1.60–1.52(1H, m) 0.94(3H, d, J=6 Hz), 0.90(3H, d, J=7 Hz).

Example 151

[3R-[3α,6α(S*),9aβ]]-6[[(S)-1-Oxo-2-thiohexyl]-amino]-octahydro-5-oxothiazol[3,2-a]azepine-3-carboxylic acid

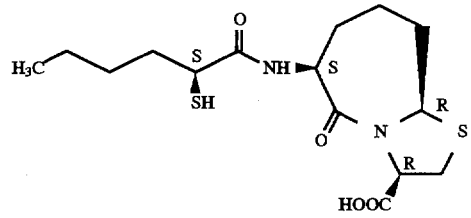

¹H-NMR (400 MHz, CDCl₃) δ; 7.58(1H, d, J=6 Hz) 5.30(1H, dd, J=7, 2 Hz), 5.07(1H, t like, J=5 Hz) 4.59–4.64 (1H, m), 3.36(1H, dd, J=12, 3 Hz) 3.30(1H, dt, J=8, 7 Hz), 3.22(1H, dd, J=12, 7 Hz) 2.10–1.90(6H, m), 2.00(1H, d, J=8 Hz) 1.76–1.64(2H, m), 1.46–1.24(4H, m) 0.90(3H, t, J=7 Hz).

Example 152

[3R-[3α,6α(S*),9aβ]]-6[[(2S,3S)-2-Benzoylthio-3-methyl-1-oxopentyl]amino]-octahydro-5-oxothiazol-[3,2-a]azepine-3-carboxylic acid

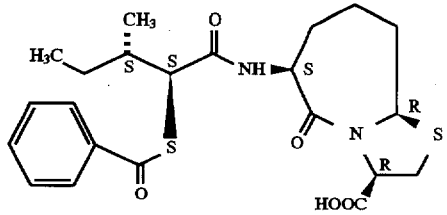

In the same procedure as that of Example 146 except that benzoyl chloride was used in place of the acetic anhydride, the title compound was obtained as a white product (147 mg, yield 51%).

¹H-NMR (400 MHz, CDCl₃) δ; 0.92(3H, t, J=7 Hz) 1.06(3H, d, J=6 Hz), 1.20–1.30(1H, m) 1.58–1.72(2H, m), 1.90–2.03(5H, m) 2.13–2.23(1H, m), 3.19(1H, dd, J=7, 12 Hz) 3.33(1H, dd, J=2, 12 Hz), 4.20(1H, d, J=7 Hz) 4.62(1H, dd, J=7, 11 Hz), 5.02–5.08(1H, m) 5.28(1H, dd, J=2, 7 Hz), 7.43–7.61(4H, m) 7.97–7.99(2H, m).

We claim:

1. A compound comprising a therapeutically or prophylactically available dose of an amino acid derivative represented by the following general formula or a pharmacologically acceptable salt thereof:

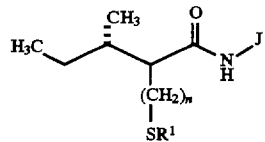

wherein $R^1$ represents a hydrogen atom or an acyl group; and n represent an integer of 0, 1 or 2; and J represents a cyclic group directly bound to N having an angiotensin I-converting enzyme inhibition activity.

2. The compound as set forth in claim 1, wherein J in the general formula (I) is represented

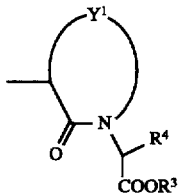

wherein $R^3$ represents a hydrogen atom or a carboxyl-protecting group;

$Y^1$ represents a group represented by the formula —$(CR^5R^6)_p$—Z—$(CR^7R^8)_q$— (wherein $R^5$, $R^6$, $R^9$ and $R^8$ are the same or different from one another and each represents a hydrogen atom, a lower alkyl group, an aryl group which may have a substituent, a heteroaryl group which may have a substituent, an arylalkyl group which may have a substituent or a heteroarylalkyl group which may have a substituent; Z represents a group represented by the formula —$(CH_2)_r$— (wherein r represents an integer of 0 or 1), a group represented by the formula —S—, a group represented by the formula —SO—, a group represented by the formula —$SO_2$—, a group represented by the formula —O— or a group represented by the formula —$NR^9$— (wherein $R^9$ represents a hydrogen atom or a lower alkyl group); and p and q represents each independently an integer of 0 or 1 to 4 and the sum of p and q is 6 or less;

with the proviso that in $R^5$, $R^6$, $R^7$, $R^8$ and $R^9$, when two carbon atoms each having an arbitrary substituent selected from among $R^5$ to $R^9$ bonded thereto are adjacent to each other, said two carbon atoms and said two substituents bonded thereto may be combined together to form a benzene ring or a heteroaryl ring, which may have a substituent;

and that when $R^2$ is an aryl group, p is 2, q is 2, Z represents a group represented by the formula —$(CH_2)_{r'}$— (wherein r' represents 0), and two substituents arbitrary selected from among $R^5$'s, $R^6$'s, $R^7$'s and $R^8$'s which are bonded to two adjacent carbon atoms are combined together to form a benzene ring, said benzene ring must be substituted by an aryl group which may have a substituent); and $R^4$ represents a hydrogen atom, a lower alkyl group or an arylalkyl group, or a group used to form a 5- to 7-membered ring which may contain one sulfur or oxygen atom in combination with $R^7$ or $R^8$.

3. An amino acid derivative represented by formula (II):

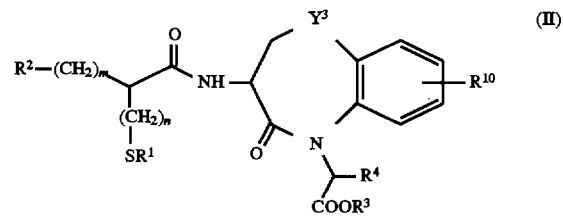

wherein $R^1$ represents a hydrogen atom or an acyl group;

$R^2$ represents a hydrogen atom, a lower alkyl group, a cycloalkyl group, an aryl group which may have a substituent, a heteroaryl group which may have a substituent, an arylalkyl group which may have a substituent or a heteroarylalkyl group which may have a substituent;

$R^3$ represents a hydrogen atom or a carboxyl-protecting group;

$R^4$ represents a hydrogen atom, or a lower alkyl group $Y^3$ represents a group represented by the formula —$(CH_2)_w$— (wherein w represents 0 or 1), a group represented by the formula —S—, a group represented by the formula —SO—, a group represented by the formula —$SO_2$—, a group represented by the formula —O— or a group represented by the formula —$NR^{16}$— (wherein $R^{16}$ represents a hydrogen atom or a lower alkyl group);

$R^{10}$ represents a hydrogen atom, a lower alkyl group, a lower alkoxy group, a hydroxyl group, a halogen atom, an aryl group which may have a substituent or a heteroaryl group which may have a substituent; and m and n represent each independently an integer of 0, 1 or 2.

4. An amino acid derivative represented by formula (III):

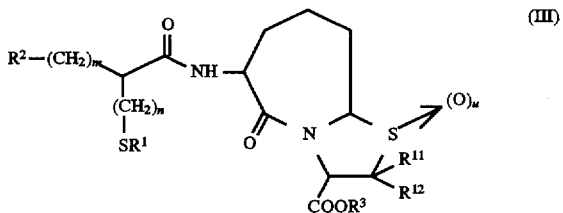

wherein $R^1$ represents a hydrogen atom or an acyl group;

$R^2$ represents a hydrogen atom, a lower alkyl group, a cycloalkyl group, an aryl group which may have a substituent, a heteroaryl group which may have a substituent, an arylalkyl group which may have a substituent or a heteroarylalkyl group which may have a substituent;

$R^3$ represents a hydrogen atom or a carboxyl-protecting group;

$R^{11}$ and $R^{12}$ are the same or different from each other and each represents a hydrogen atom or a lower alkyl group; and u, m and n represent each independently 0, 1 or 2.

5. An amino acid derivative represented by formula (IV):

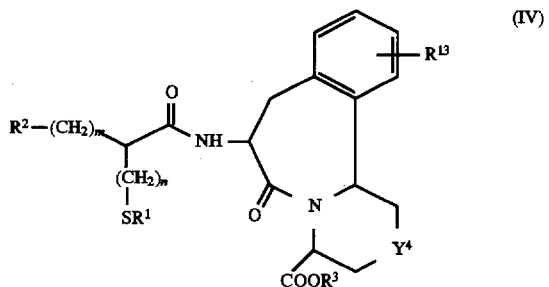

wherein R¹ represents a hydrogen atom or an acyl group;

R² represents a hydrogen atom, a lower alkyl group, a cycloalkyl group, an aryl group which may have a substituent, a heteroaryl group which may have a substituent, an arylalkyl group which may have a substituent or a heteroarylalkyl group which may have a substituent;

R³ represents a hydrogen atom or a carboxyl-protecting group;

Y⁴ represents —SO— or a group represented by the formula —SO₂—, a

R¹³ represents a group represented by the formula

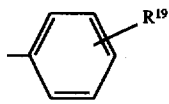

(wherein R¹⁹ represents a hydrogen atom, a lower alkyl group, a lower alkoxy group, a hydroxyl group or a halogen atom) or a group represented by the formula —NHSO₂R¹⁸ (wherein R¹⁸ represents a hydrogen atom, a lower alkyl group or an arylalkyl group which may have a substituent); and m and n represent each independently 0, 1 or 2.

6. An amino acid derivative represented by formula (V):

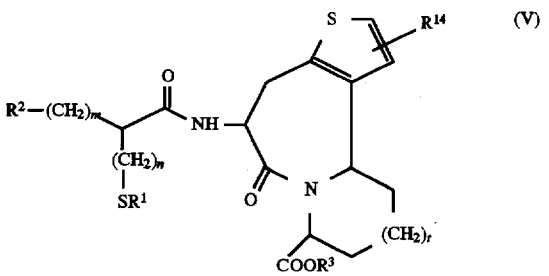

wherein R¹ represents a hydrogen atom or an acyl group;

R² represents a hydrogen atom, a lower alkyl group, a cycloalkyl group, an aryl group which may have a substituent, a heteroaryl group which may have a substituent, an arylalkyl group which may have a substituent or a heteroarylalkyl group which may have a substituent; and m, n and t represent each independently an integer of 0, 1 or 2.

7. An amino acid derivative represented by formula (VI):

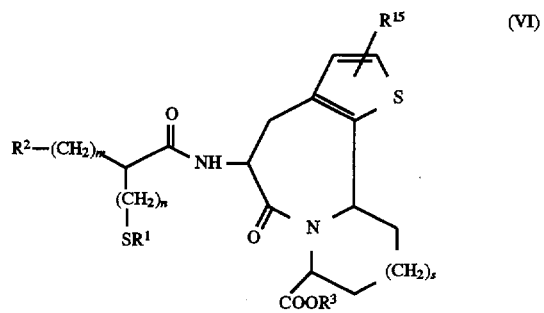

wherein R¹ represents a hydrogen atom or an acyl group;

R² represents a hydrogen atom, a lower alkyl group, a cycloalkyl group, an aryl group which may have a substituent, a heteroaryl group which may have a substituent, an arylalkyl group which may have a substituent or a heteroarylalkyl group which may have a substituent;

R³ represents a hydrogen atom or a carboxyl-protecting group;

R¹⁵ represents a hydrogen atom, a lower alkyl group, a lower alkoxy group, a hydroxyl group, a halogen atom, an aryl group which may have a substituent or a heteroaryl group which may have a substituent; and m, n and s represent each independently an integer of 0, 1 or 2.

8. An amino acid derivative represented by the formula (VI-2):

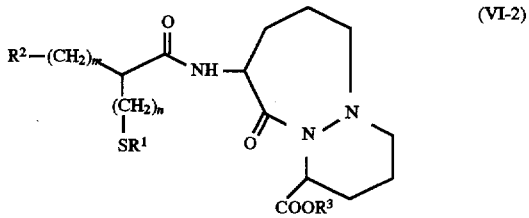

wherein R¹ represents a hydrogen atom or an acyl group;
R² represents a hydrogen atom, a lower alkyl group, a cycloalkyl group, an aryl group which may have a substituent, a heteroaryl group which may have a substituent, an arylalkyl group which may have a substituent or a heteroarylalkyl group which may have a substituent, and R³ represents a hydrogen atom or a carboxyl-protecting group, with m and n independently representing an integer of 0, 1, or 2.

9. The compound as set forth in claim 1, wherein the amino acid derivative is represented by the general formula (I'):

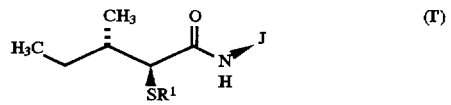

wherein R¹ represents a hydrogen atom or an acyl group; and J represents a cyclic group having an angiotensin I-converting enzyme inhibition activity.

10. The compound composition as set forth in claim 1, wherein J in the general formula (I) is represented

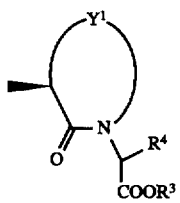

wherein R³ represents a hydrogen atom or a carboxyl-protecting group;

Y¹ represents a group represented by the formula —(CR⁵R⁶)$_p$—Z—(CR⁷R⁸)$_q$— (wherein R⁵, R⁶ R⁷ and R⁸ are the same or different from one another and each represents a hydrogen atom, a lower alkyl group, an aryl group which may have a substituent, a heteroaryl group which may have a substituent, an arylalkyl group which may have a substituent or a heteroarylalkyl group which may have a substituent; Z represents a group represented by the formula —(CH₂)$_r$— (wherein r represents an integer of 0 or 1), a group represented by the formula —S—, a group represented by the formula —SO—, a group represented by the formula —SO₂—, a group represented by the formula —O— or a group represented by the formula —NR⁹— (wherein R⁹ represents a hydrogen atom or a lower alkyl group);

and p and q represents each independently an integer of 0 or 1 to 4 and the sum of p and q is 6 or less;

with the proviso that in R⁵, R⁶, R⁷, R⁸ and R⁹, when two carbon atoms each having a substituent independently selected from R⁵, R⁶, R⁷, R⁸, or R⁹ bonded thereto are adjacent to each other, said two carbon atoms and said two substituents bonded thereto may be combined together to form a benzene ring or a heteroaryl ring, which may have a substituent;

and that when R² is an aryl group, p is 2, q is 2, Z represents a group represented by the formula —(CH₂) $_r$— (wherein r' represents 0), and two substituents independently selected from among R⁵, R⁶, R⁷, and R⁸ which are bonded to two adjacent carbon atoms are combined together to form a benzene ring, said benzene ring must be substituted by an aryl group which may have a substituent): and R⁴ represents a hydrogen atom, sulfur or oxygen atom in combination with R⁷ or R⁸.

11. The compound composition as set forth in claim 1, wherein the amino acid derivative represented by the general formula (I) is represented by the general formula (VII'):

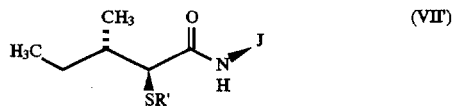

wherein R¹ represents a hydrogen atom or an acyl group; and

J represents a cyclic group having an angiotensin I-converting enzyme inhibition activity.

12. The compound composition as set forth in claim 11, wherein J in the general formula (VII') is represented by

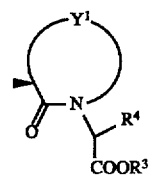

wherein R³ represents a hydrogen atom or a carboxyl-protecting group;

Y¹ represents a group represented by the formula —(CR⁵R⁶)$_p$—Z—(CR⁷R⁸)$_q$— (wherein R⁵, R⁶, R⁷ and R⁸ are the same or different from one another and each represents a hydrogen atom, a lower alkyl group, an aryl group which may have a substituent, a heteroaryl group which may have a substituent, an arylalkyl group which may have a substituent or a heteroarylalkyl group which may have a substituent; Z represents a group represented by the formula —(CH₂)$_r$— (wherein r represents an integer of 0 or 1), a group represented by the formula —S—, a group represented by the formula —SO—, a group represented by the formula —SO₂—, a group represented by the formula —O— or a group represented by the formula —NR⁹— (wherein R⁹ represents a hydrogen atom or a lower alkyl group);

and p and q represents each independently an integer of 0 or 1 to 4 and the sum of p and q is 6 or less;

with the proviso that in R⁵, R⁶, R⁷, R⁸ and R⁹, when two carbon atoms each having an arbitrary substituent selected from among R⁵ to R⁹ bonded thereto are adjacent to each other, said two carbon atoms and said two substituents bonded thereto may be combined together to form a benzene ring or a heteroaryl ring, which may have a substituent;

and that when R² is an aryl group, p is 2, q is 2, Z represents a group represented by the formula —(CH₂) $_r$— (wherein r' represents 0), and two substituents arbitrary selected from among R⁵'s, R⁶'s, R⁷'s and R⁸'s which are bonded to two adjacent carbon atoms are combined together to form a benzene ring, said benzene ring must be substituted by an aryl group which may have a substituent); and R⁴ represents a hydrogen atom, or a group used to form a 5- to 7-membered ring which may contain one sulfur or oxygen atom in combination with R⁷ or R⁸.

13. The compound composition as set forth in claim 1, wherein the amino acid derivative represented by the general formula (I) is represented by the general formula (IIa):

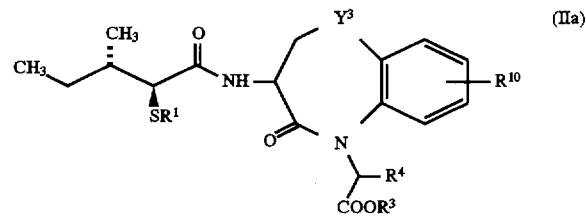

wherein R¹ represents a hydrogen atom or an acyl group;

R³ represents a hydrogen atom or a carboxyl-protecting group;

R10 represents a hydrogen atom, a lower alkyl group, a lower alkoxy group, a hydroxyl group, a halogen atom, an aryl group which may have a substituent or a heteroaryl group which may have a substituent;

$Y^3$ represents a group represented by the formula —(CH$_2$)$_w$— (wherein w represents 0 or 1), a group represented by the formula —S—, a group represented by the formula —SO—, a group represented by the formula —SO$_2$—, a group represented by the formula —O— or a group represented by the formula —NR$^{16}$— (wherein R$^{16}$ represents a hydrogen atom or a lower alkyl group); and m and n represent each independently an integer of 0, 1 or 2.

14. The compound composition as set forth in claim 1, wherein the amino acid derivative represented by the general formula (I) is represented by the general formula (IIIa):

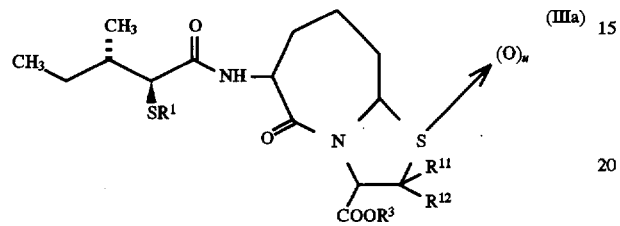

wherein R$^1$ represents a hydrogen atom or an acyl group;
R$^3$ represents a hydrogen atom or a carboxyl-protecting group;
R$^{11}$ and R$^{12}$ are the same or different from each other and each represents a hydrogen atom or a lower alkyl group; and
u, m and n represent each independently 0, 1 or 2.

15. The compound composition as set forth in claim 1, wherein the amino acid derivative represented by the general formula (I) is represented by the general formula (IVa):

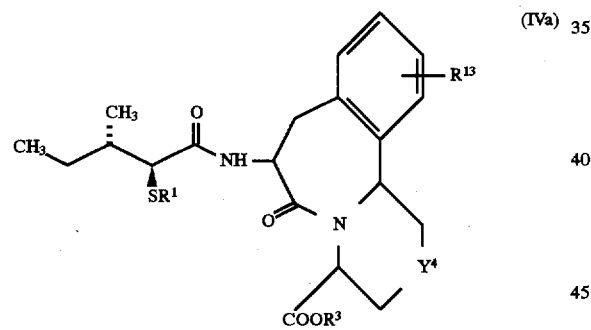

wherein R$^1$ represents a hydrogen atom or an acyl group;
R$^3$ represents a hydrogen atom or a carboxyl-protecting group;
Y$^4$ represents a group represented by the formula —(CH$_2$)$_x$— (wherein x represents 0 or 1), a group represented by the formula —S—, a group represented by the formula —SO—, a group represented by the formula —SO$_2$—, a group represented by the formula —O— or a group represented by the formula —NR$^{17}$— (wherein R$^{17}$ represents a hydrogen atom or a lower alkyl group);
R$^{13}$ represents a group represented by the formula

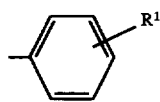

(wherein R$^{19}$ represents a hydrogen atom, a lower alkyl group, a lower alkoxy group, a hydroxyl group or a halogen atom) or a group represented by the formula —NHSO$_2$R$^{18}$ (wherein R$^{18}$ represents a hydrogen atom, a lower alkyl group or an arylalkyl group which may have a substituent); and m and n represent each independently 0, 1 or 2.

16. The compound composition as set forth in claim 1, wherein the amino acid derivative represented by the general formula (I) is represented by the general formula (Va):

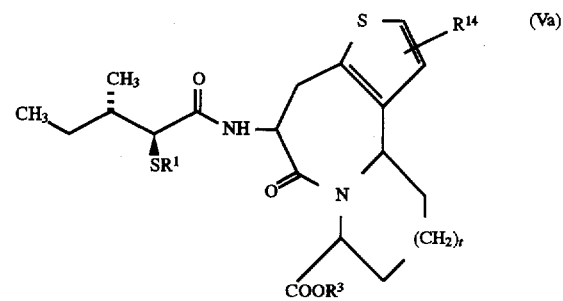

wherein R$^1$ represents a hydrogen atom or an acyl group;
R$^3$ represents a hydrogen atom or a carboxyl-protecting group;
R$^{14}$ represents a hydrogen atom, a lower alkyl group, a lower alkoxy group, a hydroxyl group, a halogen atom, an aryl group which may have a substituent or a heteroaryl group which may have a substituent; and
t represents an integer of 0, 1 or 2.

17. The compound composition as set forth in claim 1, wherein the amino acid derivative represented by the general formula (I) is represented by the general formula (VIa):

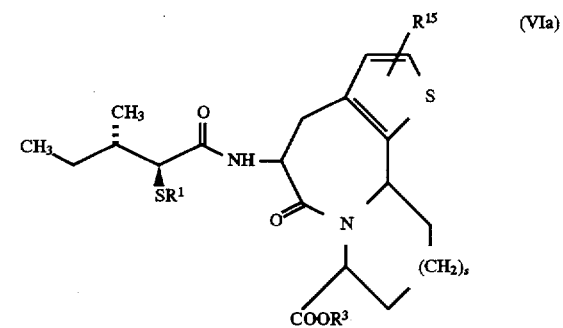

wherein R$^1$ represents a hydrogen atom or an acyl group;
R$^3$ represents a hydrogen atom or a carboxyl-protecting group;
R$^{15}$ represents a hydrogen atom, a lower alkyl group, a lower alkoxy group, a hydroxyl group, a halogen atom, an aryl group which may have a substituent or a heteroaryl group which may have a substituent; and
s represents an integer of 0, 1 or 2.

18. The amino acid derivative as set forth in claim 7, wherein the amino acid derivative represented by the general formula (I) is

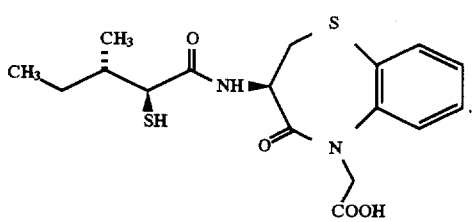

19. The amino acid derivative as set forth in claim 7, wherein the amino acid derivative represented by the general formula (I) is

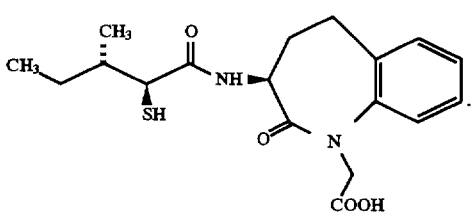

20. The amino acid derivative as set forth in claim 7, wherein the amino acid derivative represented by the general formula (I) is

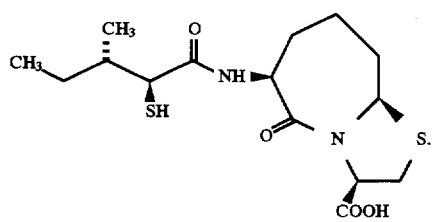

21. The amino acid derivative as set forth in claim 7, wherein the amino acid derivative represented by the general formula (I) is

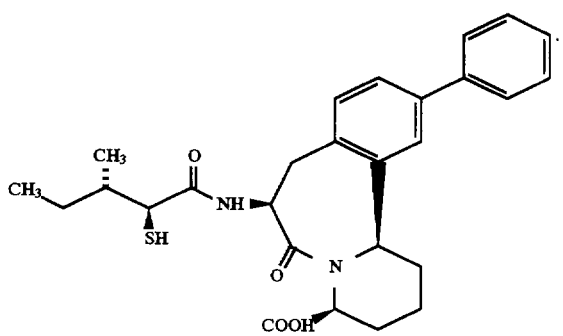

22. The medicinal composition as set forth in claim 7, wherein the amino acid derivative represented by the general formula (I) is

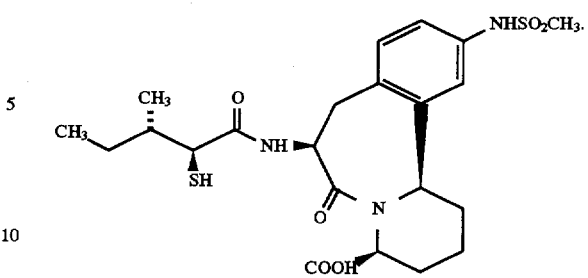

23. The amino acid derivative as set forth in claim 7, wherein the amino acid derivative represented by the general formula (I) is

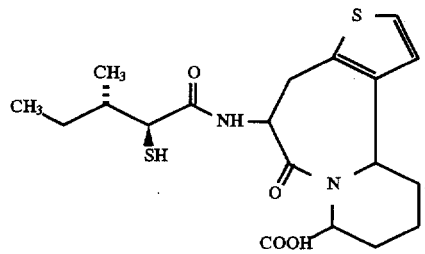

24. The amino acid derivative as set forth in claim 7, wherein the amino acid derivative represented by the general formula (I) is

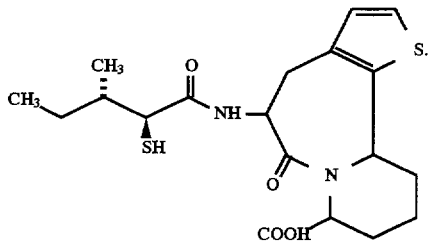

25. A pharmaceutical composition comprising an effective amount of a compound according to claim 1; and a pharmaceutically acceptable carrier.

26. A pharmaceutical composition comprising an effective amount of a amino acid derivative according to claim 3; and a pharmaceutically acceptable carrier.

27. A pharmaceutical composition comprising an effective amount of a amino acid derivative according to claim 4; and a pharmaceutically acceptable carrier.

28. A pharmaceutical composition comprising an effective amount of a amino acid derivative according to claim 5; and a pharmaceutically acceptable carrier.

29. A pharmaceutical composition comprising an effective amount of a amino acid derivative according to claim 6; and a pharmaceutically acceptable carrier.

30. A pharmaceutical composition comprising an effective amount of a amino acid derivative according to claim 7; and a pharmaceutically acceptable carrier.

31. A pharmaceutical composition comprising an effective amount of a amino acid derivative according to claim 8; and a pharmaceutically acceptable carrier.

32. The amino acid derivative as set forth in claim 1, wherein the amino acid derivative is represented by the general formula (II'):

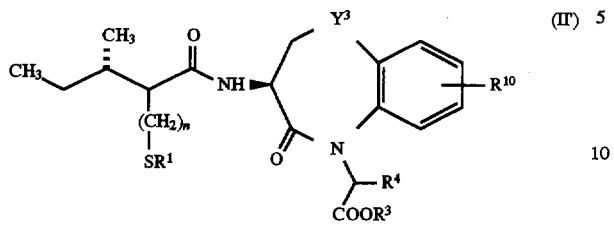

wherein $R^1$ represents a hydrogen atom or an acyl group;

$R^2$ represents a hydrogen atom, a lower alkyl group, a cycloalkyl group, an aryl group which may have a substituent, a heteroaryl group which may have a substituent, an arylalkyl group which may have a substituent or a heteroarylalkyl group which may have a substituent;

$R^3$ represents a hydrogen atom or a carboxy-protecting group;

$Y^3$ represents a group represented by the formula —(CH$_2$)$_w$— (wherein w represents 0 or 1), a group represented by the formula —S—, a group represented by the formula —SO—, a group represented by the formula —SO$_2$—, a group represented by the formula —O— or a group represented by the formula —NR$^{16}$— (wherein $R^{16}$ represents a hydrogen atom or a lower alkyl group); and $R^{10}$ represents a hydrogen atom, a lower alkyl group, a lower alkoxy group, a hydroxyl group, a halogen atom, an aryl group which may have a substituent or a heteroaryl group which may have a substituent; and n represents an integer of 0, 1 or 2.

33. The amino acid derivative as set forth in claim 4, represented by the general formula (III'):

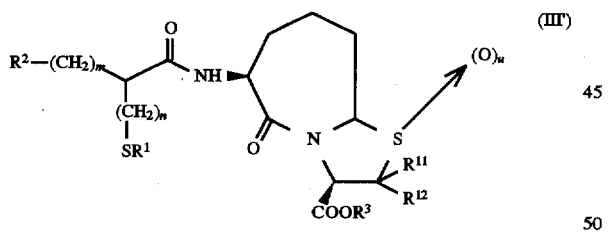

wherein $R^1$ represents a hydrogen atom or an acyl group;

$R^2$ represents a hydrogen atom, a lower alkyl group, a cycloalkyl group, an aryl group which may have a substituent, a heteroaryl group which may have a substituent, an arylalkyl group which may have a substituent or a heteroarylalkyl group which may have a substituent;

$R^3$ represents a hydrogen atom or a carboxyl-protecting group;

$R^{11}$ and $R^{12}$ are the same or different from each other and each represents a hydrogen atom or a lower alkyl group; and u, m and n represent each independently 0, 1 or 2.

34. The amino acid derivative as set forth in claim 5, represented by the general-formula (IV'):

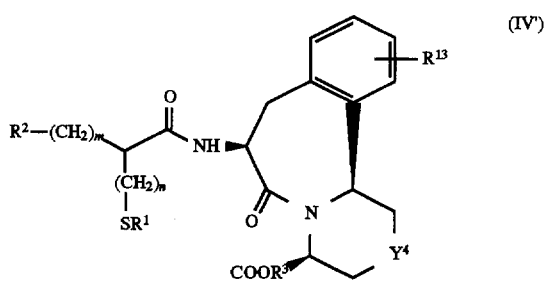

wherein $R^1$ represents a hydrogen atom or an acyl group;

$R^2$ represents a hydrogen atom, a lower alkyl group, a cycloalkyl group, an aryl group which may have a substituent, a heteroaryl group which may have a substituent, an arylalkyl group which may have a substituent or a heteroarylalkyl group which may have a substituent;

$R^3$ represents a hydrogen atom or a carboxyl-protecting group;

$Y^4$ represents a group represented by the formula —(CH$_2$)$_x$— (wherein X represents 0 or 1), a group represented by the formula —S—, a group represented by the formula —SO—, a group represented by the formula —SO$_2$—, a group represented by the formula —O— or a group represented by the formula —NR$^{17}$— (wherein $R^{17}$ represents a hydrogen atom or a lower alkyl group);

$R^{13}$ represents a group represented by the formula

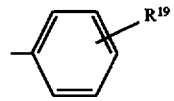

(wherein $R^{19}$ represents a hydrogen atom, a lower alkyl group, a lower alkoxy group, a hydroxyl group or a halogen atom) or a group represented by the formula —NHSO$_2$R$^{18}$ (wherein $R^{18}$ represents a hydrogen atom, a lower alkyl group or an arylalkyl group which may have a substituent); and m and n represent each independently 0, 1 or 2.

35. The amino acid derivative as set forth in claim 6, represented by the general formula (V'):

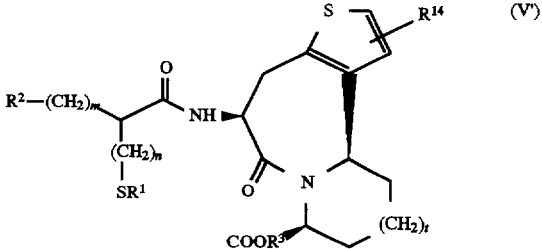

wherein $R^1$ represents a hydrogen atom or an acyl group;

$R^2$ represents a hydrogen atom, a lower alkyl group, a cycloalkyl group, an aryl group which may have a substituent, a heteroaryl group which may have a substituent, an arylalkyl group which may have a substituent or a heteroarylalkyl group which may have a substituent;

$R^3$ represents a hydrogen atom or a carboxyl-protecting group;

$R^{14}$ represents a hydrogen atom, a lower alkyl group, a lower alkoxy group, a hydroxyl group, a halogen atom, an aryl group which may have a substituent or a heteroaryl group which may have a substituent; and m, n and t represent each independently and integer of 0, 1 or 2.

36. The amino acid derivative as set forth in claim 7, represented by the general formula (VI'):

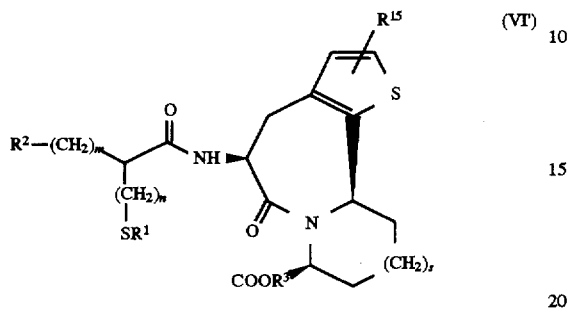

wherein $R^1$ represents a hydrogen atom or an acyl group;

$R^2$ represents a hydrogen atom, a lower alkyl group, a cycloalkyl group, an aryl group which may have a substituent, a heteroaryl group which may have a substituent, an arylalkyl group which may have a substituent or a heteroarylalkyl group which may have a substituent;

$R^3$ represents a hydrogen atom or a carboxyl-protecting group;

$R^{15}$ represents a hydrogen atom, a lower alkyl group, a lower alkoxy group, a hydroxyl group, a halogen atom, an aryl group which may have a substituent or a heteroaryl group which may have a substituent; and m, n and s represent each independently an integer of 0, 1 or 2.

37. The amino acid derivative as set forth in claim 7, represented by the general formula (VI-2'):

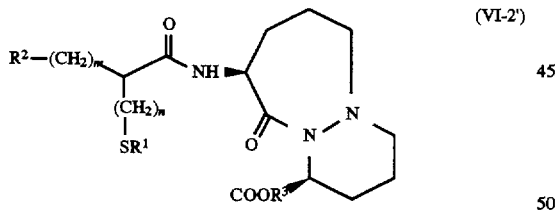

wherein $R^1$ represents a hydrogen atom or an acyl group;

$R^2$ represents a hydrogen atom, a lower alkyl group, a cycloalkyl group, an aryl group which may have a substituent, a heteroaryl group which may have a substituent, an arylalkyl group which may have a substituent or a heteroarylalkyl group which may have a substituent;

$R^3$ represents a hydrogen atom or a carboxyl-protecting group; and m and n represent each independently an integer of 0, 1 or 2.

38. The amino acid derivative as set forth in claim 3, represented by the general formula (II''):

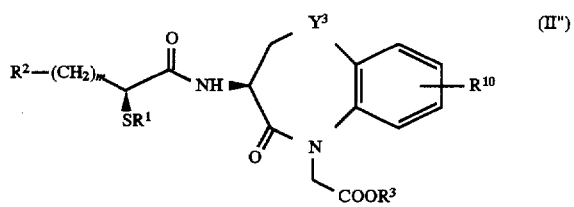

wherein $R^1$ represents a hydrogen atom or an acyl group;

$R^2$ represents a hydrogen atom, a lower alkyl group, a cycloalkyl group, an aryl group which may have a substituent, a heteroaryl group which may have a substituent, an arylalkyl which may have a substituent or a heteroarylalkyl group which may have a substituent;

$R^3$ represents a hydrogen atom or a carboxyl-protecting group;

$Y^3$ represents a group represented by the formula —(CH$_2$)$_w$— (wherein w represents 0 or 1), a group represented by the formula —S—, a group represented by the formula —SO—, a group represented by the formula —SO$_2$, a group represented by the formula —O— or a group represented by the formula —NR$^{16}$— (wherein $R^{16}$ represents a hydrogen atom or a lower alkyl group);

$R^{10}$ represents a hydrogen atom, a lower alkyl group, a lower alkoxy group, a hydroxyl group, a halogen atom, an aryl group which may have a substituent or a heteroaryl group which may have a substituent; and m represents independently an integer of 0, 1 or 2.

39. The amino acid derivative as set forth in claim 4, represented by the general formula (III''):

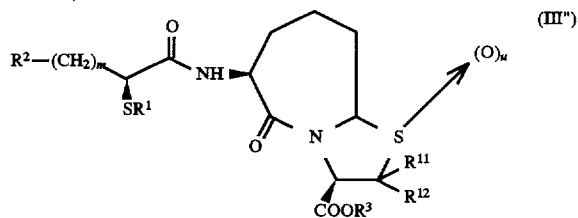

wherein $R^1$ represents a hydrogen atom or an acyl group;

$R^2$ represents a hydrogen atom, a lower alkyl group, a cycloalkyl group, an aryl group which may have a substituent, a heteroaryl group which may have a substituent, an arylalkyl group which may have a substituent or a heteroarylalkyl group which may have a substituent;

$R^3$ represents a hydrogen atom or a carboxyl-protecting group;

$R^{11}$ and $R^{12}$ are the same or different from each other and each represents a hydrogen atom or a lower alkyl group; and m and u represent each independently 0, 1 or 2.

40. The amino acid derivative as set forth in claim 5, represented by the general formula (IV''):

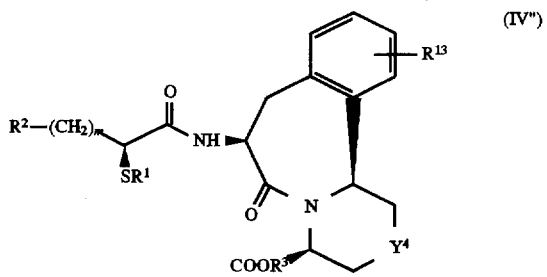

wherein R¹ represents a hydrogen atom or an acyl group;

R² represents a hydrogen atom, a lower alkyl group, a cycloalkyl group, an aryl group which may have a substituent, a heteroaryl group which may have a substituent, an arylalkyl group which may have a substituent or a heteroarylalkyl group which may have a substituent;

R³ represents a hydrogen atom or a carboxyl-protecting group;

Y⁴ represents a group represented by the formula —(CH₂)$_x$— (wherein x represents 0 or 1), a group represented by the formula —S—, a group represented by the formula —SO—, a group represented by the formula —SO₂—, a group represented by the formula —O— or a group represented by the formula —NR¹⁷— (wherein R¹⁷ represents a hydrogen atom or a lower alkyl group);

R¹³ represents a group represented by the formula

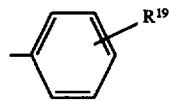

(wherein R¹⁹ represents a hydrogen atom, a lower alkyl group, a lower alkoxy group, a hydroxyl group or a halogen atom) or a group represented by the formula —NHSO₂R¹⁸ (wherein R¹⁸ represents a hydrogen atom, a lower alkyl group or an arylalkyl group which may have a substituent); and m represents independently 0, 1 or 2.

41. The compound as set forth in claim 6, represented by the general formula (V"):

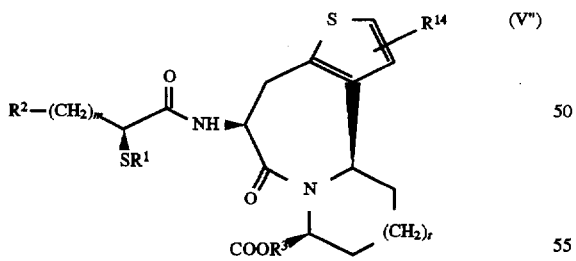

wherein R¹ represents a hydrogen atom or an acyl group;

R² represents a hydrogen atom, a lower alkyl group, a cycloalkyl group, an aryl group which may have a substituent, a heteroaryl group which may have a substituent, an arylalkyl group which may have a substituent or a heteroarylalkyl group which may have a substituent;

R³ represents a hydrogen atom or a carboxyl-protecting group;

R¹⁴ represents a hydrogen atom, a lower alkyl group, a lower alkoxy group, a hydroxyl group, a halogen atom, an aryl group which may have a substituent or a heteroaryl group which may have a substituent; and m and t represent each independently and integer of 0, 1 or 2.

42. The amino acid derivative as set forth in claim 7, represented by the general formula (VI"):

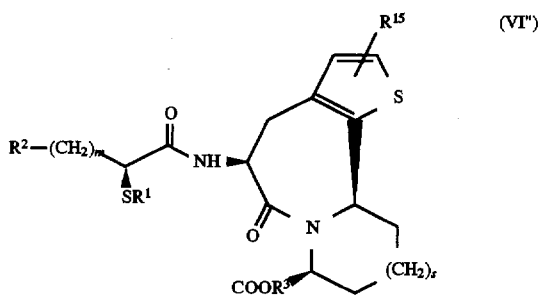

wherein R¹ represents a hydrogen atom or an acyl group;

R² represents a hydrogen atom, a lower alkyl group, a cycloalkyl group, an aryl group which may have a substituent, a heteroaryl group which may have a substituent, an arylalkyl group which may have a substituent or a heteroarylalkyl group which may have a substituent;

R³ represents a hydrogen atom or a carboxyl-protecting group;

R¹⁵ represents a hydrogen atom, a lower alkyl group, a lower alkoxy group, a hydroxyl group, a halogen atom, an aryl group which may have a substituent; and m and s represent each independently an integer of 0, 1 or 2.

43. The amino acid derivative as set forth in claim 3, represented by the general formula (IIa'):

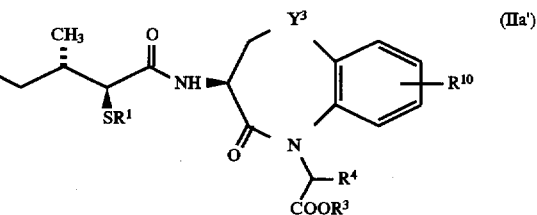

wherein R¹ represents a hydrogen atom or an acyl group;

R³ represents a hydrogen atom or a carboxyl-protecting group;

R⁴ represents a hydrogen atom, or a group used to form a 5- to 7-membered ring which may contain one sulfur or oxygen atom in combination with R⁷ or R⁸;

Y³ represents a group represented by the formula —(CH₂)$_w$— (wherein w represents 0 or 1), a group represented by the formula —S—, a group represented by the formula —SO—, a group represented by the formula —SO₂—, a group represented by the formula —O— or a group represented by the formula —NR¹⁶— (wherein R¹⁶ represents a hydrogen atom or a lower alkyl group); and R¹⁰ represents a hydrogen atom, a lower alkyl group, a lower alkoxy group, a hydroxyl group, a halogen atom, an aryl group which may have a substituent or a heteroaryl group which may have a substituent.

44. The amino acid derivative as set forth in claim 4, represented by the general formula (IIIa'):

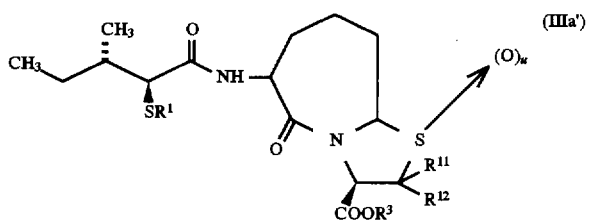

wherein $R^1$ represents a hydrogen atom or an acyl group;

$R^3$ represents a hydrogen atom or a carboxyl-protecting group;

$R^{11}$ and $R^{12}$ are the same or different from each other and each represents a hydrogen atom or a lower alkyl group; and u represents independently 0, 1 or 2.

45. The amino acid derivative as set forth in claim 5, represented by the general formula (IVa):

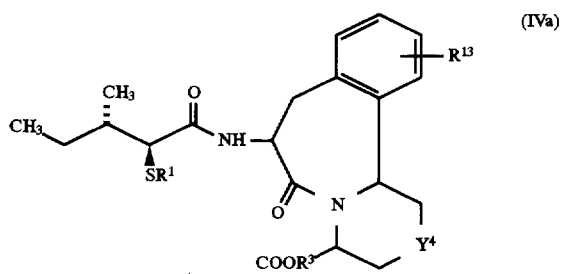

wherein $R^1$ represents a hydrogen atom or an acyl group;

$R^2$ represents a hydrogen atom, a lower alkyl group, a cycloalkyl group, an aryl group which may have a substituent, a heteroaryl group which may have a substituent, an arylalkyl group which may have a substituent or a heteroarylalkyl group which may have a substituent;

$R^3$ represents a hydrogen atom or a carboxyl-protecting group;

$Y^4$ represents a group represented by the formula —(CH$_2$)$_x$— (wherein x represents 0 or 1), a group represented by the formula —S—, a group represented by the formula —SO—, a group represented by the formula —SO$_2$—, a group represented by the formula —O— or a group represented by the formula —NR$^{17}$— (wherein $R^{17}$ represents a hydrogen atom or a lower alkyl group); and $R^{13}$ represents a group represented by the formula

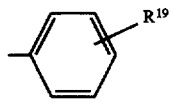

(wherein $R^{19}$ represents a hydrogen atom, a lower alkyl group, a lower alkoxy group, a hydroxyl group or a halogen atom) or a group represented by the formula —NHSO$_2$R$^{18}$ (wherein $R^{18}$ represents a hydrogen atom, a lower alkyl group or an arylalkyl group which may have a substituent).

46. The amino acid derivative as set forth in claim 6, represented by the general formula (Va):

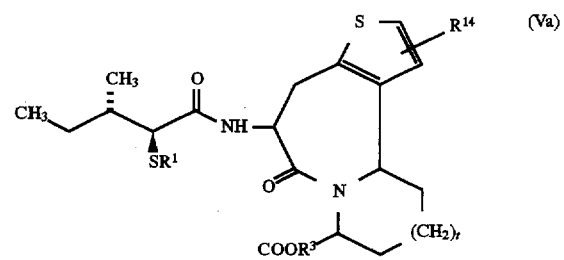

wherein $R^1$ represents a hydrogen atom or an acyl group;

$R^3$ represents a hydrogen atom or a carboxyl-protecting group;

$R^{14}$ represents a hydrogen atom, a lower alkyl group, a lower alkoxy group, a hydroxyl group, a halogen atom, an aryl group which may have a substituent or a heteroaryl group which may have a substituent; and t represents independently and integer of 0, 1 or 2.

47. The amino acid derivative as set forth in claim 7, represented by the general formula (VIa'):

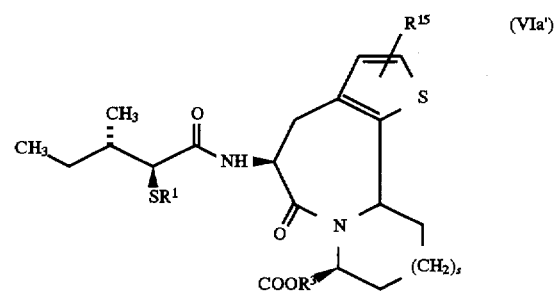

wherein $R^1$ represents a hydrogen atom or an acyl group;

$R^3$ represents a hydrogen atom or a carboxyl-protecting group;

$R^{15}$ represents a hydrogen atom, a lower alkyl group, a lower alkoxy group, a hydroxyl group, a halogen atom, an aryl group which may have a substituent or a heteroaryl group which may have a substituent; and s represents independently an integer of 0, 1 or 2.

48. The amino acid derivative as set forth in claim 7, represented by the general formula (VI-2a'):

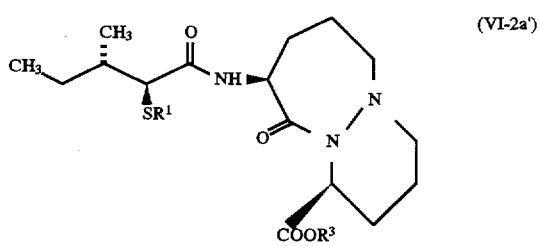

wherein $R^1$ represents a hydrogen atom or an acyl group; and $R^3$ represents a hydrogen atom or a carboxyl-protecting group.

49. The amino acid derivative as set forth in claim 3, represented by the general formula:

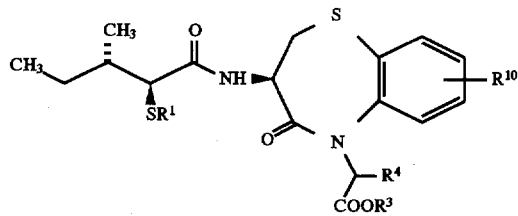

wherein R¹ represents a hydrogen atom or an acyl group;
R³ represents a hydrogen atom or a carboxyl-protecting group;
R⁴ represents a hydrogen atom, or a group used to form a 5- to 7-membered ring which may contain one sulfur or oxygen atom in combination with R⁷ or R⁸; and
R¹⁰ represents a hydrogen atom, a lower alkyl group, a lower alkoxy group, a hydroxyl group, a halogen atom, an aryl group which may have a substituent or a heteroaryl group which may have a substituent.

50. The amino acid derivative as set forth in claim 3, represented by the general formula:

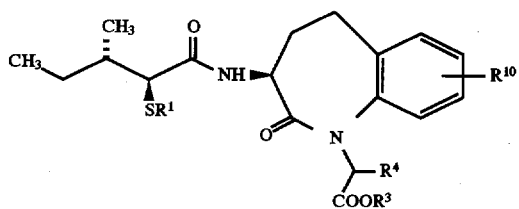

wherein R¹ represents a hydrogen atom or an acyl group;
R³ represents a hydrogen atom or a carboxyl-protecting group;
R⁴ represents a hydrogen atom, or a group used to form a 5- to 7-membered ring which may contain one sulfur or oxygen atom in combination with R⁷ or R⁸; and
R¹⁰ represents a hydrogen atom, a lower alkyl group, a lower alkoxy group, a hydroxyl group, a halogen atom, an aryl group which may have a substituent or a heteroaryl group which may have a substituent.

51. The amino acid derivative as set forth in claim 4, represented by the general formula:

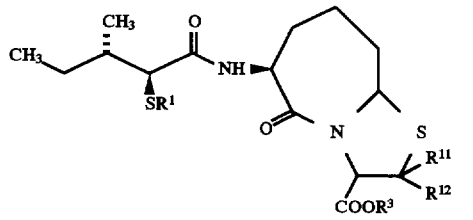

wherein R¹ represents a hydrogen atom or an acyl group;
R³ represents a hydrogen atom or a carboxyl-protecting group; and
R¹¹ and R¹² are the same or different from each other and each represents a hydrogen atom or a lower alkyl group.

52. The amino acid derivative as set forth in claim 5, represented by the general formula:

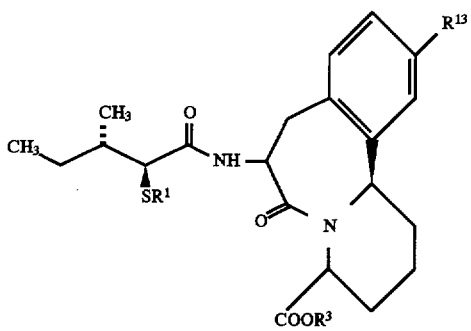

wherein R¹ represents a hydrogen atom or an acyl group;
R³ represents a hydrogen atom or a carboxyl-protecting group; and
R¹³ represents a group represented by the formula

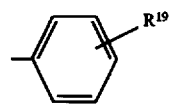

(wherein R¹⁹ represents a hydrogen atom, a lower alkyl group, a lower alkoxy group, a hydroxyl group or a halogen atom) or a group represented by the formula —NHSO₂R¹⁸ (wherein R¹⁹ represents a hydrogen atom, a lower alkyl group or an arylalkyl group which may have a substituent).

53. The amino acid derivative as set forth in claim 6, represented by the general formula (Va'):

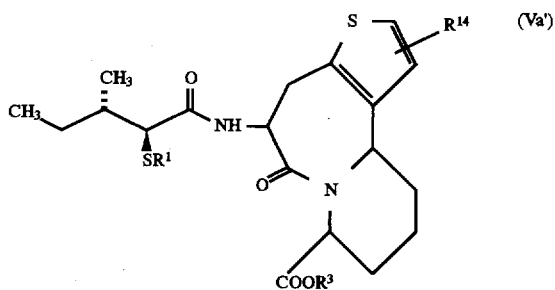

wherein R¹ represents a hydrogen atom or an acyl group;
R³ represents a hydrogen atom or a carboxyl-protecting group; and
R¹⁴ represents a hydrogen atom, a lower alkyl group, a lower alkoxy group, a hydroxyl group, a halogen atom, an aryl group which may have a substituent or a heteroaryl group which may have a substituent.

54. The compound as set forth in claim 7, represented by the general formula (VIa'):

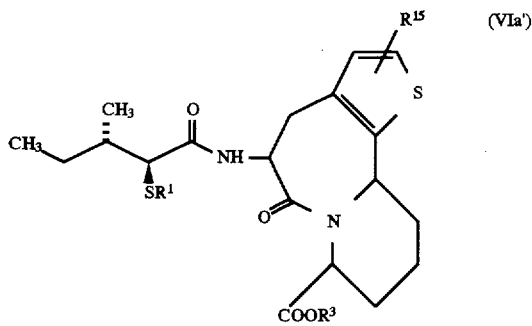

wherein $R^1$ represents a hydrogen atom or an acyl group; $R^3$ represents a hydrogen atom or a carboxyl-protecting group; and $R^{15}$ represents a hydrogen atom, a lower alkyl group, a lower alkoxy group, a hydroxyl group, a halogen atom, an aryl group which may have a substituent or a heteroaryl group which may have a substituent.

55. A method for treating or preventing diseases against which angiotensin I—converting enzyme inhibiting activity is efficacious which comprises administering a therapeutically or prophylactically available dose of an amino acid derivative or a pharmacologically acceptable salt thereof as set forth in claim 1 to a patient in need thereof.

56. A method for treating diseases against which a vasopressin antagonism is efficacious which comprises administering a therapeutically or prophylactically available dose of an amino acid derivative or a pharmacologically acceptable salt thereof as set forth in claim 1 to a patient with a disease in need thereof.

57. A method for treating diseases against which an atrial natriuretic peptide hydrolase is efficacious which comprises administering a therapeutically or prophylactically available dose of an amino acid derivative or a pharmacologically acceptable salt thereof as set forth in claim 1 to a patient in need thereof.

58. A method for treating heart failure which comprises administering a therapeutically or prophylactically available dose of an amino acid derivative or a pharmacologically acceptable salt thereof as set forth in claim 1 to a patient in need thereof.

59. A method for treating hypertension which comprises administering a therapeutically or prophylactically available dose of an amino acid derivative or a pharmacologically acceptable salt thereof as set forth in claim 1 to a patient in need thereof.

60. A method for treating a disease against which a diuretic activity is efficacious which comprises administering a therapeutically or prophylactically available dose of an amino acid derivative or a pharmacologically acceptable salt thereof as set forth in claim 1 to a patient in need thereof.

61. A compound having the formula (VII):

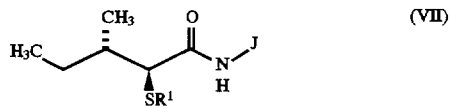

wherein $R^1$ represents a hydrogen atom or an acyl group;

J in the general formula (VII) is represented by

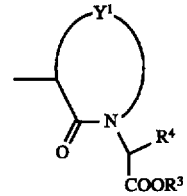

wherein $R^3$ represents a hydrogen atom or a carboxyl-protecting group;

$Y^1$ represents a group represented by the formula —$(CR^5R^6)p$—Z— $(CR^7R^8)q$— wherein $R^5$, $R^6$, $R^7$ and $R^8$ are the same or different from one another and each represents a hydrogen atom, a lower alkyl group, an aryl group which may have a substituent, a heteroaryl group which may have a substituent, an arylalkyl group which may have a substituent or a heteroarylalkyl group which may have a substituent; Z represents a group represented by the formula —$(CH_2)_x$— (wherein r represents an integer of 0 or 1), a group represented by the formula —S—, a group represented by the formula —SO—, a group represented by the formula —$SO_2$—, a group represented by the formula —O— or a group represented by the formula —$NR^9$— (wherein $R^9$ represents a hydrogen atom or a lower alkyl group); and p and q represents each independently an integer of 0,1,2,3, or 4 and the sum of p and q is 6 or less;

with the proviso that in $R^5$, $R^6$, $R^7$, $R^8$ and $R^9$, when two carbon atoms each having a substituent independently selected from among $R^5$, $R^6$, $R^7$, $R^8$, $R^9$ bonded thereto are adjacent to each other, said two carbon atoms and said two substituents bonded thereto may be combined together to form a benzene ring or a heteroaryl ring, which may have a substituent;

and that when $R^2$ is an aryl group, p is 2, q is 2, Z represents a group represented by the formula —$(CH_2)$ $_{r'}$— (wherein r' represents an integer of 0 or 1), and two substituents independently selected from among $R^5$, $R^6$, $R^7$, and $R^8$ which are bonded to two adjacent carbon atoms and are combined together to form a benzene ring, said benzene ring must be substituted by an aryl group which may have a substituent; and $R^4$ represents a hydrogen atom, a lower alkyl group or an arylalkyl group, or a group used to form a 5- to 7-membered ring which may contain one sulfur or oxygen atom in combination with $R^7$ and $R^8$.

* * * * *

UNITED STATES PATENT AND TRADEMARK OFFICE
CERTIFICATE OF CORRECTION

PATENT NO. : 5,679,671
DATED : October 21, 1997
INVENTOR(S) : Hitoshi OINUMA et al.

It is certified that error appears in the above-identified patent and that said Letters Patent is hereby corrected as shown below:

On the cover page of the Patent, left-hand column, after item [22], delete "Filed: Jan. 25, 1995" and insert the following:

```
--       PCT Filed:  June 10, 1994

[86]   PCT No.:  PCT/JP94/00947

§ 371 Date:  Jan. 25, 1995

§ 102(e) Date:  Jan. 25, 1995

[87]   PCT Pub. No.:  WO 94/28901

PCT Pub. Date:  Dec. 22, 1994--
```

Signed and Sealed this

Twenty-sixth Day of May, 1998

Attest:

BRUCE LEHMAN

*Attesting Officer*  *Commissioner of Patents and Trademarks*